US012180493B2

(12) United States Patent
Leonhardt et al.

(10) Patent No.: US 12,180,493 B2
(45) Date of Patent: Dec. 31, 2024

(54) CONSTRUCTS AND METHODS FOR CONTROLLING STOMATAL CLOSURE IN PLANTS

(71) Applicants: BIOGEMMA, Paris (FR); COMMISSARIAT A L'ENERGIE ATOMIQUE ET AUX ENERGIES ALTERNATIVES, Paris (FR)

(72) Inventors: Nathalie Leonhardt, Aix en Provence (FR); Ludovic Martin, Giat (FR); Serge Chiarenza, Aix en Provence (FR); Helene Jacquet, Vinon sur Verdon (FR); Laurent Nussaume, La Tour d'Aigues (FR); Marie Javelle, Chappes (FR)

(73) Assignees: LIMAGRAIN EUROPE, Saint Beauzire (FR); COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 876 days.

(21) Appl. No.: 16/321,644
(22) PCT Filed: Aug. 4, 2017
(86) PCT No.: PCT/EP2017/069796
§ 371 (c)(1),
(2) Date: Jan. 29, 2019
(87) PCT Pub. No.: WO2018/024883
PCT Pub. Date: Feb. 8, 2018

(65) Prior Publication Data
US 2021/0285007 A1 Sep. 16, 2021

(30) Foreign Application Priority Data
Aug. 5, 2016 (EP) .................................. 16306025

(51) Int. Cl.
*A01H 1/00* (2006.01)
*A01H 5/00* (2018.01)
*A01H 5/10* (2018.01)
*A01H 5/12* (2018.01)
*A01H 6/46* (2018.01)
*C07K 14/415* (2006.01)
*C12N 15/00* (2006.01)
*C12N 15/82* (2006.01)

(52) U.S. Cl.
CPC .......... *C12N 15/8261* (2013.01); *A01H 1/00* (2013.01); *A01H 5/10* (2013.01); *A01H 5/12* (2013.01); *A01H 6/4684* (2018.05); *C07K 14/415* (2013.01)

(58) Field of Classification Search
None
See application file for complete search history.

(56) References Cited

U.S. PATENT DOCUMENTS

| 8,577,624 B2 | 11/2013 | Palmgren et al. |
| 2005/0108791 A1* | 5/2005 | Edgerton ............. C07K 14/415 800/284 |
| 2009/0217414 A1 | 8/2009 | La Rosa et al. |
| 2013/0074202 A1 | 3/2013 | Adams et al. |
| 2016/0032312 A1 | 2/2016 | Kinoshita et al. |

FOREIGN PATENT DOCUMENTS

| EP | 1033405 A2 | 9/2000 |
| EP | 2995680 A1 | 3/2016 |
| WO | 2014012145 A1 | 1/2014 |

OTHER PUBLICATIONS

Axelsen et al., "Inventory of the Superfamily of P-Type Ion Pumps in Arabidopsis," Plant Physiol., 126:696-706 (2001).
Baunsgaard et al., "Modified plant plasma membrane H+ –ATPase with improved transport coupling efficiency Identified by mutant selection in yeast," The Plant Journal, 10(3):451-458 (1996).
Haruta et al., "Regulation of the plasma membrane proton pump (H+–ATPase) by phosphorylation," Current Opinion Plant Biology, 28:68-75 (2015).
Leonhardt et al., "Evidence for the existence of a sulfonylurea-receptor-like protein in plants: Modulation of stomatal movements and guard cell potassium channels by sulfonylureas and potassium channels by sulfonylureas and potassium channel openers," Proc. Natl. Acad. Sci. USA, 94:14156-14161 (1997).
Leonhardt et al., "ATP Binding Cassette Modulators Control Abscisic Acid-Regulated Slow Anion Channels in Guard Cells," The Plant Cells, 11:1141-1151 (1999).
Merlot et al., "Constitutive activation of a plasma membrane H+–ATPase prevents abscisic acid-mediated stomatal closure," The EMBO Journal, 26:3216-3226 (2007).
International Search Report for PCT/EP2017/069796 dated Oct. 10, 2017 (6 pages).
European Search Report for EP 16306025 dated Sep. 16, 2016 (10 pages).
Rusconi et al., "The Arabidopsis thaliana MYB60 promoter provides a tool for the spatio-temporal control of gene expression in stomatal guard cells," Journal of Experimental Botany, 64(11):3361-3371 (2013).
Ueno et al., "Biochemical Characterization of Plasma Membrane H+–ATPase Activation in Guard Cell Protoplasts of Arabidopsis thaliana in Response to Blue Light," Plant Cell Physiol., 46(6):955-963 (2005).
Yang et al., "Isolation of a strong Arabidopsis guard cell promoter and its potential as a research tool," Plant Methods, 4(6):1-15 (2008).

(Continued)

Primary Examiner — Phuong T Bui
(74) Attorney, Agent, or Firm — Arrigo, Lee, Guttman & Mouta-Bellum LLP

(57) ABSTRACT

The present invention is related to expressing an AHA5 protein in plants, and preferentially a mutated AHA5 protein leading to a constitutive activity of AHA5, to control stomatal closure and improve tolerance to drought conditions and yield in plants.

7 Claims, 11 Drawing Sheets
Specification includes a Sequence Listing.

(56) References Cited

OTHER PUBLICATIONS

Palmgren, Michael, " Plant Plasma Membrane H+ –ATPases: Powerhouses for Nutrient Uptake," Annual Rev. Plant Physiol. Plant Mol. Biol., 52:817-845 (2001).
Bates et al., "A Comparative Study of the Arabidopsis thaliana Guard-Cell Transcriptome and Its Modulation by Sucrose," PLoS One, 7(11):e49641 (2012).

* cited by examiner

SEQUENCE LISTING

```
<160> NUMBER OF SEQ ID NOS: 66

<210> SEQ ID NO 1
<211> LENGTH: 931
<212> TYPE: PRT
<213> ORGANISM: Arabidopsis thaliana
<220> FEATURE:
<221> NAME/KEY: misc_feature
<223> OTHER INFORMATION: AtAHA5 wild-type

<400> SEQUENCE: 1

Met Glu Glu Val Phe Glu Glu Leu Lys Cys Thr Lys Gln Gly Leu Thr
1               5                   10                  15

Ala Asn Glu Ala Ser His Arg Leu Asp Val Phe Gly Pro Asn Lys Leu
            20                  25                  30

Glu Glu Lys Lys Glu Ser Lys Leu Leu Lys Phe Leu Gly Phe Met Trp
        35                  40                  45

Asn Pro Leu Ser Trp Val Met Glu Val Ala Ala Leu Met Ala Ile Ala
    50                  55                  60

Leu Ala Asn Gly Gly Arg Pro Pro Asp Trp Gln Asp Phe Val Gly
65                  70                  75                  80

Ile Val Cys Leu Leu Leu Ile Asn Ser Thr Ile Ser Phe Ile Glu Glu
                85                  90                  95

Asn Asn Ala Gly Asn Ala Ala Ala Leu Met Ala Gly Leu Ala Pro
            100                 105                 110

Lys Thr Lys Val Leu Arg Asp Asn Gln Trp Ser Glu Gln Glu Ala Ser
        115                 120                 125

Ile Leu Val Pro Gly Asp Val Ile Ser Ile Lys Leu Gly Asp Ile Ile
    130                 135                 140

Pro Ala Asp Ala Arg Leu Leu Asp Gly Asp Pro Leu Lys Ile Asp Gln
145                 150                 155                 160
```

```
Ser Ser Leu Thr Gly Glu Ser Ile Pro Val Thr Lys Asn Pro Ser Asp
            165                 170                 175

Glu Val Phe Ser Gly Ser Ile Cys Lys Gln Gly Glu Ile Glu Ala Ile
            180                 185                 190

Val Ile Ala Thr Gly Val His Thr Phe Phe Gly Lys Ala Ala His Leu
            195                 200                 205

Val Asp Asn Thr Asn Gln Ile Gly His Phe Gln Lys Val Leu Thr Ser
            210                 215                 220

Ile Gly Asn Phe Cys Ile Cys Ser Ile Ala Leu Gly Ile Ile Val Glu
225                 230                 235                 240

Leu Leu Val Met Tyr Pro Ile Gln Arg Arg Tyr Arg Asp Gly Ile
            245                 250                 255

Asp Asn Leu Leu Val Leu Ile Gly Gly Ile Pro Ile Ala Met Pro
            260                 265                 270

Ser Val Leu Ser Val Thr Met Ala Thr Gly Ser His Arg Leu Phe Gln
            275                 280                 285

Gln Gly Ala Ile Thr Lys Arg Met Thr Ala Ile Glu Glu Met Ala Gly
            290                 295                 300

Met Asp Val Leu Cys Cys Asp Lys Thr Gly Thr Leu Thr Leu Asn Lys
305                 310                 315                 320

Leu Thr Val Asp Lys Asn Leu Val Glu Val Phe Ala Lys Gly Val Gly
            325                 330                 335

Lys Glu His Val Phe Leu Leu Ala Ala Arg Ala Ser Arg Ile Glu Asn
            340                 345                 350

Gln Asp Ala Ile Asp Ala Ala Ile Val Gly Met Leu Ala Asp Pro Lys
            355                 360                 365

Glu Ala Arg Ala Gly Val Arg Glu Val His Phe Phe Pro Phe Asn Pro
            370                 375                 380

Val Asp Lys Arg Thr Ala Leu Thr Tyr Val Asp Ser Asp Gly Asn Trp
385                 390                 395                 400

His Arg Ala Ser Lys Gly Ala Pro Glu Gln Ile Leu Asn Leu Cys Asn
            405                 410                 415

Cys Lys Glu Asp Val Arg Arg Lys Val His Gly Val Ile Asp Lys Phe
            420                 425                 430

Ala Glu Arg Gly Leu Arg Ser Leu Ala Val Ala Arg Gln Glu Val Leu
            435                 440                 445

Glu Lys Lys Lys Asp Ala Pro Gly Gly Pro Trp Gln Leu Val Gly Leu
            450                 455                 460

Leu Pro Leu Phe Asp Pro Pro Arg His Asp Ser Ala Glu Thr Ile Arg
465                 470                 475                 480

Arg Ala Leu Asn Leu Gly Val Asn Val Lys Met Ile Thr Gly Asp Gln
            485                 490                 495

Leu Ala Ile Gly Lys Glu Thr Gly Arg Arg Leu Gly Met Gly Thr Asn
            500                 505                 510

Met Tyr Pro Ser Ser Ala Leu Leu Gly Gln Val Lys Asp Ser Ser Leu
            515                 520                 525

Gly Ala Leu Pro Val Asp Glu Leu Ile Glu Lys Ala Asp Gly Phe Ala
            530                 535                 540

Gly Val Phe Pro Glu His Lys Tyr Glu Ile Val His Arg Leu Gln Gln
545                 550                 555                 560

Arg Asn His Ile Cys Gly Met Thr Gly Asp Gly Val Asn Asp Ala Pro
            565                 570                 575
```

```
Ala Leu Lys Lys Ala Asp Ile Gly Ile Ala Val Val Asp Ala Thr Asp
            580                 585                 590
Ala Ala Arg Gly Ala Ser Asp Ile Val Leu Thr Glu Pro Gly Leu Ser
        595                 600                 605
Val Ile Ile Ser Ala Val Leu Thr Ser Arg Ala Ile Phe Gln Arg Met
    610                 615                 620
Lys Asn Tyr Thr Ile Tyr Ala Val Ser Ile Thr Ile Arg Ile Val Phe
625                 630                 635                 640
Gly Phe Met Phe Ile Ala Leu Ile Trp Gln Phe Asp Phe Ser Pro Phe
            645                 650                 655
Met Val Leu Ile Ile Ala Ile Leu Asn Asp Gly Thr Ile Met Thr Ile
        660                 665                 670
Ser Lys Asp Arg Met Lys Pro Ser Pro Gln Pro Asp Ser Trp Lys Leu
    675                 680                 685
Arg Asp Ile Phe Ser Thr Gly Val Val Leu Gly Gly Tyr Gln Ala Leu
690                 695                 700
Met Thr Val Val Phe Phe Trp Val Met Lys Asp Ser Asp Phe Phe Ser
705                 710                 715                 720
Asn Tyr Phe Gly Val Arg Pro Leu Ser Gln Arg Pro Glu Gln Met Met
            725                 730                 735
Ala Ala Leu Tyr Leu Gln Val Ser Ile Ile Ser Gln Ala Leu Ile Phe
        740                 745                 750
Val Thr Arg Ser Arg Ser Trp Ser Tyr Ala Glu Cys Pro Gly Leu Leu
    755                 760                 765
Leu Leu Gly Ala Phe Val Ile Ala Gln Leu Val Ala Thr Phe Ile Ala
770                 775                 780
Val Tyr Ala Asn Trp Ser Phe Ala Arg Ile Glu Gly Ala Gly Trp Gly
785                 790                 795                 800
Trp Ala Gly Val Ile Trp Leu Tyr Ser Phe Leu Thr Tyr Ile Pro Leu
            805                 810                 815
Asp Leu Leu Lys Phe Gly Ile Arg Tyr Val Leu Ser Gly Lys Ala Trp
        820                 825                 830
Leu Asn Leu Leu Glu Asn Lys Thr Ala Phe Thr Thr Lys Lys Asp Tyr
    835                 840                 845
Gly Lys Glu Glu Arg Glu Ala Gln Trp Ala Ala Ala Gln Arg Thr Leu
850                 855                 860
His Gly Leu Gln Pro Ala Glu Lys Asn Asn Ile Phe Asn Glu Lys Asn
865                 870                 875                 880
Ser Tyr Ser Glu Leu Ser Gln Ile Ala Glu Gln Ala Lys Arg Arg Ala
            885                 890                 895
Glu Val Val Arg Leu Arg Glu Ile Asn Thr Leu Lys Gly His Val Glu
        900                 905                 910
Ser Val Val Lys Leu Lys Gly Leu Asp Ile Asp Thr Ile Gln Gln His
    915                 920                 925
Tyr Thr Val
    930

<210> SEQ ID NO 2
<211> LENGTH: 961
<212> TYPE: PRT
<213> ORGANISM: Zea mays
<220> FEATURE:
<221> NAME/KEY: misc_feature
<223> OTHER INFORMATION: ZmAHA5 wild-type
```

<400> SEQUENCE: 2

```
Met Gly Pro Leu Gln Arg Arg Pro Thr Ala Met Gly Gly Leu Glu Glu
1               5                   10                  15

Ile Lys Asn Glu Ala Val Asp Leu Glu Asn Ile Pro Ile Glu Glu Val
            20                  25                  30

Phe Glu Gln Leu Lys Cys Thr Arg Glu Gly Leu Ser Ser Ser Glu Gly
            35                  40                  45

Gln Gln Arg Leu Glu Ile Phe Gly Pro Asn Arg Leu Glu Glu Lys Lys
        50                  55                  60

Glu Ser Lys Ile Leu Lys Phe Leu Gly Phe Met Trp Asn Pro Leu Ser
65                  70                  75                  80

Trp Val Met Glu Met Ala Ala Val Met Ala Ile Ala Leu Ala Asn Gly
                85                  90                  95

Gly Gly Lys Pro Pro Asp Trp Glu Asp Phe Val Gly Ile Ile Val Leu
            100                 105                 110

Leu Val Ile Asn Ser Thr Ile Ser Phe Ile Glu Glu Asn Asn Ala Gly
            115                 120                 125

Asn Ala Ala Ala Ala Leu Met Ala Asn Leu Ala Pro Lys Thr Lys Val
        130                 135                 140

Leu Arg Asp Gly Arg Trp Gly Glu Gln Glu Ala Ala Ile Leu Val Pro
145                 150                 155                 160

Gly Asp Ile Val Ser Ile Lys Leu Gly Asp Ile Val Pro Ala Asp Ala
                165                 170                 175

Arg Leu Leu Glu Gly Asp Pro Leu Lys Val Asp Gln Ser Ala Leu Thr
            180                 185                 190

Gly Glu Ser Leu Pro Val Thr Lys Gly Pro Gly Asp Glu Val Phe Ser
            195                 200                 205

Gly Ser Thr Cys Lys Gln Gly Glu Ile Glu Ala Val Val Ile Ala Thr
        210                 215                 220

Gly Val His Thr Phe Phe Gly Lys Ala Ala His Leu Val Asp Ser Thr
225                 230                 235                 240

Asn Gln Val Gly His Phe Gln Gln Val Leu Thr Ala Ile Gly Asn Phe
                245                 250                 255

Cys Ile Cys Ser Ile Ala Val Gly Ile Val Val Glu Ile Ile Val Met
            260                 265                 270

Phe Pro Ile Gln His Arg Arg Tyr Arg Ser Gly Ile Glu Asn Leu Leu
            275                 280                 285

Val Leu Leu Ile Gly Gly Ile Pro Ile Ala Met Pro Thr Val Leu Ser
        290                 295                 300

Val Thr Met Ala Ile Gly Ser His Lys Leu Ser Gln Gln Gly Ala Ile
305                 310                 315                 320

Thr Lys Arg Met Thr Ala Ile Glu Glu Met Ala Gly Met Asp Val Leu
                325                 330                 335

Cys Ser Asp Lys Thr Gly Thr Leu Thr Leu Asn Lys Leu Ser Val Asp
            340                 345                 350

Lys Asn Leu Val Glu Val Phe Cys Lys Gly Val Asp Lys Asp His Val
            355                 360                 365

Leu Leu Leu Ala Ala Arg Ala Ser Arg Thr Glu Asn Gln Asp Ala Ile
        370                 375                 380

Asp Ala Ala Met Val Gly Met Leu Ala Asp Pro Lys Glu Ala Arg Ala
385                 390                 395                 400
```

```
Gly Ile Arg Glu Ile His Phe Leu Pro Phe Asn Pro Val Asp Lys Arg
                405                 410                 415

Thr Ala Leu Thr Tyr Ile Asp Ala Asp Gly His Trp His Arg Val Ser
            420                 425                 430

Lys Gly Ala Pro Glu Gln Ile Leu Asp Leu Cys His Cys Lys Glu Asp
        435                 440                 445

Leu Arg Arg Lys Val His Gly Ile Ile Asp Lys Tyr Ala Glu Arg Gly
    450                 455                 460

Leu Arg Ser Leu Ala Val Ala Arg Gln Glu Val Pro Glu Arg Asn Lys
465                 470                 475                 480

Glu Ser Pro Gly Gly Pro Trp Gln Phe Val Gly Leu Leu Pro Leu Phe
                485                 490                 495

Asp Pro Pro Arg His Asp Ser Ala Glu Thr Ile Arg Lys Ala Leu Val
            500                 505                 510

Leu Gly Val Asn Val Lys Met Ile Thr Gly Asp Gln Leu Ala Ile Gly
        515                 520                 525

Lys Glu Thr Gly Arg Arg Leu Gly Met Gly Thr Asn Met Tyr Pro Ser
    530                 535                 540

Ser Ala Leu Leu Gly Gln Asn Lys Asp Ala Thr Leu Glu Ala Leu Pro
545                 550                 555                 560

Val Asp Glu Leu Ile Glu Lys Ala Asp Gly Phe Ala Gly Val Phe Pro
                565                 570                 575

Glu His Lys Tyr Glu Ile Val Lys Arg Leu Gln Glu Lys Lys His Ile
            580                 585                 590

Val Gly Met Thr Gly Asp Gly Val Asn Asp Ala Pro Ala Leu Lys Lys
        595                 600                 605

Ala Asp Ile Gly Ile Ala Val Ala Asp Ala Thr Asp Ala Ala Arg Ser
    610                 615                 620

Ala Ser Asp Ile Val Leu Thr Glu Pro Gly Leu Ser Val Ile Ile Ser
625                 630                 635                 640

Ala Val Leu Thr Ser Arg Cys Ile Phe Gln Arg Met Lys Asn Tyr Thr
                645                 650                 655

Ile Tyr Ala Val Ser Ile Thr Ile Arg Ile Val Leu Gly Phe Met Leu
            660                 665                 670

Ile Ala Leu Ile Trp Gln Tyr Asp Phe Ser Pro Phe Met Val Leu Ile
        675                 680                 685

Ile Ala Ile Leu Asn Asp Gly Thr Ile Met Thr Ile Ser Lys Asp Arg
    690                 695                 700

Val Lys Pro Ser Pro Leu Pro Asp Ser Trp Lys Leu Lys Glu Ile Phe
705                 710                 715                 720

Ala Thr Gly Ile Val Leu Gly Ser Tyr Leu Ala Leu Met Thr Val Ile
                725                 730                 735

Phe Phe Trp Ala Met His Lys Thr Asp Phe Phe Ser Asp Lys Phe Gly
            740                 745                 750

Val Arg Ser Ile Arg Asp Ser Glu His Glu Met Met Ser Ala Leu Tyr
        755                 760                 765

Leu Gln Val Ser Ile Val Ser Gln Ala Leu Ile Phe Val Thr Arg Ser
    770                 775                 780

Arg Ser Trp Ser Phe Val Glu Arg Pro Gly Leu Leu Leu Val Thr Ala
785                 790                 795                 800

Phe Leu Leu Ala Gln Leu Val Ala Thr Phe Leu Ala Val Tyr Ala Asn
                805                 810                 815
```

```
Trp Gly Phe Ala Arg Ile Lys Gly Ile Gly Trp Gly Trp Ala Gly Val
            820                 825                 830

Val Trp Leu Tyr Ser Ile Val Phe Tyr Phe Pro Leu Asp Leu Ile Lys
        835                 840                 845

Phe Phe Ile Arg Phe Val Leu Ser Gly Arg Ala Trp Asp Asn Leu Leu
    850                 855                 860

Glu Asn Lys Thr Ala Phe Thr Thr Lys Lys Asp Tyr Gly Arg Glu Glu
865                 870                 875                 880

Arg Glu Ala Gln Trp Ala Thr Ala Gln Arg Thr Leu His Gly Leu Gln
                885                 890                 895

Pro Pro Glu Ala Ala Thr Ser Thr Leu Phe His Asp Lys Asn Ser Tyr
            900                 905                 910

Arg Glu Leu Ser Glu Ile Ala Glu Gln Ala Lys Arg Arg Ala Glu Ile
        915                 920                 925

Ala Arg Leu Arg Glu Leu Asn Thr Leu Lys Gly His Val Glu Ser Val
    930                 935                 940

Val Lys Leu Lys Gly Leu Asp Ile Asp Thr Ile Gln Gln Asn Tyr Thr
945                 950                 955                 960

Val

<210> SEQ ID NO 3
<211> LENGTH: 954
<212> TYPE: PRT
<213> ORGANISM: Helianthus annuus
<220> FEATURE:
<221> NAME/KEY: misc_feature
<223> OTHER INFORMATION: HaRA11741_4232_Helianthus_annuus

<400> SEQUENCE: 3

Met Gly Thr Asp Lys Ala Leu Gly Leu Glu Glu Ile Lys Asn Glu Thr
1               5                   10                  15

Val Asp Leu Glu Lys Val Pro Ile Glu Glu Val Phe Gln Gln Leu Lys
            20                  25                  30

Cys Asn Arg Glu Gly Leu Thr Ser Asp Glu Gly Ala Ala Arg Leu Gln
        35                  40                  45

Ile Phe Gly Pro Asn Lys Leu Glu Glu Lys Glu Ser Lys Ile Leu
    50                  55                  60

Lys Phe Leu Gly Phe Met Trp Asn Pro Leu Ser Trp Val Met Glu Ala
65                  70                  75                  80

Ala Ala Ile Met Ala Ile Ala Met Ala Asn Gly Gly Lys Pro Pro
                85                  90                  95

Asp Trp Gln Asp Phe Val Gly Ile Val Cys Leu Leu Val Ile Asn Ser
            100                 105                 110

Thr Ile Ser Phe Ile Glu Glu Asn Asn Ala Gly Asn Ala Ala Ala Ala
        115                 120                 125

Leu Met Ala Gly Leu Ala Pro Lys Thr Lys Val Leu Arg Asp Gly Arg
    130                 135                 140

Trp Ser Glu Gln Glu Ala Ser Ile Leu Val Pro Gly Asp Ile Ile Ser
145                 150                 155                 160

Ile Lys Leu Gly Asp Ile Val Pro Ala Asp Ala Arg Leu Leu Glu Gly
                165                 170                 175

Asp Pro Leu Lys Ile Asp Gln Ser Ala Leu Thr Gly Glu Ser Leu Pro
            180                 185                 190

Val Asn Lys Asn Pro Tyr Asp Glu Val Phe Ser Gly Ser Thr Cys Lys
        195                 200                 205
```

-continued

Gln Gly Glu Ile Glu Ala Val Val Ile Ala Thr Gly Val His Thr Phe
210                 215                 220

Phe Gly Lys Ala Ala His Leu Val Asp Ser Thr Asn Gln Val Gly His
225                 230                 235                 240

Phe Gln Gln Val Leu Thr Ala Ile Gly Asn Phe Cys Ile Cys Ser Ile
                245                 250                 255

Ala Val Gly Met Leu Val Glu Ile Ile Val Met Tyr Pro Ile Gln His
            260                 265                 270

Arg Gln Tyr Arg Ser Gly Ile Asp Asn Leu Leu Val Leu Leu Ile Gly
        275                 280                 285

Gly Ile Pro Ile Ala Met Pro Thr Val Leu Ser Val Thr Met Ala Ile
290                 295                 300

Gly Ser His Arg Leu Ser Gln Gln Gly Ala Ile Thr Lys Arg Met Thr
305                 310                 315                 320

Ala Ile Glu Glu Met Ala Gly Met Asp Val Leu Cys Ser Asp Lys Thr
                325                 330                 335

Gly Thr Leu Thr Leu Asn Lys Leu Thr Val Asp Lys Asn Leu Ile Glu
            340                 345                 350

Val Phe Ala Lys Gly Val Asp Lys Glu Gln Val Leu Leu Tyr Ala Ala
        355                 360                 365

Arg Ala Ser Arg Thr Glu Asn Gln Asp Ala Ile Asp Ala Ala Ile Val
370                 375                 380

Gly Thr Leu Ala Asp Pro Lys Glu Ala Arg Ala Gly Ile Arg Glu Val
385                 390                 395                 400

His Phe Phe Pro Phe Asn Pro Val Asp Lys Arg Thr Ala Leu Thr Tyr
                405                 410                 415

Ile Asp Glu Arg Gly Asn Trp His Arg Thr Ser Lys Gly Ala Pro Glu
            420                 425                 430

Gln Ile Leu Thr Leu Cys Gly Cys Lys Glu Asp Met Lys Lys Lys Val
        435                 440                 445

His Ala Met Ile Asp Lys Phe Ala Glu Arg Gly Leu Arg Ser Leu Ala
450                 455                 460

Val Gly Lys Gln Glu Val Pro Glu Lys Thr Lys Glu Gly Pro Gly Gly
465                 470                 475                 480

Pro Trp Gln Phe Val Gly Leu Leu Ser Leu Phe Asp Pro Pro Arg His
                485                 490                 495

Asp Ser Ala Glu Thr Ile Arg Gln Ala Leu His Leu Gly Val Asn Val
            500                 505                 510

Lys Met Ile Thr Gly Asp Gln Leu Ala Ile Ala Lys Glu Thr Gly Arg
        515                 520                 525

Arg Leu Gly Met Gly Thr Asn Met Tyr Pro Ser Ser Ser Leu Leu Gly
530                 535                 540

Asp His Lys Asp Ala Ser Ile Ala Thr Leu Pro Ile Glu Glu Leu Ile
545                 550                 555                 560

Glu Lys Ala Asp Gly Phe Ala Gly Val Phe Pro Glu His Lys Tyr Glu
                565                 570                 575

Ile Val Lys Lys Leu Gln Glu Arg Lys His Ile Cys Gly Met Thr Gly
            580                 585                 590

Asp Gly Val Asn Asp Ala Pro Ala Leu Lys Lys Ala Asp Ile Gly Ile
        595                 600                 605

Ala Val Ala Asp Ala Thr Asp Ala Ala Arg Ser Ala Ser Asp Ile Val
610                 615                 620

Leu Thr Glu Pro Gly Leu Ser Val Ile Ile Ser Ala Val Leu Thr Ser
625                 630                 635                 640

Arg Ala Ile Phe Gln Arg Met Lys Asn Tyr Thr Ile Tyr Ala Val Ser
            645                 650                 655

Ile Thr Ile Arg Ile Val Phe Gly Phe Met Phe Ile Ala Leu Ile Trp
            660                 665                 670

Lys Phe Asp Phe Ser Pro Phe Met Val Leu Ile Ile Ala Ile Leu Asn
            675                 680                 685

Asp Gly Thr Ile Met Thr Ile Ser Lys Asp Arg Val Lys Pro Ser Pro
            690                 695                 700

Leu Pro Asp Ser Trp Lys Leu Lys Glu Ile Phe Ala Thr Gly Ile Val
705                 710                 715                 720

Leu Gly Gly Tyr Leu Ala Leu Met Thr Val Ile Phe Phe Trp Ile Met
                725                 730                 735

Lys Asp Thr Asp Phe Phe Thr Glu Lys Phe Gly Val Arg Ser Leu Arg
            740                 745                 750

Asn Ser Glu Val Glu Met Met Ala Ala Leu Tyr Leu Gln Val Ser Ile
            755                 760                 765

Val Ser Gln Ala Leu Ile Phe Val Thr Arg Ser Arg Ser Trp Ser Phe
770                 775                 780

Ile Glu Arg Pro Gly Leu Leu Leu Gly Ala Phe Leu Ala Ala Gln
785                 790                 795                 800

Leu Val Ala Thr Leu Ile Ala Val Tyr Ala Glu Trp Glu Phe Ala Arg
                805                 810                 815

Ile Lys Gly Val Gly Trp Gly Trp Ala Gly Val Ile Trp Leu Tyr Ser
            820                 825                 830

Ile Val Phe Tyr Phe Pro Leu Asp Ile Met Lys Phe Ala Ile Arg Tyr
            835                 840                 845

Ile Leu Ser Gly Lys Ala Trp Arg Asn Met Leu Glu Asn Lys Thr Ala
            850                 855                 860

Phe Thr Thr Lys Lys Asp Tyr Gly Arg Glu Glu Arg Glu Ala Gln Trp
865                 870                 875                 880

Ala Leu Ala Gln Arg Thr Leu His Gly Leu Gln Ala Pro Glu Thr Ser
                885                 890                 895

Asn Ile Phe Asn Glu Lys Ser Ser Tyr Arg Glu Leu Ser Glu Ile Ala
            900                 905                 910

Glu Gln Ala Lys Arg Arg Ala Glu Val Ala Arg Leu Arg Glu Val Leu
            915                 920                 925

Thr Leu Lys Gly His Val Glu Ser Val Val Lys Leu Lys Gly Leu Asp
            930                 935                 940

Ile Asp Thr Ile Gln Gln His Tyr Thr Val
945                 950

<210> SEQ ID NO 4
<211> LENGTH: 952
<212> TYPE: PRT
<213> ORGANISM: Helianthus annuus
<220> FEATURE:
<221> NAME/KEY: misc_feature
<223> OTHER INFORMATION: HaRA11742_4232_Helianthus_annuus

<400> SEQUENCE: 4

Met Gly Gly Asp Lys Ala Leu Ser Leu Glu Glu Ile Lys Asn Glu Thr
1               5                   10                  15

```
Val Asp Leu Glu Lys Val Pro Ile Glu Glu Val Phe Glu Gln Leu Lys
     20                  25                  30

Cys Asn Arg Glu Gly Leu Ser Ser Asp Glu Gly Ala Ala Arg Leu Gln
         35                  40                  45

Ile Phe Gly Pro Asn Lys Leu Glu Glu Lys Lys Glu Ser Lys Leu Leu
 50                  55                  60

Lys Phe Leu Gly Phe Met Asn Pro Leu Ser Trp Val Met Glu Ala Ala
 65                  70                  75                  80

Ala Ile Met Ala Ile Ala Leu Ala Asn Gly Gly Lys Pro Pro Asp
                 85                  90                  95

Trp Gln Asp Phe Val Gly Ile Val Cys Leu Leu Val Ile Asn Ser Thr
             100                 105                 110

Ile Ser Phe Ile Glu Glu Asn Asn Ala Gly Asn Ala Ala Ala Ala Leu
         115                 120                 125

Met Ala Gly Leu Ala Pro Lys Thr Lys Val Leu Arg Asp Gly Asn Trp
 130                 135                 140

Ser Glu Gln Glu Ala Ala Ile Leu Val Pro Gly Asp Ile Ile Ser Ile
145                 150                 155                 160

Lys Leu Gly Asp Ile Val Pro Ala Asp Ala Arg Leu Leu Glu Gly Asp
                 165                 170                 175

Pro Leu Lys Ile Asp Gln Ser Ala Leu Thr Gly Glu Ser Leu Pro Val
             180                 185                 190

Asn Lys Asn Pro Tyr Asp Glu Val Phe Ser Gly Ser Thr Cys Lys Gln
         195                 200                 205

Gly Ile Glu Ala Val Val Ile Ala Thr Gly Val His Thr Phe Phe Gly
 210                 215                 220

Lys Ala Ala His Leu Val Asp Ser Thr Asn Gln Val Gly His Phe Gln
225                 230                 235                 240

Gln Val Leu Thr Ala Ile Gly Asn Phe Cys Ile Cys Ser Ile Ala Val
                 245                 250                 255

Gly Met Leu Val Glu Ile Val Val Met Tyr Pro Ile Gln His Arg Glu
             260                 265                 270

Tyr Arg Asn Gly Ile Asp Asn Leu Leu Val Leu Leu Ile Gly Gly Ile
         275                 280                 285

Pro Ile Ala Met Pro Thr Val Leu Ser Val Thr Met Ala Ile Gly Ser
 290                 295                 300

His Arg Leu Ser Gln Gln Gly Ala Ile Thr Lys Arg Met Thr Ala Ile
305                 310                 315                 320

Glu Glu Met Ala Gly Met Asp Val Leu Cys Ser Asp Lys Thr Gly Thr
                 325                 330                 335

Leu Thr Leu Asn Lys Leu Ser Val Asp Lys Asn Leu Ile Glu Val Phe
             340                 345                 350

Ala Lys Gly Val Asp Lys Asp Gln Val Leu Leu Tyr Ala Ala Arg Ala
         355                 360                 365

Ser Arg Thr Glu Asn Gln Asp Ala Ile Asp Ala Ala Ile Val Gly Thr
 370                 375                 380

Leu Ala Asp Pro Lys Glu Ala Arg Ala Gly Ile Arg Glu Val His Phe
385                 390                 395                 400

Phe Pro Phe Asn Pro Val Asp Lys Arg Thr Ala Leu Thr Tyr Ile Asp
                 405                 410                 415

Glu Arg Gly Asn Trp His Arg Thr Ser Lys Gly Ala Pro Glu Gln Ile
             420                 425                 430
```

```
Leu Thr Leu Cys Gly Cys Lys Glu Asp Met Lys Lys Val His Ala
            435                 440                 445
Met Ile Asp Lys Phe Ala Glu Arg Gly Leu Arg Ser Leu Ala Val Ala
450                 455                 460
Lys Gln Glu Val Pro Glu Lys Asn Lys Glu Ser Pro Gly Gly Pro Trp
465                 470                 475                 480
Thr Phe Ile Gly Leu Leu Ser Leu Phe Asp Pro Pro Arg His Asp Ser
                485                 490                 495
Ala Glu Thr Ile Arg Arg Ala Leu Asn Leu Gly Val Asn Val Lys Met
            500                 505                 510
Ile Thr Gly Asp Gln Leu Ala Ile Ala Lys Glu Thr Gly Arg Arg Leu
        515                 520                 525
Gly Met Gly Thr Asn Met Tyr Pro Ser Ser Ser Leu Leu Gly Asn His
530                 535                 540
Lys Asp Ala Ser Ile Ala Ala Ile Pro Ile Glu Glu Leu Ile Glu Lys
545                 550                 555                 560
Ala Asp Gly Phe Ala Gly Val Phe Pro Glu His Lys Tyr Glu Ile Val
                565                 570                 575
Lys Lys Leu Gln Glu Arg Lys His Ile Cys Gly Met Thr Gly Asp Gly
            580                 585                 590
Val Asn Asp Ala Pro Ala Leu Lys Lys Ala Asp Ile Gly Ile Ala Val
        595                 600                 605
Ala Asp Ala Thr Asp Ala Arg Gly Ala Ser Asp Ile Val Leu Thr
610                 615                 620
Glu Pro Gly Leu Ser Val Ile Ser Ala Val Leu Thr Ser Arg Ala
625                 630                 635                 640
Ile Phe Gln Arg Met Lys Asn Tyr Thr Ile Tyr Ala Val Ser Ile Thr
                645                 650                 655
Ile Arg Ile Val Phe Gly Phe Leu Phe Ile Ala Leu Ile Trp Lys Phe
            660                 665                 670
Asp Phe Ser Pro Phe Met Val Leu Ile Ile Ala Ile Leu Asn Asp Gly
        675                 680                 685
Thr Ile Met Thr Ile Ser Lys Asp Arg Val Lys Pro Ser Pro Leu Pro
690                 695                 700
Asp Ser Trp Lys Leu Lys Glu Ile Phe Ala Thr Gly Ile Val Leu Gly
705                 710                 715                 720
Gly Tyr Leu Ala Leu Met Thr Val Ile Phe Phe Trp Ile Met Lys Asp
                725                 730                 735
Thr Asn Phe Phe Ser Asp Thr Phe Gly Val Arg Ser Leu Arg His Ser
            740                 745                 750
Glu Val Glu Met Met Ala Ala Leu Tyr Leu Gln Val Ser Ile Val Ser
        755                 760                 765
Gln Ala Leu Ile Phe Val Thr Arg Ser Arg Ser Trp Ser Phe Ile Glu
770                 775                 780
Arg Pro Gly Leu Leu Leu Leu Gly Ala Phe Leu Ala Ala Gln Leu Val
785                 790                 795                 800
Ala Thr Leu Ile Ala Val Tyr Ala Asn Trp Glu Phe Ala Arg Ile Lys
                805                 810                 815
Gly Val Gly Trp Gly Trp Ala Gly Val Ile Trp Leu Tyr Ser Ile Val
            820                 825                 830
Phe Tyr Phe Pro Leu Asp Leu Met Lys Phe Ala Ile Arg Tyr Ile Leu
        835                 840                 845
```

```
Ser Gly Lys Ala Trp Asn Asn Leu Leu Glu Asn Lys Thr Ala Phe Thr
    850                 855                 860

Ser Lys Lys Asp Tyr Gly Arg Glu Arg Glu Ala Gln Trp Ala Leu
865                 870                 875                 880

Ala Gln Arg Thr Leu His Gly Leu Gln Gln Pro Glu Thr Ser Asn Ile
                885                 890                 895

Phe Asn Glu Lys Ser Ser Tyr Arg Glu Leu Ser Glu Ile Ala Glu Gln
            900                 905                 910

Ala Lys Arg Arg Ala Glu Val Ala Arg Leu Arg Glu Val Leu Thr Leu
        915                 920                 925

Lys Gly His Val Glu Ser Val Val Lys Leu Lys Gly Leu Asp Ile Asp
930                 935                 940

Thr Ile Gln Gln His Tyr Thr Val
945                 950
```

<210> SEQ ID NO 5
<211> LENGTH: 952
<212> TYPE: PRT
<213> ORGANISM: Lycopersicon esculentum
<220> FEATURE:
<221> NAME/KEY: misc_feature
<223> OTHER INFORMATION: LeAHA_XP_004242908.1_Lycopersicon_esculentum

<400> SEQUENCE: 5

```
Met Ala Lys Ala Ile Ser Leu Glu Glu Ile Lys Asn Glu Thr Val Asp
1               5                   10                  15

Leu Glu Lys Ile Pro Ile Glu Glu Val Phe Glu Gln Leu Lys Cys Ser
            20                  25                  30

Arg Glu Gly Leu Thr Ser Asp Glu Gly Ala Asn Arg Leu Gln Ile Phe
        35                  40                  45

Gly Pro Asn Lys Leu Glu Glu Lys Lys Glu Ser Lys Ile Leu Lys Phe
    50                  55                  60

Leu Gly Phe Met Trp Asn Pro Leu Ser Trp Val Met Glu Met Ala Ala
65                  70                  75                  80

Ile Met Ala Ile Ala Leu Ala Asn Gly Asp Gly Lys Pro Pro Asp Trp
                85                  90                  95

Gln Asp Phe Val Gly Ile Val Cys Leu Leu Val Ile Asn Ser Thr Ile
            100                 105                 110

Ser Phe Ile Glu Glu Asn Asn Ala Gly Asn Ala Ala Ala Ala Leu Met
        115                 120                 125

Ala Gly Leu Ala Pro Lys Thr Lys Val Leu Arg Asp Gly Arg Trp Ser
    130                 135                 140

Glu Gln Glu Ala Ala Ile Leu Val Pro Gly Asp Ile Ile Ser Val Lys
145                 150                 155                 160

Leu Gly Asp Ile Val Pro Ala Asp Ala Arg Leu Leu Glu Gly Asp Pro
                165                 170                 175

Leu Lys Ile Asp Gln Ser Ala Leu Thr Gly Glu Ser Leu Pro Val Thr
            180                 185                 190

Lys Asn Pro Gly Asp Glu Val Phe Ser Gly Ser Thr Cys Lys Gln Gly
        195                 200                 205

Glu Leu Glu Ala Val Val Ile Ala Thr Gly Val His Thr Phe Phe Gly
    210                 215                 220

Lys Ala Ala His Leu Val Asp Ser Thr Asn Asn Val Gly His Phe Gln
225                 230                 235                 240
```

```
Lys Val Leu Thr Ala Ile Gly Asn Phe Cys Ile Cys Ser Ile Ala Ile
                    245                 250                 255

Gly Met Leu Val Glu Ile Ile Val Met Tyr Pro Ile Gln His Arg Lys
                260                 265                 270

Tyr Arg Asp Gly Ile Asp Asn Leu Leu Val Leu Leu Ile Gly Gly Ile
            275                 280                 285

Pro Ile Ala Met Pro Thr Val Leu Ser Val Thr Met Ala Ile Gly Ser
290                 295                 300

His Arg Leu Ser Gln Gln Gly Ala Ile Thr Lys Arg Met Thr Ala Ile
305                 310                 315                 320

Glu Glu Met Ala Gly Met Asp Val Leu Cys Ser Asp Lys Thr Gly Thr
                325                 330                 335

Leu Thr Leu Asn Lys Leu Ser Val Asp Arg Ser Leu Val Glu Val Phe
                340                 345                 350

Thr Lys Gly Val Asp Lys Glu Tyr Val Leu Leu Leu Ala Ala Arg Ala
            355                 360                 365

Ser Arg Val Glu Asn Gln Asp Ala Ile Asp Ala Cys Met Val Gly Met
            370                 375                 380

Leu Ala Asp Pro Lys Glu Ala Arg Ala Gly Ile Arg Glu Val His Phe
385                 390                 395                 400

Leu Pro Phe Asn Pro Val Asp Lys Arg Thr Ala Leu Thr Tyr Ile Asp
                405                 410                 415

Ser Asn Gly Asn Trp His Arg Ala Ser Lys Gly Ala Pro Glu Gln Ile
                420                 425                 430

Leu Asp Leu Cys Asn Cys Lys Glu Asp Val Arg Arg Lys Val His Ser
            435                 440                 445

Met Ile Asp Lys Tyr Ala Glu Arg Gly Leu Arg Ser Leu Ala Val Ala
450                 455                 460

Arg Gln Glu Val Pro Glu Lys Ser Lys Glu Ser Thr Gly Gly Pro Trp
465                 470                 475                 480

Gln Phe Val Gly Leu Leu Pro Leu Phe Asp Pro Pro Arg His Asp Ser
                485                 490                 495

Ala Glu Thr Ile Arg Arg Ala Leu Asn Leu Gly Val Asn Val Lys Met
                500                 505                 510

Ile Thr Gly Asp Gln Leu Ala Ile Ala Lys Glu Thr Gly Arg Arg Leu
                515                 520                 525

Gly Met Gly Thr Asn Met Tyr Pro Ser Ala Ser Leu Leu Gly Gln Asp
            530                 535                 540

Lys Asp Ser Ser Ile Ala Ser Leu Pro Val Glu Glu Leu Ile Glu Lys
545                 550                 555                 560

Ala Asp Gly Phe Ala Gly Val Phe Pro Glu His Lys Tyr Glu Ile Val
                565                 570                 575

Lys Lys Leu Gln Glu Arg Lys His Ile Val Gly Met Thr Gly Asp Gly
                580                 585                 590

Val Asn Asp Ala Pro Ala Leu Lys Lys Ala Asp Ile Gly Ile Ala Val
            595                 600                 605

Ala Asp Ala Thr Asp Ala Ala Arg Gly Ala Ser Asp Ile Val Leu Thr
            610                 615                 620

Glu Pro Gly Leu Ser Val Ile Ile Ser Ala Val Leu Thr Ser Arg Ala
625                 630                 635                 640

Ile Phe Gln Arg Met Lys Asn Tyr Thr Ile Tyr Ala Val Ser Ile Thr
                645                 650                 655
```

```
Ile Arg Ile Val Phe Gly Phe Met Leu Ile Ala Leu Ile Trp Lys Tyr
            660                 665                 670

Asp Phe Ser Ala Phe Met Val Leu Ile Ile Ala Ile Leu Asn Asp Gly
            675                 680                 685

Thr Ile Met Thr Ile Ser Lys Asp Arg Val Lys Pro Ser Pro Met Pro
        690                 695                 700

Asp Ser Trp Lys Leu Asn Glu Ile Phe Ala Thr Gly Val Val Leu Gly
705                 710                 715                 720

Gly Tyr Gln Ala Leu Met Thr Val Ile Phe Phe Trp Ala Met His Asp
                725                 730                 735

Thr Ser Phe Phe Thr Asp Lys Phe Gly Val Lys Asp Ile Arg Glu Ser
            740                 745                 750

Asp Glu Glu Met Met Ser Ala Leu Tyr Leu Gln Val Ser Ile Ile Ser
            755                 760                 765

Gln Ala Leu Ile Phe Val Thr Arg Ser Arg Ser Trp Ser Phe Val Glu
            770                 775                 780

Arg Pro Gly Ala Leu Leu Met Ile Ala Phe Leu Ile Ala Gln Leu Val
785                 790                 795                 800

Ala Thr Leu Ile Ala Val Tyr Ala Asp Trp Thr Phe Ala Arg Val Lys
                805                 810                 815

Gly Cys Gly Trp Gly Trp Ala Gly Val Ile Trp Ile Phe Ser Ile Val
            820                 825                 830

Thr Tyr Phe Pro Leu Asp Ile Met Lys Phe Ala Ile Arg Tyr Ile Leu
            835                 840                 845

Ser Gly Lys Ala Trp Asn Asn Leu Leu Asp Asn Lys Thr Ala Phe Thr
850                 855                 860

Thr Lys Lys Asp Tyr Gly Lys Glu Arg Glu Ala Gln Trp Ala Leu
865                 870                 875                 880

Ala Gln Arg Thr Leu His Gly Leu Gln Pro Pro Glu Ala Ser Asn Leu
                885                 890                 895

Phe Asn Glu Lys Asn Ser Tyr Arg Glu Leu Ser Glu Ile Ala Glu Gln
            900                 905                 910

Ala Lys Arg Arg Ala Glu Met Ala Arg Leu Arg Glu Leu His Thr Leu
            915                 920                 925

Lys Gly His Val Glu Ser Val Val Lys Leu Lys Gly Leu Asp Ile Glu
            930                 935                 940

Thr Ile Gln Gln His Tyr Thr Val
945                 950

<210> SEQ ID NO 6
<211> LENGTH: 951
<212> TYPE: PRT
<213> ORGANISM: Aeluropus littoralis
<220> FEATURE:
<221> NAME/KEY: misc_feature
<223> OTHER INFORMATION: AlAHA_G3M3G8_Aeluropus_littoralis

<400> SEQUENCE: 6

Met Gly Gly Leu Glu Glu Ile Lys Asn Glu Ala Val Asp Leu Glu Asn
1               5                   10                  15

Ile Pro Met Glu Glu Val Phe Glu Gln Leu Lys Cys Thr Arg Glu Gly
            20                  25                  30

Leu Ser Ser Glu Glu Gly Thr Gln Arg Leu Gln Val Phe Gly Pro Asn
        35                  40                  45

Lys Leu Glu Glu Lys Lys Glu Ser Lys Val Leu Lys Phe Leu Gly Phe
    50                  55                  60
```

```
Met Trp Asn Pro Leu Ser Trp Val Met Glu Met Ala Ala Ile Met Ala
 65                  70                  75                  80

Ile Ala Leu Ala Asn Gly Gly Lys Pro Pro Asp Trp Gln Asp Phe
             85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Leu Met Ala Asn Leu
            115                 120                 125

Ala Pro Lys Thr Lys Val Leu Arg Asp Gly Arg Trp Gly Glu Gln Glu
130                 135                 140

Ala Ala Ile Leu Val Pro Gly Asp Ile Ile Ser Ile Lys Leu Gly Asp
145                 150                 155                 160

Ile Val Pro Ala Asp Ala Arg Leu Leu Glu Gly Asp Pro Leu Lys Val
                165                 170                 175

Asp Gln Ser Ala Leu Thr Gly Glu Ser Leu Pro Val Thr Lys Gly Pro
                180                 185                 190

Gly Asp Glu Val Phe Ser Gly Ser Thr Cys Lys Gln Gly Glu Ile Glu
            195                 200                 205

Ala Val Val Ile Ala Thr Gly Val His Thr Phe Phe Gly Lys Ala Ala
210                 215                 220

His Leu Val Asp Ser Thr Asn Gln Val Gly His Phe Gln Gln Val Leu
225                 230                 235                 240

Thr Ala Ile Gly Asn Phe Cys Ile Cys Ser Ile Ala Val Gly Ile Val
                245                 250                 255

Ile Glu Ile Ile Val Met Phe Pro Ile Gln His Arg Lys Tyr Arg Ser
                260                 265                 270

Gly Ile Glu Asn Leu Leu Val Leu Leu Ile Gly Gly Ile Pro Ile Ala
            275                 280                 285

Met Pro Thr Val Leu Ser Val Thr Met Ala Ile Gly Ser His Lys Leu
            290                 295                 300

Ser Gln Gln Gly Ala Ile Thr Lys Arg Met Thr Ala Ile Glu Glu Met
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Ala Lys Gly
            340                 345                 350

Val Asp Lys Asp His Val Leu Leu Leu Ala Ala Arg Ala Ser Arg Thr
            355                 360                 365

Glu Asn Gln Asp Ala Ile Asp Ala Ala Met Val Gly Met Leu Ala Asp
    370                 375                 380

Pro Lys Glu Ala Arg Ala Gly Ile Arg Glu Val His Phe Leu Pro Phe
385                 390                 395                 400

Asn Pro Val Asp Lys Arg Thr Ala Leu Thr Tyr Ile Asp Ser Asp Gly
                405                 410                 415

Asn Trp His Arg Ala Ser Lys Gly Ala Pro Glu Gln Ile Ile Thr Leu
            420                 425                 430

Cys Asn Cys Arg Glu Asp Met Lys Arg Lys Val His Ser Ile Ile Asp
            435                 440                 445

Lys Tyr Ala Glu Arg Gly Leu Arg Ser Leu Ala Val Ala Arg Gln Glu
    450                 455                 460

Val Pro Glu Lys Thr Lys Glu Ser Pro Gly Gly Pro Trp Gln Phe Val
465                 470                 475                 480
```

-continued

Gly Leu Leu Pro Leu Phe Asp Pro Pro Arg His Asp Ser Ala Glu Thr
                485                 490                 495

Ile Arg Lys Ala Leu His Leu Gly Val Asn Val Lys Met Ile Thr Gly
            500                 505                 510

Asp Gln Leu Ala Ile Gly Lys Glu Thr Gly Arg Arg Leu Gly Met Gly
        515                 520                 525

Thr Asn Met Tyr Pro Ser Ser Ala Leu Leu Gly Gln Asn Lys Asp Ser
    530                 535                 540

Thr Leu Glu Ala Leu Pro Val Asp Glu Leu Ile Glu Lys Ala Asp Gly
545                 550                 555                 560

Phe Ala Gly Val Phe Pro Glu His Lys Tyr Glu Ile Val Lys Lys Leu
                565                 570                 575

Gln Glu Lys Lys His Ile Val Gly Met Thr Gly Asp Gly Val Asn Asp
            580                 585                 590

Ala Pro Ala Leu Lys Lys Ala Asp Ile Gly Ile Ala Val Ala Asp Ala
        595                 600                 605

Thr Asp Ala Ala Arg Ser Ala Ser Asp Ile Val Leu Thr Glu Pro Gly
    610                 615                 620

Leu Ser Val Ile Ile Ser Ala Val Leu Thr Ser Arg Cys Ile Phe Gln
625                 630                 635                 640

Arg Met Lys Asn Tyr Thr Ile Tyr Ala Val Ser Ile Thr Ile Arg Ile
                645                 650                 655

Val Leu Gly Phe Leu Leu Ile Ala Leu Ile Trp Lys Phe Asp Phe Ala
            660                 665                 670

Pro Phe Met Val Leu Ile Ile Ala Ile Leu Asn Asp Gly Thr Ile Met
        675                 680                 685

Thr Ile Ser Lys Asp Arg Val Lys Pro Ser Pro Leu Pro Asp Ser Trp
    690                 695                 700

Lys Leu Asn Glu Ile Phe Ala Thr Gly Ile Val Leu Gly Thr Tyr Leu
705                 710                 715                 720

Ala Ile Met Thr Val Val Phe Phe Trp Ala Ile His Lys Thr Asp Phe
                725                 730                 735

Phe Thr Glu Lys Phe Gly Val Arg Ser Ile Arg Asp Ser Glu His Glu
            740                 745                 750

Met Met Ala Ala Leu Tyr Leu Gln Val Ser Ile Val Ser Gln Ala Leu
        755                 760                 765

Ile Phe Val Thr Arg Ser Arg Ser Trp Ser Phe Val Glu Arg Pro Gly
    770                 775                 780

Val Leu Leu Val Thr Ala Phe Leu Leu Ala Gln Leu Val Ala Thr Leu
785                 790                 795                 800

Ile Ala Val Tyr Ala Asn Trp Gly Phe Ala Arg Ile Lys Gly Ile Gly
                805                 810                 815

Trp Gly Trp Ala Gly Val Val Trp Leu Tyr Ser Val Val Leu Tyr Phe
            820                 825                 830

Pro Leu Asp Val Phe Lys Phe Leu Ile Arg Phe Ala Leu Ser Gly Arg
        835                 840                 845

Ala Trp Asp Asn Leu Leu Glu Asn Lys Thr Ala Phe Thr Thr Lys Lys
    850                 855                 860

Asp Tyr Gly Arg Glu Glu Arg Glu Ala Gln Trp Ala Ala Ala Gln Arg
865                 870                 875                 880

Thr Leu His Gly Leu Gln Pro Pro Glu Val Ala Ser Asn Thr Leu Phe
                885                 890                 895

```
Asn Glu Lys Ser Ser Tyr Arg Glu Leu Ser Glu Ile Ala Glu Gln Ala
            900                 905                 910

Lys Arg Arg Ala Glu Ile Ala Arg Leu Arg Glu Leu Asn Thr Leu Lys
            915                 920                 925

Gly His Val Glu Ser Val Val Lys Leu Lys Gly Leu Asp Ile Asp Thr
            930                 935                 940

Ile Gln Gln Asn Tyr Thr Val
945                 950

<210> SEQ ID NO 7
<211> LENGTH: 951
<212> TYPE: PRT
<213> ORGANISM: Aeluropus littoralis
<220> FEATURE:
<221> NAME/KEY: misc_feature
<223> OTHER INFORMATION: AlAHA_G9MC80_Aeluropus_littoralis

<400> SEQUENCE: 7

Met Gly Gly Leu Glu Glu Ile Lys Asn Glu Ser Val Asp Leu Glu Asn
1               5                   10                  15

Ile Pro Met Glu Glu Val Phe Glu Gln Leu Lys Cys Thr Arg Glu Gly
            20                  25                  30

Leu Ser Ser Glu Glu Gly Thr Gln Arg Leu Gln Val Phe Gly Pro Asn
            35                  40                  45

Lys Leu Glu Glu Lys Lys Glu Ser Lys Val Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Gly Lys Pro Pro Asp Trp Gln Asp Phe
            85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Leu Met Ala Asn Leu
            115                 120                 125

Ala Pro Lys Thr Lys Val Leu Arg Asp Gly Arg Trp Gly Glu Gln Glu
            130                 135                 140

Ala Ala Ile Leu Val Pro Gly Asp Ile Ile Ser Ile Lys Leu Gly Asp
145                 150                 155                 160

Ile Val Pro Ala Asp Ala Arg Leu Leu Glu Gly Asp Pro Leu Lys Val
            165                 170                 175

Asp Gln Ser Ala Leu Thr Gly Glu Ser Leu Pro Val Thr Lys Gly Pro
            180                 185                 190

Gly Asp Glu Val Phe Ser Gly Ser Thr Cys Lys Gln Gly Glu Ile Glu
            195                 200                 205

Ala Val Val Ile Ala Thr Gly Val His Thr Phe Phe Gly Lys Ala Ala
            210                 215                 220

His Leu Val Asp Ser Thr Asn Gln Val Gly Leu Phe Gln Gln Val Leu
225                 230                 235                 240

Thr Ala Ile Gly Asn Phe Cys Ile Cys Ser Ile Ala Val Gly Ile Val
            245                 250                 255

Ile Glu Ile Ile Val Met Phe Pro Ile Gln His Arg Arg Tyr Arg Ser
            260                 265                 270

Gly Ile Glu Asn Leu Leu Val Leu Leu Ile Gly Gly Ile Pro Ile Ala
            275                 280                 285
```

```
Met Pro Thr Val Leu Ser Val Thr Met Ala Ile Gly Ser His Lys Leu
    290                 295                 300
Ser Gln Gln Gly Ala Ile Thr Lys Arg Met Thr Ala Ile Glu Glu Met
305                 310                 315                 320
Ala Gly Met Asp Val Leu Cys Ser Asp Lys Thr Gly Thr Leu Thr Leu
                325                 330                 335
Asn Lys Leu Ser Val Asp Lys Asn Leu Val Glu Val Phe Ala Lys Gly
                340                 345                 350
Val Asp Lys Asp His Val Leu Leu Ala Ala Arg Ala Ser Arg Thr
                355                 360                 365
Glu Asn Gln Asp Ala Ile Asp Ala Ala Met Val Gly Met Leu Ala Asp
    370                 375                 380
Pro Lys Glu Ala Arg Ala Gly Ile Arg Glu Val His Phe Leu Pro Phe
385                 390                 395                 400
Asn Pro Val Asp Lys Arg Thr Ala Leu Thr Tyr Ile Asp Ser Asp Gly
                405                 410                 415
Asn Trp His Arg Ala Ser Lys Gly Ala Pro Glu Gln Ile Ile Thr Leu
                420                 425                 430
Cys Asn Cys Arg Glu Asp Met Lys Arg Lys Val His Ser Ile Ile Asp
                435                 440                 445
Lys Tyr Ala Glu Arg Gly Leu Arg Ser Leu Ala Val Ala Arg Gln Glu
    450                 455                 460
Val Pro Glu Lys Thr Lys Glu Ser Pro Gly Gly Pro Trp Gln Phe Val
465                 470                 475                 480
Gly Leu Leu Pro Leu Phe Asp Pro Pro Arg His Asp Ser Ala Glu Thr
                485                 490                 495
Ile Arg Lys Ala Leu His Leu Gly Val Asn Val Glu Met Ile Thr Gly
                500                 505                 510
Asp Gln Leu Ala Ile Gly Lys Glu Thr Gly Arg Arg Leu Gly Met Gly
                515                 520                 525
Thr Asn Met Tyr Pro Ser Ser Ala Leu Leu Gly Gln Asn Lys Asp Ala
    530                 535                 540
Thr Leu Glu Ala Leu Pro Val Asp Glu Leu Ile Glu Lys Ala Asp Gly
545                 550                 555                 560
Phe Ala Gly Val Phe Pro Glu His Lys Tyr Glu Ile Val Lys Lys Leu
                565                 570                 575
Gln Glu Lys Lys His Ile Val Gly Met Thr Gly Asp Gly Val Asn Asp
                580                 585                 590
Ala Pro Ala Leu Lys Lys Ala Asp Ile Gly Ile Ala Val Ala Asp Ala
    595                 600                 605
Thr Asp Ala Ala Arg Gly Ala Ser Asp Ile Val Leu Thr Glu Pro Gly
    610                 615                 620
Leu Ser Val Ile Ile Ser Ala Val Leu Thr Ser Arg Cys Ile Phe Gln
625                 630                 635                 640
Arg Met Lys Asn Tyr Thr Ile Tyr Ala Val Ser Ile Thr Ile Arg Ile
                645                 650                 655
Val Leu Gly Phe Leu Leu Ile Ala Leu Ile Trp Lys Phe Asp Leu Ala
                660                 665                 670
Pro Phe Met Val Leu Ile Ile Ala Ile Leu Asn Asp Gly Thr Ile Met
                675                 680                 685
Thr Ile Ser Lys Asp Arg Val Lys Pro Ser Pro Leu Pro Asp Ser Trp
    690                 695                 700
```

```
Lys Leu Lys Glu Ile Phe Ala Thr Gly Ile Val Leu Gly Thr Tyr Leu
705                 710                 715                 720

Ala Ile Met Thr Val Val Phe Phe Trp Ala Ile His Lys Thr Asp Phe
                725                 730                 735

Phe Thr Glu Lys Phe Gly Val Arg Ser Ile Arg Asp Ser Glu Asp Glu
            740                 745                 750

Met Met Ala Ala Leu Tyr Leu Gln Val Ser Ile Val Ser Gln Ala Leu
            755                 760                 765

Ile Phe Val Thr Arg Ser Arg Ser Trp Ser Phe Val Glu Arg Pro Gly
            770                 775                 780

Val Leu Val Thr Ala Phe Leu Leu Ala Gln Leu Val Ala Thr Leu
785                 790                 795                 800

Ile Ala Val Tyr Ala Asp Trp Gly Phe Ala Arg Ile Lys Gly Ile Gly
                805                 810                 815

Trp Gly Trp Ala Gly Val Val Trp Leu Tyr Ser Val Val Phe Tyr Leu
                820                 825                 830

Pro Leu Asp Val Phe Lys Phe Leu Ile Arg Phe Ala Leu Ser Gly Arg
            835                 840                 845

Ala Trp Asp Asn Leu Leu Glu Asn Lys Thr Ala Phe Thr Thr Lys Lys
850                 855                 860

Asp Tyr Gly Arg Glu Glu Arg Glu Ala Gln Trp Ala Ala Ala Gln Arg
865                 870                 875                 880

Thr Leu His Gly Leu Gln Pro Pro Glu Val Ala Ser Asn Thr Leu Phe
                885                 890                 895

Asn Glu Lys Ser Ser Tyr Arg Glu Leu Ser Glu Ile Ala Glu Gln Ala
                900                 905                 910

Lys Arg Arg Ala Glu Ile Ala Arg Leu Arg Glu Leu Asn Thr Leu Lys
            915                 920                 925

Gly His Val Glu Ser Val Val Lys Leu Lys Gly Leu Asp Ile Asp Thr
            930                 935                 940

Ile Gln Gln Asn Tyr Thr Val
945                 950

<210> SEQ ID NO 8
<211> LENGTH: 951
<212> TYPE: PRT
<213> ORGANISM: Sorghum bicolor
<220> FEATURE:
<221> NAME/KEY: misc_feature
<223> OTHER INFORMATION: SbAHA_Sb06g031240_Sorghum_bicolor

<400> SEQUENCE: 8

Met Gly Gly Leu Glu Glu Ile Lys Asn Glu Ala Val Asp Leu Glu Asn
1               5                   10                  15

Ile Pro Ile Glu Glu Val Phe Glu Gln Leu Lys Cys Thr Arg Glu Gly
                20                  25                  30

Leu Ser Ser Ser Glu Gly Gln Gln Arg Leu Glu Ile Phe Gly Pro Asn
            35                  40                  45

Lys Leu Glu Glu Lys Lys Glu Ser Lys Ile Leu Lys Phe Leu Gly Phe
    50                  55                  60

Met Trp Asn Pro Leu Ser Trp Val Met Glu Met Ala Ala Ile Met Ala
65              70                  75                  80

Ile Ala Leu Ala Asn Gly Gly Gly Lys Pro Pro Asp Trp Glu Asp Phe
                85                  90                  95

Val Gly Ile Ile Val Leu Leu Val Ile Asn Ser Thr Ile Ser Phe Ile
            100                 105                 110
```

```
Glu Glu Asn Asn Ala Gly Asn Ala Ala Ala Leu Met Ala Asn Leu
        115                 120                 125

Ala Pro Lys Thr Lys Val Leu Arg Asp Gly Arg Trp Gly Glu Gln Glu
130                 135                 140

Ala Ala Ile Leu Val Pro Gly Asp Ile Ile Ser Ile Lys Leu Gly Asp
145                 150                 155                 160

Ile Val Pro Ala Asp Ala Arg Leu Leu Glu Gly Asp Pro Leu Lys Val
                165                 170                 175

Asp Gln Ser Ala Leu Thr Gly Glu Ser Leu Pro Val Thr Arg Gly Pro
                180                 185                 190

Gly Asp Glu Val Phe Ser Gly Ser Thr Cys Lys Gln Gly Glu Ile Glu
                195                 200                 205

Ala Val Val Ile Ala Thr Gly Val His Thr Phe Phe Gly Lys Ala Ala
                210                 215                 220

His Leu Val Asp Ser Thr Asn Gln Val Gly His Phe Gln Gln Val Leu
225                 230                 235                 240

Thr Ala Ile Gly Asn Phe Cys Ile Cys Ser Ile Ala Val Gly Ile Ile
                245                 250                 255

Val Glu Ile Ile Val Met Phe Pro Ile Gln His Arg Lys Tyr Arg Ser
        260                 265                 270

Gly Ile Glu Asn Leu Leu Val Leu Leu Ile Gly Gly Ile Pro Ile Ala
        275                 280                 285

Met Pro Thr Val Leu Ser Val Thr Met Ala Ile Gly Ser His Lys Leu
        290                 295                 300

Ser Gln Gln Gly Ala Ile Thr Lys Arg Met Thr Ala Ile Glu Glu Met
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Cys Lys Gly
                340                 345                 350

Val Asp Lys Asp His Val Leu Leu Leu Ala Ala Arg Ala Ser Arg Thr
                355                 360                 365

Glu Asn Gln Asp Ala Ile Asp Ala Ala Met Val Gly Met Leu Ala Asp
                370                 375                 380

Pro Lys Glu Ala Arg Ala Gly Ile Arg Glu Val His Phe Leu Pro Phe
385                 390                 395                 400

Asn Pro Val Asp Lys Arg Thr Ala Leu Thr Tyr Ile Asp Gly Asp Gly
                405                 410                 415

Asn Trp His Arg Val Ser Lys Gly Ala Pro Glu Gln Ile Leu Asp Leu
                420                 425                 430

Cys His Cys Lys Glu Asp Leu Arg Arg Lys Val His Gly Ile Ile Asp
                435                 440                 445

Lys Tyr Ala Glu Arg Gly Leu Arg Ser Leu Ala Val Ala Arg Gln Glu
        450                 455                 460

Val Pro Glu Lys Asn Lys Glu Ser Pro Gly Gly Pro Trp Gln Phe Val
465                 470                 475                 480

Gly Leu Leu Pro Leu Phe Asp Pro Pro Arg His Asp Ser Ala Glu Thr
                485                 490                 495

Ile Arg Lys Ala Leu Val Leu Gly Val Asn Val Lys Met Ile Thr Gly
                500                 505                 510

Asp Gln Leu Ala Ile Gly Lys Glu Thr Gly Arg Arg Leu Gly Met Gly
                515                 520                 525
```

```
Thr Asn Met Tyr Pro Ser Ser Ala Leu Leu Gly Gln Asn Lys Asp Ser
        530                 535                 540

Thr Leu Glu Ala Leu Pro Val Asp Glu Leu Ile Glu Lys Ala Asp Gly
545                 550                 555                 560

Phe Ala Gly Val Phe Pro Glu His Lys Tyr Glu Ile Val Lys Arg Leu
                565                 570                 575

Gln Glu Lys Lys His Ile Val Gly Met Thr Gly Asp Gly Val Asn Asp
            580                 585                 590

Ala Pro Ala Leu Lys Lys Ala Asp Ile Gly Ile Ala Val Ala Asp Ala
            595                 600                 605

Thr Asp Ala Ala Arg Ser Ala Ser Asp Ile Val Leu Thr Glu Pro Gly
    610                 615                 620

Leu Ser Val Ile Ile Ser Ala Val Leu Thr Ser Arg Cys Ile Phe Gln
625                 630                 635                 640

Arg Met Lys Asn Tyr Thr Ile Tyr Ala Val Ser Ile Thr Ile Arg Ile
                645                 650                 655

Val Leu Gly Phe Met Leu Ile Ala Leu Ile Trp Lys Tyr Asp Phe Ser
            660                 665                 670

Pro Phe Met Val Leu Ile Ile Ala Ile Leu Asn Asp Gly Thr Ile Met
        675                 680                 685

Thr Ile Ser Lys Asp Arg Val Lys Pro Ser Pro Leu Pro Asp Ser Trp
        690                 695                 700

Lys Leu Lys Glu Ile Phe Ala Thr Gly Ile Val Leu Gly Ser Tyr Leu
705                 710                 715                 720

Ala Ile Met Thr Val Ile Phe Phe Trp Ala Met His Lys Thr Asp Phe
                725                 730                 735

Phe Ser Asp Lys Phe Gly Val Arg Ser Ile Arg Asp Ser Glu His Glu
            740                 745                 750

Met Met Ser Ala Leu Tyr Leu Gln Val Ser Ile Val Ser Gln Ala Leu
        755                 760                 765

Ile Phe Val Thr Arg Ser Arg Ser Trp Ser Phe Val Glu Arg Pro Gly
        770                 775                 780

Leu Leu Leu Val Thr Ala Phe Leu Leu Ala Gln Leu Val Ala Thr Phe
785                 790                 795                 800

Leu Ala Val Tyr Ala Asn Trp Gly Phe Ala Arg Ile Lys Gly Ile Gly
                805                 810                 815

Trp Gly Trp Ala Gly Val Val Trp Leu Tyr Ser Ile Val Phe Tyr Phe
            820                 825                 830

Pro Leu Asp Leu Ile Lys Phe Phe Ile Arg Phe Val Leu Ser Gly Arg
        835                 840                 845

Ala Trp Asp Asn Leu Leu Glu Asn Lys Thr Ala Phe Thr Thr Lys Lys
850                 855                 860

Asp Tyr Gly Arg Glu Glu Arg Glu Ala Gln Trp Ala Thr Ala Gln Arg
865                 870                 875                 880

Thr Leu His Gly Leu Gln Pro Pro Glu Ala Ala Thr Asn Thr Leu Phe
                885                 890                 895

Asn Asp Lys Ser Ser Tyr Arg Glu Leu Ser Glu Ile Ala Glu Gln Ala
            900                 905                 910

Lys Arg Arg Ala Glu Ile Ala Arg Leu Arg Glu Leu Asn Thr Leu Lys
        915                 920                 925
```

```
Gly His Val Glu Ser Val Val Lys Leu Lys Gly Leu Asp Ile Asp Thr
    930                 935                 940

Ile Gln Gln Asn Tyr Thr Val
945                 950

<210> SEQ ID NO 9
<211> LENGTH: 951
<212> TYPE: PRT
<213> ORGANISM: Setaria italica
<220> FEATURE:
<221> NAME/KEY: misc_feature
<223> OTHER INFORMATION: SiAHA_K3Z3J5_Setaria_italica

<400> SEQUENCE: 9

Met Gly Gly Leu Glu Glu Ile Lys Asn Glu Ala Val Asp Leu Glu Asn
1               5                   10                  15

Ile Pro Ile Glu Glu Val Phe Glu Gln Leu Lys Cys Thr Arg Glu Gly
            20                  25                  30

Leu Ser Ser Asn Glu Gly Ala Gln Arg Leu Glu Ile Phe Gly Pro Asn
        35                  40                  45

Lys Leu Glu Glu Lys Lys Glu Ser Lys Ile Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Gly Lys Pro Pro Asp Trp Glu Asp Phe
                85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Ala Leu Met Ala Asn Leu
        115                 120                 125

Ala Pro Lys Thr Lys Val Leu Arg Asp Gly Arg Trp Gly Glu Gln Glu
    130                 135                 140

Ala Ala Ile Leu Val Pro Gly Asp Ile Ile Ser Ile Lys Leu Gly Asp
145                 150                 155                 160

Ile Val Pro Ala Asp Ala Arg Leu Leu Glu Gly Asp Pro Leu Lys Val
                165                 170                 175

Asp Gln Ser Ala Leu Thr Gly Glu Ser Leu Pro Val Thr Lys Gly Pro
            180                 185                 190

Gly Asp Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
    210                 215                 220

His Leu Val Asp Ser Thr Asn Gln Val Gly His Phe Gln Lys Val Leu
225                 230                 235                 240

Thr Ala Ile Gly Asn Phe Cys Ile Cys Ser Ile Ala Val Gly Ile Val
                245                 250                 255

Ile Glu Ile Ile Val Met Phe Pro Ile Gln His Arg Ala Tyr Arg Ser
            260                 265                 270

Gly Ile Glu Asn Leu Leu Val Leu Leu Ile Gly Gly Ile Pro Ile Ala
        275                 280                 285

Met Pro Thr Val Leu Ser Val Thr Met Ala Ile Gly Ser His Lys Leu
    290                 295                 300

Ser Gln Gln Gly Ala Ile Thr Lys Arg Met Thr Ala Ile Glu Glu Met
305                 310                 315                 320
```

Ala Gly Met Asp Val Leu Cys Ser Asp Lys Thr Gly Thr Leu Thr Leu
            325                 330                 335

Asn Lys Leu Ser Val Asp Lys Asn Leu Val Glu Val Phe Cys Lys Gly
            340                 345                 350

Val Asp Lys Asp His Val Leu Leu Ala Ala Arg Ala Ser Arg Thr
            355                 360                 365

Glu Asn Gln Asp Ala Ile Asp Ala Met Val Gly Met Leu Ala Asp
            370                 375                 380

Pro Lys Glu Ala Arg Ala Gly Ile Arg Glu Val His Phe Leu Pro Phe
385                 390                 395                 400

Asn Pro Val Asp Lys Arg Thr Ala Leu Thr Tyr Ile Asp Ser Asp Gly
            405                 410                 415

Asn Trp His Arg Val Ser Lys Gly Ala Pro Glu Gln Ile Leu Asp Leu
            420                 425                 430

Cys Asn Cys Arg Glu Asp Met Arg Arg Lys Val His Ser Ile Ile Asp
            435                 440                 445

Lys Tyr Ala Glu Arg Gly Leu Arg Ser Leu Ala Val Ala Arg Gln Glu
            450                 455                 460

Val Pro Glu Lys Ser Lys Asp Ala Ser Gly Gly Pro Trp Gln Phe Val
465                 470                 475                 480

Gly Leu Leu Pro Leu Phe Asp Pro Pro Arg His Asp Ser Ala Glu Thr
            485                 490                 495

Ile Arg Lys Ala Leu Val Leu Gly Val Asn Val Lys Met Ile Thr Gly
            500                 505                 510

Asp Gln Leu Ala Ile Gly Lys Glu Thr Gly Arg Arg Leu Gly Met Gly
            515                 520                 525

Thr Asn Met Tyr Pro Ser Ser Ser Leu Leu Gly Thr Asn Lys Asp Ser
            530                 535                 540

Thr Leu Glu Ser Leu Pro Val Asp Glu Leu Ile Glu Lys Ala Asp Gly
545                 550                 555                 560

Phe Ala Gly Val Phe Pro Glu His Lys Tyr Glu Ile Val Lys Arg Leu
            565                 570                 575

Gln Glu Lys Lys His Ile Val Gly Met Thr Gly Asp Gly Val Asn Asp
            580                 585                 590

Ala Pro Ala Leu Lys Lys Ala Asp Ile Gly Ile Ala Val Ala Asp Ala
            595                 600                 605

Thr Asp Ala Ala Arg Ser Ala Ser Asp Ile Val Leu Thr Glu Pro Gly
            610                 615                 620

Leu Ser Val Ile Ile Ser Ala Val Leu Thr Ser Arg Cys Ile Phe Gln
625                 630                 635                 640

Arg Met Lys Asn Tyr Thr Ile Tyr Ala Val Ser Ile Thr Ile Arg Ile
            645                 650                 655

Val Leu Gly Phe Met Leu Ile Ala Leu Ile Trp Lys Tyr Asp Phe Ser
            660                 665                 670

Pro Phe Met Val Leu Ile Ile Ala Ile Leu Asn Asp Gly Thr Ile Met
            675                 680                 685

Thr Ile Ser Lys Asp Arg Val Lys Pro Ser Pro Leu Pro Asp Ser Trp
            690                 695                 700

Lys Leu Lys Glu Ile Phe Ala Thr Gly Val Val Leu Gly Ser Tyr Leu
705                 710                 715                 720

Ala Leu Met Thr Val Ile Phe Phe Trp Ala Met His Lys Thr Asp Phe
            725                 730                 735

```
Phe Pro Glu Lys Phe Gly Val Lys Pro Ile Arg Asp Ser Glu Gly Lys
                740                 745                 750

Met Met Ser Ala Leu Tyr Leu Gln Val Ser Ile Val Ser Gln Ala Leu
            755                 760                 765

Ile Phe Val Thr Arg Ser Arg Ser Trp Ser Phe Val Glu Arg Pro Gly
        770                 775                 780

Leu Leu Leu Val Thr Ala Phe Leu Leu Ala Gln Leu Val Ala Thr Phe
785                 790                 795                 800

Leu Ala Val Tyr Ala Asn Trp Gly Phe Ala Arg Ile Glu Gly Ile Gly
                805                 810                 815

Trp Gly Trp Ala Gly Val Val Trp Leu Tyr Ser Ile Val Phe Tyr Phe
            820                 825                 830

Pro Leu Asp Leu Phe Lys Phe Phe Ile Arg Phe Val Leu Ser Gly Arg
        835                 840                 845

Ala Trp Asp Asn Leu Leu Glu Asn Lys Thr Ala Phe Thr Thr Lys Lys
850                 855                 860

Asp Tyr Gly Arg Glu Glu Arg Glu Ala Gln Trp Ala Thr Ala Gln Arg
865                 870                 875                 880

Thr Leu His Gly Leu Gln Pro Pro Glu Ala Ala Ser Asn Thr Leu Phe
                885                 890                 895

Asn Asp Lys Ser Ser Tyr Arg Glu Leu Ser Glu Ile Ala Glu Gln Ala
            900                 905                 910

Lys Arg Arg Ala Glu Ile Ala Arg Leu Arg Glu Leu Asn Thr Leu Lys
        915                 920                 925

Gly His Val Glu Ser Val Val Lys Leu Lys Gly Leu Asp Ile Asp Thr
930                 935                 940

Ile Gln Gln Asn Tyr Thr Val
945                 950

<210> SEQ ID NO 10
<211> LENGTH: 951
<212> TYPE: PRT
<213> ORGANISM: Oryza sativa
<220> FEATURE:
<221> NAME/KEY: misc_feature
<223> OTHER INFORMATION: Os04g56160_Oryza_sativa

<400> SEQUENCE: 10

Met Gly Gly Leu Glu Glu Ile Lys Asn Glu Ala Val Asp Leu Glu Asn
1               5                   10                  15

Ile Pro Ile Glu Glu Val Phe Glu Gln Leu Lys Cys Thr Arg Glu Gly
            20                  25                  30

Leu Ser Ser Glu Glu Gly Asn Arg Arg Ile Glu Met Phe Gly Pro Asn
        35                  40                  45

Lys Leu Glu Glu Lys Lys Glu Ser Lys Ile Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Gly Gly Lys Pro Pro Asp Trp Glu Asp Phe
                85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Leu Met Ala Asn Leu
        115                 120                 125

Ala Pro Lys Thr Lys Val Leu Arg Asp Gly Arg Trp Gly Glu Gln Glu
    130                 135                 140
```

```
Ala Ala Ile Leu Val Pro Gly Asp Ile Ile Ser Ile Lys Leu Gly Asp
145                 150                 155                 160

Ile Val Pro Ala Asp Ala Arg Leu Leu Glu Gly Asp Pro Leu Lys Ile
            165                 170                 175

Asp Gln Ser Ala Leu Thr Gly Glu Ser Leu Pro Val Thr Lys Asn Pro
        180                 185                 190

Gly Asp Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
210                 215                 220

His Leu Val Asp Ser Thr Asn Gln Val Gly His Phe Gln Thr Val Leu
225                 230                 235                 240

Thr Ala Ile Gly Asn Phe Cys Ile Cys Ser Ile Ala Val Gly Ile Val
            245                 250                 255

Ile Glu Ile Ile Val Met Phe Pro Ile Gln His Arg Ala Tyr Arg Ser
        260                 265                 270

Gly Ile Glu Asn Leu Leu Val Leu Leu Ile Gly Ile Pro Ile Ala
        275                 280                 285

Met Pro Thr Val Leu Ser Val Thr Met Ala Ile Gly Ser His Lys Leu
    290                 295                 300

Ser Gln Gln Gly Ala Ile Thr Lys Arg Met Thr Ala Ile Glu Glu Met
305                 310                 315                 320

Ala Gly Met Asp Val Leu Cys Ser Asp Lys Thr Gly Thr Leu Thr Leu
            325                 330                 335

Asn Lys Leu Ser Val Asp Lys Asn Leu Val Glu Val Phe Thr Lys Gly
        340                 345                 350

Val Asp Lys Asp His Val Leu Leu Leu Ala Ala Arg Ala Ser Arg Thr
        355                 360                 365

Glu Asn Gln Asp Ala Ile Asp Ala Ala Met Val Gly Met Leu Ala Asp
370                 375                 380

Pro Lys Glu Ala Arg Ala Gly Ile Arg Glu Val His Phe Leu Pro Phe
385                 390                 395                 400

Asn Pro Val Asp Lys Arg Thr Ala Leu Thr Tyr Ile Asp Ala Asp Gly
            405                 410                 415

Asn Trp His Arg Ala Ser Lys Gly Ala Pro Glu Gln Ile Leu Thr Leu
        420                 425                 430

Cys Asn Cys Lys Glu Asp Val Lys Arg Lys Val His Ala Val Ile Asp
        435                 440                 445

Lys Tyr Ala Glu Arg Gly Leu Arg Ser Leu Ala Val Ala Arg Gln Glu
    450                 455                 460

Val Pro Glu Lys Ser Lys Glu Ser Ala Gly Gly Pro Trp Gln Phe Val
465                 470                 475                 480

Gly Leu Leu Pro Leu Phe Asp Pro Pro Arg His Asp Ser Ala Glu Thr
            485                 490                 495

Ile Arg Lys Ala Leu His Leu Gly Val Asn Val Lys Met Ile Thr Gly
        500                 505                 510

Asp Gln Leu Ala Ile Gly Lys Glu Thr Gly Arg Arg Leu Gly Met Gly
        515                 520                 525

Thr Asn Met Tyr Pro Ser Ser Ala Leu Leu Gly Gln Asn Lys Asp Ala
530                 535                 540

Ser Leu Glu Ala Leu Pro Val Asp Glu Leu Ile Glu Lys Ala Asp Gly
545                 550                 555                 560
```

```
Phe Ala Gly Val Phe Pro Glu His Lys Tyr Glu Ile Val Lys Arg Leu
                565                 570                 575
Gln Glu Lys Lys His Ile Val Gly Met Thr Gly Asp Gly Val Asn Asp
            580                 585                 590
Ala Pro Ala Leu Lys Lys Ala Asp Ile Gly Ile Ala Val Ala Asp Ala
        595                 600                 605
Thr Asp Ala Ala Arg Ser Ala Ser Asp Ile Val Leu Thr Glu Pro Gly
    610                 615                 620
Leu Ser Val Ile Ile Ser Ala Val Leu Thr Ser Arg Cys Ile Phe Gln
625                 630                 635                 640
Arg Met Lys Asn Tyr Thr Ile Tyr Ala Val Ser Ile Thr Ile Arg Ile
                645                 650                 655
Val Leu Gly Phe Leu Leu Ile Ala Leu Ile Trp Lys Tyr Asp Phe Ser
            660                 665                 670
Pro Phe Met Val Leu Ile Ile Ala Ile Leu Asn Asp Gly Thr Ile Met
        675                 680                 685
Thr Ile Ser Lys Asp Arg Val Lys Pro Ser Pro Leu Pro Asp Ser Trp
    690                 695                 700
Lys Leu Lys Glu Ile Phe Ala Thr Gly Ile Val Leu Gly Ser Tyr Leu
705                 710                 715                 720
Ala Leu Met Thr Val Ile Phe Phe Trp Ala Met His Lys Thr Asp Phe
                725                 730                 735
Phe Thr Asp Lys Phe Gly Val Arg Ser Ile Arg Asn Ser Glu His Glu
            740                 745                 750
Met Met Ser Ala Leu Tyr Leu Gln Val Ser Ile Val Ser Gln Ala Leu
        755                 760                 765
Ile Phe Val Thr Arg Ser Arg Ser Trp Ser Phe Ile Glu Arg Pro Gly
    770                 775                 780
Leu Leu Leu Val Thr Ala Phe Met Leu Ala Gln Leu Val Ala Thr Phe
785                 790                 795                 800
Leu Ala Val Tyr Ala Asn Trp Gly Phe Ala Arg Ile Lys Gly Ile Gly
                805                 810                 815
Trp Gly Trp Ala Gly Val Ile Trp Leu Tyr Ser Ile Val Phe Tyr Phe
            820                 825                 830
Pro Leu Asp Ile Phe Lys Phe Ile Arg Phe Val Leu Ser Gly Arg
        835                 840                 845
Ala Trp Asp Asn Leu Leu Glu Asn Lys Ile Ala Phe Thr Thr Lys Lys
    850                 855                 860
Asp Tyr Gly Arg Glu Glu Arg Glu Ala Gln Trp Ala Thr Ala Gln Arg
865                 870                 875                 880
Thr Leu His Gly Leu Gln Pro Pro Glu Val Ala Ser Asn Thr Leu Phe
                885                 890                 895
Asn Asp Lys Ser Ser Tyr Arg Glu Leu Ser Glu Ile Ala Glu Gln Ala
            900                 905                 910
Lys Arg Arg Ala Glu Ile Ala Arg Leu Arg Glu Leu Asn Thr Leu Lys
        915                 920                 925
Gly His Val Glu Ser Val Val Lys Leu Lys Gly Leu Asp Ile Asp Thr
    930                 935                 940
Ile Gln Gln Asn Tyr Thr Val
945                 950

<210> SEQ ID NO 11
<211> LENGTH: 951
<212> TYPE: PRT
```

<210> ORGANISM: Brachypodium distachyon
<220> FEATURE:
<221> NAME/KEY: misc_feature
<223> OTHER INFORMATION: BdAHA_Bradi5g24690.1_Brachypodium_distachyon

<400> SEQUENCE: 11

```
Met Gly Gly Leu Glu Glu Ile Arg Asn Glu Ala Val Asp Leu Glu Asn
1               5                   10                  15

Ile Pro Ile Glu Glu Val Phe Glu Gln Leu Lys Cys Thr Arg Glu Gly
            20                  25                  30

Leu Thr Ser Asp Glu Gly Ala Gln Arg Val Thr Ile Phe Gly Leu Asn
        35                  40                  45

Lys Leu Glu Glu Lys Lys Glu Ser Lys Val Leu Lys Phe Leu Gly Phe
50                  55                  60

Met Trp Asn Pro Leu Ser Trp Val Met Glu Met Ala Ala Ile Met Ala
65                  70                  75                  80

Ile Ala Leu Ala Asn Gly Glu Gly Lys Pro Pro Asp Trp Gln Asp Phe
                85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Leu Met Ala Asn Leu
        115                 120                 125

Ala Pro Lys Thr Lys Val Leu Arg Asp Gly Arg Trp Gly Glu Gln Glu
130                 135                 140

Ala Ser Ile Leu Val Pro Gly Asp Ile Val Ser Ile Lys Leu Gly Asp
145                 150                 155                 160

Ile Val Pro Ala Asp Ala Arg Leu Leu Glu Gly Asp Pro Leu Lys Ile
                165                 170                 175

Asp Gln Ser Gly Leu Thr Gly Glu Ser Leu Pro Val Thr Lys Asn Pro
            180                 185                 190

Gly Asp Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
210                 215                 220

His Leu Val Asp Ser Thr Asn Gln Val Gly His Phe Gln Lys Val Leu
225                 230                 235                 240

Thr Ala Ile Gly Asn Phe Cys Ile Val Ser Ile Ala Val Gly Ile Val
                245                 250                 255

Ile Glu Ile Ile Val Met Phe Pro Ile Gln Arg Arg Lys Tyr Arg Ala
            260                 265                 270

Gly Ile Glu Asn Leu Leu Val Leu Leu Ile Gly Gly Ile Pro Ile Ala
        275                 280                 285

Met Pro Thr Val Leu Ser Val Thr Met Ala Ile Gly Ser His Lys Leu
290                 295                 300

Ser Gln Gln Gly Ala Ile Thr Lys Arg Met Thr Ala Ile Glu Glu Leu
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Ala Lys Gly
            340                 345                 350

Val Asp Lys Glu His Val Leu Leu Leu Ala Ala Arg Ala Ser Arg Val
        355                 360                 365

Glu Asn Gln Asp Ala Ile Asp Ala Cys Met Val Gly Met Leu Ala Asp
370                 375                 380
```

```
Pro Lys Glu Ala Arg Ala Gly Ile Arg Glu Val His Phe Leu Pro Phe
385                 390                 395                 400

Asn Pro Thr Asp Lys Arg Thr Ala Leu Thr Tyr Ile Asp Ala Glu Gly
            405                 410                 415

Asn Trp His Arg Ala Ser Lys Gly Ala Pro Glu Gln Ile Ile Thr Leu
        420                 425                 430

Cys Asn Cys Lys Glu Asp Val Lys Arg Lys Val His Ser Val Ile Glu
        435                 440                 445

Lys Tyr Ala Glu Arg Gly Leu Arg Ser Leu Ala Val Ala Arg Gln Glu
    450                 455                 460

Val Pro Glu Lys Ser Lys Asp Ser Pro Gly Gly Pro Trp Gln Phe Ile
465                 470                 475                 480

Gly Leu Leu Pro Leu Phe Asp Pro Pro Arg His Asp Ser Ala Glu Thr
                485                 490                 495

Ile Arg Lys Ala Leu Val Leu Gly Val Asn Val Lys Met Ile Thr Gly
                500                 505                 510

Asp Gln Leu Ala Ile Gly Lys Glu Thr Gly Arg Arg Leu Gly Met Gly
            515                 520                 525

Thr Asn Met Tyr Pro Ser Ser Ala Leu Leu Gly Gln Ser Lys Asp Gly
530                 535                 540

Ser Leu Glu Ser Leu Pro Val Asp Glu Leu Ile Glu Lys Ala Asp Gly
545                 550                 555                 560

Phe Ala Gly Val Phe Pro Glu His Lys Tyr Glu Ile Val Lys Arg Leu
                565                 570                 575

Gln Glu Lys Lys His Ile Val Gly Met Thr Gly Asp Gly Val Asn Asp
            580                 585                 590

Ala Pro Ala Leu Lys Lys Ala Asp Ile Gly Ile Ala Val Asp Asp Ala
            595                 600                 605

Thr Asp Ala Ala Arg Ser Ala Ser Asp Ile Val Leu Thr Glu Pro Gly
            610                 615                 620

Leu Ser Val Ile Ile Ser Ala Val Leu Thr Ser Arg Cys Ile Phe Gln
625                 630                 635                 640

Arg Met Lys Asn Tyr Thr Ile Tyr Ala Val Ser Ile Thr Ile Arg Ile
                645                 650                 655

Val Leu Gly Phe Met Leu Ile Ala Leu Ile Trp Lys Phe Asp Phe Ala
                660                 665                 670

Pro Phe Met Val Leu Ile Ile Ala Ile Leu Asn Asp Gly Thr Ile Met
            675                 680                 685

Thr Ile Ser Lys Asp Arg Val Lys Pro Ser Pro Leu Pro Asp Ser Trp
            690                 695                 700

Lys Leu Asn Glu Ile Phe Ala Thr Gly Val Val Leu Gly Thr Tyr Leu
705                 710                 715                 720

Ala Leu Met Thr Val Val Phe Phe Trp Ala Ile His Lys Thr Asp Phe
                725                 730                 735

Phe Thr Asn Lys Phe Gly Val Arg Ser Ile Arg Asn Ser Glu Phe Glu
            740                 745                 750

Leu Met Ser Ala Leu Tyr Leu Gln Val Ser Ile Val Ser Gln Ala Leu
            755                 760                 765

Ile Phe Val Thr Arg Ser Arg Ser Trp Ser Phe Val Glu Arg Pro Gly
            770                 775                 780

Phe Leu Leu Val Thr Ala Phe Leu Leu Ala Gln Leu Val Ala Thr Leu
785                 790                 795                 800
```

```
Ile Ala Val Tyr Ala Asn Trp Glu Phe Ala Arg Ile Lys Gly Ile Gly
                805                 810                 815

Trp Gly Trp Ala Gly Val Ile Trp Leu Phe Ser Ile Val Phe Tyr Phe
            820                 825                 830

Pro Leu Asp Val Phe Lys Phe Phe Ile Arg Phe Val Leu Ser Gly Arg
        835                 840                 845

Ala Trp Asp Asn Leu Leu Gln Asn Lys Thr Ala Phe Thr Thr Lys Lys
    850                 855                 860

Asp Tyr Gly Arg Gly Glu Arg Glu Ala Gln Trp Ala Thr Ala Gln Arg
865                 870                 875                 880

Thr Leu His Gly Leu Gln Ala Pro Glu Ser Asn Asn Asn Thr Leu Phe
                885                 890                 895

Asn Asp Lys Ser Ser Tyr Arg Glu Leu Ser Glu Ile Ala Glu Gln Ala
            900                 905                 910

Lys Arg Arg Ala Glu Ile Ala Arg Leu Arg Glu Leu Asn Thr Leu Lys
        915                 920                 925

Gly His Val Glu Ser Val Val Lys Leu Lys Gly Leu Asp Ile Asp Thr
    930                 935                 940

Ile Asn Gln Asn Tyr Thr Val
945                 950

<210> SEQ ID NO 12
<211> LENGTH: 951
<212> TYPE: PRT
<213> ORGANISM: Hordeum vulgare
<220> FEATURE:
<221> NAME/KEY: misc_feature
<223> OTHER INFORMATION: HvAHA_M0Z2H5_Hordeum_vulgare

<400> SEQUENCE: 12

Met Gly Gly Leu Glu Glu Ile Arg Asn Glu Ala Val Asp Leu Glu Asn
1               5                   10                  15

Ile Pro Ile Glu Glu Val Phe Glu Gln Leu Lys Cys Thr Arg Gln Gly
            20                  25                  30

Leu Thr Ser Asp Glu Gly Ala Gln Arg Val Glu Ile Phe Gly Leu Asn
        35                  40                  45

Lys Leu Glu Glu Lys Lys Glu Ser Lys Val Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Gly Lys Pro Pro Asp Trp Gln Asp Phe
                85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Leu Met Ala Asn Leu
        115                 120                 125

Ala Pro Lys Thr Lys Val Leu Arg Asp Gly Arg Trp Gly Glu Gln Glu
130                 135                 140

Ala Ser Ile Leu Val Pro Gly Asp Ile Val Ser Ile Lys Leu Gly Asp
145                 150                 155                 160

Ile Val Pro Ala Asp Ala Arg Leu Leu Glu Gly Asp Pro Leu Lys Ile
                165                 170                 175

Asp Gln Ser Gly Leu Thr Gly Glu Ser Leu Pro Val Thr Lys Asn Pro
            180                 185                 190
```

```
Gly Asp Glu Val Phe Ser Gly Ser Thr Cys Lys Gln Gly Glu Ile Glu
            195                 200                 205

Ala Val Val Ile Ala Thr Gly Val His Thr Phe Phe Gly Lys Ala Ala
        210                 215                 220

His Leu Val Asp Ser Thr Asn Gln Val Gly His Phe Gln Gln Val Leu
225                 230                 235                 240

Thr Ala Ile Gly Asn Phe Cys Ile Ile Ser Ile Ala Val Gly Ile Val
            245                 250                 255

Ile Glu Ile Ile Val Met Phe Pro Ile Gln Arg Arg Lys Tyr Arg Ala
        260                 265                 270

Gly Ile Glu Asn Leu Leu Val Leu Leu Ile Gly Gly Ile Pro Ile Ala
            275                 280                 285

Met Pro Thr Val Leu Ser Val Thr Met Ala Ile Gly Ser His Lys Leu
    290                 295                 300

Ser Gln Gln Gly Ala Ile Thr Lys Arg Met Thr Ala Ile Glu Glu Leu
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Ala Lys Gly
            340                 345                 350

Val Asp Lys Glu His Val Leu Leu Leu Ala Ala Arg Ala Ser Arg Val
        355                 360                 365

Glu Asn Gln Asp Ala Ile Asp Ala Cys Met Val Gly Met Leu Ala Asp
    370                 375                 380

Pro Lys Glu Ala Arg Ala Gly Ile Arg Glu Val His Phe Leu Pro Phe
385                 390                 395                 400

Asn Pro Thr Asp Lys Arg Thr Ala Leu Thr Tyr Ile Asp Ala Glu Gly
                405                 410                 415

Asn Trp His Arg Ala Ser Lys Gly Ala Pro Glu Gln Ile Ile Thr Leu
            420                 425                 430

Cys Asn Cys Lys Glu Asp Val Lys Arg Lys Val His Ser Val Ile Glu
        435                 440                 445

Lys Tyr Ala Glu Arg Gly Leu Arg Ser Leu Ala Val Ala Arg Gln Glu
    450                 455                 460

Val Pro Glu Lys Ser Lys Asp Ser Ala Gly Gly Pro Trp Gln Phe Ile
465                 470                 475                 480

Gly Leu Leu Pro Leu Phe Asp Pro Pro Arg His Asp Ser Ala Glu Thr
                485                 490                 495

Ile Arg Lys Ala Leu Val Leu Gly Val Asn Val Lys Met Ile Thr Gly
            500                 505                 510

Asp Gln Leu Ala Ile Gly Lys Glu Thr Gly Arg Arg Leu Gly Met Gly
        515                 520                 525

Thr Asn Met Tyr Pro Ser Ser Ala Leu Leu Gly Gln Ser Lys Asp Gly
    530                 535                 540

Ser Leu Glu Ser Leu Pro Val Asp Glu Leu Ile Glu Lys Ala Asp Gly
545                 550                 555                 560

Phe Ala Gly Val Phe Pro Glu His Lys Tyr Glu Ile Val Lys Arg Leu
                565                 570                 575

Gln Glu Lys Lys His Ile Val Gly Met Thr Gly Asp Gly Val Asn Asp
            580                 585                 590

Ala Pro Ala Leu Lys Lys Ala Asp Ile Gly Ile Ala Val Asp Asp Ala
        595                 600                 605
```

-continued

```
Thr Asp Ala Ala Arg Ser Ala Ser Asp Ile Val Leu Thr Glu Pro Gly
    610                 615                 620

Leu Ser Val Ile Ile Ser Ala Val Leu Thr Ser Arg Cys Ile Phe Gln
625                 630                 635                 640

Arg Met Lys Asn Tyr Thr Ile Tyr Ala Val Ser Ile Thr Ile Arg Ile
                645                 650                 655

Val Leu Gly Phe Leu Leu Ile Ala Leu Ile Trp Lys Phe Asp Phe Ala
                660                 665                 670

Pro Phe Met Val Leu Ile Ile Ala Ile Leu Asn Asp Gly Thr Ile Met
            675                 680                 685

Thr Ile Ser Lys Asp Arg Val Lys Pro Ser Pro Leu Pro Asp Ser Trp
690                 695                 700

Lys Leu Asn Glu Ile Phe Ala Thr Gly Val Val Leu Gly Thr Tyr Leu
705                 710                 715                 720

Ala Leu Met Thr Val Val Phe Phe Trp Ile Ile His Arg Thr Asp Phe
                725                 730                 735

Phe Thr Asn Lys Phe Gly Val Arg Ser Ile Arg Glu Asn Glu Thr Glu
                740                 745                 750

Lys Met Ser Ala Leu Tyr Leu Gln Val Ser Ile Val Ser Gln Ala Leu
            755                 760                 765

Ile Phe Val Thr Arg Ser Arg Ser Trp Ser Phe Val Glu Arg Pro Gly
770                 775                 780

Phe Leu Leu Val Ile Ala Phe Leu Leu Ala Gln Leu Val Ala Thr Leu
785                 790                 795                 800

Ile Ala Val Tyr Ala Asn Trp Gly Phe Ala Arg Ile Ser Gly Ile Gly
                805                 810                 815

Trp Gly Trp Ala Gly Val Ile Trp Leu Phe Ser Ile Val Phe Tyr Phe
                820                 825                 830

Pro Leu Asp Ile Phe Lys Phe Phe Ile Arg Phe Val Leu Ser Gly Arg
            835                 840                 845

Ala Trp Asp Asn Leu Leu Gln Asn Lys Thr Ala Phe Thr Thr Lys Glu
            850                 855                 860

Asn Tyr Gly Lys Gly Glu Arg Glu Ala Gln Trp Ala Thr Ala Gln Arg
865                 870                 875                 880

Thr Leu His Gly Leu Gln Ala Pro Glu Pro Ala Ser His Thr Leu Phe
                885                 890                 895

Asn Asp Lys Ser Ser Tyr Arg Glu Leu Ser Glu Ile Ala Glu Gln Ala
                900                 905                 910

Lys Arg Arg Ala Glu Ile Ala Arg Leu Arg Glu Leu Asn Thr Leu Lys
            915                 920                 925

Gly His Val Glu Ser Val Val Lys Leu Lys Gly Leu Asp Ile Asp Thr
            930                 935                 940

Ile Asn Gln Asn Tyr Thr Val
945                 950

<210> SEQ ID NO 13
<211> LENGTH: 956
<212> TYPE: PRT
<213> ORGANISM: Hordeum vulgare
<220> FEATURE:
<221> NAME/KEY: misc_feature
<223> OTHER INFORMATION: HvAHA_Q8H1X2_Hordeum_vulgare
```

<400> SEQUENCE: 13

Met Ala Asp Lys Glu Ala Gly Asn Leu Glu Ala Val Leu Lys Glu Val
1               5                   10                  15

Val Asp Leu Glu Asn Ile Pro Leu Glu Glu Val Leu Asp Asn Leu Arg
                20                  25                  30

Cys Ser Arg Glu Gly Leu Thr Ala Glu Gln Ala Gln Gln Arg Leu Gln
                35                  40                  45

Ile Leu Gly Pro Asn Lys Leu Glu Glu Lys Glu Ser Lys Phe Leu
            50                  55                  60

Lys Phe Leu Gly Phe Met Trp Asn Pro Leu Ser Trp Val Met Glu Met
65                  70                  75                  80

Ala Ala Ile Met Ala Ile Ala Leu Ala Asn Gly Gly Lys Pro Pro
                    85                  90                  95

Asp Trp Gln Asp Phe Val Gly Ile Ile Val Leu Leu Val Ile Asn Ser
                100                 105                 110

Thr Val Ser Phe Ile Glu Glu Asn Asn Ala Gly Asn Ala Ala Ala Ala
            115                 120                 125

Leu Met Ala Asn Leu Ala Pro Lys Thr Lys Val Leu Arg Asp Gly Arg
    130                 135                 140

Trp Gly Glu Gln Glu Ala Ser Ile Leu Val Pro Gly Thr Leu Ser Ala
145                 150                 155                 160

Ser Ser Leu Val Thr Ser Ser Leu Leu Met Leu Val Cys Leu Glu Gly
                165                 170                 175

Asp Pro Phe Glu Asp Ser Ser Val Trp Ala Tyr Arg Arg Val Ser Pro
                180                 185                 190

Ser Asp Gln Glu Pro Trp Gly Glu Val Phe Ser Gly Ser Thr Cys Lys
                195                 200                 205

Gln Gly Glu Ile Glu Ala Val Val Ile Ala Thr Gly Val His Thr Phe
210                 215                 220

Phe Gly Lys Ala Ala His Leu Val Asp Ser Thr Asn Gln Val Gly His
225                 230                 235                 240

Phe Gln Gln Val Leu Thr Ala Ile Gly Asn Phe Cys Ile Ile Ser Ile
                245                 250                 255

Ala Val Gly Ile Val Glu Ile Ile Val Met Phe Pro Ile Gln Arg
                260                 265                 270

Arg Lys Tyr Arg Ala Gly Ile Glu Asn Leu Leu Val Leu Leu Ile Gly
            275                 280                 285

Gly Ile Pro Ile Ala Met Pro Thr Val Leu Ser Val Thr Met Ala Ile
290                 295                 300

Gly Ser His Lys Leu Ser Gln Gln Gly Ala Ile Thr Lys Arg Met Thr
305                 310                 315                 320

Ala Ile Glu Glu Leu Ala Gly Met Asp Val Leu Cys Ser Asp Lys Thr
                325                 330                 335

Gly Thr Leu Thr Leu Asn Lys Leu Ser Val Asp Lys Asn Leu Val Glu
            340                 345                 350

Val Phe Ala Lys Gly Val Asp Lys Glu His Val Leu Leu Leu Ala Ala
            355                 360                 365

Arg Ala Ser Arg Val Glu Asn Gln Asp Ala Ile Asp Ala Cys Met Val
    370                 375                 380

Gly Met Leu Ala Asp Pro Lys Glu Ala Arg Ala Gly Ile Arg Glu Val
385                 390                 395                 400

```
His Phe Leu Pro Phe Asn Pro Thr Asp Lys Arg Thr Ala Leu Thr Tyr
            405                 410                 415

Ile Asp Ala Glu Gly Asn Trp His Arg Ala Ser Lys Gly Ala Pro Glu
        420                 425                 430

Gln Ile Ile Thr Leu Cys Asn Cys Lys Glu Asp Val Lys Arg Lys Val
            435                 440                 445

His Ser Val Ile Glu Lys Tyr Ala Glu Arg Gly Leu Arg Ser Leu Ala
    450                 455                 460

Val Ala Arg Gln Glu Val Pro Glu Lys Ser Lys Asp Ser Ala Gly Gly
465                 470                 475                 480

Pro Trp Gln Phe Ile Gly Leu Leu Pro Leu Phe Asp Pro Pro Arg His
            485                 490                 495

Asp Ser Ala Glu Thr Ile Arg Lys Ala Leu Val Leu Gly Val Asn Val
                500                 505                 510

Lys Met Ile Thr Gly Asp Gln Leu Ala Ile Gly Lys Glu Thr Gly Arg
        515                 520                 525

Arg Leu Gly Met Gly Thr Asn Met Tyr Pro Ser Ser Ala Leu Leu Gly
    530                 535                 540

Gln Ser Lys Asp Gly Ser Leu Glu Ser Leu Pro Val Asp Glu Leu Ile
545                 550                 555                 560

Glu Lys Ala Asp Gly Phe Ala Gly Val Phe Pro Glu His Lys Tyr Glu
                565                 570                 575

Ile Val Lys Arg Leu Gln Glu Lys Lys His Ile Val Gly Met Thr Gly
            580                 585                 590

Asp Gly Val Asn Asp Ala Pro Ala Leu Lys Lys Ala Asp Ile Gly Ile
        595                 600                 605

Ala Val Asp Asp Ala Thr Asp Ala Ala Arg Ser Ala Ser Asp Ile Val
    610                 615                 620

Leu Thr Glu Pro Gly Leu Ser Val Ile Ser Ala Val Leu Thr Ser
625                 630                 635                 640

Arg Cys Ile Phe Gln Arg Met Lys Asn Tyr Thr Ile Tyr Ala Val Ser
                645                 650                 655

Ile Thr Ile Arg Ile Val Leu Gly Phe Leu Leu Ile Ala Leu Ile Trp
            660                 665                 670

Lys Phe Asp Phe Ala Pro Phe Met Val Leu Ile Ile Ala Ile Leu Asn
        675                 680                 685

Asp Gly Thr Ile Met Thr Ile Ser Lys Asp Arg Val Lys Pro Ser Pro
    690                 695                 700

Leu Pro Asp Ser Trp Lys Leu Asn Glu Ile Phe Ala Thr Gly Val Val
705                 710                 715                 720

Leu Gly Thr Tyr Leu Ala Leu Met Thr Val Val Phe Phe Trp Ile Ile
                725                 730                 735

His Arg Thr Asp Phe Phe Thr Asn Lys Phe Gly Val Arg Ser Ile Arg
            740                 745                 750

Glu Asn Glu Thr Glu Lys Met Ser Ala Leu Tyr Leu Gln Val Ser Ile
        755                 760                 765

Val Ser Gln Ala Leu Ile Phe Val Thr Arg Ser Arg Ser Trp Ser Phe
    770                 775                 780

Val Glu Arg Pro Gly Phe Leu Leu Val Ile Ala Phe Leu Leu Ala Gln
785                 790                 795                 800

Leu Val Ala Thr Leu Ile Ala Val Tyr Ala Asn Trp Gly Phe Ala Arg
                805                 810                 815
```

```
Ile Ser Gly Ile Gly Trp Gly Trp Ala Gly Val Ile Trp Leu Phe Ser
            820             825                 830

Ile Val Phe Tyr Phe Pro Leu Asp Ile Phe Lys Phe Ile Arg Phe
            835                 840             845

Val Leu Ser Gly Arg Ala Trp Asp Asn Leu Leu Gln Asn Lys Thr Ala
        850                 855             860

Phe Thr Thr Lys Glu Asn Tyr Gly Lys Gly Glu Arg Glu Ala Gln Trp
865             870              875              880

Ala Thr Ala Gln Arg Thr Leu His Gly Leu Gln Ala Pro Glu Pro Ala
                885              890             895

Ser His Thr Leu Phe Asn Asp Lys Ser Ser Tyr Arg Glu Leu Ser Glu
            900             905             910

Ile Ala Glu Gln Ala Lys Arg Arg Ala Glu Ile Ala Arg Leu Arg Glu
            915             920             925

Leu Asn Thr Leu Lys Gly His Val Glu Ser Val Val Lys Leu Lys Gly
            930             935             940

Leu Asp Ile Asp Thr Ile Asn Gln Asn Tyr Thr Val
945             950             955

<210> SEQ ID NO 14
<211> LENGTH: 880
<212> TYPE: PRT
<213> ORGANISM: Triticum aestivum
<220> FEATURE:
<221> NAME/KEY: misc_feature
<223> OTHER INFORMATION: TaAHA_2BL_4AEA2109C_Triticum_aestivum

<400> SEQUENCE: 14

Met Trp Asn Pro Leu Ser Trp Val Met Glu Met Ala Ala Ile Met Ala
1               5                   10                  15

Ile Ala Leu Ala Asn Gly Gly Lys Pro Pro Asp Trp Gln Asp Phe
            20                  25                  30

Val Gly Ile Ile Val Leu Leu Val Ile Asn Ser Thr Ile Ser Phe Ile
            35                  40                  45

Glu Glu Asn Asn Ala Gly Asn Ala Ala Ala Leu Met Ala Asn Leu
        50                  55                  60

Ala Pro Lys Thr Lys Val Leu Arg Asp Gly Arg Trp Gly Glu Gln Glu
65              70                  75                  80

Ala Ser Ile Leu Val Pro Gly Asp Ile Val Ser Ile Lys Leu Gly Asp
                85                  90                  95

Ile Val Pro Ala Asp Ala Arg Leu Leu Glu Gly Asp Pro Leu Lys Ile
            100                 105                 110

Asp Gln Ser Gly Leu Thr Gly Glu Ser Leu Pro Val Thr Lys Asn Pro
            115                 120                 125

Gly Asp Glu Val Phe Ser Gly Ser Thr Cys Lys Gln Gly Glu Ile Glu
        130                 135                 140

Ala Val Val Ile Ala Thr Gly Val His Thr Phe Phe Gly Lys Ala Ala
145                 150                 155                 160

His Leu Val Asp Ser Thr Asn Gln Val Gly His Phe Gln Gln Val Leu
                165                 170                 175

Thr Ala Ile Gly Asn Phe Cys Ile Val Ser Ile Ala Val Gly Ile Val
            180                 185                 190

Ile Glu Ile Ile Val Met Phe Pro Ile Gln Arg Arg Lys Tyr Arg Ala
            195                 200                 205

Gly Ile Glu Asn Leu Leu Val Leu Leu Ile Gly Gly Ile Pro Ile Ala
        210                 215                 220
```

```
Met Pro Thr Val Leu Ser Val Thr Met Ala Ile Gly Ser His Lys Leu
225                 230                 235                 240

Ser Gln Gln Gly Ala Ile Thr Lys Arg Met Thr Ala Ile Glu Glu Leu
            245                 250                 255

Ala Gly Met Asp Val Leu Cys Ser Asp Lys Thr Gly Thr Leu Thr Leu
            260                 265                 270

Asn Lys Leu Ser Val Asp Lys Asn Leu Val Glu Val Phe Ala Lys Gly
            275                 280                 285

Val Asp Lys Glu His Val Leu Leu Ala Ala Arg Ala Ser Arg Val
290                 295                 300

Glu Asn Gln Asp Ala Ile Asp Ala Cys Met Val Gly Met Leu Ala Asp
305                 310                 315                 320

Pro Lys Glu Ala Arg Ala Gly Ile Arg Glu Val His Phe Leu Pro Phe
            325                 330                 335

Asn Pro Thr Asp Lys Arg Thr Ala Leu Thr Tyr Ile Asp Ala Glu Gly
            340                 345                 350

Asn Trp His Arg Ala Ser Lys Gly Ala Pro Glu Gln Ile Ile Thr Leu
            355                 360                 365

Cys Asn Cys Lys Glu Asp Val Lys Arg Lys Val His Ser Val Ile Glu
370                 375                 380

Lys Tyr Ala Glu Arg Gly Leu Arg Ser Leu Ala Val Ala Arg Gln Glu
385                 390                 395                 400

Val Pro Glu Lys Ser Lys Asp Ser Pro Gly Gly Pro Trp Gln Phe Ile
            405                 410                 415

Gly Leu Leu Pro Leu Phe Asp Pro Pro Arg His Asp Ser Ala Glu Thr
            420                 425                 430

Ile Arg Lys Ala Leu Val Leu Gly Val Asn Val Lys Met Ile Thr Gly
            435                 440                 445

Asp Gln Leu Ala Ile Gly Lys Glu Thr Gly Arg Arg Leu Gly Met Gly
450                 455                 460

Thr Asn Met Tyr Pro Ser Ser Ala Leu Leu Gly Gln Ser Lys Asp Gly
465                 470                 475                 480

Ser Leu Glu Ser Leu Pro Val Asp Glu Leu Ile Glu Lys Ala Asp Gly
            485                 490                 495

Phe Ala Gly Val Phe Pro Glu His Lys Tyr Glu Ile Val Lys Arg Leu
            500                 505                 510

Gln Glu Lys Lys His Ile Val Gly Met Thr Gly Asp Gly Val Asn Asp
            515                 520                 525

Ala Pro Ala Leu Lys Lys Ala Asp Ile Gly Ile Ala Val Asp Asp Ala
            530                 535                 540

Thr Asp Ala Ala Arg Ser Ala Ser Asp Ile Val Leu Thr Glu Pro Gly
545                 550                 555                 560

Leu Ser Val Ile Ile Ser Ala Val Leu Thr Ser Arg Cys Ile Phe Gln
            565                 570                 575

Arg Met Lys Asn Tyr Thr Ile Tyr Ala Val Ser Ile Thr Ile Arg Ile
            580                 585                 590

Val Leu Gly Phe Met Leu Ile Ala Leu Ile Trp Lys Phe Asp Phe Ala
            595                 600                 605

Pro Phe Met Val Leu Ile Ile Ala Ile Leu Asn Asp Gly Thr Ile Met
            610                 615                 620

Thr Ile Ser Lys Asp Arg Val Lys Pro Ser Pro Leu Pro Asp Ser Trp
625                 630                 635                 640
```

```
Lys Leu Asn Glu Ile Phe Ala Thr Gly Val Leu Gly Thr Tyr Leu
                645                 650                 655

Ala Leu Met Thr Val Val Phe Phe Trp Val Ile His Lys Thr Asp Phe
            660                 665                 670

Phe Thr Asn Lys Phe Gly Val Arg Ser Ile Arg Asp Ser Glu Phe Glu
            675                 680                 685

Met Met Ser Ala Leu Tyr Leu Gln Val Ser Ile Val Ser Gln Ala Leu
        690                 695                 700

Ile Phe Val Thr Arg Ser Arg Ser Trp Ser Phe Val Glu Arg Pro Gly
705                 710                 715                 720

Phe Leu Leu Val Thr Ala Phe Leu Leu Ala Gln Leu Val Ala Thr Leu
                725                 730                 735

Ile Ala Val Tyr Ala Asn Trp Glu Phe Ala Arg Ile Lys Gly Ile Gly
                740                 745                 750

Trp Gly Trp Ala Gly Val Ile Trp Leu Phe Ser Ile Val Phe Tyr Phe
            755                 760                 765

Pro Leu Asp Ile Phe Lys Phe Phe Ile Arg Phe Val Leu Ser Gly Arg
            770                 775                 780

Ala Trp Asp Asn Leu Leu Gln Asn Lys Thr Ala Phe Thr Thr Lys Glu
785                 790                 795                 800

Asn Tyr Gly Lys Gly Glu Arg Glu Ala Gln Trp Ala Thr Ala Gln Arg
                805                 810                 815

Thr Leu His Gly Leu Gln Ala Pro Glu Pro Ala Ser His Thr Leu Phe
                820                 825                 830

Asn Asp Lys Ser Ser Tyr Arg Glu Leu Ser Glu Ile Ala Gln Gln Ala
            835                 840                 845

Lys Arg Arg Ala Glu Ile Ala Arg Leu Arg Glu Leu Asn Thr Leu Lys
850                 855                 860

Gly His Val Glu Ser Val Val Lys Leu Lys Gly Leu Asp Ile Asp Thr
865                 870                 875                 880

<210> SEQ ID NO 15
<211> LENGTH: 951
<212> TYPE: PRT
<213> ORGANISM: Triticum aestivum
<220> FEATURE:
<221> NAME/KEY: misc_feature
<223> OTHER INFORMATION: TaAHA_2AL_2C50DEE4C.1_Triticum_aestivum

<400> SEQUENCE: 15

Met Gly Gly Leu Glu Glu Ile Arg Asn Glu Ala Val Asp Leu Glu Asn
1               5                   10                  15

Ile Pro Ile Glu Glu Val Phe Glu Gln Leu Lys Cys Thr Arg Gln Gly
            20                  25                  30

Leu Thr Ser Asp Glu Gly Ala Gln Arg Val Glu Ile Phe Gly Leu Asn
        35                  40                  45

Lys Leu Glu Glu Lys Lys Glu Ser Lys Val Leu Lys Phe Leu Gly Phe
    50                  55                  60

Met Trp Asn Pro Leu Ser Trp Val Met Glu Met Ala Ala Ile Met Ala
65              70                  75                  80

Ile Ala Leu Ala Asn Gly Gly Lys Pro Pro Asp Trp Gln Asp Phe
                85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Leu Met Ala Asn Leu
        115                 120                 125
```

-continued

Ala Pro Lys Thr Lys Val Leu Arg Asp Gly Arg Trp Gly Glu Gln Glu
130                 135                 140

Ala Ser Ile Leu Val Pro Gly Asp Ile Val Ser Ile Lys Leu Gly Asp
145                 150                 155                 160

Ile Val Pro Ala Asp Ala Arg Leu Leu Glu Gly Asp Pro Leu Lys Ile
                165                 170                 175

Asp Gln Ser Gly Leu Thr Gly Glu Ser Leu Pro Val Thr Lys Asn Pro
            180                 185                 190

Gly Asp Glu Val Phe Ser Gly Ser Thr Cys Lys Gln Gly Glu Ile Glu
        195                 200                 205

Ala Val Val Ile Ala Thr Gly Val His Thr Phe Phe Gly Lys Ala Ala
210                 215                 220

His Leu Val Asp Ser Thr Asn Gln Val Gly His Phe Gln Gln Val Leu
225                 230                 235                 240

Thr Ala Ile Gly Asn Phe Cys Ile Val Ser Ile Ala Val Gly Ile Val
                245                 250                 255

Ile Glu Ile Ile Val Met Phe Pro Ile Gln Arg Arg Lys Tyr Arg Ala
                260                 265                 270

Gly Ile Glu Asn Leu Leu Val Leu Leu Ile Gly Gly Ile Pro Ile Ala
            275                 280                 285

Met Pro Thr Val Leu Ser Val Thr Met Ala Ile Gly Ser His Lys Leu
        290                 295                 300

Ser Gln Gln Gly Ala Ile Thr Lys Arg Met Thr Ala Ile Glu Glu Leu
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Ala Lys Gly
                340                 345                 350

Val Asp Lys Glu His Val Leu Leu Leu Ala Ala Arg Ala Ser Arg Val
            355                 360                 365

Glu Asn Gln Asp Ala Ile Asp Ala Cys Met Val Gly Met Leu Ala Asp
370                 375                 380

Pro Lys Glu Ala Arg Ala Gly Ile Arg Glu Val His Phe Leu Pro Phe
385                 390                 395                 400

Asn Pro Thr Asp Lys Arg Thr Ala Leu Thr Tyr Ile Asp Ala Glu Gly
                405                 410                 415

Asn Trp His Arg Ala Ser Lys Gly Ala Pro Glu Gln Ile Ile Thr Leu
            420                 425                 430

Cys Asn Cys Lys Glu Asp Val Lys Arg Val His Ser Val Ile Glu
        435                 440                 445

Lys Tyr Ala Glu Arg Gly Leu Arg Ser Leu Ala Val Ala Arg Gln Glu
450                 455                 460

Val Pro Glu Lys Ser Lys Asp Ser Pro Gly Gly Pro Trp Gln Phe Ile
465                 470                 475                 480

Gly Leu Leu Pro Leu Phe Asp Pro Pro Arg His Asp Ser Ala Glu Thr
                485                 490                 495

Ile Arg Lys Ala Leu Val Leu Gly Val Asn Val Lys Met Ile Thr Gly
            500                 505                 510

Asp Gln Leu Ala Ile Gly Lys Glu Thr Gly Arg Arg Leu Gly Met Gly
        515                 520                 525

Thr Asn Met Tyr Pro Ser Ser Ala Leu Leu Gly Gln Ser Lys Asp Gly
530                 535                 540

```
Ser Leu Glu Ser Leu Pro Val Asp Glu Leu Ile Glu Lys Ala Asp Gly
545                 550                 555                 560

Phe Ala Gly Val Phe Pro Glu His Lys Tyr Glu Ile Val Lys Arg Leu
                565                 570                 575

Gln Glu Lys Lys His Ile Val Gly Met Thr Gly Asp Gly Val Asn Asp
            580                 585                 590

Ala Pro Ala Leu Lys Lys Ala Asp Ile Gly Ile Ala Val Asp Asp Ala
        595                 600                 605

Thr Asp Ala Ala Arg Ser Ala Ser Asp Ile Val Leu Thr Glu Pro Gly
610                 615                 620

Leu Ser Val Ile Ile Ser Ala Val Leu Thr Ser Arg Cys Ile Phe Gln
625                 630                 635                 640

Arg Met Lys Asn Tyr Thr Ile Tyr Ala Val Ser Ile Thr Ile Arg Ile
                645                 650                 655

Val Leu Gly Phe Met Leu Ile Ala Leu Ile Trp Lys Phe Asp Phe Ala
                660                 665                 670

Pro Phe Met Val Leu Ile Ile Ala Ile Leu Asn Asp Gly Thr Ile Met
            675                 680                 685

Thr Ile Ser Lys Asp Arg Val Lys Pro Ser Pro Leu Pro Asp Ser Trp
690                 695                 700

Lys Leu Asn Glu Ile Phe Ala Thr Gly Val Val Leu Gly Thr Tyr Leu
705                 710                 715                 720

Ala Leu Val Thr Val Val Phe Phe Trp Leu Ile His Lys Thr Asp Phe
                725                 730                 735

Phe Thr Asn Lys Phe Gly Val Glu Ser Ile Arg Asn Thr Glu Phe Lys
            740                 745                 750

Glu Met Ser Ala Leu Tyr Leu Gln Val Ser Ile Val Ser Gln Ala Leu
            755                 760                 765

Ile Phe Val Thr Arg Ser Arg Ser Trp Ser Phe Val Glu Arg Pro Gly
770                 775                 780

Phe Leu Leu Val Thr Ala Phe Leu Leu Ala Gln Leu Val Ala Thr Leu
785                 790                 795                 800

Ile Ala Val Tyr Ala Asn Trp Asp Phe Ala Arg Ile Lys Gly Ile Gly
                805                 810                 815

Trp Gly Trp Ala Gly Val Ile Trp Leu Phe Ser Ile Val Phe Tyr Phe
                820                 825                 830

Pro Leu Asp Ile Phe Lys Phe Phe Ile Arg Phe Val Leu Ser Gly Arg
            835                 840                 845

Ala Trp Asp Asn Leu Leu Gln Asn Lys Thr Ala Phe Thr Thr Lys Glu
        850                 855                 860

Asn Tyr Gly Lys Gly Glu Arg Glu Ala Gln Trp Ala Thr Ala Gln Arg
865                 870                 875                 880

Thr Leu His Gly Leu Gln Ala Pro Glu Pro Ala Ser His Thr Leu Phe
                885                 890                 895

Asn Asp Lys Ser Ser Tyr Arg Glu Leu Ser Ile Ala Glu Gln Ala
            900                 905                 910

Lys Arg Arg Ala Glu Ile Ala Arg Leu Arg Glu Leu Asn Thr Leu Lys
                915                 920                 925

Gly His Val Glu Ser Val Val Lys Leu Lys Gly Leu Asp Ile Asp Thr
            930                 935                 940

Ile Asn Gln Asn Tyr Thr Val
945                 950
```

```
<210> SEQ ID NO 16
<211> LENGTH: 951
<212> TYPE: PRT
<213> ORGANISM: Triticum aestivum
<220> FEATURE:
<221> NAME/KEY: misc_feature
<223> OTHER INFORMATION: TaAHA_Q5PSM6_Triticum_aestivum

<400> SEQUENCE: 16

Met Gly Gly Leu Glu Glu Ile Arg Asn Glu Ala Val Asp Leu Glu Asn
1               5                   10                  15

Ile Pro Ile Glu Glu Val Phe Glu Gln Leu Lys Cys Thr Arg Gln Gly
            20                  25                  30

Leu Thr Ser Asp Glu Gly Ala Gln Arg Val Glu Ile Phe Gly Leu Asn
        35                  40                  45

Lys Leu Glu Glu Lys Lys Glu Ser Lys Val Leu Lys Phe Leu Gly Phe
    50                  55                  60

Met Trp Asn Pro Leu Ser Trp Val Met Glu Met Ala Ala Ile Met Ala
65                  70                  75                  80

Ile Ala Leu Ala Asn Gly Gly Lys Pro Pro Asp Trp Gln Asp Phe
                85                  90                  95

Val Gly Ile Ile Val Leu Leu Val Ile Asn Ser Thr Ile Ser Phe Ile
            100                 105                 110

Glu Glu Asn Asn Ala Gly Asn Ala Ala Ala Leu Met Ala Asn Leu
        115                 120                 125

Ala Pro Lys Thr Lys Val Leu Arg Asp Gly Arg Trp Gly Glu Gln Gly
    130                 135                 140

Ala Ser Ile Leu Val Pro Gly Asp Ile Val Ser Ile Lys Leu Gly Asp
145                 150                 155                 160

Ile Val Pro Ala Asp Ala Arg Leu Leu Glu Gly Asp Pro Leu Lys Ile
                165                 170                 175

Asp Gln Ser Gly Leu Thr Gly Glu Ser Leu Pro Val Thr Lys Asn Pro
            180                 185                 190

Gly Asp Glu Val Phe Ser Gly Ser Thr Cys Lys Gln Gly Glu Ile Glu
        195                 200                 205

Ala Val Val Ile Ala Thr Gly Val Arg Thr Phe Phe Gly Lys Ala Ala
    210                 215                 220

His Leu Val Asp Ser Thr Asn Gln Val Gly His Phe Gln Gln Val Leu
225                 230                 235                 240

Thr Ala Ile Gly Asn Phe Cys Ile Val Ser Ile Ala Val Gly Ile Val
                245                 250                 255

Ile Glu Ile Ile Val Met Phe Pro Ile Gln Arg Arg Lys Tyr Arg Ala
            260                 265                 270

Gly Ile Glu Asn Leu Leu Val Leu Leu Ile Gly Gly Ile Pro Ile Ala
        275                 280                 285

Met Pro Thr Val Leu Ser Val Thr Met Ala Ile Gly Ser His Lys Leu
    290                 295                 300

Ser Gln Gln Gly Ala Ile Thr Lys Arg Met Thr Ala Ile Glu Glu Leu
305                 310                 315                 320

Ala Gly Met Asp Val Leu Cys Ser Asp Lys Thr Gly Thr Leu Thr Leu
                325                 330                 335

Asn Lys Leu Ser Val Asp Lys Asn Leu Val Glu Val Phe Ala Lys Gly
            340                 345                 350

Val Asp Lys Glu His Val Leu Leu Leu Ala Ala Arg Ala Ser Arg Val
        355                 360                 365
```

```
Glu Asn Gln Asp Ala Ile Asp Ala Cys Met Val Gly Met Leu Ala Asp
    370                 375                 380
Pro Lys Glu Ala Arg Ala Gly Ile Arg Glu Val His Phe Leu Pro Phe
385                 390                 395                 400
Asn Pro Thr Asp Lys Arg Thr Ala Leu Thr Tyr Ile Asp Ala Glu Gly
            405                 410                 415
Asn Trp His Arg Ala Ser Lys Gly Ala Pro Glu Gln Ile Ile Thr Leu
                420                 425                 430
Cys Asn Cys Lys Glu Asp Val Lys Arg Val His Ser Val Ile Glu
        435                 440                 445
Lys Tyr Ala Glu Arg Gly Leu Arg Ser Leu Ala Val Ala Arg Gln Glu
    450                 455                 460
Val Pro Glu Lys Ser Lys Asp Ser Pro Gly Gly Pro Trp Gln Phe Ile
465                 470                 475                 480
Gly Leu Leu Pro Leu Phe Asp Pro Pro Arg His Asp Ser Ala Glu Thr
            485                 490                 495
Ile Arg Lys Ala Leu Val Leu Gly Val Asn Val Lys Met Ile Thr Gly
                500                 505                 510
Asp Gln Leu Ala Ile Gly Lys Glu Thr Gly Arg Arg Leu Gly Met Gly
        515                 520                 525
Thr Asn Met Tyr Pro Ser Ser Ala Leu Leu Gly Gln Ser Lys Asp Gly
    530                 535                 540
Ser Leu Glu Ser Leu Pro Val Asp Glu Leu Ile Glu Lys Ala Asp Gly
545                 550                 555                 560
Phe Ala Gly Val Phe Pro Glu His Lys Tyr Glu Ile Val Lys Arg Leu
            565                 570                 575
Gln Glu Lys Lys His Ile Val Gly Met Thr Gly Asp Gly Val Asn Asp
                580                 585                 590
Ala Pro Ala Leu Lys Lys Ala Asp Ile Gly Ile Ala Val Asp Asp Ala
        595                 600                 605
Thr Asp Ala Ala Arg Ser Ala Ser Asp Ile Val Leu Thr Glu Pro Gly
    610                 615                 620
Leu Ser Val Ile Ile Ser Ala Val Leu Thr Ser Arg Cys Ile Phe Gln
625                 630                 635                 640
Arg Met Lys Asn Tyr Thr Ile Tyr Ala Val Ser Ile Thr Ile Arg Ile
            645                 650                 655
Val Leu Gly Phe Met Leu Ile Ala Leu Ile Trp Lys Phe Asp Phe Ala
                660                 665                 670
Pro Phe Met Val Leu Ile Ile Ala Ile Leu Asn Asp Gly Thr Ile Met
        675                 680                 685
Thr Ile Ser Lys Asp Arg Val Lys Pro Ser Pro Leu Pro Asp Ser Trp
    690                 695                 700
Lys Leu Asn Glu Ile Phe Ala Thr Gly Val Val Leu Gly Thr Tyr Leu
705                 710                 715                 720
Ala Leu Val Thr Val Val Phe Phe Trp Leu Ile His Lys Thr Asp Phe
            725                 730                 735
Phe Thr Asn Lys Phe Gly Val Glu Ser Ile Arg Asn Thr Glu Phe Lys
                740                 745                 750
Glu Met Ser Ala Leu Tyr Leu Gln Val Ser Ile Val Ser Gln Ala Leu
        755                 760                 765
Ile Phe Val Thr Arg Ser Arg Ser Trp Ser Phe Val Glu Arg Pro Gly
    770                 775                 780
```

```
Phe Leu Leu Val Thr Ala Phe Leu Ala Gln Leu Val Ala Thr Leu
785                 790                 795                 800

Ile Ala Val Tyr Ala Asn Trp Asp Phe Ala Arg Ile Lys Gly Ile Gly
            805                 810                 815

Trp Gly Trp Ala Gly Val Ile Trp Leu Phe Ser Ile Val Phe Tyr Phe
        820                 825                 830

Pro Leu Asp Ile Phe Lys Phe Phe Ile Arg Phe Val Leu Ser Gly Arg
        835                 840                 845

Ala Trp Asp Asn Leu Leu Gln Asn Lys Thr Ala Phe Thr Thr Lys Glu
850                 855                 860

Asn Tyr Gly Lys Gly Glu Arg Glu Ala Gln Trp Ala Thr Ala Gln Arg
865                 870                 875                 880

Thr Leu His Gly Leu Gln Ala Pro Glu Pro Ala Ser His Thr Leu Phe
                885                 890                 895

Asn Asp Lys Ser Ser Tyr Arg Glu Leu Ser Glu Ile Ala Glu Gln Ala
            900                 905                 910

Lys Arg Arg Ala Glu Ile Ala Arg Leu Arg Glu Leu Asn Thr Leu Lys
        915                 920                 925

Ser His Val Glu Ser Val Val Lys Leu Lys Gly Leu Asp Ile Asp Thr
930                 935                 940

Ile Asn Gln Asn Tyr Thr Val
945                 950

<210> SEQ ID NO 17
<211> LENGTH: 931
<212> TYPE: PRT
<213> ORGANISM: Capsella rubella
<220> FEATURE:
<221> NAME/KEY: misc_feature
<223> OTHER INFORMATION: CrAHA[XP]_006293643_Capsella_rubella

<400> SEQUENCE: 17

Met Glu Glu Val Phe Glu Gly Leu Lys Cys Thr Lys Gln Gly Leu Thr
1               5                   10                  15

Arg Glu Glu Ala Ser His Arg Leu Asp Leu Phe Gly Pro Asn Lys Leu
            20                  25                  30

Glu Glu Lys Lys Glu Ser Lys Val Leu Lys Phe Leu Gly Phe Met Trp
        35                  40                  45

Asn Pro Leu Ser Trp Val Met Glu Ala Ala Ala Leu Met Ala Ile Ala
    50                  55                  60

Leu Ala Asn Gly Gly Gly Arg Pro Pro Asp Trp Gln Asp Phe Val Gly
65                  70                  75                  80

Ile Val Cys Leu Leu Phe Ile Asn Ser Thr Ile Ser Phe Ile Glu Glu
                85                  90                  95

Asn Asn Ala Gly Asn Ala Ala Ala Leu Met Ala Gly Leu Ala Pro
            100                 105                 110

Lys Thr Lys Val Leu Arg Asp Asn Gln Trp Ser Glu Gln Glu Ala Ser
        115                 120                 125

Ile Leu Val Pro Gly Asp Val Ile Ser Val Lys Leu Gly Asp Ile Ile
    130                 135                 140

Pro Ala Asp Ala Arg Leu Leu Asp Gly Asp Pro Leu Lys Ile Asp Gln
145                 150                 155                 160

Ser Ser Leu Thr Gly Glu Ser Ile Pro Val Thr Lys Asn Pro Gly Asp
                165                 170                 175
```

```
Glu Val Phe Ser Gly Ser Thr Cys Lys Gln Gly Ile Glu Ala Ile
            180                 185                 190

Val Val Ala Thr Gly Val His Thr Phe Gly Lys Ala Ala His Leu
            195                 200                 205

Val Asp Ser Thr Asn Gln Ile Gly His Phe Gln Lys Val Leu Thr Ser
210                 215                 220

Ile Gly Asn Phe Cys Ile Cys Ser Ile Gly Leu Gly Ile Ile Val Glu
225                 230                 235                 240

Leu Ile Val Met Tyr Pro Ile Gln Arg Arg Lys Tyr Arg Asp Gly Ile
                245                 250                 255

Asp Asn Leu Leu Val Leu Leu Ile Gly Ile Pro Ile Ala Met Pro
            260                 265                 270

Thr Val Leu Ser Val Thr Met Ala Ile Gly Ser His Arg Leu Ser Lys
            275                 280                 285

Gln Gly Ala Ile Thr Lys Arg Met Thr Ala Ile Glu Glu Met Ala Gly
            290                 295                 300

Met Asp Val Leu Cys Ser Asp Lys Thr Gly Thr Leu Thr Leu Asn Arg
305                 310                 315                 320

Leu Thr Val Asp Arg Asn Leu Val Glu Val Phe Ala Lys Gly Val Gly
                325                 330                 335

Lys Glu His Val Phe Leu Leu Ala Ala Arg Ala Ser Arg Ile Glu Asn
                340                 345                 350

Gln Asp Ala Ile Asp Ala Ala Ile Val Gly Met Leu Gly Asp Pro Lys
            355                 360                 365

Glu Ala Arg Ala Gly Val Arg Glu Val His Phe Pro Phe Asn Pro
            370                 375                 380

Val Asp Lys Arg Thr Ala Leu Thr Tyr Ile Asp Ser Asp Gly Asn Trp
385                 390                 395                 400

His Arg Ala Ser Lys Gly Ala Pro Glu Gln Ile Leu Asn Leu Cys Asn
                405                 410                 415

Cys Lys Glu Asp Val Arg Arg Lys Val His Gly Val Ile Asp Lys Phe
            420                 425                 430

Ala Glu Arg Gly Leu Arg Ser Leu Ala Val Ala Arg Gln Lys Val Pro
            435                 440                 445

Glu Lys Lys Lys Asp Ala Ser Gly Asp Pro Trp Gln Leu Val Gly Leu
            450                 455                 460

Leu Pro Leu Phe Asp Pro Pro Arg His Asp Ser Ala Glu Thr Ile Arg
465                 470                 475                 480

Arg Ala Leu Asn Leu Gly Val Asn Val Lys Met Ile Thr Gly Asp Gln
                485                 490                 495

Leu Ala Ile Gly Lys Glu Thr Gly Arg Arg Leu Gly Met Gly Thr Asn
            500                 505                 510

Met Tyr Pro Ser Ser Ala Leu Leu Gly Gln Glu Lys Asp Ser Ser Leu
            515                 520                 525

Gly Ala Leu Pro Val Asp Glu Leu Ile Glu Lys Ala Asp Gly Phe Ala
            530                 535                 540

Gly Val Phe Pro Glu His Lys Tyr Glu Ile Val Asn Arg Leu Gln Gln
545                 550                 555                 560

Arg Lys His Ile Cys Gly Met Thr Gly Asp Gly Val Asn Asp Ala Pro
                565                 570                 575

Ala Leu Lys Lys Ala Asp Ile Gly Ile Ala Val Ala Asp Ala Thr Asp
            580                 585                 590
```

```
Ala Ala Arg Gly Ala Ser Asp Ile Val Leu Thr Glu Pro Gly Leu Ser
        595                 600                 605

Val Ile Ile Ser Ala Val Leu Thr Ser Arg Ala Ile Phe Gln Arg Met
610                 615                 620

Lys Asn Tyr Thr Ile Tyr Ala Val Ser Ile Thr Ile Arg Ile Val Phe
625                 630                 635                 640

Gly Phe Met Phe Ile Ala Leu Ile Trp Gln Phe Asp Phe Ser Pro Phe
                645                 650                 655

Met Val Leu Ile Ile Ala Ile Leu Asn Asp Gly Thr Ile Met Thr Ile
                660                 665                 670

Ser Lys Asp Arg Val Lys Pro Ser Pro Gln Pro Asp Ser Trp Lys Leu
        675                 680                 685

Arg Glu Ile Phe Ser Thr Gly Val Val Leu Gly Gly Tyr Gln Ala Leu
    690                 695                 700

Met Thr Val Val Phe Phe Trp Val Met Lys Asp Thr Asp Ile Phe Ser
705                 710                 715                 720

Asn Met Leu Gly Val Arg Pro Leu Ser Gln Arg Pro Glu Gln Met Met
                725                 730                 735

Ala Ala Leu Tyr Leu Gln Val Ser Ile Ile Ser Gln Ala Leu Ile Phe
                740                 745                 750

Val Thr Arg Ser Arg Ser Trp Ser Phe Val Glu Arg Pro Gly Leu Leu
        755                 760                 765

Leu Leu Gly Ala Phe Val Ile Ala Gln Leu Val Ala Thr Phe Ile Ala
    770                 775                 780

Val Tyr Ala Asn Trp Ser Phe Ala Arg Ile Glu Gly Ala Gly Trp Gly
785                 790                 795                 800

Trp Ala Gly Val Ile Trp Leu Tyr Ser Leu Ile Thr Tyr Ile Pro Leu
                805                 810                 815

Asp Leu Leu Lys Phe Gly Ile Arg Tyr Val Leu Ser Gly Lys Ala Trp
                820                 825                 830

Leu Asn Leu Leu Glu Asn Lys Thr Ala Phe Thr Thr Lys Lys Asp Tyr
        835                 840                 845

Gly Lys Glu Glu Arg Glu Ala Gln Trp Ala Ala Ala Gln Arg Thr Leu
    850                 855                 860

His Gly Leu Gln Pro Ala Glu Thr Asn Asn Ile Phe Asn Glu Lys Asn
865                 870                 875                 880

Ser Tyr His Asp Leu Ser Gln Ile Ala Glu Gln Ala Lys Arg Arg Ala
                885                 890                 895

Glu Val Val Arg Leu Arg Glu Ile Asn Thr Leu Lys Gly His Val Glu
                900                 905                 910

Ser Val Val Lys Leu Lys Gly Leu Asp Ile Asp Thr Ile Gln Gln His
        915                 920                 925

Tyr Thr Val
    930

<210> SEQ ID NO 18
<211> LENGTH: 957
<212> TYPE: PRT
<213> ORGANISM: Camelina sativa
<220> FEATURE:
<221> NAME/KEY: misc_feature
<223> OTHER INFORMATION: CsAHA[XP]_010472461_Camelina_sativa

<400> SEQUENCE: 18

Met Ala Ala Ala Ala Gly Lys Gly Asn Glu Leu Asp His Ile Lys Asn
1               5                   10                  15
```

```
Glu Ser Val Asp Leu Val Arg Ile Pro Met Glu Val Phe Glu Glu
         20                  25                  30

Leu Lys Cys Thr Lys Gln Gly Leu Thr Thr Asp Glu Ala Ser His Arg
         35                  40                  45

Leu Asp Leu Phe Gly Pro Asn Lys Leu Glu Glu Lys Lys Glu Ser Lys
50                   55                  60

Leu Leu Lys Phe Leu Gly Phe Met Trp Asn Pro Leu Ser Trp Val Met
65                   70                  75                  80

Glu Ala Ala Ala Leu Met Ala Ile Ala Leu Ala Asn Gly Gly Arg
             85                  90                  95

Pro Pro Asp Trp Gln Asp Phe Val Gly Ile Val Cys Leu Leu Phe Ile
             100                 105                 110

Asn Ser Thr Ile Ser Phe Ile Glu Glu Asn Asn Ala Gly Asn Ala Ala
             115                 120                 125

Ala Ala Leu Met Ala Gly Leu Ala Pro Lys Thr Lys Val Leu Arg Asp
130                  135                 140

Asn Gln Trp Ser Glu Gln Glu Ala Ser Ile Leu Val Pro Gly Asp Val
145                  150                 155                 160

Ile Ser Leu Lys Leu Gly Asp Ile Ile Pro Ala Asp Ala Arg Leu Leu
             165                 170                 175

Asp Gly Asp Pro Leu Lys Ile Asp Gln Ser Ser Leu Thr Gly Glu Ser
             180                 185                 190

Ile Pro Val Thr Lys Asn Pro Gly Asp Glu Val Phe Ser Gly Ser Thr
             195                 200                 205

Cys Lys Gln Gly Glu Ile Glu Ala Ile Val Val Ala Thr Gly Val His
             210                 215                 220

Thr Phe Phe Gly Lys Ala Ala His Leu Val Asp Ser Thr Asn Gln Ile
225                  230                 235                 240

Gly His Phe Gln Lys Val Leu Thr Ser Ile Gly Asn Phe Cys Ile Cys
             245                 250                 255

Ser Ile Ala Leu Gly Ile Val Val Glu Leu Leu Val Met Tyr Pro Ile
             260                 265                 270

Gln Arg Arg Gly Tyr Arg Asp Gly Ile Asp Asn Leu Leu Val Leu Leu
             275                 280                 285

Ile Gly Gly Ile Pro Ile Ala Met Pro Thr Val Leu Ser Val Thr Met
             290                 295                 300

Ala Ile Gly Ser His Arg Leu Ser Lys Gln Gly Ala Ile Thr Lys Arg
305                  310                 315                 320

Met Thr Ala Ile Glu Glu Met Ala Gly Met Asp Val Leu Cys Ser Asp
             325                 330                 335

Lys Thr Gly Thr Leu Thr Leu Asn Lys Leu Thr Val Asp Arg Asn Leu
             340                 345                 350

Val Glu Val Phe Ala Lys Gly Val Gly Lys Glu His Val Phe Leu Leu
             355                 360                 365

Ala Ala Arg Ala Ser Arg Ile Glu Asn Gln Asp Ala Ile Asp Ala Ala
             370                 375                 380

Ile Val Gly Met Leu Ala Asp Pro Lys Glu Ala Arg Ala Gly Val Arg
385                  390                 395                 400

Glu Val His Phe Phe Pro Phe Asn Pro Val Asp Lys Arg Thr Ala Leu
             405                 410                 415

Thr Tyr Val Asp Tyr Ser Asp Gly Asn Trp Tyr Arg Ala Ser Lys Gly
             420                 425                 430
```

```
Ala Pro Glu Gln Ile Leu Asn Leu Cys Asp Cys Lys Glu Asp Val Arg
            435                 440                 445

Arg Lys Val His Gly Val Ile Asp Lys Phe Ala Glu Arg Gly Leu Arg
450                 455                 460

Ser Leu Ala Val Ala Arg Gln Glu Val Pro Glu Lys Lys Lys Asp Ala
465                 470                 475                 480

Ser Gly Gly Pro Trp Gln Leu Val Gly Leu Pro Leu Phe Asp Pro
                485                 490                 495

Pro Arg His Asp Ser Ala Glu Thr Ile Arg Arg Ala Leu Asn Leu Gly
            500                 505                 510

Val Asn Val Lys Met Ile Thr Gly Asp Gln Leu Ala Ile Gly Lys Glu
            515                 520                 525

Thr Gly Arg Arg Leu Gly Met Gly Thr Asn Met Tyr Pro Ser Ser Ala
530                 535                 540

Leu Leu Gly Gln Glu Lys Asp Ser Ser Leu Gly Ala Leu Pro Val Asp
545                 550                 555                 560

Glu Leu Ile Glu Lys Ala Asp Gly Phe Ala Gly Val Phe Pro Glu His
                565                 570                 575

Lys Tyr Glu Ile Val Asn Arg Leu Gln Gln Arg Lys His Ile Cys Gly
            580                 585                 590

Met Thr Gly Asp Gly Val Asn Asp Ala Pro Ala Leu Lys Lys Ala Asp
            595                 600                 605

Ile Gly Ile Ala Val Ala Asp Ser Thr Asp Ala Ala Arg Gly Ala Ser
            610                 615                 620

Asp Ile Val Leu Thr Glu Pro Gly Leu Ser Val Ile Ser Ala Val
625                 630                 635                 640

Leu Thr Ser Arg Ala Ile Phe Gln Arg Met Lys Asn Tyr Thr Ile Tyr
                645                 650                 655

Ala Val Ser Ile Thr Ile Arg Ile Val Phe Gly Phe Met Phe Ile Ala
            660                 665                 670

Leu Ile Trp Gln Phe Asp Phe Ser Pro Phe Met Val Leu Ile Ile Ala
            675                 680                 685

Ile Leu Asn Asp Gly Thr Ile Met Thr Ile Ser Lys Asp Arg Val Lys
            690                 695                 700

Pro Ser Pro Gln Pro Asp Ser Trp Lys Leu Arg Glu Ile Phe Ser Thr
705                 710                 715                 720

Gly Val Val Leu Gly Gly Tyr Gln Ala Phe Met Thr Val Val Phe Phe
                725                 730                 735

Trp Val Met Lys Asp Thr Asn Ile Phe Ser Asn Met Leu Gly Val Arg
            740                 745                 750

Pro Leu Ser Gln Arg Pro Glu Gln Met Met Ala Ala Leu Tyr Leu Gln
            755                 760                 765

Val Ser Ile Ile Ser Gln Ala Leu Ile Phe Val Thr Arg Ser Arg Ser
            770                 775                 780

Trp Ser Phe Val Glu Arg Pro Gly Leu Leu Leu Leu Gly Ala Phe Val
785                 790                 795                 800

Ile Ala Gln Leu Val Ala Thr Phe Ile Ala Val Tyr Ala Asp Trp Ser
                805                 810                 815

Phe Ala Arg Ile Glu Gly Ala Gly Trp Gly Trp Ala Gly Val Ile Trp
            820                 825                 830

Leu Tyr Ser Leu Ile Thr Tyr Ile Pro Leu Asp Leu Leu Lys Phe Gly
            835                 840                 845
```

-continued

Ile Arg Tyr Val Leu Ser Gly Lys Ala Trp Leu Asn Leu Leu Glu Asn
850                 855                 860

Lys Thr Ala Phe Thr Thr Lys Lys Asp Tyr Gly Lys Glu Glu Arg Glu
865                 870                 875                 880

Ala Gln Trp Ala Ala Gln Arg Thr Leu His Gly Leu Gln Pro Ala
            885                 890                 895

Glu Thr Asn Asn Ile Phe Asn Glu Lys Asn Ser Tyr Ser Glu Leu Ser
                900                 905                 910

Gln Ile Ala Glu Gln Ala Lys Arg Arg Ala Glu Val Val Arg Leu Arg
            915                 920                 925

Glu Ile Asn Ser Leu Lys Gly His Val Glu Ser Val Val Lys Leu Lys
            930                 935                 940

Gly Leu Asp Ile Asp Thr Ile Gln Gln His Tyr Thr Val
945                 950                 955

<210> SEQ ID NO 19
<211> LENGTH: 951
<212> TYPE: PRT
<213> ORGANISM: Medicago truncatula
<220> FEATURE:
<221> NAME/KEY: misc_feature
<223> OTHER INFORMATION: MtAHA[XP]_013465721_Medicago_truncatula

<400> SEQUENCE: 19

Met Gly Gly Ile Ser Leu Glu Glu Ile Lys Asn Glu Ser Val Asp Leu
1               5                   10                  15

Glu Arg Ile Pro Ile Asp Glu Val Phe Glu Gln Leu Lys Cys Ser Arg
            20                  25                  30

Gln Gly Leu Thr Ser Glu Glu Gly Ala Asn Arg Leu Gln Val Phe Gly
        35                  40                  45

Pro Asn Lys Leu Glu Glu Lys Lys Glu Ser Lys Phe Leu Lys Phe Leu
    50                  55                  60

Gly Phe Met Trp Asn Pro Leu Ser Trp Val Met Glu Ala Ala Ala Ile
65                  70                  75                  80

Met Ala Ile Ala Leu Ala Asn Gly Ser Gly Arg Pro Pro Asp Trp Gln
                85                  90                  95

Asp Phe Val Gly Ile Ile Ala Leu Leu Val Ile Asn Ser Thr Ile Ser
            100                 105                 110

Phe Ile Glu Glu Asn Asn Ala Gly Asn Ala Ala Ala Ala Leu Met Ala
        115                 120                 125

Gly Leu Ala Pro Lys Thr Lys Val Leu Arg Asp Ser Arg Trp Ser Glu
130                 135                 140

Gln Asp Ala Ala Ile Leu Val Pro Gly Asp Ile Ile Ser Ile Lys Leu
145                 150                 155                 160

Gly Asp Ile Val Pro Ala Asp Ala Arg Leu Leu Glu Gly Asp Pro Leu
                165                 170                 175

Ser Ile Asp Gln Ser Ala Leu Thr Gly Glu Ser Leu Pro Val Thr Lys
            180                 185                 190

Ser Ser Ser Asp Glu Val Phe Ser Gly Ser Thr Val Lys Lys Gly Glu
        195                 200                 205

Ile Glu Ala Val Val Ile Ala Thr Gly Val His Thr Phe Phe Gly Lys
    210                 215                 220

Ala Ala His Leu Val Asp Ser Thr Asn Gln Val Gly His Phe Gln Lys
225                 230                 235                 240

```
Val Leu Thr Ala Ile Gly Asn Phe Cys Ile Cys Ser Ile Ala Ile Gly
                245                 250                 255

Ile Leu Val Glu Leu Ile Val Met Tyr Pro Ile Gln His Arg Lys Tyr
                260                 265                 270

Arg Asp Gly Ile Asp Asn Leu Leu Val Leu Ile Gly Gly Ile Pro
                275                 280                 285

Ile Ala Met Pro Thr Val Leu Ser Val Thr Met Ala Ile Gly Ser His
            290                 295                 300

Arg Leu Ser Gln Gln Gly Ala Ile Thr Lys Arg Met Thr Ala Ile Glu
305                 310                 315                 320

Glu Met Ala Gly Met Asp Val Leu Cys Ser Asp Lys Thr Gly Thr Leu
                325                 330                 335

Thr Leu Asn Lys Leu Ser Val Asp Arg Asn Leu Ile Glu Val Phe Ala
                340                 345                 350

Lys Gly Ile Glu Lys Glu Tyr Val Met Leu Leu Ala Ala Arg Ala Ser
                355                 360                 365

Arg Thr Glu Asn Gln Asp Ala Ile Asp Ala Ala Ile Val Gly Met Leu
                370                 375                 380

Ala Asp Pro Lys Glu Ala Arg Ala Gly Ile Arg Glu Val His Phe Leu
385                 390                 395                 400

Pro Phe Asn Pro Val Asp Lys Arg Thr Ala Leu Thr Tyr Ile Asp Ser
                405                 410                 415

Asp Gly Lys Trp His Arg Ala Ser Lys Gly Ala Pro Glu Gln Ile Ile
                420                 425                 430

Asn Leu Cys Asn Cys Lys Glu Asp Val Arg Lys Val His Ala Val
                435                 440                 445

Ile Asp Lys Phe Ala Glu Arg Gly Leu Arg Ser Leu Gly Val Ala Arg
            450                 455                 460

Gln Glu Val Pro Glu Arg Thr Lys Asp Ser Pro Gly Gly Pro Trp Gln
465                 470                 475                 480

Phe Val Gly Leu Leu Pro Leu Phe Asp Pro Pro Arg His Asp Ser Ala
                485                 490                 495

Glu Thr Ile Arg Arg Ala Leu Asn Leu Gly Val Asn Val Lys Met Ile
                500                 505                 510

Thr Gly Asp Gln Leu Ala Ile Gly Lys Glu Thr Gly Arg Arg Leu Gly
                515                 520                 525

Met Gly Thr Asn Met Tyr Pro Ser Ser Ala Leu Leu Gly Gln Asp Lys
            530                 535                 540

Asp Ser Ser Ile Ser Ala Leu Pro Val Asp Glu Leu Ile Glu Lys Ala
545                 550                 555                 560

Asp Gly Phe Ala Gly Val Phe Pro Glu His Lys Tyr Glu Ile Val Lys
                565                 570                 575

Arg Leu Gln Glu Lys Lys His Ile Cys Gly Met Thr Gly Asp Gly Val
                580                 585                 590

Asn Asp Ala Pro Ala Leu Lys Lys Ala Asp Ile Gly Ile Ala Val Ala
                595                 600                 605

Asp Ala Thr Asp Ala Ala Arg Ser Ala Ser Asp Ile Val Leu Thr Glu
                610                 615                 620

Pro Gly Leu Ser Val Ile Ile Ser Ala Val Leu Thr Ser Arg Ala Ile
625                 630                 635                 640

Phe Gln Arg Met Lys Asn Tyr Thr Ile Tyr Ala Val Ser Ile Thr Ile
                645                 650                 655
```

Arg Ile Val Phe Gly Phe Met Phe Ile Ala Leu Ile Trp Lys Phe Asp
                660                 665                 670

Phe Ala Pro Phe Met Val Leu Ile Ile Ala Ile Leu Asn Asp Gly Thr
            675                 680                 685

Ile Met Thr Ile Ser Lys Asp Arg Val Lys Pro Ser Pro Leu Pro Asp
        690                 695                 700

Ser Trp Lys Leu Arg Glu Ile Phe Ala Thr Gly Val Val Leu Gly Ser
705                 710                 715                 720

Tyr Met Ala Leu Met Thr Val Val Phe Phe Trp Ala Met Lys Asp Thr
                725                 730                 735

Asn Phe Phe Ser Asn Lys Phe Gly Val Arg Pro Ile Arg His Asn Pro
            740                 745                 750

Asp Glu Met Met Ala Ala Leu Tyr Leu Gln Val Ser Ile Ile Ser Gln
        755                 760                 765

Ala Leu Ile Phe Val Thr Arg Ser Arg Ser Trp Ser Phe Ala Glu Arg
770                 775                 780

Pro Gly Leu Leu Leu Gly Ala Phe Leu Ile Ala Gln Leu Ile Ala
785                 790                 795                 800

Thr Phe Ile Ala Val Tyr Ala Asn Trp Gly Phe Ala Arg Ile Lys Gly
                805                 810                 815

Met Gly Trp Gly Trp Ala Gly Val Ile Trp Leu Tyr Ser Leu Val Thr
            820                 825                 830

Tyr Ile Pro Leu Asp Leu Leu Lys Phe Ala Ile Arg Tyr Phe Leu Ser
        835                 840                 845

Gly Lys Ala Trp Asp Asn Leu Leu Glu Asn Lys Thr Ala Phe Thr Thr
850                 855                 860

Lys Lys Asp Tyr Gly Lys Glu Glu Arg Glu Ala Gln Trp Ala Ala Ala
865                 870                 875                 880

Gln Arg Thr Leu His Gly Leu Gln Pro Pro Glu Ala Ser Asn Val Phe
                885                 890                 895

Asn Glu Lys Asn Ser Tyr Arg Glu Leu Ser Glu Ile Ala Glu Gln Ala
            900                 905                 910

Lys Arg Arg Ala Glu Val Ala Arg Leu Arg Glu Val His Thr Leu Lys
        915                 920                 925

Gly His Val Glu Ser Val Val Lys Leu Lys Gly Leu Asp Ile Asp Thr
930                 935                 940

Ile Gln Gln His Tyr Thr Val
945                 950

<210> SEQ ID NO 20
<211> LENGTH: 955
<212> TYPE: PRT
<213> ORGANISM: Populus euphratica
<220> FEATURE:
<221> NAME/KEY: misc_feature
<223> OTHER INFORMATION: PeAHA[XP]_011031360_Populus_euphratica

<400> SEQUENCE: 20

Met Ser Ser Lys Gly Gly Ile Ser Leu Glu Glu Ile Lys Asn Glu Ser
1               5                   10                  15

Val Asp Leu Glu Arg Ile Pro Met Glu Glu Val Phe Glu Gln Leu Lys
            20                  25                  30

Cys Thr Arg Glu Gly Leu Ser Ala Asp Glu Gly Ala Ser Arg Leu Gln
        35                  40                  45

Val Phe Gly Pro Asn Lys Leu Glu Glu Lys Lys Glu Ser Lys Ile Leu
50                  55                  60

```
Lys Phe Leu Gly Phe Met Trp Asn Pro Leu Ser Trp Val Met Glu Ala
 65                  70                  75                  80

Ala Ala Leu Met Ala Ile Ala Leu Ala Asn Gly Asp Gly Arg Pro Pro
                 85                  90                  95

Asp Trp Gln Asp Phe Val Gly Ile Val Val Leu Leu Val Ile Asn Ser
            100                 105                 110

Thr Ile Ser Phe Ile Glu Glu Asn Asn Ala Gly Asn Ala Ala Ala Ala
        115                 120                 125

Leu Met Ala Gly Leu Ala Pro Lys Thr Lys Val Leu Arg Asp Gly Arg
130                 135                 140

Trp Ser Glu Gln Asp Ala Ser Ile Leu Val Pro Gly Asp Ile Ile Ser
145                 150                 155                 160

Ile Lys Leu Gly Asp Ile Val Pro Ala Asp Ala Arg Leu Leu Glu Gly
                165                 170                 175

Asp Pro Leu Lys Ile Asp Gln Ser Ala Leu Thr Gly Glu Ser Leu Pro
            180                 185                 190

Val Thr Lys Asn Pro Ser Asp Glu Val Phe Ser Gly Ser Thr Cys Lys
        195                 200                 205

Gln Gly Glu Ile Glu Ala Val Val Ile Ala Thr Gly Val His Thr Phe
210                 215                 220

Phe Gly Lys Ala Ala His Leu Val Asp Ser Thr Asn Gln Val Gly His
225                 230                 235                 240

Phe Gln Lys Val Leu Thr Ala Ile Gly Asn Phe Cys Ile Cys Ser Ile
                245                 250                 255

Ala Val Gly Ile Phe Ala Glu Leu Ile Val Met Tyr Pro Ile Gln His
            260                 265                 270

Arg Lys Tyr Arg Asp Gly Ile Asp Asn Leu Leu Val Leu Leu Ile Gly
        275                 280                 285

Gly Ile Pro Ile Ala Met Pro Thr Val Leu Ser Val Thr Met Ala Ile
290                 295                 300

Gly Ser His Arg Leu Ser Gln Gln Gly Ala Ile Thr Lys Arg Met Thr
305                 310                 315                 320

Ala Ile Glu Glu Met Ala Gly Met Asp Val Leu Cys Ser Asp Lys Thr
                325                 330                 335

Gly Thr Leu Thr Leu Asn Lys Leu Thr Val Asp Arg Ser Leu Ile Glu
            340                 345                 350

Val Phe Ala Lys Gly Val Glu Lys Glu His Val Ile Leu Leu Ala Ala
        355                 360                 365

Arg Ala Ser Arg Thr Glu Asn Gln Asp Ala Ile Asp Ala Ala Ile Val
370                 375                 380

Gly Met Leu Ala Asp Pro Lys Glu Ala Arg Ala Gly Ile Arg Glu Val
385                 390                 395                 400

His Phe Leu Pro Phe Asn Pro Val Asp Lys Arg Thr Ala Leu Thr Tyr
                405                 410                 415

Ile Asp Ser Asp Gly Asn Trp His Arg Ala Ser Lys Gly Ala Pro Glu
            420                 425                 430

Gln Ile Leu Thr Leu Cys Asn Cys Lys Glu Asp Val Lys Lys Lys Val
        435                 440                 445

His Ser Val Ile Asp Lys Phe Ala Glu Arg Gly Leu Arg Ser Leu Gly
450                 455                 460

Val Ala Lys Gln Glu Val Pro Glu Lys Ser Lys Asp Ala Ala Gly Ala
465                 470                 475                 480
```

```
Pro Trp Gln Leu Val Gly Leu Leu Pro Leu Phe Asp Pro Pro Arg His
                485                 490                 495
Asp Ser Ala Glu Thr Ile Arg Arg Ala Leu His Leu Gly Val Asn Val
            500                 505                 510
Lys Met Ile Thr Gly Asp Gln Leu Ala Ile Gly Lys Glu Thr Gly Arg
        515                 520                 525
Arg Leu Gly Met Gly Thr Asn Met Tyr Pro Ser Ser Ala Leu Leu Gly
    530                 535                 540
Gln Asp Arg Asp Ala Ser Ile Ala Ala Leu Pro Val Asp Glu Leu Ile
545                 550                 555                 560
Glu Lys Ala Asp Gly Phe Ala Gly Val Phe Pro Glu His Lys Tyr Glu
                565                 570                 575
Ile Val Lys Arg Leu Gln Asp Arg Lys His Ile Cys Gly Met Thr Gly
            580                 585                 590
Asp Gly Val Asn Asp Ala Pro Ala Leu Lys Lys Ala Asp Ile Gly Ile
        595                 600                 605
Ala Val Ala Asp Ala Thr Asp Ala Ala Arg Ser Ala Ser Asp Ile Val
    610                 615                 620
Leu Thr Glu Pro Gly Leu Ser Val Ile Ile Ser Ala Val Leu Thr Ser
625                 630                 635                 640
Arg Ala Ile Phe Gln Arg Met Lys Asn Tyr Thr Ile Tyr Ala Val Ser
                645                 650                 655
Ile Thr Ile Arg Ile Val Phe Gly Phe Met Phe Ile Ala Leu Ile Trp
            660                 665                 670
Lys Phe Asp Phe Ala Pro Phe Met Val Leu Ile Ile Ala Ile Leu Asn
        675                 680                 685
Asp Gly Thr Ile Met Thr Ile Ser Lys Asp Arg Val Lys Pro Ser Pro
    690                 695                 700
Gln Pro Asp Ser Trp Lys Leu Lys Glu Ile Phe Ser Thr Gly Ile Val
705                 710                 715                 720
Leu Gly Gly Tyr Met Ala Leu Met Thr Val Leu Phe Phe Trp Ile Met
                725                 730                 735
Lys Asp Thr Asp Phe Phe Ser Asp Lys Phe Gly Val Arg Ser Leu Arg
            740                 745                 750
Lys Asn Asp Glu Glu Met Met Ala Ala Leu Tyr Leu Gln Val Ser Ile
        755                 760                 765
Val Ser Gln Ala Leu Ile Phe Val Thr Arg Ser Arg Ser Trp Ser Phe
    770                 775                 780
Val Glu Arg Pro Gly Phe Leu Leu Leu Gly Ala Phe Val Ala Ala Gln
785                 790                 795                 800
Leu Ile Ala Thr Leu Ile Ala Val Tyr Ala Asn Trp Gly Phe Ala Arg
                805                 810                 815
Ile Lys Gly Cys Gly Trp Gly Trp Ala Gly Val Ile Trp Leu Phe Ser
            820                 825                 830
Val Val Thr Tyr Val Pro Leu Asp Ile Leu Lys Phe Ala Ile Arg Tyr
        835                 840                 845
Ile Leu Ser Gly Lys Ala Trp Asp Asn Leu Leu Glu Asn Lys Thr Ala
    850                 855                 860
Phe Thr Thr Lys Lys Asp Tyr Gly Lys Glu Glu Arg Glu Ala Gln Trp
865                 870                 875                 880
Ala Thr Ala Gln Arg Thr Leu His Gly Leu Gln Pro Pro Glu Thr Ser
                885                 890                 895
```

```
His Asn Met Phe Ser Glu Lys Asn Ser Tyr Arg Glu Leu Ser Glu Ile
            900                 905                 910

Ala Glu Gln Ala Lys Arg Arg Ala Glu Met Ala Arg Leu Arg Glu Leu
        915                 920                 925

Asn Thr Leu Lys Gly His Val Glu Ser Val Val Lys Leu Lys Gly Leu
    930                 935                 940

Asp Ile Asp Thr Ile Gln Gln His Tyr Thr Val
945                 950                 955

<210> SEQ ID NO 21
<211> LENGTH: 23
<212> TYPE: PRT
<213> ORGANISM: Artificial
<220> FEATURE:
<223> OTHER INFORMATION: Consensus sequence First transmembrane domain
<220> FEATURE:
<221> NAME/KEY: VARIANT
<222> LOCATION: (15)..(15)
<223> OTHER INFORMATION: Xaa can be replaced by  M, V, A
<220> FEATURE:
<221> NAME/KEY: VARIANT
<222> LOCATION: (18)..(18)
<223> OTHER INFORMATION: Xaa can be replaced by  L, I, V
<220> FEATURE:
<221> NAME/KEY: VARIANT
<222> LOCATION: (23)..(23)
<223> OTHER INFORMATION: Xaa can be replaced by  L, M

<400> SEQUENCE: 21

Phe Leu Gly Phe Met Trp Asn Pro Leu Ser Trp Val Met Glu Xaa Ala
1               5                   10                  15

Ala Xaa Met Ala Ile Ala Xaa
            20

<210> SEQ ID NO 22
<211> LENGTH: 23
<212> TYPE: PRT
<213> ORGANISM: Artificial
<220> FEATURE:
<223> OTHER INFORMATION: First transmembrane domain mutated at position
      8 P->S
<220> FEATURE:
<221> NAME/KEY: VARIANT
<222> LOCATION: (15)..(15)
<223> OTHER INFORMATION: Xaa can be replaced by  M, V, A
<220> FEATURE:
<221> NAME/KEY: VARIANT
<222> LOCATION: (18)..(18)
<223> OTHER INFORMATION: Xaa can be replaced by  L, I, V
<220> FEATURE:
<221> NAME/KEY: VARIANT
<222> LOCATION: (23)..(23)
<223> OTHER INFORMATION: Xaa can be replaced by  L, M

<400> SEQUENCE: 22

Phe Leu Gly Phe Met Trp Asn Ser Leu Ser Trp Val Met Glu Xaa Ala
1               5                   10                  15

Ala Xaa Met Ala Ile Ala Xaa
            20

<210> SEQ ID NO 23
<211> LENGTH: 930
<212> TYPE: PRT
<213> ORGANISM: Arabidopsis thaliana
<220> FEATURE:
<221> NAME/KEY: misc_feature
<223> OTHER INFORMATION: AtAHA5_P50S mutant
```

<400> SEQUENCE: 23

```
Met Glu Glu Val Phe Glu Glu Leu Lys Cys Thr Lys Gln Gly Leu Thr
1               5                   10                  15
Ala Asn Glu Ala Ser His Arg Leu Asp Val Phe Gly Pro Asn Lys Leu
            20                  25                  30
Glu Glu Lys Lys Glu Ser Lys Leu Leu Lys Phe Leu Gly Phe Met Trp
        35                  40                  45
Asn Ser Leu Ser Trp Val Met Glu Val Ala Ala Leu Met Ala Ile Ala
    50                  55                  60
Leu Ala Asn Gly Gly Arg Pro Pro Asp Trp Gln Asp Phe Val Gly
65                  70                  75                  80
Ile Val Cys Leu Leu Leu Ile Asn Ser Thr Ile Ser Phe Ile Glu Glu
                85                  90                  95
Asn Asn Ala Gly Asn Ala Ala Ala Leu Met Ala Gly Leu Ala Pro
            100                 105                 110
Lys Thr Lys Val Leu Arg Asp Asn Gln Trp Ser Glu Gln Glu Ala Ser
        115                 120                 125
Ile Leu Val Pro Gly Asp Val Ile Ser Ile Lys Leu Gly Asp Ile Ile
    130                 135                 140
Pro Ala Asp Ala Arg Leu Leu Asp Gly Asp Pro Leu Lys Ile Asp Gln
145                 150                 155                 160
Ser Ser Leu Thr Gly Glu Ser Ile Pro Val Thr Lys Asn Pro Ser Asp
                165                 170                 175
Glu Val Phe Ser Gly Ser Ile Cys Lys Gln Gly Glu Ile Glu Ala Ile
            180                 185                 190
Val Ile Ala Thr Gly Val His Thr Phe Phe Gly Lys Ala Ala His Leu
        195                 200                 205
Val Asp Asn Thr Asn Gln Ile Gly His Phe Gln Lys Val Leu Thr Ser
    210                 215                 220
Ile Gly Asn Phe Cys Ile Cys Ser Ile Ala Leu Gly Ile Ile Val Glu
225                 230                 235                 240
Leu Leu Val Met Tyr Pro Ile Gln Arg Arg Arg Tyr Arg Asp Gly Ile
                245                 250                 255
Asp Asn Leu Leu Val Leu Leu Ile Gly Gly Ile Pro Ile Ala Met Pro
            260                 265                 270
Ser Val Leu Ser Val Thr Met Ala Thr Gly Ser His Arg Leu Phe Gln
        275                 280                 285
Gln Gly Ala Ile Thr Lys Arg Met Thr Ala Ile Glu Glu Met Ala Gly
    290                 295                 300
Met Asp Val Leu Cys Cys Asp Lys Thr Gly Thr Leu Thr Leu Asn Lys
305                 310                 315                 320
Leu Thr Val Asp Lys Asn Leu Val Glu Val Phe Ala Lys Gly Val Gly
                325                 330                 335
Lys Glu His Val Phe Leu Leu Ala Ala Arg Ala Ser Arg Ile Glu Asn
            340                 345                 350
Gln Asp Ala Ile Asp Ala Ala Ile Val Gly Met Leu Ala Asp Pro Lys
        355                 360                 365
Glu Ala Arg Ala Gly Val Arg Glu Val His Phe Pro Phe Asn Pro
    370                 375                 380
Val Asp Lys Arg Thr Ala Leu Thr Tyr Val Asp Ser Asp Gly Asn Trp
385                 390                 395                 400
His Arg Ala Ser Lys Gly Ala Pro Glu Gln Ile Leu Asn Leu Cys Asn
                405                 410                 415
```

```
Cys Lys Glu Asp Val Arg Arg Lys Val His Gly Val Ile Asp Lys Phe
            420                 425                 430

Ala Glu Arg Gly Leu Arg Ser Leu Ala Val Ala Arg Gln Glu Val Leu
            435                 440                 445

Glu Lys Lys Lys Asp Ala Pro Gly Gly Pro Trp Gln Leu Val Gly Leu
            450                 455                 460

Leu Pro Leu Phe Asp Pro Pro Arg His Asp Ser Ala Glu Thr Ile Arg
465                 470                 475                 480

Arg Ala Leu Asn Leu Gly Val Asn Val Lys Met Ile Thr Gly Asp Gln
                485                 490                 495

Leu Ala Ile Gly Lys Glu Thr Gly Arg Arg Leu Gly Met Gly Thr Asn
            500                 505                 510

Met Tyr Pro Ser Ser Ala Leu Leu Gly Gln Val Lys Asp Ser Ser Leu
            515                 520                 525

Gly Ala Leu Pro Val Asp Glu Leu Ile Glu Lys Ala Asp Gly Phe Ala
            530                 535                 540

Gly Val Phe Pro Glu His Lys Tyr Glu Ile Val His Arg Leu Gln Gln
545                 550                 555                 560

Arg Asn His Ile Cys Gly Met Thr Gly Asp Gly Val Asn Asp Ala Pro
                565                 570                 575

Ala Leu Lys Lys Ala Asp Ile Gly Ile Ala Val Val Asp Ala Thr Asp
            580                 585                 590

Ala Ala Arg Gly Ala Ser Asp Ile Val Leu Thr Glu Pro Gly Leu Ser
            595                 600                 605

Val Ile Ile Ser Ala Val Leu Thr Ser Arg Ala Ile Phe Gln Arg Met
            610                 615                 620

Lys Asn Tyr Thr Ile Tyr Ala Val Ser Ile Thr Ile Arg Ile Val Phe
625                 630                 635                 640

Gly Phe Met Phe Ile Ala Leu Ile Trp Gln Phe Asp Phe Ser Pro Phe
                645                 650                 655

Met Val Leu Ile Ile Ala Ile Leu Asn Asp Gly Thr Ile Met Thr Ile
            660                 665                 670

Ser Lys Asp Arg Met Lys Pro Ser Pro Gln Pro Asp Ser Trp Lys Leu
            675                 680                 685

Arg Asp Ile Phe Ser Thr Gly Val Val Leu Gly Gly Tyr Gln Ala Leu
690                 695                 700

Met Thr Val Val Phe Phe Trp Val Met Lys Asp Ser Asp Phe Phe Ser
705                 710                 715                 720

Asn Tyr Phe Gly Val Arg Pro Leu Ser Gln Arg Pro Glu Gln Met Met
                725                 730                 735

Ala Ala Leu Tyr Leu Gln Val Ser Ile Ile Ser Gln Ala Leu Ile Phe
            740                 745                 750

Val Thr Arg Ser Arg Ser Trp Ser Tyr Ala Glu Cys Pro Gly Leu Leu
            755                 760                 765

Leu Leu Gly Ala Phe Val Ile Ala Gln Leu Val Ala Thr Phe Ile Ala
            770                 775                 780

Val Tyr Ala Asn Trp Ser Phe Ala Arg Ile Glu Gly Ala Gly Trp Gly
785                 790                 795                 800

Trp Ala Gly Val Ile Trp Leu Tyr Ser Phe Leu Thr Tyr Ile Pro Leu
                805                 810                 815

Asp Leu Leu Lys Phe Gly Ile Arg Tyr Val Leu Ser Gly Lys Ala Trp
            820                 825                 830
```

```
Leu Asn Leu Leu Glu Asn Lys Thr Ala Phe Thr Thr Lys Lys Asp Tyr
            835                 840                 845

Gly Lys Glu Glu Arg Glu Ala Gln Trp Ala Ala Ala Gln Arg Thr Leu
        850                 855                 860

His Gly Leu Gln Pro Ala Glu Lys Asn Asn Ile Phe Asn Glu Lys Asn
865                 870                 875                 880

Ser Tyr Ser Glu Leu Ser Gln Ile Ala Glu Gln Ala Lys Arg Arg Ala
                885                 890                 895

Glu Val Val Arg Leu Arg Glu Ile Asn Thr Leu Lys Gly His Val Glu
            900                 905                 910

Ser Val Val Lys Leu Lys Gly Leu Asp Ile Asp Thr Ile Gln Gln His
            915                 920                 925

Tyr Thr
    930

<210> SEQ ID NO 24
<211> LENGTH: 107
<212> TYPE: PRT
<213> ORGANISM: Artificial
<220> FEATURE:
<223> OTHER INFORMATION: Consensus sequence R1 domain
<220> FEATURE:
<221> NAME/KEY: VARIANT
<222> LOCATION: (4)..(4)
<223> OTHER INFORMATION: Xaa can be replaced by  R, K
<220> FEATURE:
<221> NAME/KEY: VARIANT
<222> LOCATION: (7)..(7)
<223> OTHER INFORMATION: Xaa can be replaced by  D, L, N, R
<220> FEATURE:
<221> NAME/KEY: VARIANT
<222> LOCATION: (9)..(9)
<223> OTHER INFORMATION: Xaa can be replaced by  L, M
<220> FEATURE:
<221> NAME/KEY: VARIANT
<222> LOCATION: (11)..(11)
<223> OTHER INFORMATION: Xaa can be replaced by  E, Q, D
<220> FEATURE:
<221> NAME/KEY: VARIANT
<222> LOCATION: (14)..(14)
<223> OTHER INFORMATION: Xaa can be replaced by  T, I
<220> FEATURE:
<221> NAME/KEY: VARIANT
<222> LOCATION: (18)..(18)
<223> OTHER INFORMATION: Xaa can be replaced by  T, S
<220> FEATURE:
<221> NAME/KEY: VARIANT
<222> LOCATION: (20)..(20)
<223> OTHER INFORMATION: Xaa can be replaced by  K, E
<220> FEATURE:
<221> NAME/KEY: VARIANT
<222> LOCATION: (21)..(21)
<223> OTHER INFORMATION: Xaa can be replaced by  D, N
<220> FEATURE:
<221> NAME/KEY: VARIANT
<222> LOCATION: (24)..(24)
<223> OTHER INFORMATION: Xaa can be replaced by  K, R
<220> FEATURE:
<221> NAME/KEY: VARIANT
<222> LOCATION: (25)..(25)
<223> OTHER INFORMATION: Xaa can be replaced by  E, G
<220> FEATURE:
<221> NAME/KEY: VARIANT
<222> LOCATION: (33)..(33)
<223> OTHER INFORMATION: Xaa can be replaced by  T, A, L
<220> FEATURE:
<221> NAME/KEY: VARIANT
<222> LOCATION: (43)..(43)
<223> OTHER INFORMATION: Xaa can be replaced by  P, A
<220> FEATURE:
<221> NAME/KEY: VARIANT
<222> LOCATION: (44)..(44)
```

```
<223> OTHER INFORMATION: Xaa can be replaced by  P, A
<220> FEATURE:
<221> NAME/KEY: VARIANT
<222> LOCATION: (46)..(46)
<223> OTHER INFORMATION: Xaa can be replaced by  T, V, A, P, K, S
<220> FEATURE:
<221> NAME/KEY: VARIANT
<222> LOCATION: (47)..(47)
<223> OTHER INFORMATION: Xaa can be replaced by  A, S, N
<220> FEATURE:
<221> NAME/KEY: VARIANT
<222> LOCATION: (48)..(48)
<223> OTHER INFORMATION: Xaa can be replaced by  S, T, N
<220> FEATURE:
<221> NAME/KEY: VARIANT
<222> LOCATION: (49)..(49)
<223> OTHER INFORMATION: Xaa can be replaced by  N, S, H
<220> FEATURE:
<221> NAME/KEY: VARIANT
<222> LOCATION: (50)..(50)
<223> OTHER INFORMATION: Xaa can be replaced by  N, T
<220> FEATURE:
<221> NAME/KEY: VARIANT
<222> LOCATION: (51)..(51)
<223> OTHER INFORMATION: Xaa can be replaced by  I, V, M, L
<220> FEATURE:
<221> NAME/KEY: VARIANT
<222> LOCATION: (53)..(53)
<223> OTHER INFORMATION: Xaa can be replaced by  N, S, H
<220> FEATURE:
<221> NAME/KEY: VARIANT
<222> LOCATION: (54)..(54)
<223> OTHER INFORMATION: Xaa can be replaced by  E, D
<220> FEATURE:
<221> NAME/KEY: VARIANT
<222> LOCATION: (56)..(56)
<223> OTHER INFORMATION: Xaa can be replaced by  S, N
<220> FEATURE:
<221> NAME/KEY: VARIANT
<222> LOCATION: (59)..(59)
<223> OTHER INFORMATION: Xaa can be replaced by  R, S, H
<220> FEATURE:
<221> NAME/KEY: VARIANT
<222> LOCATION: (60)..(60)
<223> OTHER INFORMATION: Xaa can be replaced by  E, D
<220> FEATURE:
<221> NAME/KEY: VARIANT
<222> LOCATION: (63)..(63)
<223> OTHER INFORMATION: Xaa can be replaced by  E, Q
<220> FEATURE:
<221> NAME/KEY: VARIANT
<222> LOCATION: (74)..(74)
<223> OTHER INFORMATION: Xaa can be replaced by  I, V, M
<220> FEATURE:
<221> NAME/KEY: VARIANT
<222> LOCATION: (75)..(75)
<223> OTHER INFORMATION: Xaa can be replaced by  A, V
<220> FEATURE:
<221> NAME/KEY: VARIANT
<222> LOCATION: (80)..(80)
<223> OTHER INFORMATION: Xaa can be replaced by  L, I, V
<220> FEATURE:
<221> NAME/KEY: VARIANT
<222> LOCATION: (81)..(81)
<223> OTHER INFORMATION: Xaa can be replaced by  N, L, H
<220> FEATURE:
<221> NAME/KEY: VARIANT
<222> LOCATION: (82)..(82)
<223> OTHER INFORMATION: Xaa can be replaced by  T, S
<220> FEATURE:
<221> NAME/KEY: VARIANT
<222> LOCATION: (85)..(85)
<223> OTHER INFORMATION: Xaa can be replaced by  G, S
<220> FEATURE:
<221> NAME/KEY: VARIANT
<222> LOCATION: (99)..(99)
<223> OTHER INFORMATION: Xaa can be replaced by  D, E
<220> FEATURE:
<221> NAME/KEY: VARIANT
```

```
<222> LOCATION: (102)..(102)
<223> OTHER INFORMATION: Xaa can be replaced by  Q, N
<220> FEATURE:
<221> NAME/KEY: VARIANT
<222> LOCATION: (104)..(104)
<223> OTHER INFORMATION: Xaa can be replaced by  N, H

<400> SEQUENCE: 24

Leu Ser Gly Xaa Ala Trp Xaa Asn Xaa Leu Xaa Asn Lys Xaa Ala Phe
1               5                   10                  15

Thr Xaa Lys Xaa Xaa Tyr Gly Xaa Xaa Glu Arg Glu Ala Gln Trp Ala
            20                  25                  30

Xaa Ala Gln Arg Thr Leu His Gly Leu Gln Xaa Xaa Glu Xaa Xaa Xaa
        35                  40                  45

Xaa Xaa Xaa Phe Xaa Xaa Lys Xaa Ser Tyr Xaa Xaa Leu Ser Xaa Ile
    50                  55                  60

Ala Glu Gln Ala Lys Arg Arg Ala Glu Xaa Xaa Arg Leu Arg Glu Xaa
65                  70                  75                  80

Xaa Xaa Leu Lys Xaa His Val Glu Ser Val Val Lys Leu Lys Gly Leu
                85                  90                  95

Asp Ile Xaa Thr Ile Xaa Gln Xaa Tyr Thr Val
            100                 105

<210> SEQ ID NO 25
<211> LENGTH: 106
<212> TYPE: PRT
<213> ORGANISM: Artificial
<220> FEATURE:
<223> OTHER INFORMATION: Consensus sequence R1 domain
<220> FEATURE:
<221> NAME/KEY: VARIANT
<222> LOCATION: (4)..(4)
<223> OTHER INFORMATION: Xaa can be replaced by  R, K
<220> FEATURE:
<221> NAME/KEY: VARIANT
<222> LOCATION: (7)..(7)
<223> OTHER INFORMATION: Xaa can be replaced by  D, L, N, R
<220> FEATURE:
<221> NAME/KEY: VARIANT
<222> LOCATION: (9)..(9)
<223> OTHER INFORMATION: Xaa can be replaced by  L, M
<220> FEATURE:
<221> NAME/KEY: VARIANT
<222> LOCATION: (11)..(11)
<223> OTHER INFORMATION: Xaa can be replaced by  E, Q, D
<220> FEATURE:
<221> NAME/KEY: VARIANT
<222> LOCATION: (14)..(14)
<223> OTHER INFORMATION: Xaa can be replaced by  T, I
<220> FEATURE:
<221> NAME/KEY: VARIANT
<222> LOCATION: (18)..(18)
<223> OTHER INFORMATION: Xaa can be replaced by  T, S
<220> FEATURE:
<221> NAME/KEY: VARIANT
<222> LOCATION: (20)..(20)
<223> OTHER INFORMATION: Xaa can be replaced by  K, E
<220> FEATURE:
<221> NAME/KEY: VARIANT
<222> LOCATION: (21)..(21)
<223> OTHER INFORMATION: Xaa can be replaced by  D, N
<220> FEATURE:
<221> NAME/KEY: VARIANT
<222> LOCATION: (24)..(24)
<223> OTHER INFORMATION: Xaa can be replaced by  K, R
<220> FEATURE:
<221> NAME/KEY: VARIANT
<222> LOCATION: (25)..(25)
<223> OTHER INFORMATION: Xaa can be replaced by  E, G
<220> FEATURE:
<221> NAME/KEY: VARIANT
```

-continued

```
<222> LOCATION: (33)..(33)
<223> OTHER INFORMATION: Xaa can be replaced by  T, A, L
<220> FEATURE:
<221> NAME/KEY: VARIANT
<222> LOCATION: (43)..(43)
<223> OTHER INFORMATION: Xaa can be replaced by  P, A
<220> FEATURE:
<221> NAME/KEY: VARIANT
<222> LOCATION: (44)..(44)
<223> OTHER INFORMATION: Xaa can be replaced by  P, A
<220> FEATURE:
<221> NAME/KEY: VARIANT
<222> LOCATION: (46)..(46)
<223> OTHER INFORMATION: Xaa can be replaced by  T, V, A, P, K, S
<220> FEATURE:
<221> NAME/KEY: VARIANT
<222> LOCATION: (47)..(47)
<223> OTHER INFORMATION: Xaa can be replaced by  S, T, N
<220> FEATURE:
<221> NAME/KEY: VARIANT
<222> LOCATION: (48)..(48)
<223> OTHER INFORMATION: Xaa can be replaced by  N, S, H
<220> FEATURE:
<221> NAME/KEY: VARIANT
<222> LOCATION: (49)..(49)
<223> OTHER INFORMATION: Xaa can be replaced by  N, T
<220> FEATURE:
<221> NAME/KEY: VARIANT
<222> LOCATION: (50)..(50)
<223> OTHER INFORMATION: Xaa can be replaced by  I, V, M, L
<220> FEATURE:
<221> NAME/KEY: VARIANT
<222> LOCATION: (52)..(52)
<223> OTHER INFORMATION: Xaa can be replaced by  N, S, H
<220> FEATURE:
<221> NAME/KEY: VARIANT
<222> LOCATION: (53)..(53)
<223> OTHER INFORMATION: Xaa can be replaced by  E, D
<220> FEATURE:
<221> NAME/KEY: VARIANT
<222> LOCATION: (55)..(55)
<223> OTHER INFORMATION: Xaa can be replaced by  S, N
<220> FEATURE:
<221> NAME/KEY: VARIANT
<222> LOCATION: (58)..(58)
<223> OTHER INFORMATION: Xaa can be replaced by  R, S, H
<220> FEATURE:
<221> NAME/KEY: VARIANT
<222> LOCATION: (59)..(59)
<223> OTHER INFORMATION: Xaa can be replaced by  E, D
<220> FEATURE:
<221> NAME/KEY: VARIANT
<222> LOCATION: (62)..(62)
<223> OTHER INFORMATION: Xaa can be replaced by  E, Q
<220> FEATURE:
<221> NAME/KEY: VARIANT
<222> LOCATION: (73)..(73)
<223> OTHER INFORMATION: Xaa can be replaced by  I, V, M
<220> FEATURE:
<221> NAME/KEY: VARIANT
<222> LOCATION: (74)..(74)
<223> OTHER INFORMATION: Xaa can be replaced by  A, V
<220> FEATURE:
<221> NAME/KEY: VARIANT
<222> LOCATION: (79)..(79)
<223> OTHER INFORMATION: Xaa can be replaced by  L, I, V
<220> FEATURE:
<221> NAME/KEY: VARIANT
<222> LOCATION: (80)..(80)
<223> OTHER INFORMATION: Xaa can be replaced by  N, L, H
<220> FEATURE:
<221> NAME/KEY: VARIANT
<222> LOCATION: (81)..(81)
<223> OTHER INFORMATION: Xaa can be replaced by  T, S
<220> FEATURE:
<221> NAME/KEY: VARIANT
<222> LOCATION: (84)..(84)
<223> OTHER INFORMATION: Xaa can be replaced by  G, S
<220> FEATURE:
```

```
<221> NAME/KEY: VARIANT
<222> LOCATION: (98)..(98)
<223> OTHER INFORMATION: Xaa can be replaced by  D, E
<220> FEATURE:
<221> NAME/KEY: VARIANT
<222> LOCATION: (101)..(101)
<223> OTHER INFORMATION: Xaa can be replaced by  Q, N
<220> FEATURE:
<221> NAME/KEY: VARIANT
<222> LOCATION: (103)..(103)
<223> OTHER INFORMATION: Xaa can be replaced by  N, H

<400> SEQUENCE: 25

Leu Ser Gly Xaa Ala Trp Xaa Asn Xaa Leu Xaa Asn Lys Xaa Ala Phe
1               5                   10                  15

Thr Xaa Lys Xaa Xaa Tyr Gly Xaa Xaa Glu Arg Glu Ala Gln Trp Ala
            20                  25                  30

Xaa Ala Gln Arg Thr Leu His Gly Leu Gln Xaa Xaa Glu Xaa Xaa Xaa
        35                  40                  45

Xaa Xaa Phe Xaa Xaa Lys Xaa Ser Tyr Xaa Xaa Leu Ser Xaa Ile Ala
        50                  55                  60

Glu Gln Ala Lys Arg Arg Ala Glu Xaa Xaa Arg Leu Arg Glu Xaa Xaa
65              70                  75                  80

Xaa Leu Lys Xaa His Val Glu Ser Val Val Lys Leu Lys Gly Leu Asp
            85                  90                  95

Ile Xaa Thr Ile Xaa Gln Xaa Tyr Thr Val
            100                 105

<210> SEQ ID NO 26
<211> LENGTH: 106
<212> TYPE: PRT
<213> ORGANISM: Artificial
<220> FEATURE:
<223> OTHER INFORMATION: Consensus sequence R1 domain
<220> FEATURE:
<221> NAME/KEY: VARIANT
<222> LOCATION: (4)..(4)
<223> OTHER INFORMATION: Xaa can be replaced by  R, K
<220> FEATURE:
<221> NAME/KEY: VARIANT
<222> LOCATION: (7)..(7)
<223> OTHER INFORMATION: Xaa can be replaced by  D, L, N, R
<220> FEATURE:
<221> NAME/KEY: VARIANT
<222> LOCATION: (9)..(9)
<223> OTHER INFORMATION: Xaa can be replaced by  L, M
<220> FEATURE:
<221> NAME/KEY: VARIANT
<222> LOCATION: (11)..(11)
<223> OTHER INFORMATION: Xaa can be replaced by  E, Q, D
<220> FEATURE:
<221> NAME/KEY: VARIANT
<222> LOCATION: (14)..(14)
<223> OTHER INFORMATION: Xaa can be replaced by  T, I
<220> FEATURE:
<221> NAME/KEY: VARIANT
<222> LOCATION: (18)..(18)
<223> OTHER INFORMATION: Xaa can be replaced by  T, S
<220> FEATURE:
<221> NAME/KEY: VARIANT
<222> LOCATION: (20)..(20)
<223> OTHER INFORMATION: Xaa can be replaced by  K, E
<220> FEATURE:
<221> NAME/KEY: VARIANT
<222> LOCATION: (21)..(21)
<223> OTHER INFORMATION: Xaa can be replaced by  D, N
<220> FEATURE:
<221> NAME/KEY: VARIANT
<222> LOCATION: (24)..(24)
<223> OTHER INFORMATION: Xaa can be replaced by  K, R
<220> FEATURE:
```

-continued

```
<221> NAME/KEY: VARIANT
<222> LOCATION: (25)..(25)
<223> OTHER INFORMATION: Xaa can be replaced by  E, G
<220> FEATURE:
<221> NAME/KEY: VARIANT
<222> LOCATION: (33)..(33)
<223> OTHER INFORMATION: Xaa can be replaced by  T, A, L
<220> FEATURE:
<221> NAME/KEY: VARIANT
<222> LOCATION: (43)..(43)
<223> OTHER INFORMATION: Xaa can be replaced by  P, A
<220> FEATURE:
<221> NAME/KEY: VARIANT
<222> LOCATION: (44)..(44)
<223> OTHER INFORMATION: Xaa can be replaced by  P, A
<220> FEATURE:
<221> NAME/KEY: VARIANT
<222> LOCATION: (46)..(46)
<223> OTHER INFORMATION: Xaa can be replaced by  T, V, A, P, K, S
<220> FEATURE:
<221> NAME/KEY: VARIANT
<222> LOCATION: (47)..(47)
<223> OTHER INFORMATION: Xaa can be replaced by  A, S, N
<220> FEATURE:
<221> NAME/KEY: VARIANT
<222> LOCATION: (48)..(48)
<223> OTHER INFORMATION: Xaa can be replaced by  N, S, H
<220> FEATURE:
<221> NAME/KEY: VARIANT
<222> LOCATION: (49)..(49)
<223> OTHER INFORMATION: :Xaa can be replaced by  N, T
<220> FEATURE:
<221> NAME/KEY: VARIANT
<222> LOCATION: (50)..(50)
<223> OTHER INFORMATION: Xaa can be replaced by  I, V, M, L
<220> FEATURE:
<221> NAME/KEY: VARIANT
<222> LOCATION: (52)..(52)
<223> OTHER INFORMATION: Xaa can be replaced by  N, S, H
<220> FEATURE:
<221> NAME/KEY: VARIANT
<222> LOCATION: (53)..(53)
<223> OTHER INFORMATION: Xaa can be replaced by  E, D
<220> FEATURE:
<221> NAME/KEY: VARIANT
<222> LOCATION: (55)..(55)
<223> OTHER INFORMATION: Xaa can be replaced by  S, N
<220> FEATURE:
<221> NAME/KEY: VARIANT
<222> LOCATION: (58)..(58)
<223> OTHER INFORMATION: Xaa can be replaced by  R, S, H
<220> FEATURE:
<221> NAME/KEY: VARIANT
<222> LOCATION: (59)..(59)
<223> OTHER INFORMATION: Xaa can be replaced by  E, D
<220> FEATURE:
<221> NAME/KEY: VARIANT
<222> LOCATION: (62)..(62)
<223> OTHER INFORMATION: Xaa can be replaced by  E, Q
<220> FEATURE:
<221> NAME/KEY: VARIANT
<222> LOCATION: (73)..(73)
<223> OTHER INFORMATION: Xaa can be replaced by  I, V, M
<220> FEATURE:
<221> NAME/KEY: VARIANT
<222> LOCATION: (74)..(74)
<223> OTHER INFORMATION: Xaa can be replaced by  A, V
<220> FEATURE:
<221> NAME/KEY: VARIANT
<222> LOCATION: (79)..(79)
<223> OTHER INFORMATION: Xaa can be replaced by  L, I, V
<220> FEATURE:
<221> NAME/KEY: VARIANT
<222> LOCATION: (80)..(80)
<223> OTHER INFORMATION: Xaa can be replaced by  N, L, H
<220> FEATURE:
<221> NAME/KEY: VARIANT
<222> LOCATION: (81)..(81)
<223> OTHER INFORMATION: Xaa can be replaced by  T, S
```

```
<220> FEATURE:
<221> NAME/KEY: VARIANT
<222> LOCATION: (84)..(84)
<223> OTHER INFORMATION: Xaa can be replaced by  G, S
<220> FEATURE:
<221> NAME/KEY: VARIANT
<222> LOCATION: (98)..(98)
<223> OTHER INFORMATION: Xaa can be replaced by  D, E
<220> FEATURE:
<221> NAME/KEY: VARIANT
<222> LOCATION: (101)..(101)
<223> OTHER INFORMATION: Xaa can be replaced by  Q, N
<220> FEATURE:
<221> NAME/KEY: VARIANT
<222> LOCATION: (103)..(103)
<223> OTHER INFORMATION: Xaa can be replaced by  N, H

<400> SEQUENCE: 26

Leu Ser Gly Xaa Ala Trp Xaa Asn Xaa Leu Xaa Asn Lys Xaa Ala Phe
1               5                   10                  15

Thr Xaa Lys Xaa Xaa Tyr Gly Xaa Xaa Glu Arg Glu Ala Gln Trp Ala
            20                  25                  30

Xaa Ala Gln Arg Thr Leu His Gly Leu Gln Xaa Xaa Glu Xaa Xaa Xaa
        35                  40                  45

Xaa Xaa Phe Xaa Xaa Lys Xaa Ser Tyr Xaa Xaa Leu Ser Xaa Ile Ala
    50                  55                  60

Glu Gln Ala Lys Arg Arg Ala Glu Xaa Xaa Arg Leu Arg Glu Xaa Xaa
65                  70                  75                  80

Xaa Leu Lys Xaa His Val Glu Ser Val Val Lys Leu Lys Gly Leu Asp
                85                  90                  95

Ile Xaa Thr Ile Xaa Gln Xaa Tyr Thr Val
            100                 105

<210> SEQ ID NO 27
<211> LENGTH: 105
<212> TYPE: PRT
<213> ORGANISM: Artificial
<220> FEATURE:
<223> OTHER INFORMATION: Consensus sequence R1 domain
<220> FEATURE:
<221> NAME/KEY: VARIANT
<222> LOCATION: (4)..(4)
<223> OTHER INFORMATION: Xaa can be replaced by  R, K
<220> FEATURE:
<221> NAME/KEY: VARIANT
<222> LOCATION: (7)..(7)
<223> OTHER INFORMATION: Xaa can be replaced by  D, L, N, R
<220> FEATURE:
<221> NAME/KEY: VARIANT
<222> LOCATION: (9)..(9)
<223> OTHER INFORMATION: Xaa can be replaced by  L, M
<220> FEATURE:
<221> NAME/KEY: VARIANT
<222> LOCATION: (11)..(11)
<223> OTHER INFORMATION: Xaa can be replaced by  E, Q, D
<220> FEATURE:
<221> NAME/KEY: VARIANT
<222> LOCATION: (14)..(14)
<223> OTHER INFORMATION: Xaa can be replaced by  T, I
<220> FEATURE:
<221> NAME/KEY: VARIANT
<222> LOCATION: (18)..(18)
<223> OTHER INFORMATION: Xaa can be replaced by  T, S
<220> FEATURE:
<221> NAME/KEY: VARIANT
<222> LOCATION: (20)..(20)
<223> OTHER INFORMATION: Xaa can be replaced by  K, E
<220> FEATURE:
<221> NAME/KEY: VARIANT
<222> LOCATION: (21)..(21)
<223> OTHER INFORMATION: Xaa can be replaced by  D, N
```

```
<220> FEATURE:
<221> NAME/KEY: VARIANT
<222> LOCATION: (24)..(24)
<223> OTHER INFORMATION: Xaa can be replaced by  K, R
<220> FEATURE:
<221> NAME/KEY: VARIANT
<222> LOCATION: (25)..(25)
<223> OTHER INFORMATION: Xaa can be replaced by  E, G
<220> FEATURE:
<221> NAME/KEY: VARIANT
<222> LOCATION: (33)..(33)
<223> OTHER INFORMATION: Xaa can be replaced by  T, A, L
<220> FEATURE:
<221> NAME/KEY: VARIANT
<222> LOCATION: (43)..(43)
<223> OTHER INFORMATION: Xaa can be replaced by  P, A
<220> FEATURE:
<221> NAME/KEY: VARIANT
<222> LOCATION: (44)..(44)
<223> OTHER INFORMATION: Xaa can be replaced by  P, A
<220> FEATURE:
<221> NAME/KEY: VARIANT
<222> LOCATION: (46)..(46)
<223> OTHER INFORMATION: Xaa can be replaced by  T, V, A, P, K, S
<220> FEATURE:
<221> NAME/KEY: VARIANT
<222> LOCATION: (47)..(47)
<223> OTHER INFORMATION: Xaa can be replaced by  N, S, H
<220> FEATURE:
<221> NAME/KEY: VARIANT
<222> LOCATION: (48)..(48)
<223> OTHER INFORMATION: Xaa can be replaced by  N, T
<220> FEATURE:
<221> NAME/KEY: VARIANT
<222> LOCATION: (49)..(49)
<223> OTHER INFORMATION: Xaa can be replaced by  I, V, M, L
<220> FEATURE:
<221> NAME/KEY: VARIANT
<222> LOCATION: (51)..(51)
<223> OTHER INFORMATION: Xaa can be replaced by  N, S, H
<220> FEATURE:
<221> NAME/KEY: VARIANT
<222> LOCATION: (52)..(52)
<223> OTHER INFORMATION: Xaa can be replaced by  E, D
<220> FEATURE:
<221> NAME/KEY: VARIANT
<222> LOCATION: (54)..(54)
<223> OTHER INFORMATION: Xaa can be replaced by  S, N
<220> FEATURE:
<221> NAME/KEY: VARIANT
<222> LOCATION: (57)..(57)
<223> OTHER INFORMATION: Xaa can be replaced by  R, S, H
<220> FEATURE:
<221> NAME/KEY: VARIANT
<222> LOCATION: (58)..(58)
<223> OTHER INFORMATION: Xaa can be replaced by  E, D
<220> FEATURE:
<221> NAME/KEY: VARIANT
<222> LOCATION: (61)..(61)
<223> OTHER INFORMATION: Xaa can be replaced by  E, Q
<220> FEATURE:
<221> NAME/KEY: VARIANT
<222> LOCATION: (72)..(72)
<223> OTHER INFORMATION: Xaa can be replaced by  I, V, M
<220> FEATURE:
<221> NAME/KEY: VARIANT
<222> LOCATION: (73)..(73)
<223> OTHER INFORMATION: Xaa can be replaced by  A, V
<220> FEATURE:
<221> NAME/KEY: VARIANT
<222> LOCATION: (78)..(78)
<223> OTHER INFORMATION: Xaa can be replaced by  L, I, V
<220> FEATURE:
<221> NAME/KEY: VARIANT
<222> LOCATION: (79)..(79)
<223> OTHER INFORMATION: Xaa can be replaced by  N, L, H
<220> FEATURE:
<221> NAME/KEY: VARIANT
<222> LOCATION: (80)..(80)
```

-continued

```
<223> OTHER INFORMATION: Xaa can be replaced by  T, S
<220> FEATURE:
<221> NAME/KEY: VARIANT
<222> LOCATION: (83)..(83)
<223> OTHER INFORMATION: Xaa can be replaced by  G, S
<220> FEATURE:
<221> NAME/KEY: VARIANT
<222> LOCATION: (97)..(97)
<223> OTHER INFORMATION: Xaa can be replaced by  D, E
<220> FEATURE:
<221> NAME/KEY: VARIANT
<222> LOCATION: (100)..(100)
<223> OTHER INFORMATION: Xaa can be replaced by  Q, N
<220> FEATURE:
<221> NAME/KEY: VARIANT
<222> LOCATION: (102)..(102)
<223> OTHER INFORMATION: Xaa can be replaced by  N, H

<400> SEQUENCE: 27

Leu Ser Gly Xaa Ala Trp Xaa Asn Xaa Leu Xaa Asn Lys Xaa Ala Phe
1               5                  10                  15

Thr Xaa Lys Xaa Xaa Tyr Gly Xaa Xaa Glu Arg Glu Ala Gln Trp Ala
            20                  25                  30

Xaa Ala Gln Arg Thr Leu His Gly Leu Gln Xaa Xaa Glu Xaa Xaa Xaa
        35                  40                  45

Xaa Phe Xaa Xaa Lys Xaa Ser Tyr Xaa Xaa Leu Ser Xaa Ile Ala Glu
    50                  55                  60

Gln Ala Lys Arg Arg Ala Glu Xaa Arg Leu Arg Glu Xaa Xaa Xaa Xaa
65                  70                  75                  80

Leu Lys Xaa His Val Glu Ser Val Val Lys Leu Lys Gly Leu Asp Ile
            85                  90                  95

Xaa Thr Ile Xaa Gln Xaa Tyr Thr Val
            100                 105

<210> SEQ ID NO 28
<211> LENGTH: 107
<212> TYPE: PRT
<213> ORGANISM: Artificial
<220> FEATURE:
<223> OTHER INFORMATION: R1 domain mutated at position 31 W->L
<220> FEATURE:
<221> NAME/KEY: VARIANT
<222> LOCATION: (4)..(4)
<223> OTHER INFORMATION: Xaa can be replaced by  R, K
<220> FEATURE:
<221> NAME/KEY: VARIANT
<222> LOCATION: (7)..(7)
<223> OTHER INFORMATION: Xaa can be replaced by  D, L, N, R
<220> FEATURE:
<221> NAME/KEY: VARIANT
<222> LOCATION: (9)..(9)
<223> OTHER INFORMATION: Xaa can be replaced by  L, M
<220> FEATURE:
<221> NAME/KEY: VARIANT
<222> LOCATION: (11)..(11)
<223> OTHER INFORMATION: Xaa can be replaced by  E, Q, D
<220> FEATURE:
<221> NAME/KEY: VARIANT
<222> LOCATION: (14)..(14)
<223> OTHER INFORMATION: Xaa can be replaced by  T, I
<220> FEATURE:
<221> NAME/KEY: VARIANT
<222> LOCATION: (18)..(18)
<223> OTHER INFORMATION: Xaa can be replaced by  T, S
<220> FEATURE:
<221> NAME/KEY: VARIANT
<222> LOCATION: (20)..(20)
<223> OTHER INFORMATION: Xaa can be replaced by  K, E
<220> FEATURE:
<221> NAME/KEY: VARIANT
<222> LOCATION: (21)..(21)
```

```
-continued

<223> OTHER INFORMATION: Xaa can be replaced by  D, N
<220> FEATURE:
<221> NAME/KEY: VARIANT
<222> LOCATION: (24)..(24)
<223> OTHER INFORMATION: Xaa can be replaced by  K, R
<220> FEATURE:
<221> NAME/KEY: VARIANT
<222> LOCATION: (25)..(25)
<223> OTHER INFORMATION: Xaa can be replaced by  E, G
<220> FEATURE:
<221> NAME/KEY: VARIANT
<222> LOCATION: (33)..(33)
<223> OTHER INFORMATION: Xaa can be replaced by  T, A, L
<220> FEATURE:
<221> NAME/KEY: VARIANT
<222> LOCATION: (43)..(43)
<223> OTHER INFORMATION: Xaa can be replaced by  P, A
<220> FEATURE:
<221> NAME/KEY: VARIANT
<222> LOCATION: (44)..(44)
<223> OTHER INFORMATION: Xaa can be replaced by  P, A
<220> FEATURE:
<221> NAME/KEY: VARIANT
<222> LOCATION: (46)..(46)
<223> OTHER INFORMATION: Xaa can be replaced by  T, V, A, P, K, S
<220> FEATURE:
<221> NAME/KEY: VARIANT
<222> LOCATION: (47)..(47)
<223> OTHER INFORMATION: Xaa can be replaced by  A, S, N
<220> FEATURE:
<221> NAME/KEY: VARIANT
<222> LOCATION: (48)..(48)
<223> OTHER INFORMATION: Xaa can be replaced by  S, T, N
<220> FEATURE:
<221> NAME/KEY: VARIANT
<222> LOCATION: (49)..(49)
<223> OTHER INFORMATION: Xaa can be replaced by  N, S, H
<220> FEATURE:
<221> NAME/KEY: VARIANT
<222> LOCATION: (50)..(50)
<223> OTHER INFORMATION: Xaa can be replaced by  N, T
<220> FEATURE:
<221> NAME/KEY: VARIANT
<222> LOCATION: (51)..(51)
<223> OTHER INFORMATION: Xaa can be replaced by  I, V, M, L
<220> FEATURE:
<221> NAME/KEY: VARIANT
<222> LOCATION: (53)..(53)
<223> OTHER INFORMATION: Xaa can be replaced by  N, S, H
<220> FEATURE:
<221> NAME/KEY: VARIANT
<222> LOCATION: (54)..(54)
<223> OTHER INFORMATION: Xaa can be replaced by  E, D
<220> FEATURE:
<221> NAME/KEY: VARIANT
<222> LOCATION: (56)..(56)
<223> OTHER INFORMATION: Xaa can be replaced by  S, N
<220> FEATURE:
<221> NAME/KEY: VARIANT
<222> LOCATION: (59)..(59)
<223> OTHER INFORMATION: Xaa can be replaced by  R, S, H
<220> FEATURE:
<221> NAME/KEY: VARIANT
<222> LOCATION: (60)..(60)
<223> OTHER INFORMATION: Xaa can be replaced by  E, D
<220> FEATURE:
<221> NAME/KEY: VARIANT
<222> LOCATION: (63)..(63)
<223> OTHER INFORMATION: Xaa can be replaced by  E, Q
<220> FEATURE:
<221> NAME/KEY: VARIANT
<222> LOCATION: (74)..(74)
<223> OTHER INFORMATION: Xaa can be replaced by  I, V, M
<220> FEATURE:
<221> NAME/KEY: VARIANT
<222> LOCATION: (75)..(75)
<223> OTHER INFORMATION: Xaa can be replaced by  A, V
<220> FEATURE:
<221> NAME/KEY: VARIANT
```

<222> LOCATION: (80)..(80)
<223> OTHER INFORMATION: Xaa can be replaced by  L, I, V
<220> FEATURE:
<221> NAME/KEY: VARIANT
<222> LOCATION: (81)..(81)
<223> OTHER INFORMATION: Xaa can be replaced by  N, L, H
<220> FEATURE:
<221> NAME/KEY: VARIANT
<222> LOCATION: (82)..(82)
<223> OTHER INFORMATION: Xaa can be replaced by  T, S
<220> FEATURE:
<221> NAME/KEY: VARIANT
<222> LOCATION: (85)..(85)
<223> OTHER INFORMATION: Xaa can be replaced by  G, S
<220> FEATURE:
<221> NAME/KEY: VARIANT
<222> LOCATION: (99)..(99)
<223> OTHER INFORMATION: Xaa can be replaced by  D, E
<220> FEATURE:
<221> NAME/KEY: VARIANT
<222> LOCATION: (102)..(102)
<223> OTHER INFORMATION: Xaa can be replaced by  Q, N
<220> FEATURE:
<221> NAME/KEY: VARIANT
<222> LOCATION: (104)..(104)
<223> OTHER INFORMATION: Xaa can be replaced by  N, H

<400> SEQUENCE: 28

Leu Ser Gly Xaa Ala Trp Xaa Asn Xaa Leu Xaa Asn Lys Xaa Ala Phe
1               5                   10                  15

Thr Xaa Lys Xaa Xaa Tyr Gly Xaa Xaa Glu Arg Glu Ala Gln Leu Ala
            20                  25                  30

Xaa Ala Gln Arg Thr Leu His Gly Leu Gln Xaa Xaa Glu Xaa Xaa Xaa
        35                  40                  45

Xaa Xaa Xaa Phe Xaa Xaa Lys Xaa Ser Tyr Xaa Xaa Leu Ser Xaa Ile
    50                  55                  60

Ala Glu Gln Ala Lys Arg Arg Ala Glu Xaa Xaa Arg Leu Arg Glu Xaa
65                  70                  75                  80

Xaa Xaa Leu Lys Xaa His Val Glu Ser Val Val Lys Leu Lys Gly Leu
                85                  90                  95

Asp Ile Xaa Thr Ile Xaa Gln Xaa Tyr Thr Val
            100                 105

<210> SEQ ID NO 29
<211> LENGTH: 107
<212> TYPE: PRT
<213> ORGANISM: Artificial
<220> FEATURE:
<223> OTHER INFORMATION: R1 domain mutated at position 31 W->A
<220> FEATURE:
<221> NAME/KEY: VARIANT
<222> LOCATION: (4)..(4)
<223> OTHER INFORMATION: Xaa can be replaced by  R, K
<220> FEATURE:
<221> NAME/KEY: VARIANT
<222> LOCATION: (7)..(7)
<223> OTHER INFORMATION: Xaa can be replaced by  D, L, N, R
<220> FEATURE:
<221> NAME/KEY: VARIANT
<222> LOCATION: (9)..(9)
<223> OTHER INFORMATION: Xaa can be replaced by  L, M
<220> FEATURE:
<221> NAME/KEY: VARIANT
<222> LOCATION: (11)..(11)
<223> OTHER INFORMATION: Xaa can be replaced by  E, Q, D
<220> FEATURE:
<221> NAME/KEY: VARIANT
<222> LOCATION: (14)..(14)
<223> OTHER INFORMATION: Xaa can be replaced by  T, I
<220> FEATURE:
<221> NAME/KEY: VARIANT

```
<222> LOCATION: (18)..(18)
<223> OTHER INFORMATION: Xaa can be replaced by  T, S
<220> FEATURE:
<221> NAME/KEY: VARIANT
<222> LOCATION: (20)..(20)
<223> OTHER INFORMATION: Xaa can be replaced by  K, E
<220> FEATURE:
<221> NAME/KEY: VARIANT
<222> LOCATION: (21)..(21)
<223> OTHER INFORMATION: Xaa can be replaced by  D, N
<220> FEATURE:
<221> NAME/KEY: VARIANT
<222> LOCATION: (24)..(24)
<223> OTHER INFORMATION: Xaa can be replaced by  K, R
<220> FEATURE:
<221> NAME/KEY: VARIANT
<222> LOCATION: (25)..(25)
<223> OTHER INFORMATION: Xaa can be replaced by  E, G
<220> FEATURE:
<221> NAME/KEY: VARIANT
<222> LOCATION: (33)..(33)
<223> OTHER INFORMATION: Xaa can be replaced by  T, A, L
<220> FEATURE:
<221> NAME/KEY: VARIANT
<222> LOCATION: (43)..(43)
<223> OTHER INFORMATION: Xaa can be replaced by  P, A
<220> FEATURE:
<221> NAME/KEY: VARIANT
<222> LOCATION: (44)..(44)
<223> OTHER INFORMATION: Xaa can be replaced by  P, A
<220> FEATURE:
<221> NAME/KEY: VARIANT
<222> LOCATION: (46)..(46)
<223> OTHER INFORMATION: Xaa can be replaced by  T, V, A, P, K, S
<220> FEATURE:
<221> NAME/KEY: VARIANT
<222> LOCATION: (47)..(47)
<223> OTHER INFORMATION: Xaa can be replaced by  A, S, N
<220> FEATURE:
<221> NAME/KEY: VARIANT
<222> LOCATION: (48)..(48)
<223> OTHER INFORMATION: Xaa can be replaced by  S, T, N
<220> FEATURE:
<221> NAME/KEY: VARIANT
<222> LOCATION: (49)..(49)
<223> OTHER INFORMATION: Xaa can be replaced by  N, S, H
<220> FEATURE:
<221> NAME/KEY: VARIANT
<222> LOCATION: (50)..(50)
<223> OTHER INFORMATION: Xaa can be replaced by  N, T
<220> FEATURE:
<221> NAME/KEY: VARIANT
<222> LOCATION: (51)..(51)
<223> OTHER INFORMATION: Xaa can be replaced by  I, V, M, L
<220> FEATURE:
<221> NAME/KEY: VARIANT
<222> LOCATION: (53)..(53)
<223> OTHER INFORMATION: Xaa can be replaced by  N, S, H
<220> FEATURE:
<221> NAME/KEY: VARIANT
<222> LOCATION: (54)..(54)
<223> OTHER INFORMATION: Xaa can be replaced by  E, D
<220> FEATURE:
<221> NAME/KEY: VARIANT
<222> LOCATION: (56)..(56)
<223> OTHER INFORMATION: Xaa can be replaced by  S, N
<220> FEATURE:
<221> NAME/KEY: VARIANT
<222> LOCATION: (59)..(59)
<223> OTHER INFORMATION: Xaa can be replaced by  R, S, H
<220> FEATURE:
<221> NAME/KEY: VARIANT
<222> LOCATION: (60)..(60)
<223> OTHER INFORMATION: Xaa can be replaced by  E, D
<220> FEATURE:
<221> NAME/KEY: VARIANT
<222> LOCATION: (63)..(63)
<223> OTHER INFORMATION: Xaa can be replaced by  E, Q
<220> FEATURE:
```

```
<221> NAME/KEY: VARIANT
<222> LOCATION: (74)..(74)
<223> OTHER INFORMATION: Xaa can be replaced by  I, V, M
<220> FEATURE:
<221> NAME/KEY: VARIANT
<222> LOCATION: (75)..(75)
<223> OTHER INFORMATION: Xaa can be replaced by  A, V
<220> FEATURE:
<221> NAME/KEY: VARIANT
<222> LOCATION: (80)..(80)
<223> OTHER INFORMATION: Xaa can be replaced by  L, I, V
<220> FEATURE:
<221> NAME/KEY: VARIANT
<222> LOCATION: (81)..(81)
<223> OTHER INFORMATION: Xaa can be replaced by  N, L, H
<220> FEATURE:
<221> NAME/KEY: VARIANT
<222> LOCATION: (82)..(82)
<223> OTHER INFORMATION: Xaa can be replaced by  T, S
<220> FEATURE:
<221> NAME/KEY: VARIANT
<222> LOCATION: (85)..(85)
<223> OTHER INFORMATION: Xaa can be replaced by  G, S
<220> FEATURE:
<221> NAME/KEY: VARIANT
<222> LOCATION: (99)..(99)
<223> OTHER INFORMATION: Xaa can be replaced by  D, E
<220> FEATURE:
<221> NAME/KEY: VARIANT
<222> LOCATION: (102)..(102)
<223> OTHER INFORMATION: Xaa can be replaced by  Q, N
<220> FEATURE:
<221> NAME/KEY: VARIANT
<222> LOCATION: (104)..(104)
<223> OTHER INFORMATION: Xaa can be replaced by  N, H

<400> SEQUENCE: 29

Leu Ser Gly Xaa Ala Trp Xaa Asn Xaa Leu Xaa Asn Lys Xaa Ala Phe
1               5                   10                  15

Thr Xaa Lys Xaa Xaa Tyr Gly Xaa Xaa Glu Arg Glu Ala Gln Ala Ala
            20                  25                  30

Xaa Ala Gln Arg Thr Leu His Gly Leu Gln Xaa Xaa Glu Xaa Xaa Xaa
        35                  40                  45

Xaa Xaa Xaa Phe Xaa Xaa Lys Xaa Ser Tyr Xaa Xaa Leu Ser Xaa Ile
    50                  55                  60

Ala Glu Gln Ala Lys Arg Arg Ala Glu Xaa Xaa Arg Leu Arg Glu Xaa
65                  70                  75                  80

Xaa Xaa Leu Lys Xaa His Val Glu Ser Val Val Lys Leu Lys Gly Leu
                85                  90                  95

Asp Ile Xaa Thr Ile Xaa Gln Xaa Tyr Thr Val
            100                 105

<210> SEQ ID NO 30
<211> LENGTH: 931
<212> TYPE: PRT
<213> ORGANISM: Arabidopsis thaliana
<220> FEATURE:
<221> NAME/KEY: misc_feature
<223> OTHER INFORMATION: AtAHA5_W857L mutant

<400> SEQUENCE: 30

Met Glu Glu Val Phe Glu Glu Leu Lys Cys Thr Lys Gln Gly Leu Thr
1               5                   10                  15

Ala Asn Glu Ala Ser His Arg Leu Asp Val Phe Gly Pro Asn Lys Leu
            20                  25                  30

Glu Glu Lys Lys Glu Ser Lys Leu Leu Lys Phe Leu Gly Phe Met Trp
        35                  40                  45
```

```
Asn Pro Leu Ser Trp Val Met Glu Val Ala Ala Leu Met Ala Ile Ala
    50              55                  60

Leu Ala Asn Gly Gly Arg Pro Pro Asp Trp Gln Asp Phe Val Gly
65              70                  75                  80

Ile Val Cys Leu Leu Leu Ile Asn Ser Thr Ile Ser Phe Ile Glu Glu
                85                  90                  95

Asn Asn Ala Gly Asn Ala Ala Ala Leu Met Ala Gly Leu Ala Pro
            100             105                 110

Lys Thr Lys Val Leu Arg Asp Asn Gln Trp Ser Glu Gln Glu Ala Ser
        115                 120                 125

Ile Leu Val Pro Gly Asp Val Ile Ser Ile Lys Leu Gly Asp Ile Ile
    130                 135                 140

Pro Ala Asp Ala Arg Leu Leu Asp Gly Asp Pro Leu Lys Ile Asp Gln
145             150                 155                 160

Ser Ser Leu Thr Gly Glu Ser Ile Pro Val Thr Lys Asn Pro Ser Asp
            165                 170                 175

Glu Val Phe Ser Gly Ser Ile Cys Lys Gln Gly Glu Ile Glu Ala Ile
            180                 185                 190

Val Ile Ala Thr Gly Val His Thr Phe Phe Gly Lys Ala Ala His Leu
    195                 200                 205

Val Asp Asn Thr Asn Gln Ile Gly His Phe Gln Lys Val Leu Thr Ser
    210                 215                 220

Ile Gly Asn Phe Cys Ile Cys Ser Ile Ala Leu Gly Ile Ile Val Glu
225             230                 235                 240

Leu Leu Val Met Tyr Pro Ile Gln Arg Arg Arg Tyr Arg Asp Gly Ile
            245                 250                 255

Asp Asn Leu Leu Val Leu Leu Ile Gly Gly Ile Pro Ile Ala Met Pro
            260                 265                 270

Ser Val Leu Ser Val Thr Met Ala Thr Gly Ser His Arg Leu Phe Gln
            275                 280                 285

Gln Gly Ala Ile Thr Lys Arg Met Thr Ala Ile Glu Glu Met Ala Gly
    290                 295                 300

Met Asp Val Leu Cys Cys Asp Lys Thr Gly Thr Leu Thr Leu Asn Lys
305             310                 315                 320

Leu Thr Val Asp Lys Asn Leu Val Glu Val Phe Ala Lys Gly Val Gly
            325                 330                 335

Lys Glu His Val Phe Leu Leu Ala Ala Arg Ala Ser Arg Ile Glu Asn
            340                 345                 350

Gln Asp Ala Ile Asp Ala Ala Ile Val Gly Met Leu Ala Asp Pro Lys
    355                 360                 365

Glu Ala Arg Ala Gly Val Arg Glu Val His Phe Phe Pro Phe Asn Pro
    370                 375                 380

Val Asp Lys Arg Thr Ala Leu Thr Tyr Val Asp Ser Asp Gly Asn Trp
385             390                 395                 400

His Arg Ala Ser Lys Gly Ala Pro Glu Gln Ile Leu Asn Leu Cys Asn
            405                 410                 415

Cys Lys Glu Asp Val Arg Arg Lys Val His Gly Val Ile Asp Lys Phe
            420                 425                 430

Ala Glu Arg Gly Leu Arg Ser Leu Ala Val Ala Arg Gln Glu Val Leu
    435                 440                 445

Glu Lys Lys Lys Asp Ala Pro Gly Gly Pro Trp Gln Leu Val Gly Leu
450                 455                 460
```

```
Leu Pro Leu Phe Asp Pro Pro Arg His Asp Ser Ala Glu Thr Ile Arg
465                 470                 475                 480

Arg Ala Leu Asn Leu Gly Val Asn Val Lys Met Ile Thr Gly Asp Gln
            485                 490                 495

Leu Ala Ile Gly Lys Glu Thr Gly Arg Arg Leu Gly Met Gly Thr Asn
        500                 505                 510

Met Tyr Pro Ser Ser Ala Leu Leu Gly Gln Val Lys Asp Ser Ser Leu
    515                 520                 525

Gly Ala Leu Pro Val Asp Glu Leu Ile Glu Lys Ala Asp Gly Phe Ala
530                 535                 540

Gly Val Phe Pro Glu His Lys Tyr Glu Ile Val His Arg Leu Gln Gln
545                 550                 555                 560

Arg Asn His Ile Cys Gly Met Thr Gly Asp Gly Val Asn Asp Ala Pro
                565                 570                 575

Ala Leu Lys Lys Ala Asp Ile Gly Ile Ala Val Val Asp Ala Thr Asp
            580                 585                 590

Ala Ala Arg Gly Ala Ser Asp Ile Val Leu Thr Glu Pro Gly Leu Ser
        595                 600                 605

Val Ile Ile Ser Ala Val Leu Thr Ser Arg Ala Ile Phe Gln Arg Met
610                 615                 620

Lys Asn Tyr Thr Ile Tyr Ala Val Ser Ile Thr Ile Arg Ile Val Phe
625                 630                 635                 640

Gly Phe Met Phe Ile Ala Leu Ile Trp Gln Phe Asp Phe Ser Pro Phe
                645                 650                 655

Met Val Leu Ile Ile Ala Ile Leu Asn Asp Gly Thr Ile Met Thr Ile
            660                 665                 670

Ser Lys Asp Arg Met Lys Pro Ser Pro Gln Pro Asp Ser Trp Lys Leu
        675                 680                 685

Arg Asp Ile Phe Ser Thr Gly Val Val Leu Gly Gly Tyr Gln Ala Leu
        690                 695                 700

Met Thr Val Val Phe Phe Trp Val Met Lys Asp Ser Asp Phe Phe Ser
705                 710                 715                 720

Asn Tyr Phe Gly Val Arg Pro Leu Ser Gln Arg Pro Glu Gln Met Met
                725                 730                 735

Ala Ala Leu Tyr Leu Gln Val Ser Ile Ile Ser Gln Ala Leu Ile Phe
            740                 745                 750

Val Thr Arg Ser Arg Ser Trp Ser Tyr Ala Glu Cys Pro Gly Leu Leu
        755                 760                 765

Leu Leu Gly Ala Phe Val Ile Ala Gln Leu Val Ala Thr Phe Ile Ala
        770                 775                 780

Val Tyr Ala Asn Trp Ser Phe Ala Arg Ile Glu Gly Ala Gly Trp Gly
785                 790                 795                 800

Trp Ala Gly Val Ile Trp Leu Tyr Ser Phe Leu Thr Tyr Ile Pro Leu
                805                 810                 815

Asp Leu Leu Lys Phe Gly Ile Arg Tyr Val Leu Ser Gly Lys Ala Trp
            820                 825                 830

Leu Asn Leu Leu Glu Asn Lys Thr Ala Phe Thr Thr Lys Lys Asp Tyr
        835                 840                 845

Gly Lys Glu Glu Arg Glu Ala Gln Leu Ala Ala Gln Arg Thr Leu
        850                 855                 860

His Gly Leu Gln Pro Ala Glu Lys Asn Asn Ile Phe Asn Glu Lys Asn
865                 870                 875                 880
```

```
Ser Tyr Ser Glu Leu Ser Gln Ile Ala Glu Gln Ala Lys Arg Arg Ala
            885                 890                 895

Glu Val Val Arg Leu Arg Glu Ile Asn Thr Leu Lys Gly His Val Glu
        900                 905                 910

Ser Val Val Lys Leu Lys Gly Leu Asp Ile Asp Thr Ile Gln Gln His
        915                 920                 925

Tyr Thr Val
    930

<210> SEQ ID NO 31
<211> LENGTH: 961
<212> TYPE: PRT
<213> ORGANISM: Zea mays
<220> FEATURE:
<221> NAME/KEY: misc_feature
<223> OTHER INFORMATION: ZmAHA5_W885L mutant

<400> SEQUENCE: 31

Met Gly Pro Leu Gln Arg Arg Pro Thr Ala Met Gly Gly Leu Glu Glu
1               5                   10                  15

Ile Lys Asn Glu Ala Val Asp Leu Glu Asn Ile Pro Ile Glu Glu Val
            20                  25                  30

Phe Glu Gln Leu Lys Cys Thr Arg Glu Gly Leu Ser Ser Ser Glu Gly
        35                  40                  45

Gln Gln Arg Leu Glu Ile Phe Gly Pro Asn Arg Leu Glu Glu Lys Lys
    50                  55                  60

Glu Ser Lys Ile Leu Lys Phe Leu Gly Phe Met Trp Asn Pro Leu Ser
65                  70                  75                  80

Trp Val Met Glu Met Ala Ala Val Met Ala Ile Ala Leu Ala Asn Gly
                85                  90                  95

Gly Gly Lys Pro Pro Asp Trp Glu Asp Phe Val Gly Ile Ile Val Leu
            100                 105                 110

Leu Val Ile Asn Ser Thr Ile Ser Phe Ile Glu Glu Asn Asn Ala Gly
        115                 120                 125

Asn Ala Ala Ala Ala Leu Met Ala Asn Leu Ala Pro Lys Thr Lys Val
    130                 135                 140

Leu Arg Asp Gly Arg Trp Gly Glu Gln Glu Ala Ala Ile Leu Val Pro
145                 150                 155                 160

Gly Asp Ile Val Ser Ile Lys Leu Gly Asp Ile Val Pro Ala Asp Ala
                165                 170                 175

Arg Leu Leu Glu Gly Asp Pro Leu Lys Val Asp Gln Ser Ala Leu Thr
            180                 185                 190

Gly Glu Ser Leu Pro Val Thr Lys Gly Pro Gly Asp Glu Val Phe Ser
        195                 200                 205

Gly Ser Thr Cys Lys Gln Gly Glu Ile Glu Ala Val Val Ile Ala Thr
    210                 215                 220

Gly Val His Thr Phe Phe Gly Lys Ala Ala His Leu Val Asp Ser Thr
225                 230                 235                 240

Asn Gln Val Gly His Phe Gln Gln Val Leu Thr Ala Ile Gly Asn Phe
                245                 250                 255

Cys Ile Cys Ser Ile Ala Val Gly Ile Val Val Glu Ile Ile Val Met
            260                 265                 270

Phe Pro Ile Gln His Arg Arg Tyr Arg Ser Gly Ile Glu Asn Leu Leu
        275                 280                 285

Val Leu Leu Ile Gly Gly Ile Pro Ile Ala Met Pro Thr Val Leu Ser
    290                 295                 300
```

```
Val Thr Met Ala Ile Gly Ser His Lys Leu Ser Gln Gln Gly Ala Ile
305                 310                 315                 320

Thr Lys Arg Met Thr Ala Ile Glu Glu Met Ala Gly Met Asp Val Leu
            325                 330                 335

Cys Ser Asp Lys Thr Gly Thr Leu Thr Leu Asn Lys Leu Ser Val Asp
            340                 345                 350

Lys Asn Leu Val Glu Val Phe Cys Lys Gly Val Asp Lys Asp His Val
            355                 360                 365

Leu Leu Leu Ala Ala Arg Ala Ser Arg Thr Glu Asn Gln Asp Ala Ile
    370                 375                 380

Asp Ala Ala Met Val Gly Met Leu Ala Asp Pro Lys Glu Ala Arg Ala
385                 390                 395                 400

Gly Ile Arg Glu Ile His Phe Leu Pro Phe Asn Pro Val Asp Lys Arg
                405                 410                 415

Thr Ala Leu Thr Tyr Ile Asp Ala Asp Gly His Trp His Arg Val Ser
            420                 425                 430

Lys Gly Ala Pro Glu Gln Ile Leu Asp Leu Cys His Cys Lys Glu Asp
            435                 440                 445

Leu Arg Arg Lys Val His Gly Ile Ile Asp Lys Tyr Ala Glu Arg Gly
    450                 455                 460

Leu Arg Ser Leu Ala Val Ala Arg Gln Glu Val Pro Glu Arg Asn Lys
465                 470                 475                 480

Glu Ser Pro Gly Gly Pro Trp Gln Phe Val Gly Leu Leu Pro Leu Phe
                485                 490                 495

Asp Pro Pro Arg His Asp Ser Ala Glu Thr Ile Arg Lys Ala Leu Val
            500                 505                 510

Leu Gly Val Asn Val Lys Met Ile Thr Gly Asp Gln Leu Ala Ile Gly
            515                 520                 525

Lys Glu Thr Gly Arg Arg Leu Gly Met Gly Thr Asn Met Tyr Pro Ser
530                 535                 540

Ser Ala Leu Leu Gly Gln Asn Lys Asp Ala Thr Leu Glu Ala Leu Pro
545                 550                 555                 560

Val Asp Glu Leu Ile Glu Lys Ala Asp Gly Phe Ala Gly Val Phe Pro
                565                 570                 575

Glu His Lys Tyr Glu Ile Val Lys Arg Leu Gln Glu Lys Lys His Ile
            580                 585                 590

Val Gly Met Thr Gly Asp Gly Val Asn Asp Ala Pro Ala Leu Lys Lys
            595                 600                 605

Ala Asp Ile Gly Ile Ala Val Ala Asp Ala Thr Asp Ala Ala Arg Ser
    610                 615                 620

Ala Ser Asp Ile Val Leu Thr Glu Pro Gly Leu Ser Val Ile Ile Ser
625                 630                 635                 640

Ala Val Leu Thr Ser Arg Cys Ile Phe Gln Arg Met Lys Asn Tyr Thr
                645                 650                 655

Ile Tyr Ala Val Ser Ile Thr Ile Arg Ile Val Leu Gly Phe Met Leu
            660                 665                 670

Ile Ala Leu Ile Trp Gln Tyr Asp Phe Ser Pro Phe Met Val Leu Ile
            675                 680                 685

Ile Ala Ile Leu Asn Asp Gly Thr Ile Met Thr Ile Ser Lys Asp Arg
    690                 695                 700

Val Lys Pro Ser Pro Leu Pro Asp Ser Trp Lys Leu Lys Glu Ile Phe
705                 710                 715                 720
```

-continued

```
Ala Thr Gly Ile Val Leu Gly Ser Tyr Leu Ala Leu Met Thr Val Ile
                725                 730                 735
Phe Phe Trp Ala Met His Lys Thr Asp Phe Phe Ser Asp Lys Phe Gly
            740                 745                 750
Val Arg Ser Ile Arg Asp Ser Glu His Glu Met Met Ser Ala Leu Tyr
        755                 760                 765
Leu Gln Val Ser Ile Val Ser Gln Ala Leu Ile Phe Val Thr Arg Ser
    770                 775                 780
Arg Ser Trp Ser Phe Val Glu Arg Pro Gly Leu Leu Leu Val Thr Ala
785                 790                 795                 800
Phe Leu Leu Ala Gln Leu Val Ala Thr Phe Leu Ala Val Tyr Ala Asn
                805                 810                 815
Trp Gly Phe Ala Arg Ile Lys Gly Ile Gly Trp Gly Trp Ala Gly Val
            820                 825                 830
Val Trp Leu Tyr Ser Ile Val Phe Tyr Phe Pro Leu Asp Leu Ile Lys
        835                 840                 845
Phe Phe Ile Arg Phe Val Leu Ser Gly Arg Ala Trp Asp Asn Leu Leu
    850                 855                 860
Glu Asn Lys Thr Ala Phe Thr Thr Lys Lys Asp Tyr Gly Arg Glu Glu
865                 870                 875                 880
Arg Glu Ala Gln Leu Ala Thr Ala Gln Arg Thr Leu His Gly Leu Gln
                885                 890                 895
Pro Pro Glu Ala Ala Thr Ser Thr Leu Phe His Asp Lys Asn Ser Tyr
            900                 905                 910
Arg Glu Leu Ser Glu Ile Ala Glu Gln Ala Lys Arg Arg Ala Glu Ile
        915                 920                 925
Ala Arg Leu Arg Glu Leu Asn Thr Leu Lys Gly His Val Glu Ser Val
    930                 935                 940
Val Lys Leu Lys Gly Leu Asp Ile Asp Thr Ile Gln Gln Asn Tyr Thr
945                 950                 955                 960
Val

<210> SEQ ID NO 32
<211> LENGTH: 40
<212> TYPE: DNA
<213> ORGANISM: Artificial
<220> FEATURE:
<223> OTHER INFORMATION: Amplification primer for the AtAHA5 gene

<400> SEQUENCE: 32
ggattctaga actagtatgg aggaagtgtt cgaggagctg                            40

<210> SEQ ID NO 33
<211> LENGTH: 42
<212> TYPE: DNA
<213> ORGANISM: Artificial
<220> FEATURE:
<223> OTHER INFORMATION: Amplification primer for the AtAHA5 gene

<400> SEQUENCE: 33
cggtatcata agcttgttaa acggtgtaat gttgctgaat cg                         42

<210> SEQ ID NO 34
<211> LENGTH: 27
<212> TYPE: DNA
<213> ORGANISM: Artificial
<220> FEATURE:
<223> OTHER INFORMATION: Primers for site directed mutagenesis of P50S
```

-continued

<400> SEQUENCE: 34
gggttcatgt ggaactcatt gtcgtgg                                          27

<210> SEQ ID NO 35
<211> LENGTH: 27
<212> TYPE: DNA
<213> ORGANISM: Artificial
<220> FEATURE:
<223> OTHER INFORMATION: Primers for site directed mutagenesis of P50S

<400> SEQUENCE: 35
ccacgacaat gagttccaca tgaaccc                                          27

<210> SEQ ID NO 36
<211> LENGTH: 29
<212> TYPE: DNA
<213> ORGANISM: Artificial
<220> FEATURE:
<223> OTHER INFORMATION: Primers for site directed mutagenesis of W857L

<400> SEQUENCE: 36
ggaaagagaa gctcaattgg ctgcagctc                                        29

<210> SEQ ID NO 37
<211> LENGTH: 29
<212> TYPE: DNA
<213> ORGANISM: Artificial
<220> FEATURE:
<223> OTHER INFORMATION: Primers for site directed mutagenesis of W857L

<400> SEQUENCE: 37
gagctgcagc caattgagct tctctttcc                                        29

<210> SEQ ID NO 38
<211> LENGTH: 48
<212> TYPE: DNA
<213> ORGANISM: Artificial
<220> FEATURE:
<223> OTHER INFORMATION: Amplification primer for the promoter pAtAHA5

<400> SEQUENCE: 38
ggggacaact ttgtatagaa aagttgcaac catcatgaca agcgtctg                   48

<210> SEQ ID NO 39
<211> LENGTH: 52
<212> TYPE: DNA
<213> ORGANISM: Artificial
<220> FEATURE:
<223> OTHER INFORMATION: Amplification primer for the promoter pAtAHA5

<400> SEQUENCE: 39
ggggactgct tttttgtaca aacttggggt attcgtacct agacccatca tt              52

<210> SEQ ID NO 40
<211> LENGTH: 922
<212> TYPE: DNA
<213> ORGANISM: Sorghum bicolor
<220> FEATURE:
<221> NAME/KEY: misc_feature
<223> OTHER INFORMATION: proSbMYB60

<400> SEQUENCE: 40
ctccgtcgct agcgttgtaa ttttatcag cctctctcca tctgattgga tgagctgctt       60
ctcctagcta gcacgttgtc aaccattggg gacgccctt aggagtgaaa gtgatgcagt      120

```
tactctactc ccatccggtc caaatcccaa cctaagggat atatgacgaa gagttttcaa    180
tttcagtata atgtgtatag caagtgattt gattttcctg cagattcttg agagagaagg    240
gccaaacctg catatgtgcc aggtgcgcac tcacagtcac acacacggtc ctcatcaatg    300
cccaagaaat ctggagagac acagacaaac gcaagcaatt actccattca tgagcgccac    360
agcagaaaaa ggagtcctcc agaaccggcc gtgttcttgg cttgcacaca cacacacaca    420
cacgcgaaag cagcgcatgc aacaaagcaa agatcacaca cggccggagc aagagagacg    480
cccatattca tgtgatcacc tggctgactt ttgcattgga aagcaacagt gcgagatcaa    540
aagcgaacgc agcacacagc acagcacagc acagggatcg agttgctcta ctccgtatat    600
gaggtcatgc agtatataag cactcacatg cagctatacc ttagctaggg cacctgtgca    660
aggggacagg taggagataa agcaatgtct gctggctaga ataaaaggag gccgatatcg    720
tatcagcaga gggttccagg ggagaaggcc gttctgcagg gccgccgtaa aaggctgtgt    780
aggaagcagc cacagcttct catatcttct tgttcttcga ctacttgcct agctactata    840
tctactagac tagccctagg ctgcttgcta gctagtaggt gtatcgatcg tccgaggtag    900
gaggagacag caggaagcag gc                                            922
```

<210> SEQ ID NO 41
<211> LENGTH: 773
<212> TYPE: DNA
<213> ORGANISM: Zea mays
<220> FEATURE:
<221> NAME/KEY: misc_feature
<223> OTHER INFORMATION: proZmMYB60

<400> SEQUENCE: 41

```
ggaagtgttt tgattttcct gcagttctcg atcgagagag ccctcttga atctgaaaga     60 ggtcgagaag ggccagcctg cgtgtcccag gagcgtgcgc tcacacacac ggtcctcatc    120
aatgcccaag aaatctggag agacacaaac aaacgcaaag caattactca cttcatgagc    180
gccacagcag aaaaggagtc ctcaagcagt acgtcaaccg gccgtgttct cgcacacgca    240
aaagcagcgc atgcaacaaa gcaaagatca cacacccgga gcgaagagac gcccattcat    300
gtgatcacct ggctgacttt tgcattggaa agctacagtc gagatcaaa agcgaacgca    360 gcacagcaca ggccggggga gtggcttata tgaggtcatg cagtatataa gcactcacat    420
gcagctagct aggtagagca cctgtgcatc aaggtaaagc agatgggggcc tgctctgctg    480 cctgcctgcc tgctggcatg cgtgtacgtc ctagaataaa aggaggcccg tatcgtatta    540
gcagagggtt ccagggagaa gagaagggag ggcgaggcca ctggctgtgt aggcagcagc    600
cagccacaca gacacagctt cgttcccatc tcttctcgtt cttcatcacc tacttgccta    660
ctatatctac tagccacgct agctagacta gccttagaaa aggctagctc actagctgct    720
tgctaggtgt gtaccgatcg tccgaggtag gagacacagc acgcagcagg ggt           773
```

<210> SEQ ID NO 42
<211> LENGTH: 674
<212> TYPE: DNA
<213> ORGANISM: Artificial
<220> FEATURE:
<223> OTHER INFORMATION: pro35S

<400> SEQUENCE: 42

```
attgagactt ttcaacaaag ggtaatatcc ggaaacctcc tcggattcca ttgcccagct     60
atctgtcact ttattgtgaa gatagtggaa aaggaaggtg gctcctacaa atgccatcat    120
```

```
tgcgataaag gaaaggccat cgttgaagat gcctctgccg acagtggtcc caaagatgga      180
ccccacccca cgaggagcat cgtggaaaaa gaagacgttc caaccacgtc ttcaaagcaa      240
gtggattgat gtgataacat ggtggagcac gacacacttg tctactccaa aaatatcaaa      300
gatacagtct cagaagacca aagggcaatt gagacttttc aacaaagggt aatatccgga      360
aacctcctcg gattccattg cccagctatc tgtcacttta ttgtgaagat agtggaaaag      420
gaaggtggct cctacaaatg ccatcattgc gataaaggaa aggccatcgt tgaagatgcc      480
tctgccgaca gtggtcccaa agatggaccc ccacccacga ggagcatcgt ggaaaaagaa      540
gacgttccaa ccacgtcttc aaagcaagtg gattgatgtg atatctccac tgacgtaagg      600
gatgacgcac aatcccacta tccttcgcaa gacccttcct ctatataagg aagttcattt      660
catttggaga ggac                                                        674

<210> SEQ ID NO 43
<211> LENGTH: 4023
<212> TYPE: DNA
<213> ORGANISM: Artificial
<220> FEATURE:
<223> OTHER INFORMATION: Cassette 35S-AtAHA5P50S

<400> SEQUENCE: 43
attgagactt ttcaacaaag gtaatatcc ggaaacctcc tcggattcca ttgcccagct       60
atctgtcact ttattgtgaa gatagtggaa aaggaaggtg ctcctacaa atgccatcat      120 tgcgataaag gaaaggccat cgttgaagat gcctctgccg acagtggtcc caaagatgga      180
ccccacccca cgaggagcat cgtggaaaaa gaagacgttc caaccacgtc ttcaaagcaa      240
gtggattgat gtgataacat ggtggagcac gacacacttg tctactccaa aaatatcaaa      300
gatacagtct cagaagacca aagggcaatt gagacttttc aacaaagggt aatatccgga      360
aacctcctcg gattccattg cccagctatc tgtcacttta ttgtgaagat agtggaaaag      420
gaaggtggct cctacaaatg ccatcattgc gataaaggaa aggccatcgt tgaagatgcc      480
tctgccgaca gtggtcccaa agatggaccc ccacccacga ggagcatcgt ggaaaaagaa      540
gacgttccaa ccacgtcttc aaagcaagtg gattgatgtg atatctccac tgacgtaagg      600
gatgacgcac aatcccacta tccttcgcaa gacccttcct ctatataagg aagttcattt      660
catttggaga ggacctcgac tctagaggat ccccgggtac cggcccccc ctcgaggcgc       720 gccaaataat gattttattt tgactgatag tgacctgttc gttgcaacaa attgatgagc      780
aatgcttttt tataatgcca actttgtaca aaaaagcagg ctccatggag gaagtgttcg      840
aggagctgaa atgtacaaaa caaggtctta cggcaaatga agcttctcac cgtcttgacg      900
tttttggtcc taacaagctt gaagagaaga ggaaagcaa gttacttaag ttttttagggt      960 tcatgtggaa ctcattgtcg tgggtgatgg aggtggctgc actaatggca atcgctttgg     1020
ccaacggagg aggacggcca ccggattggc aagactttgt gggatagtg tgtttactat     1080 taatcaactc aaccattagt ttcattgagg aaaataacgc cggtaatgct gcagccgctc     1140
tcatggccgg tctagcccct aagacaaagg ttctcagaga taatcaatgg agcgagcaag     1200
aagcatcgat tctcgtcccc ggagatgtaa tcagcatcaa gctcggcgat atcattcccg     1260
ccgatgcacg tttactcgac ggcgatcctc tcaaaatcga tcaatcatca ctcaccggtg     1320
aatcaatccc cgtcacaaaa aaccccagcg atgaagtctt ctccggctca atatgcaaac     1380
aaggcgaaat cgaagcaatc gtcatcgcca ctggagtcca cattcttc ggcaaagcag     1440 ctcatctcgt cgacaacaca aaccaaatcg gccatttcca gaaagttctc acttcgattg     1500
```

```
gtaacttctg tatctgttcg attgctttag gaatcatcgt tgagctttta gtaatgtatc    1560
cgattcaacg ccggagatat cgagacgaaa tcgataattt acttgttttg ttgatcggag    1620
ggattcctat agctatgcct agtgtgttat ctgttacaat ggcgactggt tctcatagat    1680
tgtttcaaca aggagctatt actaagaaa tgactgctat tgaggaaatg gctggtatgg    1740
atgtattgtg ttgtgataag actggtactc ttacgcttaa taagcttacg gttgataaga    1800
acttagtcga ggttttcgct aaaggagttg gtaaagaaca tgttttcctt ttggctgcga    1860
gagcttcgag gattgagaat caagatgcga ttgatgctgc tattgttgga atgcttgctg    1920
atcctaaaga ggctagagct ggtgttagag aggttcattt ttttccttt aatccggttg    1980 ataagagaac tgctttgact tatgttgact ctgatggaaa ctggcataga gctagtaaag    2040
gagctccaga gcagatactg aacctctgta attgcaagga agatgttagg aggaaagttc    2100
atggagtgat tgataagttt gctgagcgtg gacttcgctc tttggctgtt gcaagacagg    2160
aagttctcga gaagaagaaa gatgctcctg gtggcccatg gcaacttgta ggtcttttac    2220
ctctttttga tcctccgagg catgacagtg ccgagacaat caggagggct ttaaacctcg    2280
gtgttaatgt taagatgata accgggacc agcttgcaat tgggaaagag accggtcgaa    2340
ggcttggaat gggtacgaac atgtatcctt cttctgcgct gctcggacaa gtcaaagatt    2400
cttccttggg tgcacttcct gtggatgaac tgatagagaa ggctgatggg tttgcaggag    2460
tctttccaga acataagtat gagattgttc ataggctgca acaaaggaat cacatatgtg    2520
gcatgactgg agatggtgtg aatgatgccc cggctctcaa gaaggcggat attggtatag    2580
ctgttgttga tgctactgat gctgcgagag cgcttctga tatcgttctc acagaacccg    2640
gattgagtgt tatcattagt gctgtactca ccagtagagc catattccaa gaatgaaaa    2700 attacactat ttatgcggtt tcaatcacga tacgaattgt gtttggcttc atgttcattg    2760
ccctcatatg gcagttcgat ttttcgcctt tcatggttct gatcatagca atcttaaacg    2820
acggaacaat catgacaata tcaaaagaca gaatgaagcc atctccacag ccagatagct    2880
ggaaactcag agatatattc tcgaccggcg tcgtgcttgg aggttaccag gccttgatga    2940
cagtcgtttt cttctgggtg atgaaagaca gtgatttttt ctcgaactat tttggtgtga    3000
gaccactgag ccaacgtcct gaacaaatga tggctgctct gtatctacaa gttagcatca    3060
taagccaggc tctcatcttc gtcaccagat cccgtagctg gtcctacgcc gaatgccctg    3120
gccttctctt acttggtgca tttgtcatag ctcagctggt ggcgacattt atagcagttt    3180
atgcaaactg gagttttgcc cggatagaag agccggttg gggatgggct ggagtgatct    3240
ggctatacag tttcctaacg tacatccctc ttgacttact caagtttgga atccgctatg    3300
ttttgagtgg aaaagcttgg ttaaatcttc ttgagaacaa gactgccttc acgacgaaga    3360
aagactatgg gaaagaggaa agagaagctc aatgggctgc agctcaaaga accctccacg    3420
gacttcaacc agcagagaaa aacaacatct ttaacgaaaa gaatagttac agtgaactct    3480
ctcagattgc tgaacaggct aaacgccgag ctgaggttgt caggctgaga gagataaata    3540
cattaaaagg gcatgtagag tcagtggtga agcttaaagg acttgacatt gacacgattc    3600
agcaacatta caccgtttaa aacccagctt tcttgtacaa agttggcatt ataagaaagc    3660
attgcttatc aatttgttgc aacgaacagg tcactatcag tcaaaataaa atcattattt    3720
gttaattaac tagttctaga gcggccgcc accgcgtgg agctcgaatt ccccgatcg    3780 ttcaaacatt tggcaataaa gtttcttaag attgaatcct gttgccggtc ttgcgatgat    3840
```

| | |
|---|---|
| tatcatataa tttctgttga attacgttaa gcatgtaata attaacatgt aatgcatgac | 3900 |
| gttatttatg agatgggttt ttatgattag agtcccgcaa ttatacattt aatacgcgat | 3960 |
| agaaaacaaa atatagcgcg caaactagga taaattatcg cgcgcggtgt catctatgtt | 4020 |
| act | 4023 |

<210> SEQ ID NO 44
<211> LENGTH: 4023
<212> TYPE: DNA
<213> ORGANISM: Artificial
<220> FEATURE:
<223> OTHER INFORMATION: Cassette 35S-AtAHA5W857L

<400> SEQUENCE: 44

| | |
|---|---|
| attgagactt ttcaacaaag ggtaatatcc ggaaacctcc tcggattcca ttgcccagct | 60 |
| atctgtcact ttattgtgaa gatagtggaa aaggaaggtg gctcctacaa atgccatcat | 120 |
| tgcgataaag gaaaggccat cgttgaagat gcctctgccg acagtggtcc caaagatgga | 180 |
| cccccaccca cgaggagcat cgtggaaaaa gaagacgttc caaccacgtc ttcaaagcaa | 240 |
| gtggattgat gtgataacat ggtggagcac gacacacttg tctactccaa aaatatcaaa | 300 |
| gatacagtct cagaagacca aagggcaatt gagactttc aacaaaggt aatatccgga | 360 |
| aacctcctcg gattccattg cccagctatc tgtcactta ttgtgaagat agtggaaaag | 420 |
| gaaggtggct cctacaaatg ccatcattgc gataaaggaa aggccatcgt tgaagatgcc | 480 |
| tctgccgaca gtggtcccaa agatggaccc ccacccacga ggagcatcgt ggaaaaagaa | 540 |
| gacgttccaa ccacgtcttc aaagcaagtg gattgatgtg atatctccac tgacgtaagg | 600 |
| gatgacgcac aatcccacta tccttcgcaa gacccttcct ctatataagg aagttcattt | 660 |
| catttggaga ggacctcgac tctagaggat ccccgggtac cgggcccccc ctcgaggcgc | 720 |
| gccaaataat gattttattt tgactgatag tgacctgttc gttgcaacaa attgatgagc | 780 |
| aatgctttt tataatgcca actttgtaca aaaaagcagg ctccatggag gaagtgttcg | 840 |
| aggagctgaa atgtacaaaa caaggtctta cggcaaatga agcttctcac cgtcttgacg | 900 |
| tttttggtcc taacaagctt gaagagaaga aggaaagcaa gttacttaag ttttttagggt | 960 |
| tcatgtggaa cccattgtcg tgggtgatgg aggtggctgc actaatggca atcgctttgg | 1020 |
| ccaacggagg aggacggcca ccggattggc aagactttgt ggggatagtg tgtttactat | 1080 |
| taatcaactc aaccattagt ttcattgagg aaaataacgc cggtaatgct gcagccgctc | 1140 |
| tcatggccgg tctagcccct aagacaaagg ttctcagaga taatcaatgg agcgagcaag | 1200 |
| aagcatcgat tctcgtcccc ggagatgtaa tcagcatcaa gctcggcgat atcattcccg | 1260 |
| ccgatgcacg tttactcgac ggcgatcctc tcaaaatcga tcaatcatca ctcaccggtg | 1320 |
| aatcaatccc cgtcacaaaa aaccccagcg atgaagtctt ctccggctca atatgcaaac | 1380 |
| aaggcgaaat cgaagcaatc gtcatcgcca ctggagtcca cattcttc ggcaaagcag | 1440 |
| ctcatctcgt cgacaacaca aaccaaatcg gccatttcca gaaagttctc acttcgattg | 1500 |
| gtaacttctg tatctgttcg attgcttag gaatcatcgt tgagcttta gtaatgtatc | 1560 |
| cgattcaacg ccggagatat cgagacggaa tcgataattt acttgtttg ttgatcggag | 1620 |
| ggattcctat agctatgcct agtgtgttat ctgttacaat ggcgactggt tctcatagat | 1680 |
| tgtttcaaca aggagctatt actaagagaa tgactgctat tgaggaaatg gctggtatgg | 1740 |
| atgtattgtg ttgtgataag actggtactc ttacgcttaa taagcttacg gttgataaga | 1800 |
| acttagtcga ggttttcgct aaaggagttg gtaaagaaca tgttttcctt ttggctgcga | 1860 |

```
gagcttcgag gattgagaat caagatgcga ttgatgctgc tattgttgga atgcttgctg    1920
atcctaaaga ggctagagct ggtgttagag aggttcattt tttccctttt aatccggttg    1980
ataagagaac tgctttgact tatgttgact ctgatggaaa ctggcataga gctagtaaag    2040
gagctccaga gcagatactg aacctctgta attgcaagga agatgttagg aggaaagttc    2100
atggagtgat tgataagttt gctgagcgtg gacttcgctc tttggctgtt gcaagacagg    2160
aagttctcga gaagaagaaa gatgctcctg gtggcccatg gcaacttgta ggtcttttac    2220 ctcttttga tcctccgagg catgacagtg ccgagacaat caggagggct ttaaacctcg    2280
gtgttaatgt taagatgata accgggggacc agcttgcaat tgggaaagag accggtcgaa    2340
ggcttggaat gggtacgaac atgtatcctt cttctgcgct gctcggacaa gtcaaagatt    2400
cttccttggg tgcacttcct gtggatgaac tgatagagaa ggctgatggg tttgcaggag    2460
tctttccaga acataagtat gagattgttc ataggctgca acaaggaat cacatatgtg    2520 gcatgactgg agatggtgtg aatgatgccc cggctctcaa gaaggcggat attggtatag    2580
ctgttgttga tgctactgat gctgcgagag gcgcttctga tatcgttctc acagaacccg    2640
gattgagtgt tatcattagt gctgtactca ccagtagagc catattccaa gaatgaaaa    2700 attacactat ttatgcggtt tcaatcacga tacgaattgt gtttggcttc atgttcattg    2760
ccctcatatg gcagttcgat ttttcgcctt tcatggttct gatcatagca atcttaaacg    2820
acggaacaat catgacaata tcaaaagaca gaatgaagcc atctccacag ccagatagct    2880
ggaaactcag agatatattc tcgaccggcg tcgtgcttgg aggttaccag gccttgatga    2940
cagtcgtttt cttctgggtg atgaaagaca gtgatttttt ctcgaactat tttggtgtga    3000
gaccactgag ccaacgtcct gaacaaatga tggctgctct gtatctacaa gttagcatca    3060
taagccaggc tctcatcttc gtcaccagat cccgtagctg gtcctacgcc gaatgccctg    3120
gccttctctt acttggtgca tttgtcatag ctcagctggt ggcgacattt atagcagttt    3180
atgcaaactg gagttttgcc cggatagaag gagccggttg gggatgggct ggagtgatct    3240
ggctatacag tttcctaacg tacatccctc ttgacttact caagtttgga atccgctatg    3300
ttttgagtgg aaaagcttgg ttaaatcttc ttgagaacaa gactgccttc acgacgaaga    3360
aagactatgg gaaagaggaa agagaagctc aattggctgc agctcaaaga accctccacg    3420
gacttcaacc agcagagaaa aacaacatct ttaacgaaaa gaatagttac agtgaactct    3480
ctcagattgc tgaacaggct aaacgccgag ctgaggttgt caggctgaga gagataaata    3540
cattaaaagg gcatgtagag tcagtggtga agcttaaagg acttgacatt gacacgattc    3600
agcaacatta caccgtttaa aacccagctt tcttgtacaa agttggcatt ataagaaagc    3660
attgcttatc aatttgttgc aacgaacagg tcactatcag tcaaaataaa atcattattt    3720
gttaattaac tagttctaga gcggccgccc accgcggtgg agctcgaatt ccccgatcg    3780 ttcaaacatt tggcaataaa gtttcttaag attgaatcct gttgccggtc ttgcgatgat    3840
tatcatataa tttctgttga attacgttaa gcatgtaata attaacatgt aatgcatgac    3900
gttatttatg agatgggttt ttatgattag agtcccgcaa ttatacattt aatacgcgat    3960
agaaaacaaa atatagcgcg caaactagga taaattatcg cgcgcggtgt catctatgtt    4020
act                                                                  4023
```

<210> SEQ ID NO 45
<211> LENGTH: 4023
<212> TYPE: DNA

<213> ORGANISM: Artificial
<220> FEATURE:
<223> OTHER INFORMATION: Cassette 35S-AtAHA5 WT

<400> SEQUENCE: 45

```
attgagactt tcaacaaag ggtaatatcc ggaaacctcc tcggattcca ttgcccagct      60
atctgtcact ttattgtgaa gatagtggaa aaggaaggtg gctcctacaa atgccatcat    120
tgcgataaag gaaaggccat cgttgaagat gcctctgccg acagtggtcc caaagatgga   180
cccccaccca cgaggagcat cgtggaaaaa gaagacgttc aaccacgtc ttcaaagcaa    240
gtggattgat gtgataacat ggtggagcac gacacacttg tctactccaa aaatatcaaa   300
gatacagtct cagaagacca aagggcaatt gagactttc aacaagggt aatatccgga    360
aacctcctcg gattccattg cccagctatc tgtcactta ttgtgaagat agtggaaaag   420
gaaggtggct cctacaaatg ccatcattgc gataaaggaa aggccatcgt tgaagatgcc   480
tctgccgaca gtggtcccaa agatggaccc cacccacga ggagcatcgt ggaaaaagaa    540
gacgttccaa ccacgtcttc aaagcaagtg gattgatgtg atatctccac tgacgtaagg   600
gatgacgcac aatcccacta tccttcgcaa gaccttcct ctatataagg aagttcattt    660
catttggaga ggacctcgac tctagaggat ccccgggtac cgggcccccc ctcgaggcgc   720
gccaaataat gattttatt tgactgatag tgacctgttc gttgcaacaa attgatgagc    780
aatgctttt tataatgcca actttgtaca aaaaagcagg ctccatggag gaagtgttcg    840
aggagctgaa atgtacaaaa caaggtctta cggcaaatga agcttctcac cgtcttgacg    900
tttttggtcc taacaagctt gaagagaaga aggaaagcaa gttacttaag tttttagggt   960
tcatgtggaa cccattgtcg tgggtgatgg aggtggctgc actaatggca atcgctttgg  1020
ccaacggagg aggacggcca ccggattggc aagactttgt ggggatagtg tgtttactat  1080
taatcaactc aaccattagt ttcattgagg aaaataacgc cggtaatgct gcagccgctc  1140
tcatggccgg tctagcccct aagacaaagg ttctcagaga taatcaatgg agcgagcaag  1200
aagcatcgat tctcgtcccc ggagatgtaa tcagcatcaa gctcggcgat atcattcccg  1260
ccgatgcacg tttactcgac ggcgatcctc tcaaaatcga tcaatcatca ctcaccggtg  1320
aatcaatccc cgtcacaaaa aaccccagcg atgaagtctt ctccggctca atatgcaaac  1380
aaggcgaaat cgaagcaatc gtcatcgcca ctggagtcca cattcttc ggcaaagcag   1440
ctcatctcgt cgacaacaca aaccaaatcg gccatttcca gaaagttctc acttcgattg  1500
gtaacttctg tatctgttcg attgctttag gaatcatcgt tgagctttta gtaatgtatc  1560
cgattcaacg ccggagatat cgagacggaa tcgataattt acttgttttg ttgatcggag  1620
ggattcctat agctatgcct agtgtgttat ctgttacaat ggcgactggt tctcatagat  1680
tgtttcaaca aggagctatt actaagagaa tgactgctat tgaggaaatg gctggtatgg  1740
atgtattgtg ttgtgataag actggtactc ttacgcttaa taagcttacg gttgataaga  1800
acttagtcga ggttttcgct aaaggagttg gtaaagaaca tgttttcctt ttggctgcga  1860
gagcttcgag gattgagaat caagatgcga ttgatgctgc tattgttgga atgcttgctg  1920
atcctaaaga ggctagagct ggtgttagag aggttcattt tttccctttt aatccggttg  1980
ataagagaac tgctttgact tatgttgact ctgatggaaa ctggcataga gctagtaaag  2040
gagctccaga gcagatactg aacctctgta attgcaagga agatgttagg aggaaagttc  2100
atggagtgat tgataagttt gctgagcgtg gacttcgctc tttggctgtt gcaagacagg  2160
aagttctcga gaagaagaaa gatgctcctg gtggcccatg gcaacttgta ggtctttac   2220
```

| | |
|---|---|
| ctcttttga tcctccgagg catgacagtg ccgagacaat caggagggct ttaaacctcg | 2280 |
| gtgttaatgt taagatgata accggggacc agcttgcaat tgggaaagag accggtcgaa | 2340 |
| ggcttggaat gggtacgaac atgtatcctt cttctgcgct gctcggacaa gtcaaagatt | 2400 |
| cttccttggg tgcacttcct gtggatgaac tgatagagaa ggctgatggg tttgcaggag | 2460 |
| tctttccaga acataagtat gagattgttc ataggctgca acaaggaat cacatatgtg | 2520 |
| gcatgactgg agatggtgtg aatgatgccc cggctctcaa gaaggcggat attggtatag | 2580 |
| ctgttgttga tgctactgat gctgcgagag gcgcttctga tatcgttctc acagaacccg | 2640 |
| gattgagtgt tatcattagt gctgtactca ccagtagagc catattccaa gaatgaaaa | 2700 |
| attacactat ttatgcggtt tcaatcacga tacgaattgt gtttggcttc atgttcattg | 2760 |
| ccctcatatg gcagttcgat ttttcgcctt tcatggttct gatcatagca atcttaaacg | 2820 |
| acggaacaat catgacaata tcaaaagaca gaatgaagcc atctccacag ccagatagct | 2880 |
| ggaaactcag agatatattc tcgaccggcg tcgtgcttgg aggttaccag gccttgatga | 2940 |
| cagtcgtttt cttctgggtg atgaaagaca gtgatttttt ctcgaactat tttggtgtga | 3000 |
| gaccactgag ccaacgtcct gaacaaatga tggctgctct gtatctacaa gttagcatca | 3060 |
| taagccaggc tctcatcttc gtcaccagat cccgtagctg gtcctacgcc gaatgccctg | 3120 |
| gccttctctt acttggtgca tttgtcatag ctcagctggt ggcgacattt atagcagttt | 3180 |
| atgcaaactg gagttttgcc cggatagaag gagccggttg gggatgggct ggagtgatct | 3240 |
| ggctatacag tttcctaacg tacatccctc ttgacttact caagtttgga atccgctatg | 3300 |
| ttttgagtgg aaaagcttgg ttaaatcttc ttgagaacaa gactgccttc acgacgaaga | 3360 |
| aagactatgg gaaagaggaa agagaagctc aatgggctgc agctcaaaga accctccacg | 3420 |
| gacttcaacc agcagagaaa aacaacatct ttaacgaaaa gaatagttac agtgaactct | 3480 |
| ctcagattgc tgaacaggct aaacgccgag ctgaggttgt caggctgaga gagataaata | 3540 |
| cattaaaagg gcatgtagag tcagtggtga agcttaaagg acttgacatt gacacgattc | 3600 |
| agcaacatta caccgtttaa aacccagctt tcttgtacaa agttggcatt ataagaaagc | 3660 |
| attgcttatc aatttgttgc aacgaacagg tcactatcag tcaaaataaa atcattattt | 3720 |
| gttaattaac tagttctaga gcggccgccc accgcggtgg agctcgaatt ccccgatcg | 3780 |
| ttcaaacatt tggcaataaa gtttcttaag attgaatcct gttgccggtc ttgcgatgat | 3840 |
| tatcatataa tttctgttga attacgttaa gcatgtaata attaacatgt aatgcatgac | 3900 |
| gttatttatg agatgggttt ttatgattag agtcccgcaa ttatacattt aatacgcgat | 3960 |
| agaaaacaaa atatagcgcg caaactagga taaattatcg cgcgcggtgt catctatgtt | 4020 |
| act | 4023 |

```
<210> SEQ ID NO 46
<211> LENGTH: 2356
<212> TYPE: DNA
<213> ORGANISM: Arabidopsis thaliana
<220> FEATURE:
<221> NAME/KEY: misc_feature
<223> OTHER INFORMATION: pAtAHA5

<400> SEQUENCE: 46
```

| | |
|---|---|
| aaccatcatg acaagcgtct ggattttggg aatctaggat ttttgaaca tatagtgtgg | 60 |
| tgattttttg gggagaagag atcattgttg atgtatgttg cctgagttat ggccgcgacg | 120 |
| aaaaaataga ctgaaatgtg tgaaaagatg gtataaatat ctttacctag gtttctaggt | 180 |

```
tttgattact gggcatgtga aatgggtttt aataaatggg cttgggcttg taaaattgtg      240
gaattaagct attgtaatca cgcatatgag ttatctaatt ggataactta ttagattgta      300
ataatgaggg aaaaaaaaag attattataa tgagaggtcc acatttaaaa tgatgtgaca      360
ctcttagcaa ataaatataa catggcaaaa tttagaagtg ttgtcaaaaa acgataagcg      420
taaaatggaa attgtgactg aaccaccata agaagcgtct ggattttttgg agtccgagag     480 atttagaaag tggagtgtgg ttgttttttt tagagggggga atgttgttgt ttatgccatt    540
agagtcatgg tggcgtcgaa gaacaataag tatatgtggg aatcagagat gtgtgtaaga     600
gaaacaaaaa tttatttggt tgggttttga attttcaaga aatgttaaa ttatttcatc      660 gagtttcttt ttttttctct atgttaggaa atggtatggt caaaatctat tgatgatggt     720
gatgcctaac attaacaaaa ccaatagaag ggagacaaga gacataagac atcttcttga     780
aattcatcaa cattacaaac ttactaaaac tcctcctccc aatcccaaat gaatatgtac     840
ttcttaaagc cacgtgtctt tctcttttttc attaatattt atttattttt ttaaaatgtg    900
aaattatttc tttggtttaa tatctctgga tcattcttct acaatgatca caagtattta    960
gatcatgtgt aaatagtccc atcatgaagt tttaattacc aatcggtatt gcacatcacc    1020
gattggtact gatccacctg cacttttgtc gatcttttgg gacaacgaaa aagaaactaa    1080
tttaatatat tttgttatcc gctcgaagat attaattata agcttaatt tggaacttct     1140 ttatatcaat tatatatata tataacttct ttgttaatag aaaatgggaa cgatccaaaa    1200
cttaagacat ttgatctcca caaggccgtc gacgtacaga gaagaagaat ggccaaaaat    1260
aagtaaataa aagagaagaa accgagggga agatgatttt gcattgccac gacccacgag    1320
catccatcgg ccatcgcctt tttggattca catggcaaag acaaacttcg atcttccttt    1380
tttctcgtga agttattatc tctctaattt ctagtctggt cgaacctata tttcatcata    1440
tatatcatta tttaattcat atgctgatgc atgggacatt atcatgttaa gtcattacaa    1500
aaaaataaaa ataaaaataa cttacgttgg actctcagtt taccttctcc tatggatttc    1560
acttccttgt ataagaatat acatcttact caaatcatga tttatatgca attttctttt    1620
gtgagatttt ttttacatat aaaccagaaa tgttgaaaga agaatatcca aacacaacaa    1680 ataatagaa gaaatctcac gtagaacatg gaaatggaaa aagaagtgaa ctcgtgaacc      1740 gatatatta ccaaaagtgc acacatagac aagtctttct cattaaagcc caatttcaca      1800
ctttcacatt ttcgtgacgt cttttgaagt tttgaatacg aattaatgtt catgtacgct    1860
ataaagacct aaaaggttgt catatttctc cactttcatc ttctcttcac aactatccta    1920 aaccttttt ccttttcttc ttcttcactc tctttcttcc cggcgtcact atggcggctg     1980
ccgccgggta aaggcagcga actcgaccac atcaagaatg aatccgttga tctggtatat    2040
atatttacgt cttcttagtt ttctattatc tatatgtttt aaaaaatctt tggccctact    2100
aattttaaat tttctgttac ataaaagata catatatgta tagtacgtaa ctagtaacta    2160
ctttgatcta atcagttaat atatttgtcc catgcgattt actcatgttt ccattagaaa    2220
tgattagtca aaattatata aatgatgggt ctaggtacga ataccctaat atatttgtcc    2280
catgcgattt actcatgttt ccattagaaa tgattagtca aaattatata aatgatgggt    2340
ctaggtacga ataccc                                                    2356
```

<210> SEQ ID NO 47
<211> LENGTH: 6253
<212> TYPE: DNA

<213> ORGANISM: Artificial
<220> FEATURE:
<223> OTHER INFORMATION: Cassette pAtAHA5-AtAHA5W857L

<400> SEQUENCE: 47

```
aaccatcatg acaagcgtct ggattttttgg aatctaggat tttttgaaca tatagtgtgg      60
tgatttttttg gggagaagag atcattgttg atgtatgttg cctgagttat ggccgcgacg     120
aaaaaataga ctgaaatgtg tgaaaagatg gtataaatat ctttacctag gtttctaggt     180
tttgattact gggcatgtga atgggtttt aataaatggg cttgggcttg taaaattgtg      240
gaattaagct attgtaatca cgcatatgag ttatctaatt ggataactta ttagattgta     300
ataatgaggg aaaaaaaaag attattataa tgagaggtcc acatttaaaa tgatgtgaca     360
ctcttagcaa ataaatataa catggcaaaa tttagaagtg ttgtcaaaaa acgataagcg     420
taaaatggaa attgtgactg aaccaccata agaagcgtct ggattttttgg agtccgagag     480
atttagaaag tggagtgtgg ttgtttttttt tagaggggga atgttgttgt ttatgccatt     540
agagtcatgg tggcgtcgaa gaacaataag tatatgtggg aatcagagat gtgtgtaaga     600
gaaacaaaaa tttatttggt tgggttttga attttcaaga aaatgttaaa ttatttcatc     660
gagtttctttt tttttttctct atgttaggaa atggtatggt caaaatctat tgatgatggt     720
gatgcctaac attaacaaaa ccaatagaag ggagacaaga gacataagac atcttcttga     780
aattcatcaa cattacaaac ttactaaaac tcctcctccc aatcccaaat gaatatgtac     840
ttcttaaagc cacgtgtctt tctcttttttc attaatattt atttattttt ttaaaatgtg     900
aaattatttc tttggtttaa tatctctgga tcattcttct acaatgatca caagtattta     960
gatcatgtgt aaatagtccc atcatgaagt tttaattacc aatcggtatt gcacatcacc    1020
gattggtact gatccacctg cacttttgtc gatcttttgg gacaacgaaa aagaaactaa    1080
tttaatatat tttgttatcc gctcgaagat attaattata agctttaatt tggaacttct    1140
ttatatcaat tatatatata taaacttct ttgttaatag aaaatgggaa cgatccaaaa    1200
cttaagacat ttgatctcca caaggccgtc gacgtacaga gaagaagaat ggccaaaaat    1260
aagtaaataa aagagaagaa accgagggga agatgatttt gcattgccac gacccacgag    1320
catccatcgg ccatcgcctt tttggattca catggcaaag acaaacttcg atcttccttt    1380
tttctcgtga agttattatc tctctaattt ctagtctggt cgaacctata tttcatcata    1440
tatatcatta tttaattcat atgctgatgc atgggacatt atcatgttaa gtcattacaa    1500
aaaaataaaa ataaaaataa cttacgttgg actctcagtt taccttctcc tatggatttc    1560
acttccttgt ataagaatat acatcttact caaatcatga tttatatgca attttctttt    1620
gtgagatttt ttttacatat aaaccagaaa tgttgaaaga agaatatcca aacacaacaa    1680
aataatagaa gaaatctcac gtagaacatg gaaatggaaa aagaagtgaa ctcgtgaacc    1740
gatatattta ccaaaagtgc acacatagac aagtctttct cattaaagcc caatttcaca    1800
ctttcacatt ttcgtgacgt cttttgaagt tttgaatacg aattaatgtt catgtacgct    1860
ataaagacct aaaaggttgt catatttctc cactttcatc ttctcttcac aactatccta    1920
aacctttttt cctttcttc ttcttcactc tctttcttcc cggcgtcact atggcggctg    1980
ccgccgggta aaggcagcga actcgaccac atcaagaatg aatccgttga tctggtatat    2040
atatttacgt cttcttagtt ttctattatc tatatgtttt aaaaaatctt tggccctact    2100
aattttaaat tttctgttac ataaaagata catatatgta tagtacgtaa ctagtaacta    2160
ctttgatcta atcagttaat atatttgtcc catgcgattt actcatgttt ccattagaaa    2220
```

```
tgattagtca aaattatata aatgatgggt ctaggtacga ataccctaat atatttgtcc    2280
catgcgattt actcatgttt ccattagaaa tgattagtca aaattatata aatgatgggt    2340
ctaggtacga atacccatgc aagtttgtac aaaaaagcag cttaatggt gagcaagggc     2400 gaggagctgt tcaccggggt ggtgcccatc ctggtcgagc tggacggcga cgtaaacggc    2460
cacaagttca gcgtgtccgg cgagggcgag ggcgatgcca cctacggcaa gctgaccctg    2520
aagttcatct gcaccaccgg caagctgccc gtgccctggc ccaccctcgt gaccaccctg    2580
acctacggcg tgcagtgctt cagccgctac cccgaccaca tgaagcagca cgacttcttc    2640
aagtccgcca tgcccgaagg ctacgtccag gagcgcacca tcttcttcaa ggacgacggc    2700
aactacaaga cccgcgccga ggtgaagttc gagggcgaca ccctggtgaa ccgcatcgag    2760
ctgaagggca tcgacttcaa ggaggacggc aacatcctgg ggcacaagct ggagtacaac    2820
tacaacagcc acaacgtcta tatcatggcc gacaagcaga agaacggcat caaggtgaac    2880
ttcaagatcc gccacaacat cgaggacggc agcgtgcagc tcgccgacca ctaccagcag    2940
aacaccccca tcggcgacgg ccccgtgctg ctgcccgaca accactacct gagcacccag    3000
tccgccctga gcaaagaccc caacgagaag cgcgatcaca tggtcctgct ggagttcgtg    3060
accgccgccg ggatcactct cggcatggac gagctgtaca agtacccagc tttcttgtac    3120
aaagtggcta tggaggaagt gttcgaggag ctgaaatgta caaaacaagg tcttacggca    3180
aatgaagctt ctcaccgtct tgacgttttt ggtcctaaca agcttgaaga aagaaggaa    3240 agcaagttac ttaagttttt agggttcatg tggaacccat tgtcgtgggt gatggaggtg    3300
gctgcactaa tggcaatcgc tttggccaac ggaggaggac ggccaccgga ttggcaagac    3360
tttgtgggga tagtgtgttt actattaatc aactcaacca ttagtttcat tgaggaaaat    3420
aacgccggta atgctgcagc cgctctcatg gccggtctag cccctaagac aaaggttctc    3480
agagataatc aatggagcga gcaagaagca tcgattctcg tccccggaga tgtaatcagc    3540
atcaagctcg gcgatatcat tcccgccgat gcacgtttac tcgacggcga tcctctcaaa    3600
atcgatcaat catcactcac cggtgaatca atccccgtca caaaaaaccc cagcgatgaa    3660
gtcttctccg gctcaatatg caaacaaggc gaaatcgaag caatcgtcat cgccactgga    3720
gtccacacat tcttcggcaa agcagctcat ctcgtcgaca acacaaacca aatcggccat    3780
ttccagaaag ttctcacttc gattggtaac ttctgtatct gttcgattgc tttaggaatc    3840
atcgttgagc ttttagtaat gtatccgatt caacgccgga gatatcgaga cggaatcgat    3900
aatttacttg ttttgttgat cggagggatt cctatagcta tgcctagtgt gttatctgtt    3960
acaatggcga ctggttctca tagattgttt caacaaggag ctattactaa gagaatgact    4020
gctattgagg aaaatgctgg tatggatgta ttgtgttgtg ataagactgg tactcttacg    4080
cttaataagc ttacggttga taagaactta gtcgaggttt tcgctaaagg agttggtaaa    4140
gaacatgttt tccttttggc tgcgagagct tcgaggattg agaatcaaga tgcgattgat    4200
gctgctattg ttggaatgct tgctgatcct aaagaggcta gagctggtgt tagagaggtt    4260
cattttttcc ctttaatcc ggttgataag agaactgctt tgacttatgt tgactctgat    4320
ggaaactggc atagagctag taaaggagct ccagagcaga tactgaacct ctgtaattgc    4380
aaggaagatg ttaggaggaa agttcatgga gtgattgata gtttgctga gcgtggactt    4440 cgctcttttgg ctgttgcaag acaggaagtt ctcgagaaga agaaagatgc tcctggtggc    4500
ccatggcaac ttgtaggtct tttacctctt tttgatcctc cgaggcatga cagtgccgag    4560
```

| | | | | |
|---|---|---|---|---|
| acaatcagga | gggctttaaa | cctcggtgtt | aatgttaaga | tgataaccgg ggaccagctt | 4620 |
| gcaattggga | aagagaccgg | tcgaaggctt | ggaatgggta | cgaacatgta tccttcttct | 4680 |
| gcgctgctcg | acaagtcaa | agattcttcc | ttgggtgcac | ttcctgtgga tgaactgata | 4740 |
| gagaaggctg | atgggtttgc | aggagtcttt | ccagaacata | agtatgagat tgttcatagg | 4800 |
| ctgcaacaaa | ggaatcacat | atgtggcatg | actggagatg | gtgtgaatga tgccccggct | 4860 |
| ctcaagaagg | cggatattgg | tatagctgtt | gttgatgcta | ctgatgctgc gagaggcgct | 4920 |
| tctgatatcg | ttctcacaga | acccggattg | agtgttatca | ttagtgctgt actcaccagt | 4980 |
| agagccatat | tccaaagaat | gaaaaattac | actatttatg | cggtttcaat cacgatacga | 5040 |
| attgtgtttg | gcttcatgtt | cattgccctc | atatggcagt | tcgattttc gcctttcatg | 5100 |
| gttctgatca | tagcaatctt | aaacgacgga | acaatcatga | caatatcaaa agacagaatg | 5160 |
| aagccatctc | cacagccaga | tagctggaaa | ctcagagata | tattctcgac cggcgtcgtg | 5220 |
| cttggaggtt | accaggcctt | gatgacagtc | gttttcttct | gggtgatgaa agacagtgat | 5280 |
| ttttttctcga | actattttgg | tgtgagacca | ctgagccaac | gtcctgaaca atgatggct | 5340 |
| gctctgtatc | tacaagttag | catcataagc | caggctctca | tcttcgtcac cagatcccgt | 5400 |
| agctggtcct | acgccgaatg | ccctggcctt | ctcttacttg | gtgcatttgt catagctcag | 5460 |
| ctggtggcga | catttatagc | agtttatgca | aactggagtt | tgcccggat agaaggagcc | 5520 |
| ggttggggat | gggctggagt | gatctggcta | tacagtttcc | taacgtacat ccctcttgac | 5580 |
| ttactcaagt | ttggaatccg | ctatgttttg | agtggaaaag | cttggttaaa tcttcttgag | 5640 |
| aacaagactg | ccttcacgac | gaagaaagac | tatgggaaag | aggaaagaga agctcaattg | 5700 |
| gctgcagctc | aaagaaccct | ccacggactt | caaccagcag | agaaaaacaa catctttaac | 5760 |
| gaaaagaata | gttacagtga | actctctcag | attgctgaac | aggctaaacg ccagctgag | 5820 |
| gttgtcaggc | tgagagagat | aaatacatta | aagggcatg | tagagtcagt ggtgaagctt | 5880 |
| aaaggacttg | acattgacac | gattcagcaa | cattacaccg | tttaacaact ttattataca | 5940 |
| tagttgataa | ttcactggcc | gtcgttttac | aacgtcgtga | ctgggaaaac gatctaactg | 6000 |
| actagccgcg | gccatggcgg | ccgggagcgg | ccatgctaga | gtccgcaaaa atcaccagtc | 6060 |
| tctctctaca | aatctatctc | tctctatttt | tctccagaat | aatgtgtgag tagttcccag | 6120 |
| ataagggaat | tagggttctt | atagggtttc | gctcatgtgt | tgagcatata agaaaccctt | 6180 |
| agtatgtatt | tgtatttgta | aaatacttct | atcaataaaa | tttctaattc ctaaaaccaa | 6240 |
| aatccagtga | cct | | | | 6253 |

<210> SEQ ID NO 48
<211> LENGTH: 6253
<212> TYPE: DNA
<213> ORGANISM: Artificial
<220> FEATURE:
<223> OTHER INFORMATION: Cassette pAtAHA5-AtAHA5 WT

<400> SEQUENCE: 48

| | | | | |
|---|---|---|---|---|
| aaccatcatg | acaagcgtct | ggattttggg | aatctaggat | ttttgaaca tatagtgtgg | 60 |
| tgatttttg | gggagaagag | atcattgttg | atgtatgttg | cctgagttat ggccgcgacg | 120 |
| aaaaaataga | ctgaaatgtg | tgaaagatg | gtataaatat | ctttacctag gtttctaggt | 180 |
| tttgattact | gggcatgtga | atgggttttt | aataaatggg | cttgggcttg taaaattgtg | 240 |
| gaattaagct | attgtaatca | cgcatatgag | ttatctaatt | ggataactta ttagattgta | 300 |
| ataatgaggg | aaaaaaaaag | attattataa | tgagaggtcc | acatttaaaa tgatgtgaca | 360 |

```
ctcttagcaa ataaatataa catggcaaaa tttagaagtg ttgtcaaaaa acgataagcg    420
taaaatggaa attgtgactg aaccaccata agaagcgtct ggattttgg agtccgagag      480 atttagaaag tggagtgtgg ttgtttttt tagagggga atgttgttgt ttatgccatt       540
agagtcatgg tggcgtcgaa gaacaataag tatatgtggg aatcagagat gtgtgtaaga    600
gaaacaaaaa tttatttggt tgggttttga atttcaaga aaatgttaaa ttatttcatc     660
gagtttcttt tttttctct atgttaggaa atggtatggt caaaatctat tgatgatggt     720
gatgcctaac attaacaaaa ccaatagaag ggagacaaga gacataagac atcttcttga    780
aattcatcaa cattacaaac ttactaaaac tcctcctccc aatcccaaat gaatatgtac    840
ttcttaaagc cacgtgtctt tctctttttc attaatattt atttatttt ttaaaatgtg     900 aaattatttc tttggttaa tatctctgga tcattcttct acaatgatca caagtattta    960
gatcatgtgt aaatagtccc atcatgaagt tttaattacc aatcggtatt gcacatcacc   1020
gattggtact gatccacctg cacttttgtc gatcttttgg gacaacgaaa aagaaactaa   1080
tttaatatat tttgttatcc gctcgaagat attaattata agctttaatt tggaacttct   1140
ttatatcaat tatatatata taaacttct ttgttaatag aaaatgggaa cgatccaaaa    1200
cttaagacat ttgatctcca caaggccgtc gacgtacaga gaagaagaat ggccaaaaat   1260
aagtaaataa aagagaagaa accgagggga agatgatttt gcattgccac gacccacgag   1320
catccatcgg ccatcgcctt tttggattca catggcaaag acaaacttcg atcttccttt   1380
tttctcgtga agttattatc tctctaattt ctagtctggt cgaacctata tttcatcata   1440
tatatcatta tttaattcat atgctgatgc atgggacatt atcatgttaa gtcattacaa   1500
aaaaataaaa ataaaaataa cttacgttgg actctcagtt taccttctcc tatggatttc   1560
acttccttgt ataagaatat acatcttact caaatcatga tttatatgca attttctttt   1620
gtgagatttt ttttacatat aaaccagaaa tgttgaaaga agaatatcca aacacaacaa   1680
aataatagaa gaaatctcac gtagaacatg gaaatggaaa aagaagtgaa ctcgtgaacc   1740
gatatattta ccaaaagtgc acacatagac aagtctttct cattaaagcc caatttcaca   1800 cttcacatt ttcgtgacgt cttttgaagt tttgaatacg aattaatgtt catgtacgct    1860
ataaagacct aaaaggttgt catatttctc cactttcatc ttctcttcac aactatccta   1920 aaccttttt ccttttcttc ttcttcactc tctttcttcc cggcgtcact atggcggctg    1980
ccgccgggta aaggcagcga actcgaccac atcaagaatg aatccgttga tctggtatat   2040
atatttacgt cttcttagtt ttctattatc tatatgtttt aaaaaatctt tggccctact   2100 aatttttaaat tttctgttac ataaaagata catatatgta tagtacgtaa ctagtaacta   2160
ctttgatcta atcagttaat atatttgtcc catgcgattt actcatgttt ccattagaaa   2220
tgattagtca aaattatata aatgatgggt ctaggtacga ataccctaat atatttgtcc   2280
catgcgattt actcatgttt ccattagaaa tgattagtca aaattatata aatgatgggt   2340
ctaggtacga atacccatgc aagtttgtac aaaaaagcag gcttaatggt gagcaagggc   2400
gaggagctgt tcaccggggt ggtgcccatc ctggtcgagc tggacggcga cgtaaacggc   2460
cacaagttca gcgtgtccgg cgagggcgag ggcgatgcca cctacggcaa gctgaccctg   2520
aagttcatct gcaccaccgg caagctgccc gtgccctggc ccaccctcgt gaccaccctg   2580
acctacggcg tgcagtgctt cagccgctac cccgaccaca tgaagcagca cgacttcttc   2640
aagtccgcca tgcccgaagg ctacgtccag gagcgcacca tcttcttcaa ggacgacggc   2700
```

```
aactacaaga cccgcgccga ggtgaagttc gagggcgaca ccctggtgaa ccgcatcgag    2760
ctgaagggca tcgacttcaa ggaggacggc aacatcctgg ggcacaagct ggagtacaac    2820
tacaacagcc acaacgtcta tatcatggcc gacaagcaga agaacggcat caaggtgaac    2880
ttcaagatcc gccacaacat cgaggacggc agcgtgcagc tcgccgacca ctaccagcag    2940
aacacccca tcggcgacgg ccccgtgctg ctgcccgaca ccactacct gagcacccag    3000
tccgccctga gcaaagaccc caacgagaag cgcgatcaca tggtcctgct ggagttcgtg    3060
accgccgccg ggatcactct cggcatggac gagctgtaca agtacccagc tttcttgtac    3120
aaagtggcta tggaggaagt gttcgaggag ctgaaatgta caaaacaagg tcttacggca    3180
aatgaagctt ctcaccgtct tgacgttttt ggtcctaaca gcttgaaga gaagaaggaa    3240
agcaagttac ttaagttttt agggttcatg tggaacccat tgtcgtgggt gatggaggtg    3300
gctgcactaa tggcaatcgc tttggccaac ggaggaggac ggccaccgga ttggcaagac    3360
tttgtgggga tagtgtgttt actattaatc aactcaacca ttagtttcat tgaggaaaat    3420
aacgccggta atgctgcagc cgctctcatg gccggtctag cccctaagac aaaggttctc    3480
agagataatc aatggagcga gcaagaagca tcgattctcg tccccggaga tgtaatcagc    3540
atcaagctcg gcgatatcat tcccgccgat gcacgtttac tcgacggcga tcctctcaaa    3600
atcgatcaat catcactcac cggtgaatca atccccgtca caaaaaaccc cagcgatgaa    3660
gtcttctccg gctcaatatg caaacaaggc gaaatcgaag caatcgtcat cgccactgga    3720
gtccacacat tcttcggcaa agcagctcat ctcgtcgaca cacaaaccaa atcggccat    3780
ttccagaaag ttctcacttc gattggtaac ttctgtatct gttcgattgc tttaggaatc    3840
atcgttgagc ttttagtaat gtatccgatt caacgccgga gatatcgaga cggaatcgat    3900
aatttacttg ttttgttgat cggagggatt cctatagcta tgcctagtgt gttatctgtt    3960
acaatggcga ctggttctca tagattgttt caacaaggag ctattactaa gagaatgact    4020
gctattgagg aaatggctgg tatggatgta ttgtgttgtg ataagactgg tactcttacg    4080
cttaataagc ttacggttga taagaactta gtcgaggttt cgctaaagg agttggtaaa    4140
gaacatgttt tcctttttggc tgcgagagct tcgaggattg agaatcaaga tgcgattgat    4200
gctgctattg ttggaatgct tgctgatcct aaagaggcta gagctggtgt tagagaggtt    4260
cattttttcc cttttaatcc ggttgataag agaactgctt tgacttatgt tgactctgat    4320
ggaaactggc atagagctag taaaggagct ccagagcaga tactgaacct ctgtaattgc    4380
aaggaagatg ttaggaggaa agttcatgga gtgattgata gtttgctga gcgtggactt    4440
cgctctttgg ctgttgcaag acaggaagtt ctcgagaaga agaaagatgc tcctggtggc    4500
ccatggcaac ttgtaggtct tttacctctt tttgatcctc cgaggcatga cagtgccgag    4560
acaatcagga gggctttaaa cctcggtgtt aatgttaaga tgataaccgg ggaccagctt    4620
gcaattggga agagaccgg tcgaaggctt ggaatgggta cgaacatgta tccttcttct    4680
gcgctgctcg gacaagtcaa agattcttcc ttgggtgcac ttcctgtgga tgaactgata    4740
gagaaggctg atgggtttgc aggagtcttt ccagaacata gtatgagat tgttcatagg    4800
ctgcaacaaa ggaatcacat atgtggcatg actgagatg gtgtgaatga tgccccggct    4860
ctcaagaagg cggatattgg tatagctgtt gttgatgcta ctgatgctgc gagaggcgct    4920
tctgatatcg ttctcacaga acccggattg agtgttatca ttagtgctgt actcaccagt    4980
agagccatat tccaaagaat gaaaaattac actatttatg cggtttcaat cacgatacga    5040
attgtgtttg gcttcatgtt cattgccctc atatggcagt tcgattttc gcctttcatg    5100
```

| | |
|---|---|
| gttctgatca tagcaatctt aaacgacgga acaatcatga caatatcaaa agacagaatg | 5160 |
| aagccatctc cacagccaga tagctggaaa ctcagagata tattctcgac cggcgtcgtg | 5220 |
| cttggaggtt accaggcctt gatgacagtc gttttcttct gggtgatgaa agacagtgat | 5280 |
| tttttctcga actattttgg tgtgagacca ctgagccaac gtcctgaaca aatgatggct | 5340 |
| gctctgtatc tacaagttag catcataagc caggctctca tcttcgtcac cagatcccgt | 5400 |
| agctggtcct acgccgaatg ccctggcctt ctcttacttg gtgcatttgt catagctcag | 5460 |
| ctggtggcga catttatagc agtttatgca aactggagtt ttgcccggat agaaggagcc | 5520 |
| ggttggggat gggctggagt gatctggcta tacagtttcc taacgtacat ccctcttgac | 5580 |
| ttactcaagt ttggaatccg ctatgttttg agtggaaaag cttggttaaa tcttcttgag | 5640 |
| aacaagactg ccttcacgac gaagaaagac tatgggaaag aggaaagaga agctcaatgg | 5700 |
| gctgcagctc aaagaaccct ccacggactt caaccagcag agaaaaacaa catctttaac | 5760 |
| gaaaagaata gttacagtga actctctcag attgctgaac aggctaaacg ccgagctgag | 5820 |
| gttgtcaggc tgagagagat aaatacatta aaagggcatg tagagtcagt ggtgaagctt | 5880 |
| aaaggacttg acattgacac gattcagcaa cattacaccg tttaacaact ttattataca | 5940 |
| tagttgataa ttcactggcc gtcgttttac aacgtcgtga ctgggaaaac gatctaactg | 6000 |
| actagccgcg gccatggcgg ccgggagcgg ccatgctaga gtccgcaaaa atcaccagtc | 6060 |
| tctctctaca aatctatctc tctctatttt tctccagaat aatgtgtgag tagttcccag | 6120 |
| ataagggaat tagggttctt ataggttttc gctcatgtgt tgagcatata agaaaccctt | 6180 |
| agtatgtatt tgtatttgta aaatacttct atcaataaaa tttctaattc ctaaaaccaa | 6240 |
| aatccagtga cct | 6253 |

```
<210> SEQ ID NO 49
<211> LENGTH: 2886
<212> TYPE: DNA
<213> ORGANISM: Zea mays
<220> FEATURE:
<221> NAME/KEY: misc_feature
<223> OTHER INFORMATION: ZmAHA5W885L version 1

<400> SEQUENCE: 49
```

| | |
|---|---|
| atggggccac tgcagcggcg gcctacggct atgggggggc tggaggagat taagaacgag | 60 |
| gcggttgacc tggagaacat cccgattgag gaggtgttcg agcagctgaa gtgcacccgc | 120 |
| gagggcctct ccagctcgga ggggcagcag cgcctggaga tcttcggccc caaccgcctg | 180 |
| gaggagaaga aggagtccaa gatcctcaag ttcctgggct tcatgtggaa cccactgagc | 240 |
| tgggttatgg agatggctgc cgtgatggct atcgcgctcg ctaatggcgg gggcaagcca | 300 |
| ccagactggg aggatttcgt cggcatcatt gtgctcctgg tcatcaactc gacgatttct | 360 |
| ttcatcgagg agaacaatgc tggcaacgct gccgcggctc tgatggctaa tctcgctcct | 420 |
| aagacaaagg tgctgaggga tggccgctgg ggggagcagg aggccgcgat cctggtgccg | 480 |
| ggcgacattg tcagcatcaa gctcggggac atcgttccag ctgatgctag gctcctggag | 540 |
| ggggacccac tcaaggtgga tcagagcgct ctgacgggcg agtcgctccc tgtcacaaag | 600 |
| gggccaggcg acgaggtttt ctccggcagc acgtgcaagc agggggagat tgaggccgtg | 660 |
| gtcatcgcga ctggcgtcca caccttcttc gggaaggctg cccatctggt cgactcgact | 720 |
| aaccaggttg gccacttcca gcaggtgctc accgcgatcg ggaatttctg catttgctct | 780 |
| atcgctgtgg gcattgttgt ggagatcatt gtcatgttcc caatccagca taggcgctac | 840 |

```
cgctccggca ttgagaacct cctggtgctc ctgatcgggg gcatccccat tgcgatgcca      900
acggttctga gcgtgacaat ggccatcggc agccacaagc tctcgcagca gggggccatt      960
acgaagagga tgacagccat cgaggagatg gcggggatgg acgtcctgtg ctctgataag     1020
acaggcactc tcaccctgaa caagctgtca gtggacaaga tctcgttga ggtgttctgc      1080 aagggcgttg acaaggatca cgtgctcctg ctcgcggctc gggcctcccg caccgagaac     1140
caggacgcga tcgatgctgc gatggtgggg atgctcgccg atccaaagga ggctagggcc     1200
ggcattcggg agatccattt cctgcccttc aatccagtcg acaagaggac tgctctcacc     1260
tacatcgacg ccgatggcca ctggcatcgg gtgagcaagg ggccccaga gcagatcctc      1320 gacctgtgcc actgcaagga ggatctgcgg cgcaaggtgc atggcatcat tgacaagtac     1380
gcggagaggg ggctcaggtc gctggcggtc gctcggcagg aggttcccga cgcaacaag      1440 gagtctcctg ggggcccgtg gcagttcgtc ggcctgctcc cactcttcga cccacctcgg     1500
cacgattccg cggagactat ccgcaaggct ctcgtgctgg gcgtcaatgt taagatgatt     1560
accggggatc agctggccat cggcaaggag acggggagga ggctcgggat gggcacaaac     1620
atgtacccgt cttcagcgct gctcggccag aataaggacg ctaccctgga ggccctcccg     1680
gtggacgagc tgatcgagaa ggcggatggc ttcgctgggg tcttcccgga gcacaagtac     1740
gagattgtta agaggctgca ggagaagaag catatcgtgg gcatgacggg ggacggcgtc     1800
aacgatgctc ctgctctcaa gaaggcggat atcggcattg ctgtcgctga cgctacggat     1860
gctgctcggt cggcctctga catcgttctg acagagccgg gcctctctgt gatcatttca     1920
gcggtcctga cctcacgctg cattttccag aggatgaaga actacactat ctacgcggtt     1980
tccatcacca ttcgcatcgt gctcggcttc atgctcattg ccctgatctg gcagtacgac     2040
ttctctccgt tcatggtcct gatcattgcc atcctcaatg acggcacgat tatgacaatc     2100
tcaaaggata gggtgaagcc atcgcctctg ccggactctt ggaagctcaa ggagattttc     2160
gccacaggca tcgtgctggg gtcctacctc gctctgatga ctgtcatctt cttctgggcc     2220
atgcacaaga ccgacttctt cagcgataag ttcggcgtcc gctccatcag ggacagcgag     2280
catgagatga tgtcggcgct ctacctgcag gtctcaattg tttcccaggc cctcatcttc     2340
gtgacccggt cacgctcctg gagcttcgtt gagaggccag gctgctcct ggtgacggcc      2400 ttcctcctgg cgcagctggt cgctacattc ctcgccgttt acgcgaactg ggcttcgcg     2460 cgcattaagg ggatcggctg ggggtgggct ggcgtcgttt ggctgtactc catcgtcttc     2520
tacttcccgc tcgacctgat taagttcttc atcaggttcg tgctcagcgg ccgggcgtgg     2580
gataacctcc tggagaataa gacggccttc accacgaaga aggactacgg cagggaggag     2640
cgcgaggctc agctcgctac tgctcagcgc accctccacg gcctgcagcc accagaggct     2700
gctacgtcga cactgttcca tgacaagaac tcatacaggg agctctccga gattgctgag     2760
caggccaagc gcagggcgga gatcgctagg ctcagggagc tgaacaccct caaggggcac     2820
gtcgagtccg tggtcaagct gaagggcctc gacattgata ctatccagca gaattacacc     2880
gtgtag                                                                2886
```

<210> SEQ ID NO 50
<211> LENGTH: 2886
<212> TYPE: DNA
<213> ORGANISM: Zea mays
<220> FEATURE:
<221> NAME/KEY: misc_feature
<223> OTHER INFORMATION: ZmAHA5W885L version 2

<400> SEQUENCE: 50

```
atgggcccac tgcagaggcg cccaacagcg atgggggggcc tggaggagat caagaacgag    60
gccgtcgatc tggagaacat ccctattgag gaggtgttcg agcagctgaa gtgcacccgg   120
gagggcctca gctcctcgga gggccagcag cgcctggaga tcttcggccc aaaccggctg   180
gaggagaaga aggagagcaa gatcctcaag ttcctggggt tcatgtggaa cccgctgtcc   240
tgggtcatgg agatggctgc cgtgatggcg attgctctgg ctaatggcgg gggcaagcca   300
ccggactggg aggatttcgt ggggattatc gtcctgctcg tcatcaacag cactatctcc   360
ttcattgagg agaacaacgc tggcaacgcc gctgctgcgc tgatggcgaa cctcgctcca   420
aagactaagg tcctccgcga cggccgctgg ggggagcagg aggctgcgat tctcgtgccc   480
ggggacatcg ttagcattaa gctcggggat atcgtccctg ctgatgcccg gctgctggag   540
ggggaccccc tgaaggtcga ccagagcgct ctcaccggcg agtcgctccc agtcactaag   600
ggccctgggg acgaggtgtt cagcggctct acgtgcaagc agggcgagat cgaggcggtc   660
gtgatcgcta ccggcgtgca caccttcttc gggaaggccg cccatctcgt ggattcgaca   720
aaccaggtcg ggcacttcca gcaggtgctg acagccatcg ggaacttctg catctgctcg   780
attgccgttg ggatcgtggt tgagattatt gtgatgttcc cgattcagca ccggcgctac   840
cgctccggga tcgagaacct cctggtcctc ctcattgggg ggattccgat cgctatgccg   900
accgtcctga gcgtcactat ggctatcggg tctcacaagc tctcacagca ggggcgatt    960
accaagcgga tgacagcgat tgaggagatg gcggggatgg acgtgctgtg ctcagacaag  1020
accggcactc tgacgctcaa caagctctcc gtggacaaga acctcgtcga ggtgttctgc  1080
aaggggggtgg acaaggatca tgtcctgctg ctggcggcca gggcctcccg gacagagaac  1140
caggacgcca ttgacgccgc tatggtgggg atgctggccg accctaagga ggcgagggcc  1200
ggcatccgcg agattcactt cctgccattc aatcccgttg acaagcgcac tgcgctgacg  1260
tacattgatg cggacgggca ctggcacagg gtgtccaagg gggctccaga gcagatcctc  1320
gatctgtgcc actgcaagga ggatctgcgc cgcaaggtgc atgggatcat tgacaagtac  1380
gcggagaggg ggctccggag cctggcggtg gccaggcagg aggtgccgga cgcaacaag   1440
gagtcgccgg ggggcccttg gcagttcgtc gggctgctcc ctctgttcga tcccccgagg  1500
cacgacagcg cggagactat ccgcaaggcc ctcgttctgg gggtgaatgt caagatgatt  1560
accggggacc agctggccat tgggaaggag acaggccggc gcctcgggat gggcacgaac  1620
atgtacccgt catccgccct gctggggcag aataaggacg ccactctgga ggccctgccg  1680
gtcgatgagc tcatcgagaa ggctgacggg ttcgcgggcg tcttccccga gcataagtac  1740
gagatcgtga gcggctgca ggagaagaag catattgtgg ggatgactgg cgacggggtg   1800
aatgatgctc ccgccctgaa gaaggctgac atcggcattg ccgtcgcgga cgccacagat  1860
gctgcccgct cggcgtccga tatcgttctc acggagcctg gctgagcgt tattatctcg   1920
gcggttctga caagcaggtg catcttccag cgcatgaaga actacaccat ctacgctgtg  1980
tcgatcacta tcaggatcgt gctgggcttc atgctgattg cgctcatctg gcagtacgac  2040
ttctccccctt tcatggtcct gatcattgct atcctcaacg acggcacaat catgactatc  2100
tcgaaggacc gcgtgaagcc gagcccactc cccgactctt ggaagctcaa ggagattttc  2160
gccactggga tcgttctcgg gtcttacctc gctctgatga ccgtgatttt cttctgggct  2220
atgcacaaga ccgacttctt cagcgacaag ttcggggttc gctcgattcg cgactcggag  2280
```

```
cacgagatga tgtctgcgct gtacctccag gtttcaattg tttcacaggc gctcattttc    2340
gtgactaggt cacggtcttg gtccttcgtc gagaggcctg gcctgctcct ggtcactgct    2400
ttcctgctcg cccagctggt ggccactttc ctcgctgttt acgctaattg ggggttcgct    2460
aggatcaagg ggatcggctg ggggtgggcg ggcgtggtct ggctctactc catcgttttc    2520
tacttcccac tcgacctcat caagttcttc attcggttcg tgctgtcagg gagggcgtgg    2580
gacaacctcc tggagaacaa gaccgcgttc accactaaga aggactacgg ccgcgaggag    2640
agggaggcgc agctggctac agcgcagcgc accctccacg ggctccagcc cccagaggct    2700
gcgacatcta cactcttcca cgacaagaat tcttaccgcg agctgtcaga gattgccgag    2760
caggctaagc gcagggcgga gattgctagg ctgagggagc tcaacacact gaagggccac    2820
gtggagtcag tggtcaagct gaagggcctg gacatcgata caattcagca gaactacacc    2880
gtttag                                                              2886

<210> SEQ ID NO 51
<211> LENGTH: 504
<212> TYPE: DNA
<213> ORGANISM: Cassava vein mosaic virus
<220> FEATURE:
<221> NAME/KEY: misc_feature
<223> OTHER INFORMATION: proCsVMV

<400> SEQUENCE: 51
aaggtaatta tccaagatgt agcatcaaga atccaatgtt tacgggaaaa actatggaag      60
tattatgtga gctcagcaag aagcagatca atatgcggca catatgcaac ctatgttcaa     120
aaatgaagaa tgtacagata caagatccta tactgccaga atacgaagaa gaatacgtag     180
aaattgaaaa agaagaacca ggcgaagaaa agaatcttga agacgtaagc actgacgaca     240
acaatgaaaa gaagaagata aggtcggtga ttgtgaaaga gacatagagg acacatgtaa     300
ggtggaaaat gtaagggcgg aaagtaacct tatcacaaag gaatcttatc ccccactact     360 tatccttttta tattttccg tgtcatttt gcccttgagt tttcctatat aaggaaccaa     420
gttcggcatt tgtgaaaaca agaaaaaatt tggtgtaagc tattttcttt gaagtactga     480
ggatacaact tcagagaaat ttgt                                            504

<210> SEQ ID NO 52
<211> LENGTH: 557
<212> TYPE: DNA
<213> ORGANISM: Artificial
<220> FEATURE:
<223> OTHER INFORMATION: Rice actin intron

<400> SEQUENCE: 52
accaccacca ccaccaccac ctccacctcc tccccctcg ctgccggacg acgagctcct       60 ccccctccc cctccgccgc cgccgcgccg gtaaccaccc cgcccctctc ctctttcttt      120
ctccgttttt ttttccgtc tcggtctcga tctttggcct tggtagtttg ggtgggcgag      180
aggcggcttc gtgcgcgccc agatcggtgc gcggagggg cggatctcg cggctggggc      240 tctcgccggc gtggatccgg cccggatctc gcggggaatg gggctctcgg atgtagatct      300
gcgatccgcc gttgttgggg gagatgatgg ggggtttaaa atttccgcca tgctaaacaa      360
gatcaggaag aggggaaaag ggcactatgg tttatatttt tatatatttc tgctgcttcg      420
tcaggcttag atgtgctaga tcttcttc ttcttttgt gggtagaatt tgaatccctc        480
```

```
agcattgttc atcggtagtt tttcttttca tgatttgtga caaatgcagc ctcgtgcgga        540
gcttttttgt aggtaga                                                      557

<210> SEQ ID NO 53
<211> LENGTH: 509
<212> TYPE: DNA
<213> ORGANISM: Arabidopsis thaliana
<220> FEATURE:
<221> NAME/KEY: misc_feature
<223> OTHER INFORMATION: terSac66

<400> SEQUENCE: 53
ctaaatgctc ttaactgagc taattatgta atgcacatac acatatttac atagatatgc        60
atatttatat atagcatgta tattgtacta catgcattgc ttcttaatac atgtagtaaa       120
gatatatgca aaaatagtcg aaagatttgt ttacatataa aatcaccaat atttattgtt       180
attgtatttt catgaataaa gtaataagat tatttgtcta atattttgat ttactagtac       240
tagaaatgaa aaggaatatg cacaatttca gcattatagt ttggtaggca aaatggagtg       300
agaatagagt ttcatagtat atactaaggt tcttaattgt gcaaatagtt gatacaagtc       360
acatgggcca agtttgtaaa tcttaaatcg aaatatgcct tcttcttttt ttgcatgaaa       420
atgctagtaa tttataagtg tgttttcaa taagagatgc taaataccaa aattaaccta       480
gttttcagtg agcgcttgca ttattgtgg                                        509

<210> SEQ ID NO 54
<211> LENGTH: 968
<212> TYPE: DNA
<213> ORGANISM: Zea mays
<220> FEATURE:
<221> NAME/KEY: misc_feature
<223> OTHER INFORMATION: proZmrbcS_Mut_a1

<400> SEQUENCE: 54 tcccttttaat ctggcgctag atctgcatcc gcggcttgca aagataaatg gcacatttag       60
tgtgttattt tgcaataccct ttcatagtag atatccttaa atgcagtttt aggcatgttt      120
gggtaattaa ataacatttt taggaggagt tttagattta cctttctttc gtgatgactg       180
atgacagacg tggggaattc aaatgcaact ctagcgaaag ttcatatatt tttcataaat       240
agctgaggct ggggtaatta ttttttttgt agaaaaatag aataggtgga atggttgggg       300
aaggcgtagg cgctcgtgga cgacgcccga taaaagacaa gaggcggaat tgccatgaat       360
tcgaggtagc taagtaaggc gcatatatat gccaaaaaat tctactgtca ctttccaatt       420
tcaatgcgct gccaaacaag ccatcctgga aactgacttg aattcagccc aattctgtag       480
atccaaacag ggccggcgtc agtgcctcag gtgagagagc agcagacgat tcaaagagcc       540
aaaactgcaa gcagacgcag ccgaagccga agccgaagcc caagcccaaa actgttttgt       600
ctttgcccag aaccgcgacg agcctaaact gcgcttcctc ctatctacaa gtccctggca       660
catcacgcat agtccaacct aggcgcgcag gcgataaggc gcgccacggg gacgcgacat       720
gtggtggcgg acgcgatcag gatagggcca ggctggccgg gcgcggccac gggagaacgg       780
tggccactcg tcccacatcc gcttcgtcct gtcctgtact gcgtcctgcc cccaacgaga       840
gccggagccg gccatcccgt cgcacactct ccccctctat atatgccgtc ggtgtggggg       900
agcctactac aggacgaccc aagcaagcaa gcaagcagcg agtacataca tactaggcag       960
ccaggcag                                                              968
```

<210> SEQ ID NO 55
<211> LENGTH: 537
<212> TYPE: DNA
<213> ORGANISM: Zea mays
<220> FEATURE:
<221> NAME/KEY: misc_feature
<223> OTHER INFORMATION: terZmRbcs

<400> SEQUENCE: 55

| | | | | | |
|---|---|---|---|---|---|
| tagaccgcgc ccgccggccg cccccgccg gctagctagc tagctagcta gctcctgcgt | | | | | 60 |
| gagctagtag ctagtgccat gcgtcgtctc tgtcgttcgg ttttgcttcg ggtcaccgta | | | | | 120 |
| ccctttgctt gcttggtttc ttctttcctt ttttcctttt tttttcttc ttttccccgg | | | | | 180 |
| ccatggttcc tttgctttca gcagttctct gctggatgtg atgtatccat tgttgcaagc | | | | | 240 |
| atggccttgc attggctacc tctatacctg ctacaaacta ctgcaacgcc tatatatact | | | | | 300 |
| tggggtgagg aacatgtgaa tgcaagctcc ggctatcata tacatgtaat atggatacaa | | | | | 360 |
| actatatata taaatccgcc gaggcgccga ctaatactat acgacgacac cgtgttaagt | | | | | 420 |
| taatatataa ctggtgcttt ttatttatat atctgtctca tcatatatat atgctaatta | | | | | 480 |
| atggatgtgt gtcctcttca cttcaattcc ttctttcctt tcctatgctt tgagatc | | | | | 537 |

<210> SEQ ID NO 56
<211> LENGTH: 444
<212> TYPE: DNA
<213> ORGANISM: Zea mays
<220> FEATURE:
<221> NAME/KEY: misc_feature
<223> OTHER INFORMATION: proZmRAB17_del

<400> SEQUENCE: 56

| | | | | | |
|---|---|---|---|---|---|
| aaatgttatg cagttcgctc tggacttttc tgctgcgcct acacttgggt gtactgggcc | | | | | 60 |
| taaattcagc ctgaccgacc gcctgcattg aataatggat gagcaccggt aaaatccgcg | | | | | 120 |
| tacccaactt tcgagaagaa ccgagacgtg cgggccggg ccaccgacgc acggcaccag | | | | | 180 |
| cgactgcaca cgtcccgccg gcgtacgtgt acgtgctgtt ccctcactgg ccgcccaatc | | | | | 240 |
| cactcatgca tgcccacgta cacccctgcc gtggcgcgcc cagatcctaa tccttttcgcc | | | | | 300 |
| gttctgcact tctgctgcct ataaatggcg gcatcgaccg tcacctgctt caccaccggc | | | | | 360 |
| gagccacatc gagaacacga tcgagcacac aagcacgaag actcgtttag gagaaaccac | | | | | 420 |
| aaaccaccaa gccgtgcaag catc | | | | | 444 |

<210> SEQ ID NO 57
<211> LENGTH: 500
<212> TYPE: DNA
<213> ORGANISM: Zea mays
<220> FEATURE:
<221> NAME/KEY: misc_feature
<223> OTHER INFORMATION: terZmRab17

<400> SEQUENCE: 57

| | | | | | |
|---|---|---|---|---|---|
| gcggcgccta tacgtggctg tgctgtgctg tctggcgcgt caaagccgta ctcttcagcg | | | | | 60 |
| ttccatagat aataagataa acccatgaat aagtgtccct acccttgat catgtgacag | | | | | 120 |
| ggacagggac agtttcctgt acttgtgggg tgaatttgta cgtgtgatac ggtaacttgg | | | | | 180 |
| tccgtgtact gtttatgctg ctacgttttcc ttcctaaaag tacgtatata tatacagcac | | | | | 240 |
| ttgcgagtgg ctttacttgt gtgcactgcc taaaagtgtc gatattacct ccagcggtaa | | | | | 300 |
| ataaatgacc cttgtaagaa acttacacag catgtcttac taattaacag ccgttattat | | | | | 360 |

| | |
|---|---|
| gttcggcgca gtactcacac tggaacttac gaacaagaat tgctctatca atcaccatct | 420 |
| actttagata tatcttctga aactttttc aaatccaaaa gttcagtatc ttcctacaaa | 480 |
| ttagtgaatt aggaatccaa | 500 |

<210> SEQ ID NO 58
<211> LENGTH: 4416
<212> TYPE: DNA
<213> ORGANISM: Artificial
<220> FEATURE:
<223> OTHER INFORMATION: Cassette_T02781_CsVMV ZmAHA5_W885L

<400> SEQUENCE: 58

| | |
|---|---|
| aaggtaatta tccaagatgt agcatcaaga atccaatgtt tacgggaaaa actatggaag | 60 |
| tattatgtga gctcagcaag aagcagatca atatgcggca catatgcaac ctatgttcaa | 120 |
| aaatgaagaa tgtacagata caagatccta tactgccaga atacgaagaa gaatacgtag | 180 |
| aaattgaaaa agaagaacca ggcgaagaaa agaatcttga agacgtaagc actgacgaca | 240 |
| acaatgaaaa gaagaagata aggtcggtga ttgtgaaaga gacatagagg acacatgtaa | 300 |
| ggtggaaaat gtaagggcgg aaagtaacct tatcacaaag gaatcttatc ccccactact | 360 |
| tatccttta tattttccg tgtcattttt gcccttgagt tttcctatat aaggaaccaa | 420 |
| gttcggcatt tgtgaaaaca agaaaaaatt tggtgtaagc tattttcttt gaagtactga | 480 |
| ggatacaact tcagagaaat ttgtccctcc ccctcccc tccgccgccg ccgcgccggt | 540 |
| aaccaccccg cccctctcct ctttctttct ccgttttttt tttccgtctc ggtctcgatc | 600 |
| tttggccttg gtagtttggg tgggcgagag gcggcttcgt gcgcgcccag atcggtgcgc | 660 |
| gggaggggcg ggatctcgcg gctggggctc tcgccggcgt ggatccggcc cggatctcgc | 720 |
| ggggaatggg gctctcggat gtagatctgc gatccgccgt tgttggggga gatgatgggg | 780 |
| ggtttaaaat ttccgccatg ctaaacaaga tcaggaagag gggaaaaggg cactatggtt | 840 |
| tatatttta tatatttctg ctgcttcgtc aggcttagat gtgctagatc tttcttctt | 900 |
| ctttttgtgg gtagaatttg aatccctcag cattgttcat cggtagtttt tcttttcatg | 960 |
| atttgtgaca aatgcagcct cgtgcggagc tttttgtag gtagacgata tctccaccat | 1020 |
| ggggccactg cagcggcggc ctacggctat gggggggctg gaggagatta agaacgaggc | 1080 |
| ggttgacctg gagaacatcc cgattgagga ggtgttcgag cagctgaagt gcacccgcga | 1140 |
| gggcctctcc agctcggagg ggcagcagcg cctggagatc ttcggcccca accgcctgga | 1200 |
| ggagaagaag gagtccaaga tcctcaagtt cctgggcttc atgtggaacc cactgagctg | 1260 |
| ggttatggag atggctgccg tgatggctat cgcgctcgct aatggcgggg gcaagccacc | 1320 |
| agactgggag gatttcgtcg gcatcattgt gctcctggtc atcaactcga cgatttcttt | 1380 |
| catcgaggag aacaatgctg gcaacgctgc cgcggctctg atggctaatc tcgctcctaa | 1440 |
| gacaaaggtg ctgagggatg gccgctgggg ggagcaggag gccgcgatcc tggtgccggg | 1500 |
| cgacattgtc agcatcaagc tcggggacat cgttccagct gatgctaggc tcctggaggg | 1560 |
| ggacccactc aaggtggatc agagcgctct gacgggcgag tcgctccctg tcacaaaggg | 1620 |
| gccaggcgac gaggttttct ccggcagcac gtgcaagcag gggagattg aggccgtggt | 1680 |
| catcgcgact ggcgtccaca ccttcttcgg gaaggctgcc catctggtcg actcgactaa | 1740 |
| ccaggttggc cacttccagc aggtgctcac cgcgatcggg aatttctgca tttgctctat | 1800 |
| cgctgtgggc attgttgtgg agatcattgt catgttccca atccagcata ggcgctaccg | 1860 |
| ctccggcatt gagaacctcc tggtgctcct gatcgggggc atccccattg cgatgccaac | 1920 |

```
ggttctgagc gtgacaatgg ccatcggcag ccacaagctc tcgcagcagg gggccattac    1980
gaagaggatg acagccatcg aggagatggc ggggatggac gtcctgtgct ctgataagac    2040
aggcactctc accctgaaca agctgtcagt ggacaagaat ctcgttgagg tgttctgcaa    2100
gggcgttgac aaggatcacg tgctcctgct cgcggctcgg gcctcccgca ccgagaacca    2160
ggacgcgatc gatgctgcga tggtggggat gctcgccgat ccaaaggagg ctagggccgg    2220
cattcgggag atccatttcc tgcccttcaa tccagtcgac aagaggactg ctctcaccta    2280
catcgacgcc gatggccact ggatcgggt gagcaagggg ccccagagc agatcctcga    2340 cctgtgccac tgcaaggagg atctgcggcg caaggtgcat ggcatcattg acaagtacgc    2400
ggagaggggg ctcaggtcgc tggcggtcgc tcggcaggag gttcccgagc gcaacaagga    2460
gtctcctggg ggccgtggc agttcgtcgg cctgctccca ctcttcgacc cacctcggca    2520
cgattccgcg gagactatcc gcaaggctct cgtgctgggc gtcaatgtta agatgattac    2580
cggggatcag ctggccatcg gcaaggagac ggggaggagg ctcgggatgg cacaaacat    2640 gtaccgtct tcagcgctgc tcggccagaa taaggacgct accctggagg ccctcccggt    2700
ggacgagctg atcgagaagg cggatggctt cgctggggtc ttcccggagc acaagtacga    2760
gattgttaag aggctgcagg agaagaagca tatcgtgggc atgacggggg acggcgtcaa    2820
cgatgctcct gctctcaaga aggcggatat cggcattgct gtcgctgacg ctacggatgc    2880
tgctcggtcg gcctctgaca tcgttctgac agagccgggc ctctctgtga tcatttcagc    2940
ggtcctgacc tcacgctgca ttttccagag gatgaagaac tacactatct acgcggtttc    3000
catcaccatt cgcatcgtgc tcggcttcat gctcattgcc ctgatctggc agtacgactt    3060
ctctccgttc atggtcctga tcattgccat cctcaatgac ggcacgatta tgacaatctc    3120
aaaggatagg gtgaagccat cgcctctgcc ggactcttgg aagctcaagg agattttcgc    3180
cacaggcatc gtgctggggt cctacctcgc tctgatgact gtcatcttct tctgggccat    3240
gcacaagacc gacttcttca cgcataagtt cggcgtccgc tccatcaggg acagcgagca    3300
tgagatgatg tcggcgctct acctgcaggt ctcaattgtt tcccaggccc tcatcttcgt    3360
gacccggtca cgctcctgga gcttcgttga gaggccaggc ctgctcctgg tgacggcctt    3420
cctcctggcg cagctggtcg ctacattcct cgccgtttac gcgaactggg gcttcgcgcg    3480
cattaagggg atcggctggg ggtgggctgg cgtcgtttgg ctgtactcca tcgtcttcta    3540
cttcccgctc gacctgatta agttcttcat caggttcgtg ctcagcggcc gggcgtggga    3600
taacctcctg gagaataaga cggccttcac cacgaagaag gactacgca gggaggagcg    3660 cgaggctcag ctcgctactg ctcagcgcac cctccacggc ctgcagccac cagaggctgc    3720
tacgtcgaca ctgttccatg acaagaactc atacagggag ctctccgaga ttgctgagca    3780
ggccaagcgc agggcggaga tcgctaggct cagggagctg aacaccctca aggggcacgt    3840
cgagtccgtg gtcaagctga agggcctcga cattgatact atccagcaga attacaccgt    3900
gtagaaccta atgctctta actgagctaa ttatgtaatg cacatacaca tatttacata    3960
gatatgcata tttatatata gcatgtatat tgtactacat gcattgcttc ttaatacatg    4020
tagtaaagat atatgcaaaa atagtcgaaa gatttgttta catataaaat caccaatatt    4080
tattgttatt gtattttcat gaataaagta ataagattat tgtctaata ttttgattta    4140 ctagtactag aaatgaaaag gaatatgcac aatttcagca ttatagtttg gtaggcaaaa    4200
tggagtgaga atagagtttc atagtatata ctaaggttct taattgtgca aatagttgat    4260
```

| | |
|---|---|
| acaagtcaca tgggccaagt tgtaaatct taaatcgaaa tatgccttct tcttttttg | 4320 |
| catgaaaatg ctagtaattt ataagtgtgt ttttcaataa gagatgctaa ataccaaaat | 4380 |
| taacctagtt ttcagtgagc gcttgcatta ttgtgg | 4416 |

<210> SEQ ID NO 59
<211> LENGTH: 4402
<212> TYPE: DNA
<213> ORGANISM: Artificial
<220> FEATURE:
<223> OTHER INFORMATION: Cassette_T02784_rbcS_Mut_al ZmAHA5_W885L

<400> SEQUENCE: 59

| | |
|---|---|
| tcccttttaat ctggcgctag atctgcatcc gcggcttgca agataaatg gcacatttag | 60 |
| tgtgttattt tgcaatacct ttcatagtag atatccttaa atgcagtttt aggcatgttt | 120 |
| gggtaattaa ataacatttt taggaggagt tttagattta cctttctttc gtgatgactg | 180 |
| atgacagacg tggggaattc aaatgcaact ctagcgaaag ttcatatatt tttcataaat | 240 |
| agctgaggct ggggtaatta ttttttttgt agaaaaatg aataggtgga atggttgggg | 300 |
| aaggcgtagg cgctcgtgga cgacgcccga taaaagacaa gaggcggaat tgccatgaat | 360 |
| tcgaggtagc taagtaaggc gcatatatat gccaaaaaat tctactgtca ctttccaatt | 420 |
| tcaatgcgct gccaaacaag ccatcctgga aactgacttg aattcagccc aattctgtag | 480 |
| atccaaacag ggccggcgtc agtgcctcag gtgagagagc agcagacgat tcaaagagcc | 540 |
| aaaactgcaa gcagacgcag ccgaagccga agccgaagcc caagcccaaa actgttttgt | 600 |
| cttttgcccag aaccgcgacg agcctaaact gcgcttcctc ctatctacaa gtccctggca | 660 |
| catcacgcat agtccaacct aggcgcgcag gcgataaggc gcgccacggg gacgcgacat | 720 |
| gtggtggcgg acgcgatcag gatagggcca ggctggccgg gcgcggccac gggagaacgg | 780 |
| tggccactcg tcccacatcc gcttcgtcct gtcctgtact gcgtcctgcc cccaacgaga | 840 |
| gccgagccg gccatcccgt cgcacactct ccccctctat atatgccgtc ggtgtggggg | 900 |
| agcctactac aggacgaccc aagcaagcaa gcaagcagcg agtacataca tactaggcag | 960 |
| ccaggcagtc tccaccatgg ggccactgca gcggcggcct acggctatgg gggggctgga | 1020 |
| ggagattaag aacgaggcgg ttgacctgga gaacatcccg attgaggagg tgttcgagca | 1080 |
| gctgaagtgc acccgcgagg gcctctccag ctcggagggg cagcagcgcc tggagatctt | 1140 |
| cggccccaac cgcctggagg agaagaagga gtccaagatc ctcaagttcc tgggcttcat | 1200 |
| gtggaaccca ctgagctggg ttatggagat ggctgccgtg atggctatcg cgctcgctaa | 1260 |
| tggcggggc aagccaccag actgggagga tttcgtcggc atcattgtgc tcctggtcat | 1320 |
| caactcgacg atttctttca tcgaggagaa caatgctggc aacgctgccg cggctctgat | 1380 |
| ggctaatctc gctcctaaga caaaggtgct gagggatggc cgctgggggg agcaggaggc | 1440 |
| cgcgatcctg gtgccgggcg acattgtcag catcaagctc ggggacatcg ttccagctga | 1500 |
| tgctaggctc ctgagggggg acccactcaa ggtggatcag agcgctctga cgggcgagtc | 1560 |
| gctccctgtc acaaagggc caggcgacga ggttttctcc ggcagcacgt gcaagcaggg | 1620 |
| ggagattgag gccgtggtca tcgcgactgg cgtccacacc ttcttcggga aggctgccca | 1680 |
| tctggtcgac tcgactaacc aggttggcca cttccagcag gtgctcaccg cgatcgggaa | 1740 |
| tttctgcatt tgctctatcg ctgtgggcat tgttgtggag atcattgtca tgttcccaat | 1800 |
| ccagcatagg cgctaccgct ccggcattga gaacctcctg gtgctcctga tcgggggcat | 1860 |
| ccccattgcg atgccaacgg ttctgagcgt gacaatggcc atcggcagcc acaagctctc | 1920 |

```
gcagcagggg gccattacga agaggatgac agccatcgag gagatggcgg ggatggacgt    1980
cctgtgctct gataagacag gcactctcac cctgaacaag ctgtcagtgg acaagaatct    2040
cgttgaggtg ttctgcaagg gcgttgacaa ggatcacgtg ctcctgctcg cggctcgggc    2100
ctcccgcacc gagaaccagg acgcgatcga tgctgcgatg gtggggatgc tcgccgatcc    2160
aaaggaggct agggccggca ttcgggagat ccatttcctg cccttcaatc cagtcgacaa    2220
gaggactgct ctcacctaca tcgacgccga tggccactgg catcgggtga gcaaggggc    2280 cccagagcag atcctcgacc tgtgccactg caaggaggat ctgcggcgca aggtgcatgg    2340
catcattgac aagtacgcgg agaggggct caggtcgctg gcggtcgctc ggcaggaggt    2400
tcccgagcgc aacaaggagt ctcctggggg cccgtggcag ttcgtcggcc tgctcccact    2460
cttcgaccca cctcggcacg attccgcgga gactatccgc aaggctctcg tgctgggcgt    2520
caatgttaag atgattaccg gggatcagct ggccatcggc aaggagacgg ggaggaggct    2580
cgggatgggc acaaacatgt acccgtcttc agcgctgctc ggccagaata aggacgctac    2640
cctggaggcc ctcccggtgg acgagctgat cgagaaggcg gatggcttcg ctgggtctt    2700 cccggagcac aagtacgaga ttgttaagag gctgcaggaa aagaagcata tcgtgggcat    2760
gacgggggac ggcgtcaacg atgctcctgc tctcaagaag gcggatatcg gcattgctgt    2820
cgctgacgct acggatgctg ctcggtcggc ctctgacatc gttctgacag agccgggcct    2880
ctctgtgatc atttcagcgg tcctgacctc acgctgcatt ttccagagga tgaagaacta    2940
cactatctac gcggttttcca tcaccattcg catcgtgctc ggcttcatgc tcattgccct    3000
gatctggcag tacgacttct ctccgttcat ggtcctgatc attgccatcc tcaatgacgg    3060
cacgattatg acaatctcaa aggatagggt gaagccatcg cctctgccgg actcttggaa    3120
gctcaaggag attttcgcca caggcatcgt gctggggtcc tacctcgctc tgatgactgt    3180
catcttcttc tgggccatgc acaagaccga cttcttcagc gataagttcg gcgtccgctc    3240
catcagggac agcgagcatg agatgatgtc ggcgctctac ctgcaggtct caattgtttc    3300
ccaggccctc atcttcgtga cccggtcacg ctccctggagc ttcgttgaga ggccaggcct    3360
gctcctggtg acggccttcc tcctggcgca gctggtcgct acattcctcg ccgtttacgc    3420 gaactgggc ttcgcgcgca ttaagggga cggctggggg tgggctggcg tcgtttggct    3480
gtactccatc gtcttctact tcccgctcga cctgattaag ttcttcatca ggttcgtgct    3540
cagcggccgg gcgtgggata acctcctgga gaataagacg gccttcacca cgaagaagga    3600
ctacggcagg gaggagcgcg aggctcagct cgctactgct cagcgcaccc tccacggcct    3660
gcagccacca gaggctgcta cgtcgacact gttccatgac aagaactcat acaggagct    3720 ctccgagatt gctgagcagg ccaagcgcag ggcggagatc gctaggctca gggagctgaa    3780
caccctcaag gggcacgtcg agtccgtggt caagctgaag ggcctcgaca ttgatactat    3840
ccagcagaat tacaccgtgt agaactagac cgcgcccgcc ggccgcccc cgccggctag    3900 ctagctagct agctagctcc tgcgtgagct agtagctagt gccatgcgtc gtctctgtcg    3960
ttcggttttg cttcgggtca ccgtaccctt tgcttgcttg gtttcttctt tccttttttc    4020
cttttttttt tcttcttttc cccggccatg gttcctttgc tttcagcagt tctctgctgg    4080
atgtgatgta tccattgttg caagcatggc cttgcattgg ctacctctat acctgctaca    4140
aactactgca acgcctatat atacttgggg tgaggaacat gtgaatgcaa gctccggcta    4200
tcatatacat gtaatatgga tacaaactat atatataaat ccgccgaggc gccgactaat    4260
```

| | |
|---|---|
| actatacgac gacaccgtgt taagttaata tataactggt gcttttttatt tatatatctg | 4320 |
| tctcatcata tatatatgct aattaatgga tgtgtgtcct cttcacttca attccttctt | 4380 |
| tccttttccta tgctttgaga tc | 4402 |

<210> SEQ ID NO 60
<211> LENGTH: 3841
<212> TYPE: DNA
<213> ORGANISM: Artificial
<220> FEATURE:
<223> OTHER INFORMATION: Cassette_T10401_RAB17_del ZmAHA5_W885L

<400> SEQUENCE: 60

| | |
|---|---|
| aaatgttatg cagttcgctc tggacttttc tgctgcgcct acacttgggt gtactgggcc | 60 |
| taaattcagc ctgaccgacc gcctgcattg aataatggat gagcaccggt aaaatccgcg | 120 |
| tacccaactt tcgagaagaa ccgagacgtg gcgggccggg ccaccgacgc acggcaccag | 180 |
| cgactgcaca cgtcccgccg gcgtacgtgt acgtgctgtt ccctcactgg ccgcccaatc | 240 |
| cactcatgca tgcccacgta caccccctgcc gtggcgcgcc cagatcctaa tccttcgcc | 300 |
| gttctgcact tctgctgcct ataaatggcg gcatcgaccg tcacctgctt caccaccggc | 360 |
| gagccacatc gagaacacga tcgagcacac aagcacgaag actcgtttag gagaaaccac | 420 |
| aaaccaccaa gccgtgcaag catctctcca ccatgggccc actgcagagg cgcccaacag | 480 |
| cgatgggggg cctggaggag atcaagaacg aggccgtcga tctggagaac atccctattg | 540 |
| aggaggtgtt cgagcagctg aagtgcaccc gggagggcct cagctcctcg gagggccagc | 600 |
| agcgcctgga gatcttcggc ccaaaccggc tggaggagaa gaaggagagc aagatcctca | 660 |
| agttcctggg gttcatgtgg aacccgctgt cctgggtcat ggagatggct gccgtgatgg | 720 |
| cgattgctct ggctaatggc gggggcaagc caccggactg gaggattttc gtggggatta | 780 |
| tcgtcctgct cgtcatcaac agcactatct ccttcattga ggagaacaac gctggcaacg | 840 |
| ccgctgctgc gctgatggcg aacctcgctc caaagactaa ggtcctccgc gacggccgct | 900 |
| gggggggagca ggaggctgcg attctcgtgc ccggggacat cgttagcatt aagctcgggg | 960 |
| atatcgtccc tgctgatgcc cggctgctgg aggggacccc cctgaaggtc gaccagagcg | 1020 |
| ctctcaccgg cgagtcgctc ccagtcacta agggccctgg ggacgaggtg ttcagcggct | 1080 |
| ctacgtgcaa gcagggcgag atcgaggcgg tcgtgatcgc taccggcgtg cacaccttct | 1140 |
| tcgggaaggc cgcccatctc gtggattcga caaaccaggt cgggcacttc cagcaggtgc | 1200 |
| tgacagccat cggaacttc tgcatctgct cgattgccgt tgggatcgtg ttgagatta | 1260 |
| ttgtgatgtt cccgattcag caccggcgct accgctccgg gatcgagaac ctcctggtcc | 1320 |
| tcctcattgg ggggattccg atcgctatgc cgaccgtcct gagcgtcact atggctatcg | 1380 |
| ggtctcacaa gctctcacag caggggggcga ttaccaagcg gatgacagcg attgaggaga | 1440 |
| tggcggggat ggacgtgctg tgctcagaca gaaccggcac tctgacgctc aacaagctct | 1500 |
| ccgtggacaa gaacctcgtc gaggtgttct gcaagggggt ggacaaggat catgtcctgc | 1560 |
| tgctggcggc cagggcctcc cggacagaga accaggacgc cattgacgcc gctatggtgg | 1620 |
| ggatgctggc cgaccctaag gaggcgaggg ccggcatccg cgagattcac ttcctgccat | 1680 |
| tcaatcccgt tgacaagcgc actgcgctga cgtacattga tgcggacggg cactggcaca | 1740 |
| gggtgtccaa ggggggctcca gagcagatcc tcgatctgtg ccactgcaag gaggatctgc | 1800 |
| ggcgcaaggt gcatgggatc attgacaagt acgcggagag ggggctccgg agcctggcgg | 1860 |
| tggccaggca ggaggtgccg gagcgcaaca aggagtcgcc ggggggccct tggcagttcg | 1920 |

```
tcgggctgct ccctctgttc gatcccccga ggcacgacag cgcggagact atccgcaagg    1980
ccctcgttct gggggtgaat gtcaagatga ttaccgggga ccagctggcc attgggaagg    2040
agacaggccg gcgcctcggg atgggcacga acatgtaccc gtcatccgcc ctgctggggc    2100
agaataagga cgccactctg gaggccctgc cggtcgatga gctcatcgag aaggctgacg    2160
ggttcgcggg cgtcttcccc gagcataagt acgagatcgt gaagcggctg caggagaaga    2220
agcatattgt ggggatgact ggcgacgggg tgaatgatgc tcccgccctg aagaaggctg    2280
acatcggcat tgccgtcgcg gacgccacag atgctgcccg ctcggcgtcc gatatcgttc    2340
tcacggagcc tgggctgagc gttattatct cggcggttct gacaagcagg tgcatcttcc    2400
agcgcatgaa gaactacacc atctacgctg tgtcgatcac tatcaggatc gtgctgggct    2460
tcatgctgat tgcgctcatc tggcagtacg acttctcccc tttcatggtc ctgatcattg    2520
ctatcctcaa cgacggcaca atcatgacta tctcgaagga ccgcgtgaag ccgagcccac    2580
tccccgactc ttggaagctc aaggagattt tcgccactgg gatcgttctc gggtcttacc    2640
tcgctctgat gaccgtgatt ttcttctggg ctatgcacaa gaccgacttc ttcagcgaca    2700
agttcggggt tcgctcgatt cgcgactcgg agcacgagat gatgtctgcg ctgtacctcc    2760
aggtttcaat tgtttcacag gcgctcattt tcgtgactag gtcacggtct tggtccttcg    2820
tcgagaggcc tggcctgctc ctggtcactg cttttcctgct cgcccagctg gtggccactt    2880
tcctcgctgt ttacgctaat tgggggttcg ctaggatcaa ggggatcggc tgggggtggg    2940
cgggcgtggt ctggctctac tccatcgttt tctacttccc actcgacctc atcaagttct    3000
tcattcggtt cgtgctgtca gggagggcgt gggacaacct cctggagaac aagaccgcgt    3060
tcaccactaa gaaggactac ggccgcgagg agagggaggc gcagctggct acagcgcagc    3120
gcaccctcca cgggctccag cccccagagg ctgcgacatc tacactcttc cacgacaaga    3180
attcttaccg cgagctgtca gagattgccg agcaggctaa gcgcagggcg gagattgcta    3240
ggctgaggga gctcaacaca ctgaagggcc acgtggagtc agtggtcaag ctgaagggcc    3300
tggacatcga tacaattcag cagaactaca ccgtttagaa cgcggcgcct atacgtggct    3360
gtgctgtgct gtctggcgcg tcaaagccgt actcttcagc gttccataga taataagata    3420
aacccatgaa taagtgtccc tacccttga tcatgtgaca gggacaggga cagtttcctg    3480
tacttgtggg gtgaatttgt acgtgtgata cggtaacttg gtccgtgtac tgtttatgct    3540
gctacgtttc cttcctaaaa gtacgtatat atatacagca cttgcgagtg gctttacttg    3600
tgtgcactgc ctaaaagtgt cgatattacc tccagcggta aataaatgac ccttgtaaga    3660
aacttacaca gcatgtctta ctaattaaca gccgttatta tgttcggcgc agtactcaca    3720
ctggaactta cgaacaagaa ttgctctatc aatcaccatc tactttagat atatcttctg    3780
aaactttttt caaatccaaa agttcagtat cttcctacaa attagtgaat taggaatcca    3840
a                                                                  3841
```

<210> SEQ ID NO 61
<211> LENGTH: 4328
<212> TYPE: DNA
<213> ORGANISM: Artificial
<220> FEATURE:
<223> OTHER INFORMATION: Cassette_T10584_MYB60 ZmAHA5_W885L

<400> SEQUENCE: 61

```
ctccgtcgct agcgttgtaa tttttatcag cctctctcca tctgattgga tgagctgctt     60
ctcctagcta gcacgttgtc aaccattggg gacgcccttt aggagtgaaa gtgatgcagt    120
tactctactc ccatccggtc caaatcccaa cctaagggat atatgacgaa gagttttcaa    180
tttcagtata atgtgtatag caagtgattt gattttcctg cagattcttg agagagaagg    240
gccaaacctg catatgtgcc aggtgcgcac tcacagtcac acacacggtc tcatcaatg     300
cccaagaaat ctggagagac acagacaaac gcaagcaatt actccattca tgagcgccac    360
agcagaaaaa ggagtcctcc agaaccggcc gtgttcttgg cttgcacaca cacacacaca    420
cacgcgaaag cagcgcatgc aacaaagcaa agatcacaca cggccggagc aagagagacg    480
cccatattca tgtgatcacc tggctgactt ttgcattgga aagcaacagt gcagatcaa     540
aagcgaacgc agcacacagc acagcacagc acagggatcg agttgctcta ctccgtatat    600
gaggtcatgc agtatataag cactcacatg cagctatacc ttagctaggg cacctgtgca    660
aggggacagg taggagataa agcaatgtct gctggctaga ataaaaggag gccgatatcg    720
tatcagcaga gggttccagg ggagaaggcc gttctgcagg gccgccgtaa aaggctgtgt    780
aggaagcagc cacagcttct catatcttct tgttcttcga ctacttgcct agctactata    840
tctactagac tagccctagg ctgcttgcta gctagtaggt gtatcgatcg tccgaggtag    900
gaggagacag caggaagcag gctctccacc atgggcccac tgcagaggcg cccaacagcg    960
atgggggggcc tggaggagat caagaacgag gccgtcgatc tggagaacat ccctattgag   1020
gaggtgttcg agcagctgaa gtgcacccgg gagggcctca gctcctcgga gggccagcag   1080
cgcctggaga tcttcggccc aaaccggctg gaggagaaga aggagagcaa gatcctcaag   1140
ttcctggggt tcatgtggaa cccgctgtcc tgggtcatgg agatggctgc cgtgatggcg   1200
attgctctgg ctaatggcgg gggcaagcca ccggactggg aggatttcgt ggggattatc   1260
gtcctgctcg tcatcaacag cactatctcc ttcattgagg agaacaacgc tggcaacgcc   1320
gctgctgcgc tgatggcgaa cctcgctcca aagactaagg tcctccgcga cggccgctgg   1380
ggggagcagg aggctgcgat tctcgtgccc ggggacatcg ttagcattaa gctcggggat   1440
atcgtccctg ctgatgcccg gctgctggag ggggacccccc tgaaggtcga ccagagcgct   1500
ctcaccggcg agtcgctccc agtcactaag ggccctgggg acgaggtgtt cagcggctct   1560
acgtgcaagc agggcgagat cgaggcggtc gtgatcgcta ccggcgtgca caccttcttc   1620
gggaaggccc ccatctcgt ggattcgaca aaccaggtcg ggcacttcca gcaggtgctg   1680
acagccatcg ggaacttctg catctgctcg attgccgttg ggatcgtggt tgagattatt   1740
gtgatgttcc cgattcagca ccggcgctac cgctccggga tcgagaacct cctggtcctc   1800
ctcattgggg ggattccgat cgctatgccg accgtcctga gcgtcactat ggctatcggg   1860
tctcacaagc tctcacagca gggggcgatt accaagcgga tgcagcgat tgaggagatg    1920
gcggggatgg acgtgctgtg ctcagacaag accggcactc tgacgctcaa caagctctcc   1980
gtggacaaga acctcgtcga ggtgttctgc aagggggtgg acaaggatca tgtcctgctg   2040
ctggcggcca gggcctcccg gacagagaac caggacgcca ttgacgccgc tatggtgggg   2100
atgctggccg accctaagga ggcgagggcc ggcatccgcg agattcactt cctgccattc   2160
aatcccgttg acaagcgcac tgcgctgacg tacattgatg cggacgggca ctggcacagg   2220
gtgtccaagg gggctccaga gcagatcctc gatctgtgcc actgcaagga ggatctgcgg   2280
```

```
cgcaaggtgc atgggatcat tgacaagtac gcggagaggg ggctccggag cctggcggtg    2340
gccaggcagg aggtgccgga gcgcaacaag gagtcgccgg ggggcccttg gcagttcgtc    2400
gggctgctcc ctctgttcga tcccccgagg cacgacagcg cggagactat ccgcaaggcc    2460
ctcgttctgg gggtgaatgt caagatgatt accggggacc agctggccat tgggaaggag    2520
acaggccggc gcctcgggat gggcacgaac atgtacccgt catccgccct gctggggcag    2580
aataaggacg ccactctgga ggccctgccg gtcgatgagc tcatcgagaa ggctgacggg    2640
ttcgcgggcg tcttccccga gcataagtac gagatcgtga agcggctgca ggagaagaag    2700
catattgtgg ggatgactgg cgacggggtg aatgatgctc ccgccctgaa gaaggctgac    2760
atcggcattg ccgtcgcgga cgccacagat gctgcccgct cggcgtccga tatcgttctc    2820
acggagcctg gctgagcgt tattatctcg gcggttctga caagcaggtg catcttccag    2880
cgcatgaaga actacaccat ctacgctgtg tcgatcacta tcaggatcgt gctgggcttc    2940
atgctgattg cgctcatctg gcagtacgac ttctccccctt tcatggtcct gatcattgct    3000
atcctcaacg acggcacaat catgactatc tcgaaggacc gcgtgaagcc gagcccactc    3060
cccgactctt ggaagctcaa ggagattttc gccactggga tcgttctcgg gtcttacctc    3120
gctctgatga ccgtgatttt cttctgggct atgcacaaga ccgacttctt cagcgacaag    3180
ttcggggttc gctcgattcg cgactcggag cacgagatga tgtctgcgct gtacctccag    3240
gtttcaattg tttcacaggc gctcattttc gtgactaggt cacggtcttg gtccttcgtc    3300
gagaggcctg gctgctcct ggtcactgct ttcctgctcg cccagctggt ggccactttc    3360
ctcgctgttt acgctaattg gggttcgct aggatcaagg gatcggctg ggggtgggcg    3420 ggcgtggtct ggctctactc catcgttttc tacttcccac tcgacctcat caagttcttc    3480
attcggttcg tgctgtcagg gagggcgtgg acaacctcc tggagaacaa gaccgcgttc    3540
accactaaga aggactacgg ccgcgaggag agggaggcgc agctggctac agcgcagcgc    3600
accctccacg ggctccagcc cccagaggct gcgacatcta cactcttcca cgacaagaat    3660
tcttaccgcg agctgtcaga gattgccgag caggctaagc gcagggcgga gattgctagg    3720
ctgagggagc tcaacacact gaagggccac gtgggagtcag tggtcaagct gaagggcctg    3780
gacatcgata caattcagca gaactacacc gtttagaacc taaatgctct taactgagct    3840
aattatgtaa tgcacataca catatttaca tagatatgca tatttatata tagcatgtat    3900
attgtactac atgcattgct tcttaataca tgtagtaaag atatatgcaa aaatagtcga    3960
aagatttgtt tacatataaa atcaccaata tttattgtta ttgtatttc atgaataaag    4020 taataagatt atttgtctaa tattttgatt tactagtact agaaatgaaa aggaatatgc    4080
acaatttcag cattatagtt tggtaggcaa aatggagtga gaatagagtt tcatagtata    4140
tactaaggtt cttaattgtg caaatagttg atacaagtca catgggccaa gtttgtaaat    4200
cttaaatcga aatatgcctt cttctttttt tgcatgaaaa tgctagtaat ttataagtgt    4260
gtttttcaat aagagatgct aaataccaaa attaacctag ttttcagtga gcgcttgcat    4320
tattgtgg                                                            4328
```

<210> SEQ ID NO 62
<211> LENGTH: 2796
<212> TYPE: DNA
<213> ORGANISM: Arabidopsis thaliana
<220> FEATURE:
<221> NAME/KEY: misc_feature
<223> OTHER INFORMATION: AtAHA5W857L

<400> SEQUENCE: 62

```
atggaggagg ttttcgagga gctgaagtgc accaagcagg ggctgaccgc taatgaggcg      60
tcccacaggc tggatgtttt cgggccaaac aagctggagg agaagaagga gtctaagctc     120
ctgaagttcc tgggcttcat gtggaacccc ctctcatggg ttatggaggt ggctgctctg     180
atggctatcg ctctcgccaa tggcgggggc aggccgcccg actggcagga tttcgtcggc     240
attgtttgcc tcctgctcat caactctacg atttcattca tcgaggagaa caatgctggc     300
aatgctgccg cggctctgat ggccgggctc gcgccaaaga caaaggtgct cagggacaac     360
cagtggtctg agcaggaggc gtcaatcctg gtgccaggcg atgtcatctc cattaagctc     420
ggggacatca ttccagctga tgctaggctg ctcgacggcg atccactgaa gatcgaccag     480
tccagcctca cgggcgagtc gattcccgtc acaaagaacc catctgatga ggttttcagc     540
ggctcgattt gcaagcaggg ggagatcgag gccatcgtca ttgcgactgg cgttcacacc     600
ttcttcggga aggccgcgca tctggtggac aacactaatc agatcggcca cttccagaag     660
gtcctgacct caattgggaa cttctgcatt tgctccatcg ccctcggcat cattgttgag     720
ctgctcgtga tgtacccaat ccagaggagg cgctaccgcg acggcattga taatctgctc     780
gtgctgctca tcgggggcat ccctattgcg atgccgtccg tgctgagcgt cacgatggct     840
acaggctccc accgcctctt ccagcagggg gctattacga agcgcatgac agctatcgag     900
gagatggccg gatggacgt gctgctgctgc gataagacag gcactctgac cctcaacaag     960
ctgaccgtcg acaagaatct cgtcgaggtt ttcgcgaagg gggtgggcaa ggagcatgtc    1020
ttcctgctcg ctgccgcgc ctcccgcatc gagaaccagg acgccattga tgctgctatc    1080
gtcggcatgc tggccgaccc aaaggaggcc agggcgggcg ttcgggaggt gcacttcttc    1140
cctttcaacc cggtggacaa cgcactgcg ctcacctacg tcgacagcga tggcaattgg    1200
cataggctt cgaaggggc cccagagcag atcctgaacc tctgcaattg caaggaggac    1260
gtgcgcagga aggtccacgg cgttatcgat aagttcgctg agaggggct gaggtcgctc    1320
gctgttgccc ggcaggaggt gctggagaag aagaaggacg ctccaggggg cccgtggcag    1380
ctggtcggcc tgctccctct cttcgaccca cctcgccatg atagcgctga cacgatccgg    1440
cgcgctctga acctcggcgt gaatgtcaag atgattacag gggaccagct ggccatcggc    1500
aaggagacgg ggaggaggct cgggatgggc acaaacatgt acccgtcgtc tgctctgctc    1560
ggccaggtca aggactcatc cctgggggcg ctccctgttg acgagctcat cgagaaggcg    1620
gatggcttcg ctgggtttt cccggagcac aagtacgaga tcgtgcatcg cctgcagcag    1680
aggaaccaca tctgcggcat gacgggggac ggcgtgaatg atgcgcctgc tctcaagaag    1740
gccgacatcg gcattgccgt ggtcgacgct acggatgctg cgaggggggc gagcgatatc    1800
gtcctgacag agccgggcct ctcagtcatc atttccgccg ttctgacctc ccgggcgatt    1860
ttccagcgca tgaagaacta cactatctac gccgttagca tcaccattcg catcgtgttc    1920
ggcttcatgt tcattgcgct catctggcag ttcgacttct cgccgttcat ggtgctgatc    1980
attgccatcc tcaatgacgg cacgattatg acaatctcta aggataggat gaagccgtcc    2040
ccacagccag acagctggaa gctgagggat atcttctcca ctggcgttgt gctgggggc    2100
taccaggctc tcatgaccgt cgtgttcttc tgggtcatga aggacagcga cttcttctcc    2160
aactacttcg gcgtcaggcc tctgagccag aggccagagc agatgatggc tgctctgtac    2220
ctccaggtgt cgatcatttc tcaggccctc atcttcgtca cccggtctcg ctcatggtcc    2280
tacgctgagt gcccaggcct gctcctgctc ggggctttcg tgattgccca gctggtcgcg    2340
```

```
accttcatcg ctgtgtacgc caactggtca ttcgcgagga tcgaggggc tggctggggg    2400 tgggctggcg tcatttggct gtactccttc ctcacctaca tcccactcga cctgctcaag   2460
ttcggcattc gctacgtgct gagcgggaag gcctggctca acctcctgga gaataagact   2520
gcgttcacca cgaagaagga ctacggcaag gaggagcgcg aggctcagct ggcggctgcc   2580
cagaggaccc tgcacggcct ccagccggcg gagaagaaca atatcttcaa cgagaagaat   2640
agctactcgg agctctcgca gatcgctgag caggctaagc gcagggccga ggtggtcagg   2700
ctgagggaga tcaacacgct caagggccac gtggagtctg ttgtgaagct gaagggcctc   2760
gacattgata ctatccagca gcattacacc gtctag                             2796
```

<210> SEQ ID NO 63
<211> LENGTH: 4326
<212> TYPE: DNA
<213> ORGANISM: Artificial
<220> FEATURE:
<223> OTHER INFORMATION: Cassette_T02780_CsVMV AtAHA5_W857L

<400> SEQUENCE: 63

```
aaggtaatta tccaagatgt agcatcaaga atccaatgtt tacgggaaaa actatggaag     60
tattatgtga gctcagcaag aagcagatca atatgcggca catatgcaac ctatgttcaa    120
aaatgaagaa tgtacagata caagatccta ctgccagaga atacgaagaa gaatacgtag    180
aaattgaaaa agaagaacca ggcgaagaaa agaatcttga agacgtaagc actgacgaca    240
acaatgaaaa gaagaagata aggtcggtga ttgtgaaaga gacatagagg acacatgtaa    300
ggtggaaaat gtaagggcgg aaagtaacct tatcacaaag gaatcttatc ccccactact    360 tatccttta tattttccg tgtcattttt gcccttgagt tttcctatat aaggaaccaa    420
gttcggcatt tgtgaaaaca agaaaaaatt tggtgtaagc tattttcttt gaagtactga    480
ggatacaact tcagagaaat ttgtccctcc cccctccccc tccgccgccg ccgcgccggt    540
aaccaccccg cccctctcct ctttctttct ccgttttttt tttccgtctc ggtctcgatc    600
tttggccttg gtagtttggg tgggcgagag gcggcttcgt gcgcgcccag atcggtgcgc    660 gggagggggcg ggatctcgcg gctggggctc tcgccggcgt ggatccggcc cggatctcgc    720
ggggaatggg gctctcggat gtagatctgc gatccgccgt tgttggggga gatgatgggg    780
ggtttaaaat ttccgccatg ctaaacaaga tcaggaagag gggaaaaggg cactatggtt    840
tatattttta tatatttctg ctgcttcgtc aggcttagat gtgctagatc tttctttctt    900 cttttgtgg gtagaatttg aatccctcag cattgttcat cggtagtttt tcttttcatg    960
atttgtgaca aatgcagcct cgtgcggagc ttttttgtag gtagacgata tctccaccat   1020
ggaggaggtt tcgaggagc tgaagtcac caagcagggg ctgaccgcta atgaggcgtc   1080
ccacaggctg gatgttttcg ggccaaacaa gctggaggag aagaaggagt ctaagctcct   1140
gaagttcctg gcttcatgt ggaaccccct ctcatgggtt atggaggtgg ctgctctgat   1200
ggctatcgct ctcgccaatg gcgggggcag gccgcccgac tggcaggatt tcgtcggcat   1260
tgtttgcctc ctgctcatca actctacgat tcattcatc gaggagaaca atgctggcaa   1320
tgctgccgcg gctctgatgg ccgggctcgc gccaaagaca aaggtgctca gggacaacca   1380
gtggtctgag caggaggcgt caatcctggt gccaggcgat gtcatctcca ttaagctcgg   1440
ggacatcatt ccagctgatg ctaggctgct cgacggcgat ccactgaaga tcgaccagtc   1500
cagcctcacg ggcgagtcga ttcccgtcac aaagaaccca tctgatgagg ttttcagcgg   1560
```

-continued

```
ctcgatttgc aagcaggggg agatcgaggc catcgtcatt gcgactggcg ttcacacctt    1620
cttcgggaag gccgcgcatc tggtggacaa cactaatcag atcggccact tccagaaggt    1680
cctgacctca attgggaact tctgcatttg ctccatcgcc ctcggcatca ttgttgagct    1740
gctcgtgatg tacccaatcc agaggaggcg ctaccgcgac ggcattgata atctgctcgt    1800
gctgctcatc gggggcatcc ctattgcgat gccgtccgtg ctgagcgtca cgatggctac    1860
aggctcccac cgcctcttcc agcagggggc tattacgaag cgcatgacag ctatcgagga    1920
gatggccggg atggacgtgc tctgctgcga taagacaggc actctgaccc tcaacaagct    1980
gaccgtcgac aagaatctcg tcgaggtttt cgcgaagggg gtgggcaagg agcatgtctt    2040
cctgctcgct gcccgcgcct cccgcatcga gaaccaggac gccattgatg ctgctatcgt    2100
cggcatgctg gccgacccaa aggaggccag ggcgggcgtt cgggaggtgc acttcttccc    2160
tttcaacccg gtggacaagc gcactgcgct cacctacgtc gacagcgatg gcaattggca    2220
tagggcttcg aagggggccc cagagcagat cctgaacctc tgcaattgca aggaggacgt    2280
gcgcaggaag gtccacggcg ttatcgataa gttcgctgag agggggctga ggtcgctcgc    2340
tgttgcccgg caggaggtgc tggagaagaa aaggacgct ccaggggcc cgtggcagct    2400
ggtcggcctg ctccctctct tcgacccacc tcgccatgat agcgctgaga cgatccggcg    2460
cgctctgaac ctcggcgtga atgtcaagat gattacaggg gaccagctgg ccatcggcaa    2520
ggagacgggg aggaggctcg ggatgggcac aaacatgtac ccgtcgtctg ctctgctcgg    2580
ccaggtcaag gactcatccc tgggggcgct ccctgttgac gagctcatcg agaaggcgga    2640
tggcttcgct ggggttttcc cggagcacaa gtacagagatc gtgcatcgcc tgcagcagag    2700
gaaccacatc tgcggcatga cggggggacgg cgtgaatgat gcgcctgctc tcaagaaggc    2760
cgacatcggc attgccgtgg tcgacgctac ggatgctgcg agggggggcga gcgatatcgt    2820
cctgacagag ccgggcctct cagtcatcat ttccgccgtt ctgacctccc gggcgatttt    2880
ccagcgcatg aagaactaca ctatctacgc cgttagcatc accattcgca tcgtgttcgg    2940
cttcatgttc attgcgctca tctggcagtt cgacttctcg ccgttcatgg tgctgatcat    3000
tgccatcctc aatgacggca cgattatgac aatctctaag gataggatga agccgtcccc    3060
acagccagac agctggaagc tgagggatat cttctccact ggcgttgtgc tgggggggcta    3120
ccaggctctc atgaccgtcg tgttcttctg ggtcatgaag acagcgact tcttctccaa    3180
ctacttcggc gtcaggcctc tgagccagag gccagagcag atgatggctg ctctgtacct    3240
ccaggtgtcg atcatttctc aggccctcat cttcgtcacc cggtctcgct catggtccta    3300
cgctgagtgc ccaggcctgc tcctgctcgg ggctttcgtg attgcccagc tggtcgcgac    3360
cttcatcgct gtgtacgcca actggtcatt cgcgaggatc gagggggctg gctgggggtg    3420
ggctggcgtc atttggctgt actccttcct cacctacatc ccactcgacc tgctcaagtt    3480
cggcattcgc tacgtgctga gcgggaaggc ctggctcaac ctcctggaga ataagactgc    3540
gttcaccacg aagaaggact acggcaagga ggagcgcgag gctcagctgg cggctgccca    3600
gaggaccctg cacggcctcc agccggcgga gaagaacaat atcttcaacg agaagaatag    3660
ctactcggag ctctcgcaga tcgctgagca ggctaagcgc agggccgagg tggtcaggct    3720
gagggagatc aacacgctca agggccacgt ggagtctgtt gtgaagctga agggcctcga    3780
cattgatact atccagcagc attacaccgt ctagaaccta aatgctctta actgagctaa    3840
ttatgtaatg cacatacaca tatttacata gatatgcata tttatatata gcatgtatat    3900
tgtactacat gcattgcttc ttaatacatg tagtaaagat atatgcaaaa atagtcgaaa    3960
```

```
gatttgttta catataaaat caccaatatt tattgttatt gtattttcat gaataaagta    4020
ataagattat ttgtctaata ttttgattta ctagtactag aaatgaaaag gaatatgcac    4080
aatttcagca ttatagtttg gtaggcaaaa tggagtgaga atagagtttc atagtatata    4140
ctaaggttct taattgtgca aatagttgat acaagtcaca tgggccaagt ttgtaaatct    4200
taaatcgaaa tatgccttct tctttttttg catgaaaatg ctagtaattt ataagtgtgt    4260
ttttcaataa gagatgctaa ataccaaaat taacctagtt ttcagtgagc gcttgcatta    4320
ttgtgg                                                               4326
```

<210> SEQ ID NO 64
<211> LENGTH: 4312
<212> TYPE: DNA
<213> ORGANISM: Artificial
<220> FEATURE:
<223> OTHER INFORMATION: Cassette_T02783_rbcS_Mut_a1 AtAHA5_W857L

<400> SEQUENCE: 64

```
tcccttttaat ctggcgctag atctgcatcc gcggcttgca agataaatg gcacatttag     60 tgtgttattt tgcaatacct ttcatagtag atatccttaa atgcagtttt aggcatgttt    120
gggtaattaa ataacatttt taggaggagt tttagattta cctttctttc gtgatgactg    180
atgacagacg tggggaattc aaatgcaact ctagcgaaag ttcatatatt tttcataaat    240
agctgaggct ggggtaatta ttttttttgt agaaaaatag aataggtgga atggttgggg    300
aaggcgtagg cgctcgtgga cgacgcccga taaaagacaa gaggcggaat tgccatgaat    360
tcgaggtagc taagtaaggc gcatatatat gccaaaaaat tctactgtca ctttccaatt    420
tcaatgcgct gccaaacaag ccatcctgga aactgacttg aattcagccc aattctgtag    480
atccaaacag ggccggcgtc agtgcctcag gtgagagagc agcagacgat tcaaagagcc    540
aaaactgcaa gcagacgcag ccgaagccga agccgaagcc caagcccaaa actgttttgt    600
ctttgcccag aaccgcgacg agcctaaact gcgcttcctc ctatctacaa gtccctggca    660
catcacgcat agtccaacct aggcgcgcag gcgataaggc gcgccacggg gacgcgacat    720
gtggtggcgg acgcgatcag gatagggcca ggctggccgg gcgcggccac gggagaacgg    780
tggccactcg tcccacatcc gcttcgtcct gtcctgtact gcgtcctgcc cccaacgaga    840 gccgagccg gccatcccgt cgcacactct ccccctctat atatgccgtc ggtgtggggg    900
agcctactac aggacgaccc aagcaagcaa gcaagcagcg agtacataca tactaggcag    960
ccaggcagtc tccaccatgg aggaggtttt cgaggagctg aagtgcacca agcaggggct   1020
gaccgctaat gaggcgtccc acaggctgga tgttttcggg ccaaacaagc tggaggagaa   1080
gaaggagtct aagctcctga agttcctggg cttcatgtgg aaccccctct catgggttat   1140
ggaggtggct gctctgatgg ctatcgctct cgccaatggc ggggcaggc cgcccgactg   1200 gcaggatttc gtcggcattg tttgcctcct gctcatcaac tctacgattt cattcatcga   1260
ggagaacaat gctggcaatg ctgccgcggc tctgatggcc gggctcgcgc aaagacaaa   1320 ggtgctcagg gacaaccagt ggtctgagca ggaggcgtca atcctggtgc caggcgatgt   1380
catctccatt aagctcgggg acatcattcc agctgatgct aggctgctcg acggcgatcc   1440
actgaagatc gaccagtcca gcctcacggg cgagtcgatt cccgtcacaa agaacccatc   1500
tgatgaggtt ttcagcggct cgatttgcaa gcaggggggag atcgaggcca tcgtcattgc   1560
gactggcgtt cacaccttct tcgggaaggc cgcgcatctg gtggacaaca ctaatcagat   1620
```

```
cggccacttc cagaaggtcc tgacctcaat tgggaacttc tgcatttgct ccatcgccct    1680
cggcatcatt gttgagctgc tcgtgatgta cccaatccag aggaggcgct accgcgacgg    1740
cattgataat ctgctcgtgc tgctcatcgg gggcatccct attgcgatgc cgtccgtgct    1800
gagcgtcacg atggctacag gctcccaccg cctcttccag caggggggcta ttacgaagcg    1860 catgacagct atcgaggaga tggccgggat ggacgtgctc tgctgcgata gacaggcac    1920 tctgacccct caacaagctga ccgtcgacaa gaatctcgtc gaggttttcg caaggggt    1980 gggcaaggag catgtcttcc tgctcgctgc ccgcgcctcc cgcatcgaga accaggacgc    2040
cattgatgct gctatcgtcg gcatgctggc cgacccaaag gaggccaggg cgggcgttcg    2100
ggaggtgcac ttcttcccctt tcaacccggt ggacaagcgc actgcgctca cctacgtcga    2160
cagcgatggc aattggcata gggcttcgaa gggggcccca gagcagatcc tgaacctctg    2220
caattgcaag gaggacgtgc gcaggaaggt ccacggcgtt atcgataagt tcgctgagag    2280
ggggctgagg tcgctcgctg ttgcccggca ggaggtgctg gagaagaaga aggacgctcc    2340
agggggcccg tggcagctgg tcggcctgct ccctctcttc gacccacctc gccatgatag    2400
cgctgagacg atccggcgcg ctctgaacct cggcgtgaat gtcaagatga ttacagggga    2460
ccagctggcc atcggcaagg agacggggag gaggctcggg atgggcacaa acatgtaccc    2520
gtcgtctgct ctgctcggcc aggtcaagga ctcatccctg ggggcgctcc ctgttgacga    2580
gctcatcgag aaggcggatg gcttcgctgg ggttttcccg gagcacaagt acgagatcgt    2640
gcatcgcctg cagcagagga accacatctg cggcatgacg ggggacggcg tgaatgatgc    2700
gcctgctctc aagaaggccg acatcggcat tgccgtggtc gacgctacgg atgctgcgag    2760
gggggcgagc gatatcgtcc tgacagagcc gggcctctca gtcatcattt ccgccgttct    2820
gacctcccgg gcgattttcc agcgcatgaa gaactacact atctacgccg ttagcatcac    2880
cattcgcatc gtgttcggct tcatgttcat tgcgctcatc tggcagttcg acttctcgcc    2940
gttcatggtg ctgatcattg ccatcctcaa tgacggcacg attatgacaa tctctaagga    3000
taggatgaag ccgtccccac agccagacag ctggaagctg agggatatct tctccactgg    3060
cgttgtgctg ggggggctacc aggctctcat gaccgtcgtg ttcttctggg tcatgaagga    3120
cagcgacttc ttctccaact acttcggcgt caggcctctg agccagaggc cagagcagat    3180
gatggctgct ctgtacctcc aggtgtcgat catttctcag gccctcatct tcgtcacccg    3240
gtctcgctca tggtcctacg ctgagtgccc aggcctgctc ctgctcgggg ctttcgtgat    3300
tgcccagctg gtcgcgacct tcatcgctgt gtacgccaac tggtcattcg cgaggatcga    3360
gggggctggc tggggggtggg ctggcgtcat ttggctgtac tccttcctca cctacatccc    3420
actcgacctg ctcaagttcg gcattcgcta cgtgctgagc gggaaggcct ggctcaacct    3480
cctggagaat aagactgcgt tcaccacgaa gaaggactac ggcaaggagg agcgcgaggc    3540
tcagctggcg gctgcccaga ggaccctgca cggcctccag ccggcggaga gaacaatat    3600 cttcaacgag aagaatagct actcggagct ctcgcagatc gctgagcagg ctaagcgcag    3660
ggccgaggtg gtcaggctga gggagatcaa cacgctcaag ggccacgtgg agtctgttgt    3720
gaagctgaag ggcctcgaca ttgatactat ccagcagcat acaccgtct agaactagac    3780 cgcgcccgcc ggccgccccc cgccggctag ctagctagct agctagctcc tgcgtgagct    3840
agtagctagt gccatgcgtc gtctctgtcg ttcggttttg cttcgggtca ccgtacccctt    3900 tgcttgcttg gtttcttctt tccttttttc ctttttttt tcttctttc cccggccatg    3960 gttcctttgc tttcagcagt tctctgctgg atgtgatgta tccattgttg caagcatggc    4020
```

```
cttgcattgg ctacctctat acctgctaca aactactgca acgcctatat atacttgggg    4080
tgaggaacat gtgaatgcaa gctccggcta tcatatacat gtaatatgga tacaaactat    4140
atatataaat ccgccgaggc gccgactaat actatacgac gacaccgtgt taagttaata    4200
tataactggt gcttttattt tatatatctg tctcatcata tatatatgct aattaatgga    4260
tgtgtgtcct cttcacttca attccttctt tcctttccta tgctttgaga tc            4312
```

<210> SEQ ID NO 65
<211> LENGTH: 5181
<212> TYPE: DNA
<213> ORGANISM: Artificial
<220> FEATURE:
<223> OTHER INFORMATION: Cassette_T10191_RAB17_del AtAHA5_W857L
<400> SEQUENCE: 65

```
aaatgttatg cagttcgctc tggactttc tgctgcgcct acacttgggt gtactgggcc    60
taaattcagc ctgaccgacc gcctgcattg aataatggat gagcaccggt aaaatccgcg    120
tacccaactt tcgagaagaa ccgagacgtg gcgggccggg ccaccgacgc acggcaccag    180
cgactgcaca cgtcccgccg gcgtacgtgt acgtgctgtt ccctcactgg ccgcccaatc    240
cactcatgca tgcccacgta caccctgcc gtggcgcgcc cagatcctaa tcctttcgcc    300
gttctgcact tctgctgcct ataaatggcg gcatcgaccg tcacctgctt caccaccggc    360
gagccacatc gagaacacga tcgagcacac aagcacgaag actcgtttag gagaaaccac    420
aaaccaccaa gccgtgcaag catctctcca ccatggagga ggttttcgag gagctgaagt    480
gcaccaagca ggggctgacc gctaatgagg cgtcccacag gctggatgtt tcgggccaa    540 acaagctgga ggagaagaag gagtctaagc tcctgaagtt cctgggcttc atgtggaacc    600
ccctctcatg ggttatggag gtggctgctc tgatggctat cgctctcgcc aatggcgggg    660
gcaggccgcc cgactggcag gatttcgtcg gcattgtttg cctcctgctc atcaactcta    720
cgatttcatt catcgaggag aacaatgctg gcaatgctgc cgcggctctg atggccgggc    780
tcgcgccaaa gacaaaggtg ctcagggaca ccagtggtc tgagcaggag gcgtcaatcc    840
tggtgccagg cgatgtcatc tccattaagc tcggggacat cattccagct gatgctaggc    900
tgctcgacgg cgatccactg aagatcgacc agtccagcct cacgggcgag tcgattcccg    960
tcacaaagaa cccatctgat gaggttttca gcggctcgat tgcaagcag ggggagatcg    1020 aggccatcgt cattgcgact ggcgttcaca ccttcttcgg gaaggccgcg catctggtgg    1080
acaacactaa tcagatcggc cacttccaga aggtcctgac ctcaattggg aacttctgca    1140
tttgctccat cgccctcggc atcattgttg agctgctcgt gatgtaccca atccagagga    1200
ggcgctaccg cgacggcatt gataatctgc tcgtgctgct catcggggc atccctattg    1260 cgatgccgtc cgtgctgagc gtcacgatgg ctacaggctc ccaccgcctc ttccagcagg    1320
gggctattac gaagcgcatg acagctatcg aggagatggc cgggatggac gtgctctgct    1380
gcgataagac aggcactctg accctcaaca agctgaccgt cgacaagaat ctcgtcgagg    1440
ttttcgcgaa gggggtgggc aaggagcatg tcttcctgct cgctgcccgc gcctcccgca    1500
tcgagaacca ggacgccatt gatgctgcta tcgtcggcat gctggccgac ccaaaggagg    1560
ccagggcggg cgttcgggag gtgcacttct ccctttcaa cccggtggac aagcgcactg    1620 cgctcacccta cgtcgacagc gatggcaatt ggcataggc ttcgaagggg gccccagagc    1680
agatcctgaa cctctgcaat tgcaaggagg acgtgcgcag gaaggtccac ggcgttatcg    1740
```

```
ataagttcgc tgagaggggg ctgaggtcgc tcgctgttgc ccggcaggag gtgctggaga    1800
agaagaagga cgctccaggg ggcccgtggc agctggtcgg cctgctccct ctcttcgacc    1860
cacctcgcca tgatagcgct gagacgatcc ggcgcgctct gaacctcggc gtgaatgtca    1920
agatgattac aggggaccag ctggccatcg gcaaggagac ggggaggagg ctcgggatgg    1980
gcacaaacat gtacccgtcg tctgctctgc tcggccaggt caaggactca tccctggggg    2040 cgctcccctgt tgacgagctc atcgagaagg cggatggctt cgctgggggtt ttcccggagc    2100 acaagtacga gatcgtgcat cgcctgcagc agaggaacca catctgcggc atgacggggg    2160
acggcgtgaa tgatgcgcct gctctcaaga aggccgacat cggcattgcc gtggtcgacg    2220
ctacggatgc tgcgagggggg gcgagcgata tcgtcctgac agagccgggc ctctcagtca    2280
tcatttccgc cgttctgacc tcccgggcga ttttccagcg catgaagaac tacactatct    2340
acgccgttag catcaccatt cgcatcgtgt tcggcttcat gttcattgcg ctcatctggc    2400
agttcgactt ctcgccgttc atggtgctga tcattgccat cctcaatgac ggcacgatta    2460
tgacaatctc taaggatagg atgaagccgt ccccacagcc agacagctgg aagctgaggg    2520
atatcttctc cactggcgtt gtgctggggg gctaccaggc tctcatgacc gtcgtgttct    2580
tctgggtcat gaaggacagc gacttcttct ccaactactt cggcgtcagg cctctgagcc    2640
agaggccaga gcagatgatg gctgctctgt acctccaggt gtcgatcatt tctcaggccc    2700
tcatcttcgt cacccggtct cgctcatggt cctacgctga gtgccaggc ctgctcctgc    2760 tcggggcttt cgtgattgcc cagctggtcg cgaccttcat cgctgtgtac gccaactggt    2820
cattcgcgag gatcgagggg gctggctggg ggtgggctgg cgtcatttgg ctgtactcct    2880
tcctcaccta catcccactc gacctgctca gttcggcat tcgctacgtg ctgagcggga    2940
aggcctggct caacctcctg gagaataaga ctgcgttcac cacgaagaag gactacggca    3000
aggaggagcg cgaggctcag ctggcggctg cccagaggac cctgcacggc ctccagccgg    3060
cggagaagaa caatatcttc aacgagaaga atagctactc ggagctctcg cagatcgctg    3120
agcaggctaa gcgcagggcc gaggtggtca ggctgaggga gatcaacacg ctcaagggcc    3180
acgtggagtc tgttgtgaag ctgaagggcc tcgacattga tactatccag cagcattaca    3240
ccgtctagaa cgcggcgcct atacgtggct gtgctgtgct gtctggcgcg tcaaagccgt    3300
actcttcagc gttccataga taataagata aacccatgaa taagtgtccc tacccctttga    3360 tcatgtgaca gggacaggga cagtttcctg tacttgtggg gtgaatttgt acgtgtgata    3420
cggtaacttg gtccgtgtac tgtttatgct gctacgtttc cttcctaaaa gtacgtatat    3480
atatacagca cttgcgagtg gctttacttg tgtgcactgc ctaaaagtgt cgatattacc    3540
tccagcggta aataaatgac ccttgtaaga aacttacaca gcatgtctta ctaattaaca    3600
gccgttatta tgttcggcgc agtactcaca ctggaactta cgaacaagaa ttgctctatc    3660
aatcaccatc tactttagat atatcttctg aaactttttt caaatccaaa agttcagtat    3720
cttcctacaa attagtgaat taggaatcca agtggttaaa cgaattcggc cggcggtac    3780 cccttaggcc tagggctaga ggacccagct ttgagtggcc gtagatttgc aaaagcaatg    3840
gctaacagac acatattctg ccaaaccccca agaaggataa tcactttttct tagataaaaa    3900 agaacagacc aatatacaaa catccacact tctgcaaaca atacatcaga actaggatta    3960
cgccgattac gtggctttag cagactgtcc aaaaatctgt tttgcaaagc tccaattgct    4020
ccttgcttat ccagcttctt ttgtgttggc aaactgcgct tttccaaccg attttgttct    4080
tctcgcgctt tcttcttagc ctaaacaaac ctcaccgtgc acgcagccat ggtcctgaac    4140
```

```
cttcacctcg tccctataaa agcctagcca accttcacaa tcttatcatc acccacaaca      4200
ccgagcacca caaactagag atcctctcca ccatggctca gtcaaagcac gggctcacaa      4260
aggagatgac tatgaagtac aggatggagg gctgcgtcga tgggcacaag ttcgttatca      4320
ccggcgaggg gatcggctac ccgttcaagg gcaagcaggc gattaacctg tgcgtggtcg      4380
agggcgggcc actgcccttc gctgaggata tcctctccgc cgcgttcatg tacggcaaca      4440
gggttttcac cgagtacccg caggacattg tcgattactt caagaattcc tgcccagctg      4500
ggtacacgtg ggacaggagc ttcctcttcg aggatggcgc tgtgtgcatc tgcaacgccg      4560
acattaccgt ttcggtggag gagaattgca tgtaccacga gtctaagttc tacggggtga      4620
acttcccagc tgacggcccc gtcatgaaga agatgacgga taattgggag ccatcatgcg      4680
agaagatcat tccagtgcct aagcagggga tcctgaaggg cgacgtctcc atgtacctcc      4740
tgctcaagga tggcggcagg ctcaggtgcc agttcgacac agtctacaag gccaagagcg      4800
ttccacgcaa gatgcctgac tggcacttca tccagcataa gctgactcgg gaggaccgct      4860
cggatgcgaa gaaccagaag tggcacctga ctgagcacgc tatcgcctcg gggtccgccc      4920
tcccttgaaa cgatcgttca aacatttggc aataaagttt cttaagattg aatcctgttg      4980
ccggtcttgc gatgattatc atataatttc tgttgaatta cgttaagcat gtaataatta      5040
acatgtaatg catgacgtta tttatgagat gggttttat gattagagtc ccgcaattat       5100
acatttaata cgcgatagaa aacaaaatat agcgcgcaaa ctaggataaa ttatcgcgcg      5160
cggtgtcatc tatgttacta g                                                5181

<210> SEQ ID NO 66
<211> LENGTH: 4238
<212> TYPE: DNA
<213> ORGANISM: Artificial
<220> FEATURE:
<223> OTHER INFORMATION: Cassette_T10586_MYB60 AtAHA5_W857L

<400> SEQUENCE: 66
ctccgtcgct agcgttgtaa tttttatcag cctctctcca tctgattgga tgagctgctt        60
ctcctagcta gcacgttgtc aaccattggg gacgcccttt aggagtgaaa gtgatgcagt       120
tactctactc ccatccggtc caaatcccaa cctaagggat atatgacgaa gagttttcaa       180
tttcagtata atgtgtatag caagtgattt gattttcctg cagattcttg agagagaagg       240
gccaaacctg catatgtgcc aggtgcgcac tcacagtcac acacacggtc ctcatcaatg       300
cccaagaaat ctggagagac acagacaaac gcaagcaatt actccattca tgagcgccac       360
agcagaaaaa ggagtcctcc agaaccggcc gtgttcttgg cttgcacaca cacacacaca       420
cacgcgaaag cagcgcatgc aacaaagcaa agatcacaca cggccggagc aagagagacg       480
cccatattca tgtgatcacc tggctgactt ttgcattgga aagcaacagt gcgagatcaa       540
aagcgaacgc agcacacagc acagcacagc acagggatcg agttgctcta ctccgtatat       600
gaggtcatgc agtatataag cactcacatg cagctatacc ttagctaggg cacctgtgca       660
aggggacagg taggagataa agcaatgtct gctggctaga ataaaaggag gccgatatcg       720
tatcagcaga gggttccagg ggagaaggcc gttctgcagg gccgccgtaa aaggctgtgt       780
aggaagcagc cacagcttct catatcttct tgttcttcga ctacttgcct agctactata       840
tctactagac tagccctagg ctgccttgcta gctagtaggt gtatcgatcg tccgaggtag      900
gaggagacag caggaagcag gctctccacc atggaggagg ttttcgagga gctgaagtgc       960
```

-continued

```
accaagcagg ggctgaccgc taatgaggcg tcccacaggc tggatgtttt cgggccaaac   1020
aagctggagg agaagaagga gtctaagctc ctgaagttcc tgggcttcat gtggaacccc   1080
ctctcatggg ttatggaggt ggctgctctg atggctatcg ctctcgccaa tggcgggggc   1140
aggccgcccg actggcagga tttcgtcggc attgtttgcc tcctgctcat caactctacg   1200
atttcattca tcgaggagaa caatgctggc aatgctgccg cggctctgat ggccgggctc   1260
gcgccaaaga caaaggtgct cagggacaac cagtggtctg agcaggaggc gtcaatcctg   1320
gtgccaggcg atgtcatctc cattaagctc ggggacatca ttccagctga tgctaggctg   1380
ctcgacggcg atccactgaa gatcgaccag tccagcctca cgggcgagtc gattcccgtc   1440
acaaagaacc catctgatga ggttttcagc ggctcgattt gcaagcaggg ggagatcgag   1500
gccatcgtca ttgcgactgg cgttcacacc ttcttcggga aggccgcgca tctggtggac   1560
aacactaatc agatcggcca cttccagaag gtcctgacct caattgggaa cttctgcatt   1620
tgctccatcg ccctcggcat cattgttgag ctgctcgtga tgtacccaat ccagaggagg   1680
cgctaccgcg acggcattga taatctgctc gtgctgctca tcgggggcat ccctattgcg   1740

atgccgtccg tgctgagcgt cacgatggct acaggctccc accgcctctt ccagcagggg   1800
gctattacga agcgcatgac agctatcgag gagatggccg ggatggacgt gctctgctgc   1860
gataagacag gcactctgac cctcaacaag ctgaccgtcg acaagaatct cgtcgaggtt   1920
ttcgcgaagg gggtgggcaa ggagcatgtc ttcctgctcg ctgcccgcgc ctcccgcatc   1980
gagaaccagg acgccattga tgctgctatc gtcggcatgc tggccgaccc aaaggaggcc   2040
agggcgggcg ttcgggaggt gcacttcttc cctttcaacc cggtggacaa gcgcactgcg   2100
ctcacctacg tcgacagcga tggcaattgg catagggctt cgaagggggc cccagagcag   2160
atcctgaacc tctgcaattg caaggaggac gtgcgcagga aggtccacgg cgttatcgat   2220
aagttcgctg agagggggct gaggtcgctc gctgttgccc ggcaggaggt gctggagaag   2280
aagaaggacg ctccaggggg cccgtggcag ctggtcggcc tgctccctct cttcgaccca   2340
cctcgccatg atagcgctga gacgatccgg cgcgctctga acctcggcgt gaatgtcaag   2400
atgattacag gggaccagct ggccatcggc aaggagacgg ggaggaggct cgggatgggc   2460
acaaacatgt acccgtcgtc tgctctgctc ggccaggtca aggactcatc cctgggggcg   2520
ctccctgttg acgagctcat cgagaaggcg gatggcttcg ctggggtttt cccggagcac   2580
aagtacgaga tcgtgcatcg cctgcagcag aggaaccaca tctgcggcat gacgggggac   2640
ggcgtgaatg atgcgcctgc tctcaagaag gccgacatcg gcattgccgt ggtcgacgct   2700
acggatgctg cgagggggcc gagcgatatc gtcctgacag agccgggcct ctcagtcatc   2760
atttccgccg ttctgacctc ccgggcgatt ttccagcgca tgaagaacta cactatctac   2820
gccgttagca tcaccattcg catcgtgttc ggcttcatgt tcattgcgct catctggcag   2880
ttcgacttct cgccgttcat ggtgctgatc attgccatcc tcaatgacgg cacgattatg   2940
acaatctcta aggataggat gaagccgtcc ccacagccag acagctggaa gctgagggat   3000
atcttctcca ctggcgttgt gctgggggc taccaggctc tcatgaccgt cgtgttcttc   3060
tgggtcatga aggacagcga cttcttctcc aactacttcg gcgtcaggcc tctgagccag   3120
aggccagagc agatgatggc tgctctgtac ctccaggtgt cgatcatttc tcaggccctc   3180
atcttcgtca cccggtctcg ctcatggtcc tacgctgagt gcccaggcct gctcctgctc   3240
ggggctttcg tgattgccca gctggtcgcg accttcatcg ctgtgtacgc caactggtca   3300
ttcgcgagga tcgagggggc tggctggggg tgggctggcg tcatttggct gtactccttc   3360
```

```
ctcacctaca tcccactcga cctgctcaag ttcggcattc gctacgtgct gagcgggaag    3420
gcctggctca acctcctgga gaataagact gcgttcacca cgaagaagga ctacggcaag    3480
gaggagcgcg aggctcagct ggcggctgcc cagaggaccc tgcacggcct ccagccggcg    3540
gagaagaaca atatcttcaa cgagaagaat agctactcgg agctctcgca gatcgctgag    3600
caggctaagc gcagggccga ggtggtcagg ctgagggaga tcaacacgct caagggccac    3660
gtggagtctg ttgtgaagct gaagggcctc gacattgata ctatccagca gcattacacc    3720
gtctagaacc taaatgctct taactgagct aattatgtaa tgcacataca catatttaca    3780
tagatatgca tatttatata tagcatgtat attgtactac atgcattgct tcttaataca    3840
tgtagtaaag atatatgcaa aaatagtcga aagatttgtt tacatataaa atcaccaata    3900
tttattgtta ttgtattttc atgaataaag taataagatt atttgtctaa tattttgatt    3960
tactagtact agaaatgaaa aggaatatgc acaatttcag cattatagtt tggtaggcaa    4020
aatggagtga gaatagagtt tcatagtata tactaaggtt cttaattgtg caaatagttg    4080
atacaagtca catgggccaa gtttgtaaat cttaaatcga aatatgcctt cttctttttt    4140
tgcatgaaaa tgctagtaat ttataagtgt gttttcaat aagagatgct aaataccaaa    4200
attaacctag ttttcagtga gcgcttgcat tattgtgg                            4238
```

CONSTRUCTS AND METHODS FOR CONTROLLING STOMATAL CLOSURE IN PLANTS

BACKGROUND

Drought is one of the greatest limitations to crop expansion outside the present-day agricultural areas. It will become increasingly important in regions of the globe where, in the past, the problem was negligible, due to the recognized changes in global climate. Today there is a concern with improving cultural practices and crop genotypes for drought-prone areas.

In plants, the majority of all water loss occurs through pores on the leaf surface, which are called stomata. The size of the stomatal pores in a leaf is variable and controls the rate of diffusion of water vapour out of the plant. In addition to controlling water loss, stomata allow $CO_2$ to diffuse into the leaf for photosynthesis. Thereby, stomata permanently control the trade-off between carbon uptake and water loss. Regulation of stomatal movements by guard cells in response to environmental stimuli and stress conditions is a primary factor in determining water use efficiency and productivity of crop plants.

In plants, the primary ion pumps, the $H^+$-ATPases, are the major protein of the plasma membrane. Using the chemical energy of ATP, plasma membrane $H^+$-ATPases extrude protons from cells of plants to generate electrochemical proton gradients. This gradient has a major role in providing the energy for secondary active transport across the plasma membrane. Molecular studies have shown that plant $H^+$-ATPases are encoded by a multigene family. Notably, eleven isoforms named from AHA1 to AHA11 have been identified in the *Arabidopsis* genome (Axelsen et al. 2001). Alignments between members of this family have shown that they share at least 66% protein sequence identity (Axelsen et al., 2001). They share a common structure with a 100-amino acid long C-terminal domain referred as the R (regulatory) or auto-inhibitory domain, comprising a 14-3-3 binding site and a phosphorylation site at the penultimate Thr residue.

An overview of the expression profiles of members of the *Arabidopsis* plasma membrane $H^+$-ATPase (AHA) family can be found in the Genevestigator database (genevestigator.org). Two genes, AHA1 and AHA2, are expressed in almost all tissues and organs. Thus, these genes appear to function as housekeeping genes required for ion homeostasis. Relatively more AHA1 transcripts are found in shoots, whereas AHA2 is predominantly expressed in roots, especially in root hairs. AHA3, AHA4 and AHA11 also show broad expression throughout the plant, but are not expressed to the same degree. Some degree of specialization is seen as AHA4 has high expression in root endodermis in accordance with reporter gene analysis studies (Vitart et al., 2001). Real time RT-PCR analysis has confirmed that AHA1, AHA2, AHA3 and AHA11 are the major transcripts found in leaves (Alsterfjord et al., 2004). Reporter gene analyses show that the AHA3 promoter is active in leaf phloem companion cells (DeWitt et al., 1991). Expression patterns of AHA6 and AHA9 (predominantly expressed in anthers), AHA7 and AHA8 (almost exclusive expression in pollen) and AHA10 (highest transcript levels in siliques) suggest that the pumps encoded by these genes have more specialized function. Reporter gene analyses have verified the expression of AHA9 in anthers (Houlne et al., 1994) and AHA10 in the endothelium of the developing seed coat (Baxter et al., 2005). AHA5 was found to be predominantly expressed in guard cells (Ueno et al. 2005). In *Arabidopsis* guard cells, the expression of all 11 $H^+$-ATPase isogenes can be detected, but AHA1, AHA2 and AHA5 are the predominant isoforms (Ueno et al. 2005).

Plant plasma membrane $H^+$-ATPases play a central role in different physiological functions including nutrient uptake, intracellular pH regulation and stomatal opening (Haruta et al., 2015). Besides regulation of physiological processes, the plasma membrane proton pumps also play roles in adaptation of plants to changing conditions. Thus, $H^+$-ATPases can be mutual elements for resistance mechanisms that are activated in stress conditions.

To determine the function of the different isoforms in planta, single loss-of-function mutants have been obtained in the plant model *Arabidopsis* for 10 of the 11 genes. However these mutants exhibited no phenotype under normal growth conditions probably due to functional redundancy. For example aha1 and aha2 knock-down mutants grow normally in standard conditions whereas the double homozygous mutant is embryo-lethal (Haruta et al., 2010). This clearly illustrates these two proteins are essential for plant physiology. In addition, using physiological genetic screens, two *Arabidopsis* ost2 (open stomata2) mutants have been identified and the positional cloning of the OST2 locus revealed its identity with the known AHA1 gene that codes for a plasma membrane $H^+$-ATPase (Merlot et al., 2007). Two dominant change-of-function alleles of OST2 were identified as coding for $AHA1_{P68S}$ and $AHA1_{L169F-G867S}$ pump variants, respectively. Both mutations disrupt the auto-inhibitory regulation of the AHA1 pump and cause its constitutive activity. Interestingly, this pump deregulation induced pleiotropic effects including the development of spontaneous necrosis on leaves correlated with an increase in the salicylic acid content (SA), an increase of $H^+$ excretion (acidification) in roots, but also an aberrant control of stomatal aperture, resulting in abnormally high water loss from leaves.

Several studies demonstrate that substitutions at several residues result in activated $H^+$-ATPases including the two substitutions in AHA1 detected in ost2 mutants. Indeed, mutant forms of AHA1 including $W_{875}L$, $G_{867}L$ or $P_{68}S$ rise to high-affinity $H^+$-ATPase with increase molecular activity (Baunsgaard et al., 1996; Merlot et al., 2007). Using functional assay based on yeast complementation these substitutions were shown to rescue lethal growth defect in yeast mutant RS-72 disrupted in its endogenous plasma membrane PMA1 but not its wild-type counter (Cid et al., 1987; Baunsgaard et al., 1996; Merlot et al., 2007). In addition, Merlot et al. (2007) teaches that AHA1 is involved in the regulation of stomatal aperture in plants and the stomata of two ost2 mutants are more open especially under dark conditions compared to wild type.

There are many different documents describing the mechanisms for controlling the stomatal closure. However, none of them provide a solution to improve drought tolerance.

In EP2995680, inventors overexpressed AHA2 in *Arabidopsis thaliana* plants under the control of a guard cell specific promoter. They observed that the stomata were more open in the transformed plants, facilitating photosynthesis and possibly improving yield. AHA2 promotes the opening of the stomata so the person skilled in the art would not consider this gene interesting for improving drought tolerance in plants.

WO2014/012145 intends to inhibit stomatal closure by overexpressing AHA1 in order to increase transpiration. The person skilled in the art would not consider this document when trying to improve drought tolerance.

The sequences of AHA5 from *Arabidopsis thaliana* and *Zea mays* are listed in the sequence listing of EP1033405, US20130074202 and US20090217414. However, there is no indication of a possible use for AHA5.

A protein closed to ZmAHA5 was described in U.S. Pat. No. 8,577,624. This patent deals with a method to identify a potential inhibitor of a type III P-type ATPase, a method to produce such modulator and a computer-assisted method to perform the invention.

There is still a strong interest to develop solutions for controlling the closing of the stomata in order to improve the drought tolerance in plants and the efficient use of water by plants.

SUMMARY OF THE INVENTION

The invention consists in expressing an AHA5 protein in plants, and preferentially a mutated AHA5 protein leading to a constitutive activity of AHA5, to control stomatal closure and improve tolerance to drought conditions in plants.

The invention is based on the surprising effect that transformation of plants with a nucleic acid encoding an AHA5 protein, and preferentially a mutated AHA5 protein leading to a constitutive activity of AHA5, gives rise to transgenic plants having an increase tolerance to drought stress compared to a corresponding non-transgenic plant.

The invention thus consists in either (i) overexpressing a wild-type AHA5 protein, or (ii) expressing or overexpressing a mutated AHA5 protein leading to a constitutive activity of AHA5, for controlling stomatal closure and improve tolerance to drought conditions in plants. The invention also consists in methods to obtain drought tolerant plants through stomatal closure.

In a first aspect, the present invention is related to a method to control stomatal closure in a plant, said method comprising expressing or overexpressing an AHA5 protein. Said method allows conferring drought tolerance or drought resistance through the control of stomatal closure due to AHA5 protein activity.

Preferably, the expression or overexpression of AHA5 is obtained by overexpression of a nucleic acid encoding a mutated AHA5 which leads to a constitutive activity of AHA5 protein.

In a second aspect, the present invention is related to a method to identify a plant with closed stomata comprising the step of identifying in a population of plants, the plants overexpressing an AHA5 protein or with an AHA5 constitutively active, in particular the plants overexpressing a wild-type AHA5 protein or a constitutively active AHA5 protein.

In another aspect, the present invention is also related to a method of growing plants comprising the step of sowing plant seeds, wherein said plant seeds originate from plants expressing or overexpressing an AHA5 protein, and the step of growing plants from these sowed seeds, wherein the growing phase is made under drought/water deficit stress conditions.

In one other aspect, the present invention is related to a nucleic acid sequence encoding a constitutively active AHA5 protein, preferably with genetic modifications leading to amino acid modifications in either the first transmembrane segment or in the R1 domain in the auto inhibitory C-terminus of AHA5 protein or to the deletion of at least part of the R1 domain in the auto inhibitory C-terminus of AHA5 protein, and more preferably with genetic modifications leading to either amino acid substitution(s) in the first transmembrane segment or in the R1 domain in the auto inhibitory C-terminus of AHA5 protein.

In a further aspect, the present invention is also related to nucleic acid constructs comprising a promoter functional in plants and allowing at least an expression in the guard cells, which is operably linked to a nucleic acid sequence encoding an AHA5 protein according to the invention.

Transgenic plants comprising a nucleic acid construct comprising a promoter functional in plants and allowing at least an expression in the guard cells which is operably linked to a nucleic acid sequence encoding a constitutively active AHA5 protein, or comprising a nucleic acid encoding a wild-type AHA5 protein linked to a promoter which allows at least an expression in guard cells and wherein the promoter is not the endogenous promoter of the nucleic acid encoding said wild-type AHA5 protein, are other aspects of the present invention.

Still another aspect of the present invention provides methods for decreasing water loss in a plant, by expression or overexpression of an AHA5 protein.

In yet another aspect, the present invention provides a method for increasing plant yield under non-stress or stress conditions for water supply or at least maintaining plant yield under drought/water deficit stress conditions said method comprising a step of growing a transgenic plant overexpressing a wild-type AHA5 protein or a constitutively active AHA5 protein under non-stress conditions or stress conditions for water supply or drought/water deficit conditions.

Suitably, the methods for decreasing water loss or for increasing plant yield comprise expression or overexpression of a constitutively active AHA5 protein, preferably by amino acid substitution(s) in the first transmembrane segment or in the R1 domain in the auto inhibitory C-terminus of AHA5 protein.

In all these aspects related to control of stomatal closure and improvement of tolerance to drought conditions in plants the present invention encompasses expression of an AHA5 protein by either (i) overexpressing a wild-type AHA5 protein, or (ii) expressing or overexpressing a mutated AHA5 protein leading to a constitutively active AHA5 protein in plants and methods thereof.

DETAILED DESCRIPTION OF THE INVENTION

Figure 1:
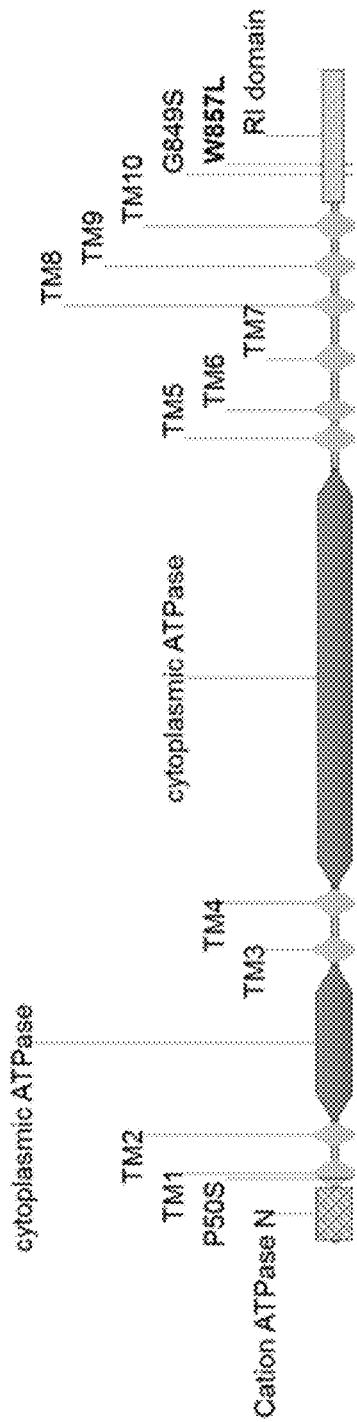
FIG. 1 is a schematic representation of *Arabidopsis thaliana* AHA5 (AtAHA5) wild-type protein (931 amino acids) with its different functional domains (TM=transmembrane domains; R1 domain in the auto-inhibitory C-terminus). Three positions of amino acid substitutions to obtain a constitutively active AHA5 are represented: $P_{50}S$, $G_{849}S$, $W_{857}L$.

The present invention is based on the fact that overexpression or expression of an AHA5 protein or a constitutively active AHA5 protein controls stomatal closure in plants, which confers drought tolerance, thus leading to improved, or at least maintained, yield.

According to the present invention, stomatal closure in a plant may be controlled by overexpressing a wild-type AHA5 protein, by overexpressing a mutated AHA5 protein which is constitutively active, or by expressing a constitutively active AHA5 directly in said plant.

In a first aspect, the present invention is related to a method to control stomatal closure in a plant, said method comprising expressing or overexpressing an AHA5 protein, preferably overexpressing an AHA5 protein.

In one embodiment, the method to control stomatal closure in a plant comprises overexpression of an AHA5 protein is a method comprising overexpression of a wild-type AHA5 protein or a constitutively active AHA5 protein. It may be obtained by any conventional methods of overexpression useful in plants such as transformation with a vector comprising said nucleic acid sequence encoding an AHA5 protein. Said transformation may be performed with bacterial strains such as *Agrobacterium tumefaciens* or by direct methods such as electroporation, gene gun bombardment or other method known by the person skilled in the art. Preferably, the AHA5 protein is overexpressed by transformation of a plant with a vector comprising a promoter functional in plants and a nucleic acid sequence encoding an AHA5 protein, and regenerating said cell to obtain a whole plant. Said vector may be introduced into the plant by *Agrobacterium tumefaciens*. In particular, it is possible to use the method described by Ishida et al. (1996) for the transformation of Monocotyledons.

In one other embodiment, the method to control stomatal closure in a plant comprises expressing a constitutively active AHA5 protein directly in the plant. It may be obtained by direct mutation of the gene in the plant cell with gene editing techniques, such as CRISPR/Cas9 or TALEN according to the mutations disclosed in the present application. Such techniques are also well known by the skilled person.

The term "stomatal closure" or "closed stomata" as used herein is both referring to a stomata completely closed and to a stomata partially closed. According to the present invention, a stomata is considered closed or partially closed when the aperture between the two guard cells of the stomata is reduced by at least 50% compared to an open stomata in a given plant. Stomata are considered open when the plant is placed under light conditions and non-water stress conditions. In particular, in a preferred embodiment of the present invention, a stomata is considered partially closed when the aperture is reduced by at least 50%, at least 60%, at least 70%, at least 80% and up to 85% compared to an open stomata. Also in a preferred embodiment, the stomata is considered closed when the aperture is reduced by more than 85% compared to an open stomata.

Stomatal closure or aperture may be measured by any classical methods known from the person skilled in the art.

For example, stomatal closure or aperture may be measured by direct methods such as but not limited to visual measures, in particular using microscopy and measuring the aperture between the two guard cells of the stomata under light or dark conditions (Leonhardt N et al.; 1997).

Stomatal closure or aperture may also be measured by indirect methods based on parameters measurements, such as but not limited to:
  (i) Rosette leaf adaxial surface temperature, in particular using thermography and for example by infra-red thermography (Merlot S et al., 2002),
  (ii) Channel activities, such as potassium or calcium channels, in particular using patch-clamp experiments on guard cells protoplasts (Perfus-Barbeoch L et al., 2002),
  (iii) Stomatal conductance, in particular leaf using analysis hand-held porometer which monitors the resistance to gas exchanges, and for example by measuring the leaf temperature and the relative humidity (Clement M et al., 2011), or using gas exchange measurement chambers.
  (iv) transpiration rate, in particular based on plant weight loss divided by plant leaf area (Caldeira et al., 2014)

According to a preferred embodiment, the method of controlling stomatal closure comprises expression or overexpression of an AHA5 protein at least in guard cells, and more preferably overexpression of a mutated AHA5 protein which is constitutively active at least in guard cells.

The expression "controlling stomatal closure" or "control of stomatal closure" as used herein means acting on stomatal closure and in particular promoting stomatal closure.

In one embodiment, the method for controlling stomatal closure comprises overexpression a wild-type AHA5 protein in the plant is.

As used herein the term "wild-type" means the amino acid sequence which is a naturally occurring in at least one given organism and which is not changed, modified or mutated by man.

Said wild-type AHA5 protein may be from any plant (genus, species), such as *Arabidopsis thaliana* (SEQ ID NO: 1), *Zea mays* (SEQ ID NO: 2), *Helianthus annuus* (SEQ ID NO: 3 and SEQ ID NO: 4), *Lycopersicon esculentum* (SEQ ID NO: 5), *Aeluropus littoralis* (SEQ ID NO: 6 and SEQ ID NO: 7), *Sorghum bicolor* (SEQ ID NO: 8), *Setaria italica* (SEQ ID NO: 9), *Oryza sativa* (SEQ ID NO: 10), *Brachypodium distachyon* (SEQ ID NO: 11), *Hordeum vulgare* (SEQ ID NO: 12 and SEQ ID NO: 13), *Triticum aestivum*

(SEQ ID NO: 14 and SEQ ID NO: 15 and SEQ ID NO: 16), *Capsella rubella* (SEQ ID NO: 17), *Camelina sativa* (SEQ ID NO: 18), *Medicago truncatula* (SEQ ID NO: 19), *Populus euphratica* (SEQ ID NO: 20).

In a preferred embodiment, said wild-type AHA5 protein is selected within the group consisting of the sequence as set forth as SEQ ID NO: 1 and SEQ ID NO: 2.

In another embodiment, and which represents a preferred embodiment, the method for controlling stomatal closure comprises expression or overexpression of a mutated AHA5 which leads to a constitutive activity of the AHA5 protein.

The term "constitutively active AHA5" or "constitutive AHA5 activity" means a mutated AHA5 H$^+$-ATPase so as to be always active. This may be obtained for example by amino acid modifications in either the first transmembrane domain or the R1 regulatory domain of AHA5 protein or by deletion of at least part of the R1 domain in the auto inhibitory C-terminus of AHA5 protein. Preferably the constitutive AHA5 activity may be obtained by either amino acid substitution(s) in the first transmembrane segment or in the R1 regulatory domain of AHA5 protein.

In one embodiment, the method for controlling stomatal closure according to the present invention comprises the expression or overexpression of a constitutively active AHA5 protein which is an AHA5 protein mutated in the first transmembrane domain.

As used herein, the first transmembrane domain consists in the 23 amino acid consensus sequence (SEQ ID NO: 21)
FLGFMWNPLSWVMEX$_1$AAX$_2$MAIAX$_3$ wherein:
X$_1$: M, V, A
X$_2$: L, I, V
X$_3$: L, M

Preferably, the method for controlling stomatal closure comprises the expression or overexpression of an AHA5 protein mutated in the first transmembrane domain by substituting the amino acid P at position 8 with the amino acid S with reference to the above consensus sequence (SEQ ID NO: 21)

(SEQ ID NO: 22)
FLGFMWNSLSWVMEX$_1$AAX$_2$MAIAX$_3$.

In a preferred embodiment, the method for controlling stomatal closure comprises the expression or overexpression of a mutated AHA5 protein from *Arabidopsis thaliana* as represented by SEQ ID NO: 23.

In one other embodiment, the method for controlling stomatal closure according to the present invention comprises the expression or overexpression of a constitutively active AHA5 protein which is a AHA5 protein modified by amino acid substitution or deletion in the R1 domain.

As used herein, the R1 domain consists in the 107 amino acid consensus sequence (SEQ ID NOS: 24-27)
LSGX$_4$AWX$_5$NX$_6$LX$_7$NKX$_8$AFTX$_9$KX$_{10}$X$_{11}$YGX$_{12}$X$_{13}$EREAQWAX$_{14}$

AQRTLHGLQX$_{15}$X$_{16}$EX$_{17}$X$_{18}$X$_{19}$X$_{20}$X$_{21}$X$_{22}$FX$_{23}$X$_{24}$KX$_{25}$SYX$_{26}$

X$_{27}$LSX$_{28}$IAEQAKRRAEX$_{29}$X$_{30}$RLREX$_{31}$X$_{32}$X$_{33}$LKX$_{34}$HVESVVK

LKGLDIX$_{35}$TIX$_{36}$QX$_{37}$YTV, wherein:
X$_4$: R, K
X$_5$: D, L, N, R
X$_6$: L, M
X$_7$: E, Q, D
X$_3$: T, I
X$_9$: T, S
X$_{10}$: K, E
X$_{11}$: D, N
X$_{12}$: K, R
X$_{13}$: E, G
X$_{14}$: T, A, L
X$_{15}$: P, A
X$_{16}$: P, A
X$_{17}$: T, V, A, P, K, S
X$_{18}$: no amino acid, A, S, N
X$_{19}$: no amino acid, S, T, N
X$_{20}$: N, S, H
X$_{21}$: N, T
X$_{22}$: I, V, M, L
X$_{23}$: N, S, H
X$_{24}$: E, D
X$_{25}$: S, N
X$_{28}$: R, S, H
X$_{27}$: E, D
X$_{28}$: E, Q
X$_{20}$: I, V, M
X$_{30}$: A, V
X$_{31}$: L, I, V
X$_{32}$: N, L, H
X$_3$: T, S
X$_{34}$: G, S
X$_{35}$: D, E
X$_{36}$: Q, N
X$_{37}$: N, H Preferably, the method for controlling stomatal closure comprises the expression or overexpression of an AHA5 protein mutated in the R1 domain at one or more, more preferably at one, of the following positions with reference to above consensus sequence SEQ ID NOs: 24-27:
22 wherein the amino acid Y is substituted with A or;
23 wherein the amino acid G is substituted with S or A or;
24 wherein the amino acid K or R is substituted with A or;
27 wherein the amino acid R is substituted with A or;
31 wherein the amino acid W is substituted with L or A or;
32 wherein the amino acid A is substituted with S or;
35 wherein the amino acid Q is substituted with A or;
36 wherein the amino acid R is substituted with A or;
41 wherein the amino acid L is substituted with A or;
68 wherein the amino acid A is substituted with S or T or;
70 wherein the amino acid R is substituted with A or;
71 wherein the amino acid R is substituted with A or;
74 wherein the amino acid I is substituted with A Among the above substitutions, one or more, preferably one, of the following positions is preferred:
23 wherein the amino acid G is substituted with S or A or;
31 wherein the amino acid W is substituted with L or A or;
36 wherein the amino acid R is substituted with A or;
41 wherein the amino acid L is substituted with A or;
69 wherein the amino acid R is substituted with A.

The most preferred substitution for obtaining a constitutively active AHA5 protein is at position 31 wherein the amino acid W is substituted with L or A. Therefore, in an advantageous embodiment of the present invention, the method for controlling stomatal closure comprises the expression or overexpression of an AHA5 protein mutated in the R1 domain at position 31 wherein the amino acid W is substituted with L or A with reference to the above consensus sequence

```
SEQ ID NOs: 24-27
                                             (SEQ ID NO: 28)
LSGX4AWX5NX6LX7NKX8AFTX9KX10X11YGX12X13EREAQLAX14
AQRTLHGLQX15X16EX17X18X19X20X21X22FX23X24KX25SYX26
X27LSX28IAEQAKRRAEX29X30RLREX31X32X33LKX34HVESVVK
LKGLDIX35TIX36QX37YTV
or
                                             (SEQ ID NO: 29)
LSGX4AWX5NX6LX7NKX8AFTX9KX10X11YGX12X13EREAQAAX14
AQRTLHGLQX15X16EX17X18X19X20X21X22FX23X24KX25SYX26
X27LSX28IAEQAKRRAEX29X30RLREX31X32X33LKX34HVESVVK
LKGLDIX35TIX36QX37YTV.
```

In a preferred embodiment, the method for controlling stomatal closure comprises the expression or overexpression of a mutated AHA5 protein from *Arabidopsis thaliana* as represented by SEQ ID NO: 30 or the expression or overexpression of a mutated AHA5 protein from *Zea mays* as represented by SEQ ID NO: 31.

In a further embodiment of the present invention, the method for controlling stomatal closure comprises the expression or overexpression of an AHA5 protein lacking at least part of the R1 domain in the auto inhibitory C-terminus.

In this particular embodiment, the R1 domain may be completely deleted, thus lacking the 107 amino acids of sequence SEQ ID NOs: 24-27 at the C-terminus of the AHA5 protein. The R1 domain may also be deleted in part, and preferably of at least the 67 amino acids, preferably of at least the 78 amino acids, preferably of at least the 93 amino acids, preferably of at least the 96 amino acids from the C-terminal end of the AHA5 protein. The above positions are with reference to above-mentioned R1 domain consensus sequence SEQ ID NOs: 24-27.

The method for controlling stomatal closure according to the present invention may be for controlling stomatal closure in any type of plant, such as: monocotyledons like maize, wheat, sorgho, rice, barley, sugarcane, or dicotyledons like sunflower or plants from the Brassicaceae family like *Arabidopsis thaliana*, rapeseed, *Brassica* or from the Solanaceae family like tomato and potato.

Preferably, the method is for controlling stomatal closure in monocotyledons, and more preferably selected in the group consisting of maize and wheat and most preferably in maize.

In a specific embodiment, the method of the present invention is for controlling stomatal closure in maize by overexpression of the AHA5 protein from the genus *Arabidopsis*, in particular *Arabidopsis thaliana* or by overexpression of the AHA5 protein from *Zea mays*.

In a second aspect, the present invention is related to a method to identify a plant with closed stomata comprising the step of identifying in a population of plants, the plants overexpressing AHA5 protein or with an AHA5 protein constitutively active, in particular the plants overexpressing a wild-type AHA5 protein or an AHA5 protein constitutively active.

In a specific embodiment, the identification is performed through the use of a marker that is specific to the transgene. In this embodiment, the identification step is thus preferably preceded by a step comprising genotyping said population of plants.

In a specific embodiment, the identification step is preceded by a step comprising extracting the RNA from the individuals in said population.

In a specific embodiment, the identification step is preceded by a step comprising extracting proteins from the individuals in said population. Any classical method known in the art for detecting and quantifying the level of the AHA5 protein may be used, such as Western Blot.

In another aspect, the present invention is also related to a method of growing plants comprising the step of:
sowing plant seeds, wherein said plant seeds originate from plants overexpressing an AHA5 protein,
growing plants from these sowed seeds, wherein the growing phase is made under drought/water deficit stress conditions.

This method may also comprise a step of harvesting said plants.

As used herein, the expressions "drought stress" and "water deficit stress" are synonymous conditions. The term "drought stress" refers to a condition without normal watering in plant growth, which is utilized as a very common term including all kind of abiotic stresses that induce harmful effects on plant growth and survival, for example "drought stress" as used herein includes such stresses as e.g., soil water deficit, vapor pressure deficit, heat stress or light radiation. More specifically, the term "drought" and "water-deficit" refers to environmental conditions where the amount of water (e.g., rainfall or other available water source for plant life) is less than the average water conditions for the particular environment, or the amount of water available is less than the amount of water typically needed by a certain species of plant or by a plant growing in a particular environment.

According to the present application, a drought stressed location is for example a location where the grain yield potential of the site has not been reached due to a drought stress.

A non-stressed location is for example a location where the grain yield potential has been reached by a commercial hybrid variety.

The drought stress intensity may be evaluated by measuring the yield lost between the drought stress treatment (WUE) and a reference treatment irrigated with an optimal amount of water, which is at least, equivalent to the maximum evapotranspiration (ETM) of the crop.

A yield loss of −30% is generally targeted with a common distribution of the drought location between −10% and −40% of yield.

A low drought stressed location may typically be a location with a yield lost between 0% and up to −20% a moderate stressed location between −20% and up to −30%.

The targeted growth stage period may typically be from tasseling to R2 growth stage.

In a common drought location, the drought stress period can spread out from a period between V10 and R4 growth stage.

The terms "drought-resistance" or "drought-tolerance" refer to the ability of a plant to recover from periods of drought stress (i.e., little or no water for a period of days). In the context of the present invention, drought tolerance refers to the ability of a plant to achieve a yield performance as close as possible to the optimal yield whatever the intensity and the duration of the stress.

Yield is normally defined as the measurable produce of economic value from a crop. This may be defined in terms of quantity and/or quality. Yield is directly dependent on several factors, for example, the number and size of the organs, plant architecture (for example, the number of branches), seed production, leaf senescence and more. The term "yield" in general means a measurable produce of economic value, typically related to a specified crop, to an area, and to a period of time. Individual plant parts directly contribute to yield based on their number, size and/or weight, or the actual yield is the yield per square meter for a crop and year, which is determined by dividing total production (includes both harvested and appraised production) by planted square meters. The term "yield" of a plant may relate to vegetative biomass (root and/or shoot biomass), to reproductive organs, and/or to propagules (such as seeds) of that plant. The yield may be expressed for example in q/ha (q means quintal which correspond to 100 kg and ha means hectare).

For the present invention, the yield may be calculated as follows:

During harvest, grain weight and grain moisture are measured using on-board equipment on the combine harvester.

Grain weight is then normalized to moisture at 15%, using the following formula:

Normalized grain weight=measured grain weight×(100−measured moisture (as a percentage))/85 (which is 100−normalized moisture at 15%). As an example, if the measured grain moisture is 25%, the normalized grain weight will be: normalized grain weight=measured grain weight×75/85.

Yield is then expressed in a conventional unit (such as quintal per hectare).

In a specific embodiment, the method of growing plants according to the invention comprises the step of sowing plant seeds originate from plants overexpressing a constitutively active AHA5 protein, and preferably overexpressing a constitutively active AHA5 protein as defined above.

In one other aspect, the present invention is related to a nucleic acid sequence encoding a constitutively active AHA5 protein, preferably with genetic modifications leading to amino acid modifications in either the first transmembrane segment as described above as SEQ ID NO: 21, or in the R1 domain in the auto-inhibitory C-terminus of AHA5 protein or by deletion of at least part of the R1 domain in the auto-inhibitory C terminus of AHA5 as described above as SEQ ID Nos: 24-27, and more preferably leading to either amino acid substitution(s) in said first transmembrane segment or in said R1 domain in the auto inhibitory C-terminus of AHA5 protein.

In a preferred embodiment, the nucleic acid sequence encodes a constitutively active AHA5 protein mutated in the first transmembrane domain and in a more preferred embodiment the AHA5 protein is mutated in the first transmembrane domain by substituting the amino acid P at position 8 with the amino acid S with reference to the above consensus sequence (SEQ ID NO: 21).

In a most preferred embodiment, the nucleic acid sequence encodes a constitutively active AHA5 protein from *Arabidopsis thaliana*, said protein being represented by SEQ ID NO: 23.

In one other preferred embodiment, the nucleic acid sequence encodes a constitutively active AHA5 protein modified by amino acid substitution or deletion in the R1 domain. More preferably, said AHA5 protein is mutated in the R1 domain at one or more, and preferentially one, of the following positions with reference to consensus sequence SEQ ID NOs: 24-27:

22 wherein the amino acid Y is substituted with A or;
23 wherein the amino acid G is substituted with S or A or;
24 wherein the amino acid K or R is substituted with A or;
27 wherein the amino acid R is substituted with A or;
31 wherein the amino acid W is substituted with L or A or;
32 wherein the amino acid A is substituted with S or;
35 wherein the amino acid Q is substituted with A or;
36 wherein the amino acid R is substituted with A or;
41 wherein the amino acid L is substituted with A or;
68 wherein the amino acid A is substituted with S or T or;
70 wherein the amino acid R is substituted with A or;
71 wherein the amino acid R is substituted with A or;
74 wherein the amino acid I is substituted with A.

In an even more preferred embodiment, the nucleic acid sequence encodes a constitutively active AHA5 protein mutated in the R1 domain at one or more, preferentially one, of the following positions with reference to consensus sequence SEQ ID NOs: 24-27:

23 wherein the amino acid G is substituted with S or A or;
31 wherein the amino acid W is substituted with L or A or;
36 wherein the amino acid R is substituted with A or;
41 wherein the amino acid L is substituted with A or;
69 wherein the amino acid R is substituted with A.

In the most preferred embodiment, the nucleic acid sequence encodes a constitutively active AHA5 protein mutated in the R1 domain at position 31 wherein the amino acid W is substituted with L or A (SEQ ID NO: 28 and SEQ ID NO: 29, respectively).

In a preferred embodiment, the nucleic acid sequence encodes a mutated AHA5 protein from *Arabidopsis thaliana*, said protein being represented by SEQ ID NO: 30 or the nucleic acid encodes a mutated AHA5 protein from *Zea mays*, said protein being represented by SEQ ID NO: 31.

In another preferred embodiment, the nucleic acid sequence encodes an AHA5 protein lacking at least part of the R1 domain in the auto inhibitory C-terminus.

In a further aspect, the present invention is also related to nucleic acid constructs comprising a promoter functional in plants and allowing at least an expression in the guard cells, which is operably linked to a nucleic acid sequence encoding a constitutively active AHA5 protein as defined above.

A promoter functional in plants refers to a nucleotide sequence capable of initiating transcription of a nucleic acid molecule in a cell of a plant. A promoter functional in plants can be for example a constitutive promoter, an inducible promoter, a developmentally regulated promoter or a tissue-specific promoter such as a leaf-specific promoter, a seed-specific, a guard cell-specific promoter and the like.

According to the present invention, the nucleic acid constructs comprise a promoter functional in plants and allowing at least an expression in the guard cells of the stomata.

The nucleic acid constructs of the present invention may comprise a promoter which is specific of the guard cells such as the SbMYB60 or a promoter allowing expression in the whole plant such as the CsvMV promoter, or a promoter driving expression in leaf such as the rbcs promoter or a drought inducible promoter such as RAB17.

In another aspect the present invention is also related to nucleic acid constructs comprising a nucleic acid encoding a wild-type AHA5 protein linked to promoter which is not the endogenous promoter of the nucleic acid encoding said wild-type AHA5 protein and which allows at least an expression in the guard cells.

All the nucleic acid constructs of the present invention, either containing a nucleic acid sequence encoding a constitutively active AHA5 protein with an endogenous or non-endogenous promoter or containing a nucleic acid sequence encoding a wild-type AHA5 protein under the control of a non-endogenous promoter, are stomata closure-controlling constructs.

A further aspect of the invention consists in transgenic plants comprising a nucleic acid construct comprising a promoter functional in plants operably linked to a nucleic acid sequence encoding a constitutively active AHA5 protein or transgenic plants comprising a nucleic acid construct comprising a promoter operably linked to a nucleic acid sequence encoding a wild-type AHA5 protein, said promoter being non-endogenous as described above.

All the above preferred embodiments concerning the nucleic acid sequence encoding a constitutively active AHA5 protein also apply to the nucleic acid constructs according to the invention.

Still another aspect of the present invention provides methods for decreasing water loss in a plant, by expressing or overexpression of an AHA5 protein in said plant, in particular by overexpressing a wild-type AHA5 protein or by expressing or overexpressing a constitutively active AHA5 protein in said plant.

In yet another aspect, the present invention provides a method for increasing plant yield under non-stress or stress conditions for water supply or at least maintaining plant yield under drought/water deficit stress conditions said method comprising a step of growing a transgenic plant overexpressing a wild-type AHA5 protein or a constitutively active AHA5 protein under non-stress conditions or stress conditions for water supply or under drought/water deficit conditions.

As used herein, the expression "non-stress conditions for water supply" means a condition with normal or sufficient water supply with respect to the species of plant and to the particular environment wherein the plant is growing.

All the preferred embodiments described herein for expression or overexpression of AHA5 protein for controlling stomatal closure in a plant apply mutatis mutandis for expression or overexpression of AHA5 protein in the methods according to the invention for decreasing water loss in a plant or for increasing plant yield.

Suitably, the methods for decreasing water loss or for increasing plant yield comprise expression or overexpression of a constitutively active AHA5 protein, which is preferably an AHA5 mutated by amino acid modifications in either the first transmembrane or the R1 regulatory domain of AHA5 protein or by deletion of at least part of the R1 domain in the auto inhibitory C-terminus of AHA5 protein. More preferably, the constitutively active AHA5 protein is an AHA5 mutated by amino acid substitution(s) in the first transmembrane segment or in the R1 regulatory domain of AHA5 protein.

According to the present invention, the increasing of plant yield is wherein:

the yield obtained from said transgenic plant grown under said water deficit stress conditions is increased as compared to the yield obtained from a plant not overexpressing an AHA5 protein, grown under said stress conditions, or the yield obtained from said transgenic plants grown under non-stress conditions for water supply is increased as compared to the yield obtained from a plant not overexpressing an AHA5 protein grown under said non-stress conditions, or the yield obtained from said transgenic plants grown under said water deficit stress conditions is maintained as compared to the yield obtained from said transgenic plant grown in non-stress conditions for water supply.

In yet another aspect, the present invention provides a promoter of sequence with at least 80%, preferably with at least 85%, more preferably with at least 90%, and even more preferably with at least 95% sequence identity with SEQ ID NO: 40. This promoter is able to drive expression specifically in the guard cells of a plant. This promoter is also able to be induced by drought stress, viz. is a drought stress-inducible promoter. The identity percentage is calculated by any sequence analysis method known by the skilled person, and particularly with algorithms such as Needleman-Wunsch. The identity percentage is calculated over the whole length of the query sequence.

In a preferred embodiment, the promoter is SEQ ID NO: 40.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The following examples illustrate certain aspects of the invention. The examples in no way limit the invention.

EXAMPLES

Example 1—Identification of Two Mutations Involved in the Activity Regulation of Plasma Membrane Proton Pumps H$^+$-ATPases The AtAHA5 gene was synthetized by the gene synthesis provider GeneArt and cloned into the pMK vector. Subsequently, AtAHA5 was amplified by PCR using the following primers:

```
                                           (SEQ ID NO: 32)
5'-GGATTCTAGAACTAGTATGGAGGAAGTGTTCGAGGAGCTG-3'
and (SEQ ID NO: 33)
5'-CGGTATCATAAGCTTGTTAAACGGTGTAATGTTGCTGAATCG-3'
``` and cloned into the pAG425GPD excised by SpeI and HindIII using In-Fusion strategy (Clontech), following the manufacturer's instructions. Then, to test substitutions previously identified in AHA1, AtAHA5 variants were generated by introducing point mutations into AtAHA5. In AHA1, these mutations give rise to high-affinity H$^+$-ATPase with increase molecular activity.

Single amino acid substitution, $P_{50}S$ or $W_{857}L$, was introduced into AtAHA5 by site-directed mutagenesis using Site-Directed Mutagenesis kit (Agilent technology), following the manufacturer's instructions and using the following primers:

```
                                           (SEQ ID NO: 34)
5'-GGGTTCATGTGGAACTCATTGTCGTGG-3'
and (SEQ ID NO: 35)
5'-CCACGACAATGAGTTCCACATGAACCC-3'
or
```

-continued (SEQ ID NO: 36)
5'-GGAAAGAGAAGCTCAATTGGCTGCAGCTC-3' and (SEQ ID NO: 37)
5'-GAGCTGCAGCCAATTGAGCTTCTCTTTCC-3', respectively.

To evaluate the impact of these substitutions, functional assay based on yeast complementation was performed using the yeast mutant RS-72 disrupted in its endogenous plasma membrane ATPase. In the RS-72 yeast strain, the native promoter of the yeast $H^+$-ATPase (PMA1) has been replaced by a galactose-dependent (GAL1) promoter. Expression of plasmid-born plant $H^+$-ATPase is under the control of the constitutive PMA1 promoter. Thus, when the yeasts are maintained on galactose medium, both the yeast and the plant $H^+$-ATPases are expressed. After transfer to glucose medium only plant $H^+$-ATPase is being produced and, in order to grow, yeasts are dependent on the plant enzyme (Cid et al., 1987).

Figure 2:
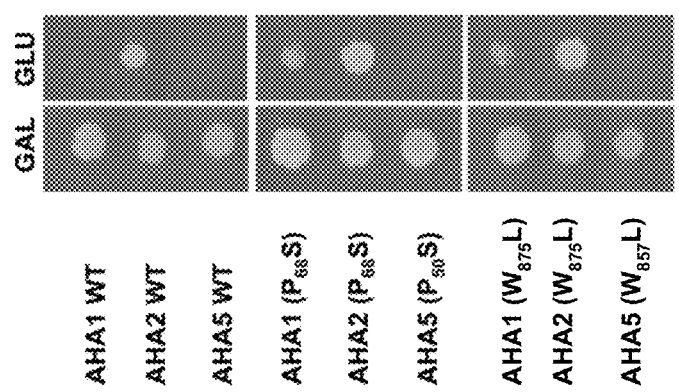
FIG. 2: Complementation of the yeast mutant RS-72 in which the essential gene encoding the $H^+$-ATPase PMA1 was replaced under the strict control of a galactose (GAL)-inducible promoter.

Yeast expressing wild-type AtAHA5 but no endogenous yeast ATPase do not grow at all on glucose medium as previously observe for AHA1 (FIG. 2). Surprisingly, none of the amino acid substitution, $P_{50}S$ or $W_{857}L$ is able to rescue the growth phenotype of the yeast compare to AHA1 or AHA2. Using Western analysis with antibodies directed against the plant $H^+$-ATPases on membrane proteins from yeast, the expression of AtAHA5 protein in yeast was confirmed (Data not shown).

These results show that amino acid substitutions $P_{68}S$ and $W_{875}L$ in AHA1 and AHA2 proteins, but not the corresponding amino acid substitutions $P_{50}S$ and $W_{857}L$ in AHA5, are able to complement the growth defect of RS-72.

These variants were then used to transform *Arabidopsis thaliana* plants to evaluate the impact of these proteins in stomatal closure and water loss rate coupled to biomass evaluation in response to drought stress.

Example 2—Guard Cell Specific Expression of the Marker Gene GUS Under Control of AtAHA5 Promoter Region Previous studies based on RT-PCR indicate that AtAHA5 is expressed in stomata (Ueno et al., 2005, Leonhardt et al, 1999). To determine the AtAHA5 expression profile in detail, transgenic plants expressing the reporter β-glucuronidase (GUS) gene under the control of the putative AtAHA5 promoter were generated. The genomic region located upstream of the translation initiation codon, 2356 bp in length, was amplified by PCR on genomic DNA from *Arabidopsis* Columbia ecotype (Col) using the primers (SEQ ID NO: 38)
5'-GGG GAC AAC TTT GTA TAG AAA AGT TGC AAC CAT

CAT GAC AAG CGT CTG-3' and (SEQ ID NO: 39)
5'-GGG GAC TGC TTT TTT GTA CAA ACT TGG GGT ATT

CGT ACC TAG ACC CAT CAT T-3'.

Figure 3:
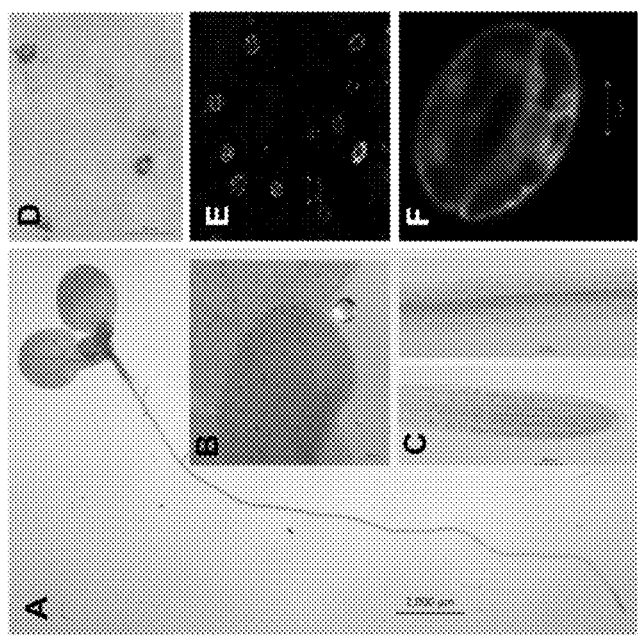
FIG. 3: Expression profile of AtAHA5 gene in plants (Col) transformed with pAHA5: EGFP-GUS construct.

This 2356 bp genomic fragment was then cloned upstream the EGFP (Enhance Green Fluorescence Protein) and GUS (β-glucuronidase) reporter genes in the pBGWFS7 vector. The construct obtained was introduced in *Arabidopsis* and the resulting transgenic lines were histologically analyzed to detect the reporter expression domains. In all samples examined, reporter gene expression was only detected in guard cells from all plant aerial organs provided with stomata (FIG. 3).

These results show that GUS and GFP were detected only in guard cell (B, D, E, F). No GUS activity or EGFP were detected in roots (A, B, C) or in vascular tissues and mesophyll in leaves (A).

Example 3—Identification of Guard-Cell Promoters SbMYB60 and ZmMYB60

Using AtMYB60 protein sequence, first hits by blastp against the *Arabidopsis* genome (TAIR_V9), rice genome (MSU Rice Genome Release 7), maize genome (B73 RefGen_v2), and *sorghum* genome (MIPS 1.4) were selected and aligned using Muscle module of seaview4 (Gouy M. et al., (2010). Conserved blocks were identified and provided to the phyML 3.0 software (Guindon S. et al., 2010). Closest homologous genes were identified in rice (LOC_Os11g35390), sorgho (Sb05g021820) and maize (GRMZM2G108959). The upstream region up to the next repetitive region were isolated and aligned to identify conserved blocks and cis-elements. From a region of 922 bp upstream of Sb05g021820, one ABRE box was identified 149 bp upstream of the putative start codon. The ABRE box was mutated from ACGTG in order to create a DOF element AAAAG. An additional base was modified 682 bp upstream of the putative start codon for cloning purposes. Similarly in maize from a region of 773 bp upstream of the GRMZM2G108959 gene, one ABRE box was identified 71 bp upstream of the putative start codon. The ABRE box was mutated from ACGTG in order to create a DOF element AAAAG. An additional base was modified 702 bp upstream of the putative start codon for cloning purposes.

The regulatory region upstream of the putative start codon of SbMYB60 as exemplified above (SEQ ID NO: 40) was cloned and fused to the reporter gene ZsGreen (Clonetech; Matz et al., 1999) and the *Arabidopsis thaliana* Sac66 polyadenylation sequence, and transformed into maize. Guard cell specific expression of the ZsGreen fluorescence protein was verified by confocal microscopy of primary transformants seedlings. The guard cell specific *Sorghum bicolor* MYB60 promoter allows strong expression in guard cells. The *Sorghum bicolor* gene was identified as the closest homologue of AtMYB60 (Rusconi et al., 2013).

Figure 4:
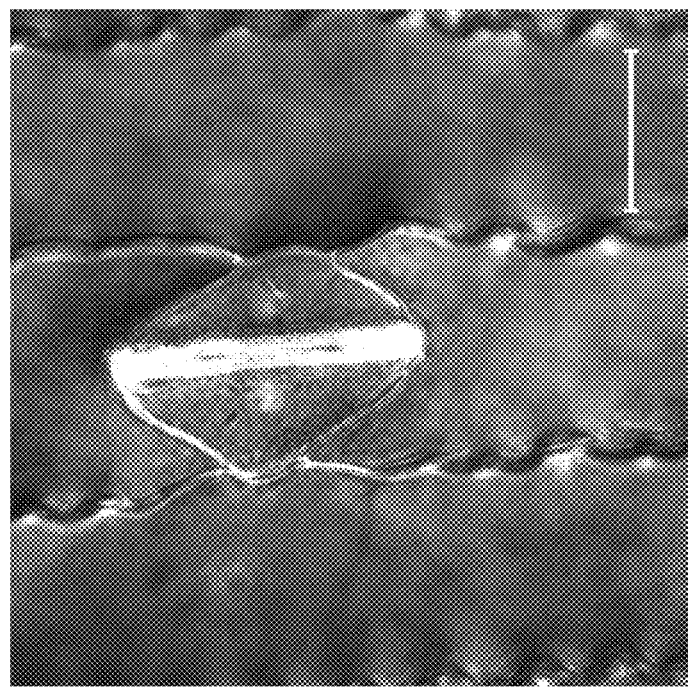
FIG. 4: Expression profile of SbMYB60 gene in plants (*Zea mays*) transformed with pSbMYB60: ZsGreen construct. Scale bar, 20 μm.

The maize T0 plantlets stably transformed with the fusion proSMYB60: ZsGreen were analyzed by confocal microscopy. As shown in FIG. 4, fluorescence of the ZsGreen marker gene was detected in guard cells but not subsidiary cells neither in epidermal pavement cells of maize leaves.

The maize MYB60 promoter was also identified (SEQ ID NO: 41) as described above.

Example 4—Cloning of AtAHA5 Downstream the 35S Promoter and Downstream the AtAHA5 Promoter and Transformation of *Arabidopsis* Plants The AtAHA5 gene was synthetized by the gene synthesis provider GeneArt and cloned into the pMK vector. AtAHA5 was subsequently excised by AscI, PacI cleavage and cloned in the AscI, PacI sites of the gateway constitutive expression vector, pMDC32, harboring a dual 35S promoter (SEQ ID NO: 42). Then, single amino acid substitution, $P_{50}S$ or $W_{857}L$, was introduced into pMDC32 by site-directed mutagenesis using the following primers:

5'-GGGTTCATGTGGAACTCATTGTCGTGG-3'  (SEQ ID NO: 34)

and

5'-CCACGACAATGAGTTCCACATGAACCC-3'  (SEQ ID NO: 35)

or

5'-GGAAAGAGAAGCTCAATTGGCTGCAGCTC-3'  (SEQ ID NO: 36)

and

5'-GAGCTGCAGCCAATTGAGCTTCTCTTTCC-3',  (SEQ ID NO: 37)

respectively.

The p35S: AtAHA5$P_{50}$S construct corresponds to SEQ ID NO: 43 and the p35S: AtAHA5$W_{857}L$ construct corresponds to SEQ ID NO: 44.

The AtAHA5 wild-type gene was also cloned downstream of the dual 35S promoter to make the construct SEQ ID NO: 45.

The promoter of AtAHA5 (SEQ ID NO: 46) was fused to the EGFP and the AtAHA5 gene into the pB7m34G vector using the gateway cloning strategy. Then, single amino acid substitution, $W_{857}L$, was introduced into pB7m34G by site-directed mutagenesis using the following primers:

5'-GGAAAGAGAAGCTCAATTGGCTGCAGCTC-3'  (SEQ ID NO: 36)

and

5'-GAGCTGCAGCCAATTGAGCTTCTCTTTCC-3'.  (SEQ ID NO: 37)

The construct (SEQ ID NO: 47) was introduced in *Arabidopsis*.

The AtAHA5 wild-type gene was also cloned downstream of the promoter of AtAHA5 (SEQ ID NO: 48).

All of the plant transformation plasmid vectors were introduced into *Agrobacterium tumefaciens*, which was then used to transform *Arabidopsis* plants belonging to the Columbia ecotype or ost2-2D mutant using a standard method (Weigel and Glazebrook. 2006). F3 homozygous plants were used for the experiments.

Example 5—Cloning of the Mutated ZmAHA5 Downstream of CsVMV, Rbcs, ZmRAB17 and SbMYB60 Promoters and Transformation in Corn The ZmAHA5 coding sequence (GRMZM2G006894) with the mutation W885L (SEQ ID NO: 49 or SEQ ID NO: 50 corresponding to two optimized versions with respect to allergenicity issue) was codon optimized for maize expression by a gene synthesis service provider and cloned into the pUC57 vector (Genscript). The mutated ZmAHA5 sequence was then cloned via restriction enzyme digestion and ligation between a CsVMV promoter (Verdaguer et al (1996)) (SEQ ID NO: 51) plus a rice actin intron (McElroy et al 1990) (SEQ ID NO: 52), and an *Arabidopsis* Sac66 polyadenylation sequence (Jenkins et al., 1999) (SEQ ID NO: 53), into the destination binary plasmid pBIOS03092 forming pBIOS03580. (The destination vector is a derivative of pSB12 (Komari et al. (1996)) containing a pActin+actin intron-selectable marker-nos polyA chimeric gene for selection of maize transformants and cassette between a HMWG promoter, the reporter gene ZsGreen (Clonetech; Matz et al., 1999) and a Sac66 polyadenylation sequence).

Similarly, the mutated ZmAHA5 was linked to the Rbcs promoter (Matsuoka and Sanada, 1991) (SEQ ID NO: 54) and a *Zea mays* Rbcs polyadenylation sequence (SEQ ID NO: 55), by performing a restriction enzyme digestion and ligation and the destination binary plasmid pBIOS03092 forming pBIOS03583.

Similarly, the mutated ZmAHA5 was linked to the drought inducible *Zea mays* Rab17 promoter (Vilardell et al., 1991) (SEQ ID NO: 56) and a *Zea mays* Rab17 polyadenylation sequence (SEQ ID NO: 57), by performing a restriction enzyme digestion and ligation and the destination binary plasmid pBIOS03092 forming pBIOS10481.

The mutated ZmAHA5 was linked to the guard cell specific *Sorghum bicolor* MYB60 promoter (SEQ ID NO: 40) and an *Arabidopsis thaliana* Sac66 polyadenylation sequence (SEQ ID NO: 53), by performing a restriction enzyme digestion and ligation and the destination binary plasmid pBIOS03092 forming pBIOS10646.

pBIOS03580, pBIOS03583, pBIOS10481, and pBIOS10646 were transferred into agrobacteria LBA4404_+pSB1 according to Komari et al (1996) forming respectively strain T02781, strain T02784, strain T10401 and strain T10584. Maize cultivar A188 was transformed with these agrobacterial strains essentially as described by Ishida et al (1996).

Analysis of the pCsVMV-ZmAHA5$W_{885L}$-AtSac66 term (SEQ ID NO: 58), pRbcs-ZmAHA5$W_{885L}$-Rbcs term (SEQ ID NO: 59), pZmRAB17-ZmAHA5 $W_{885L}$-ZmRab17 term (SEQ ID NO: 60), and pSbMYB60-ZmAHA5$W_{885L}$-AtSac66 term (SEQ ID NO: 61) transformed maize plants indicated that plants overexpressed the mutated ZmAHA5. Overexpression of the transgene was verified by quantitative reverse-transcription polymerase chain reaction (q-RT-PCR). Total RNA was extracted from TO plantlets leaf. RNA was reverse transcribed into cDNA; mutated ZmAHA5 expression was quantified on those cDNA and normalized with endogenous ZmEF1α (GRMZM2G001327) and ZmUbiquitin (GRMZM2G110983) genes expression.

Example 6—Cloning of the Mutated AtAHA5 Downstream of CsVMV, Rbcs, ZmRAB17 and SbMYB60 Promoters and Transformation in Corn The AtAHA5 coding sequence (AT2G24520) with the mutation W857L (SEQ ID NO: 62) was codon optimized for maize expression by a gene synthesis service provider and cloned into the pUC57 vector (Genscript). The AtAHA5 sequence was then cloned via restriction enzyme digestion and ligation between a CsVMV promoter (Verdaguer et al (1996)) (SEQ ID NO: 51) plus a rice actin intron (McElroy et al 1990) (SEQ ID NO: 52), and an *Arabidopsis* Sac66 polyadenylation sequence (Jenkins et al (1999)) (SEQ ID NO: 53), into the destination binary plasmid pBIOS3091 forming pBIOS03579.

Similarly, the mutated AtAHA5 was linked to the rbcs promoter (SEQ ID NO: 54) by performing restriction enzyme digestion and ligation between a rbcs promoter, and a *Zea mays* rbcs polyadenylation sequence (SEQ ID NO: 55), into the destination binary plasmid pBIOS03092 forming pBIOS03582.

Similarly, the mutated AtAHA5 was linked to the drought inducible *Zea mays* Rab17 promoter (Vilardell et al., 1991) (SEQ ID NO: 56) and a *Zea mays* Rab17 polyadenylation sequence (SEQ ID NO: 57), by performing a restriction enzyme digestion and ligation and the destination binary plasmid pBIOS03092 forming pBIOS10231.

The mutated AtAHA5 was linked to the guard cell specific *Sorghum bicolor* MYB60 promoter (SEQ ID NO: 40) and an *Arabidopsis thaliana* Sac66 polyadenylation sequence (SEQ ID NO: 53), by performing a restriction enzyme digestion and ligation and the destination binary plasmid pBIOS03092 forming pBIOS10648.

pBIOS03579, pBIOS03582, pBIOS10231, and pBIOS10648 were transferred into agrobacteria LBA4404 (pSB1) forming respectively strain T02780, strain T02783, strain T10191 and strain T10586. Maize cultivar A188 was transformed with these agrobacterial strains essentially as described by Ishida et al (1996).

Analysis of the pCsVMV-AtAHA5$W_{857L}$-AtSac66 term (SEQ ID NO: 63), pRbcs-AtAHA5 $W_{857L}$-ZmRbcs term (SEQ ID NO: 64), pZmRAB17-AtAHA5$W_{857L}$-ZmRAB17 term (SEQ ID NO: 65), and pSbMYB60-AtAHA5$W_{857L}$-AtSac66 term (SEQ ID NO: 66) transformed maize plants indicated that plants overexpressed the mutated AtAHA5. Overexpression of the transgene was verified by quantitative reverse-transcription polymerase chain reaction (q-RT-PCR) as previously described.

Example 7—Maize Field Trials

A—Field Trials

Hybrids were obtained from a cross of T3 plants issued from the AHA5 transgenic maize line (pCsVMV-ZmAHA5$W_{885L}$-AtSac66 term (SEQ ID NO: 58), pRbcs-ZmAHA5$W_{885L}$-Rbcs term (SEQ ID NO: 59), pZmRAB17-ZmAHA5 $W_{885L}$-ZmRab17 term (SEQ ID NO: 60), pSbMYB60-ZmAHA5$W_{885L}$-AtSac66 term (SEQ ID NO: 61), pCsVMV-AtAHA5$W_{857L}$-AtSac66 term (SEQ ID NO: 63), pRbcs-AtAHA5 $W_{857L}$-ZmRbcs term (SEQ ID NO: 64), pZmRAB17-AtAHA5$W_{857L}$-ZmRAB17 term (SEQ ID NO: 65), and pSbMYB60-AtAHA5$W_{857L}$-AtSac66 term (SEQ ID NO: 66)) chosen according to the previous example with a tester line.

The transformant (TO) plant was first crossed with the A188 line thereby producing T1 plants. T1 plants were then self-pollinated twice, producing T3 plants which are homozygous lines containing the transgene. These T3 plants were then crossed with the tester line thereby leading to a hybrid. This hybrid is at a T4 level with regards to the transformation step and is heterozygous for the transgene. These hybrid plants are used in field experiments.

Control hybrids are obtained as follows:

Control Equivalent corresponds to a cross between a A188 line (the line used for transformation) and the tester line.

Yield was calculated as follows:

During harvest, grain weight and grain moisture are measured using on-board equipment on the combine harvester.

Grain weight is then normalized to moisture at 15%, using the following formula: Normalized grain weight=measured grain weight×(100−measured moisture (as a percentage))/85 (which is 100−normalized moisture at 15%).

As an example, if the measured grain moisture is 25%, the normalized grain weight will be: normalized grain weight=measured grain weight×75/85.

Yield is then expressed in a conventional unit (such as quintal per hectare).

B—Experimental Design:

Field trials are on 3 different locations.

The experimental block comprises 4 replicates. The experimental design was Randomized Lattice blocks in drought stressed locations. Each replicate comprised of two row plots with about up to 70 plants per plot at a density of 75 000 plants/ha.

Controls were used present in this experiment as described above a control equivalent (A188 crossed with the tester line).

A drought stressed location is a location where the grain yield potential of the site has not been reached due to a drought stress.

A non-stressed location is a location where the grain yield potential has been reached by a commercial hybrid variety.

The drought stress intensity is evaluated by measuring the yield lost between the drought stress treatment (WUE) and a reference treatment irrigated with an optimal amount of water, which is at least, equivalent to the maximum evapotranspiration (ETM) of the crop.

A yield loss of −30% is targeted with a common distribution of the drought location between −10% and −40% of yield.

A low drought stressed location is typically a location with a yield lost between 0% and up to −20% a moderate stressed location between −20% and up to −30%.

The targeted growth stage period is typically from tasseling to R2 growth stage.

In a common drought location, the drought stress period can spread out from a period between V10 and R4 growth stage.

Example 8: Water Loss Experiments

Figure 5:
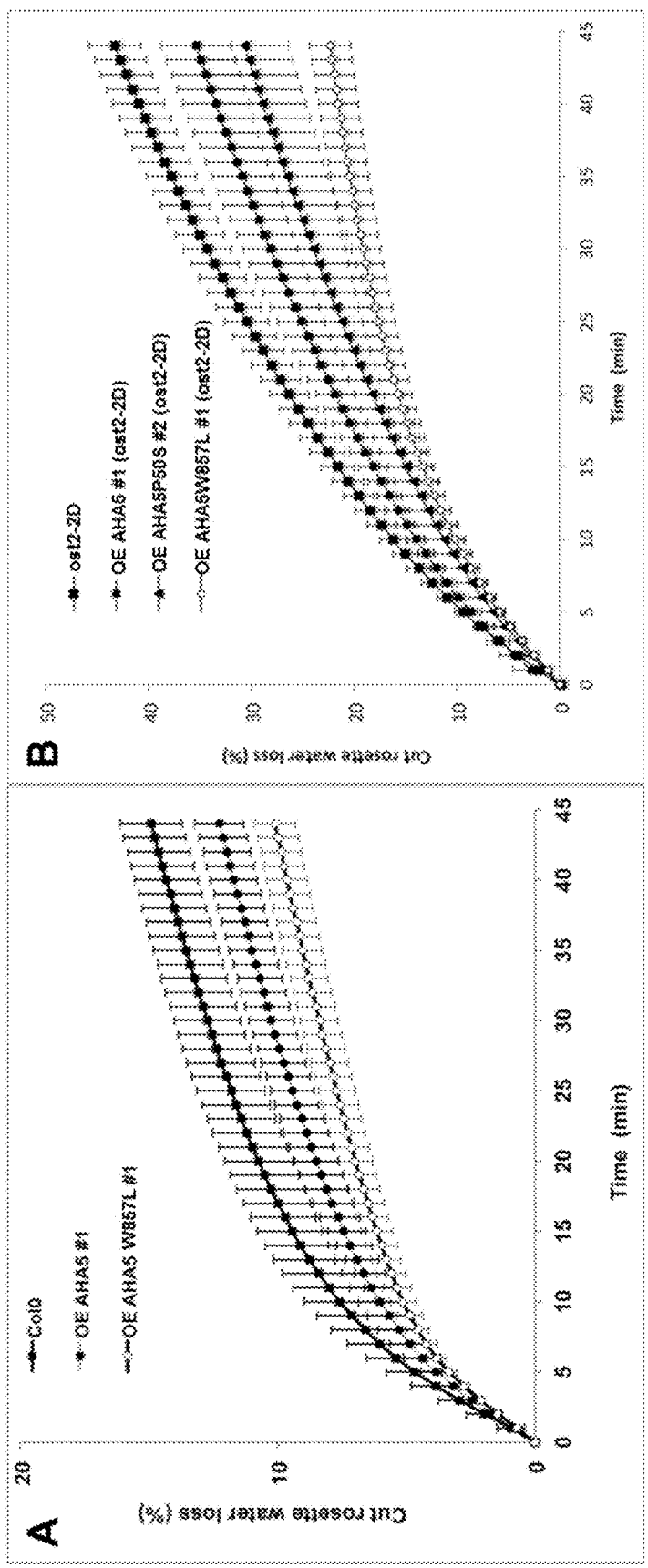
FIGS. 5A and B: Water loss experiments in plants transformed with AtAHA5, $AtAHA5_{P50S}$ or $AtAHA5_{W857L}$ under the control of the 35S promoter (OE means overexpression).

Transpirational water loss is one of the most important factors related to drought tolerance. To assess the rate of water loss, rosettes from plants (Col0 or ost2-2D) transformed with AtAHA5, AtAHA5$_{P50S}$ or AtAHA5$_{W857L}$ under the control of the 35S promoter, were detached and their fresh weight changes were measured over a 45 min period. The increase activity of AtAHA5 results in decreased water loss from excised rosettes. Rosettes from different ecotypes were grown on soil in growth chamber (21° C., 70% relative humidity, 8 h/16 h light/dark, 300 μmol·m-2·s-1) were excised at least 4 h after the beginning of the light period and transferred to darkness. Water loss was determined by monitoring the decrease in fresh weight of the excised rosettes. Means±SE of at least 3 independent measurements are shown on FIG. 5.

These data show that the leaves from plants that overexpressed AtAHA5 showed a slower rate of water loss compare to wild-type (FIG. 5A) or ost2-2D leaves (FIG. 5B). Moreover, the amino acid substitutions $P_{50}$S or $W_{857}$L enhance this effect showing that a constitutive activity of the AtAHA5 proton pump allows reducing rate of water loss.

Figure 6:
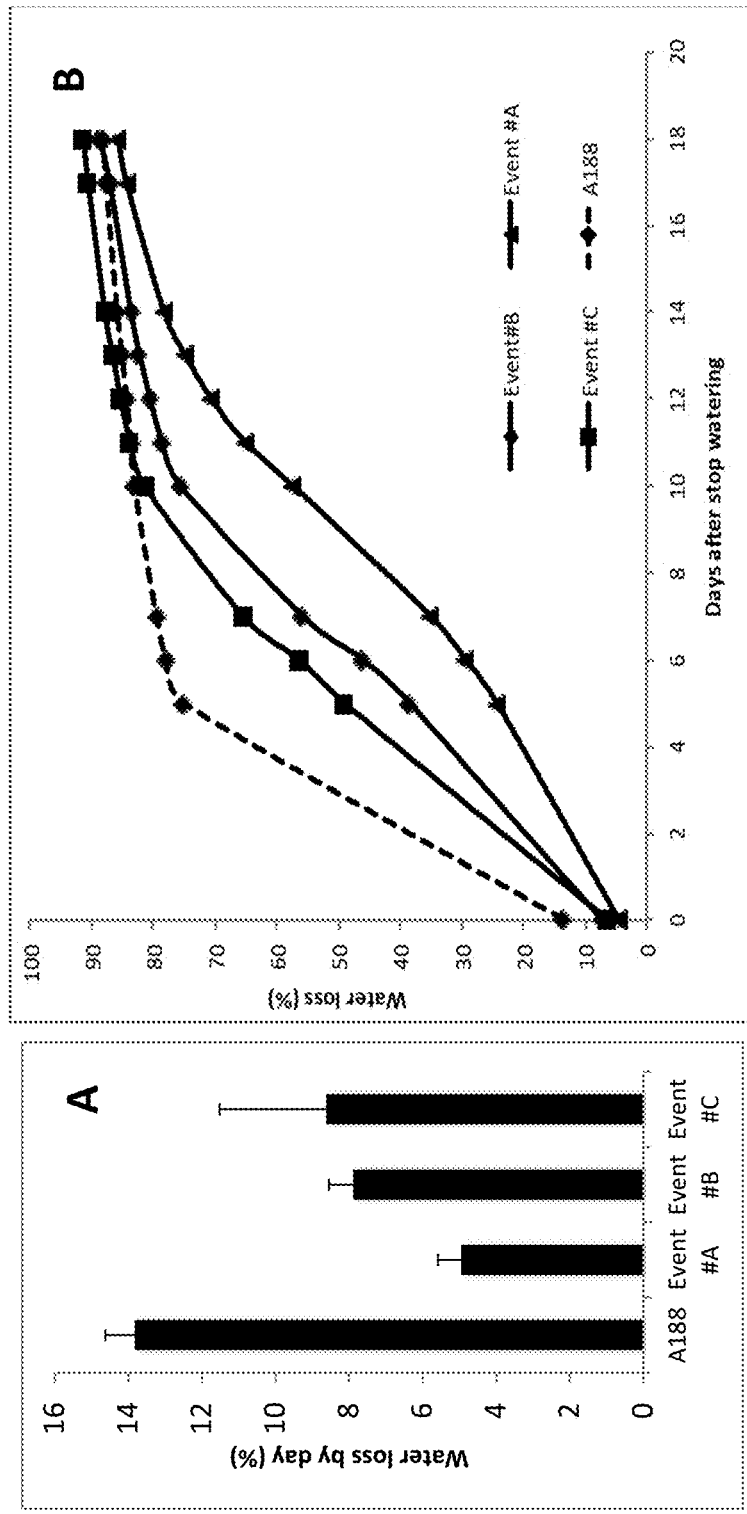
FIGS. 6A and B: Water loss experiments (A) by day and (B) in kinetics measured in maize plantlets transformed with ZmAHA5$_{W885L}$ under the control of the pZmRAB17 promoter for three events #A, #B, #C compared to A188 control.

Maize plantlets transformed with ZmAHA5$_{W885L}$ under the control of the promoter pZmRAB17 are grown on soil in a growth chamber under controlled conditions. After 5 weeks, plants are submitted to water stress and water loss is determined daily by monitoring the decrease of plantlets fresh weight while irrigation is stopped. The results are shown in FIGS. 6A and 6B. The data show that the leaves from plantlets that overexpress ZmAHA5$_{W885L}$ under the control of the promoter pZmRAB17 showed a slower rate of water loss as compared to A188 non-transformed plantlets leaves. The three events (Event #A, Event #B, Event #C) present a similar pattern of slower water loss compared to the control.

Figure 7:
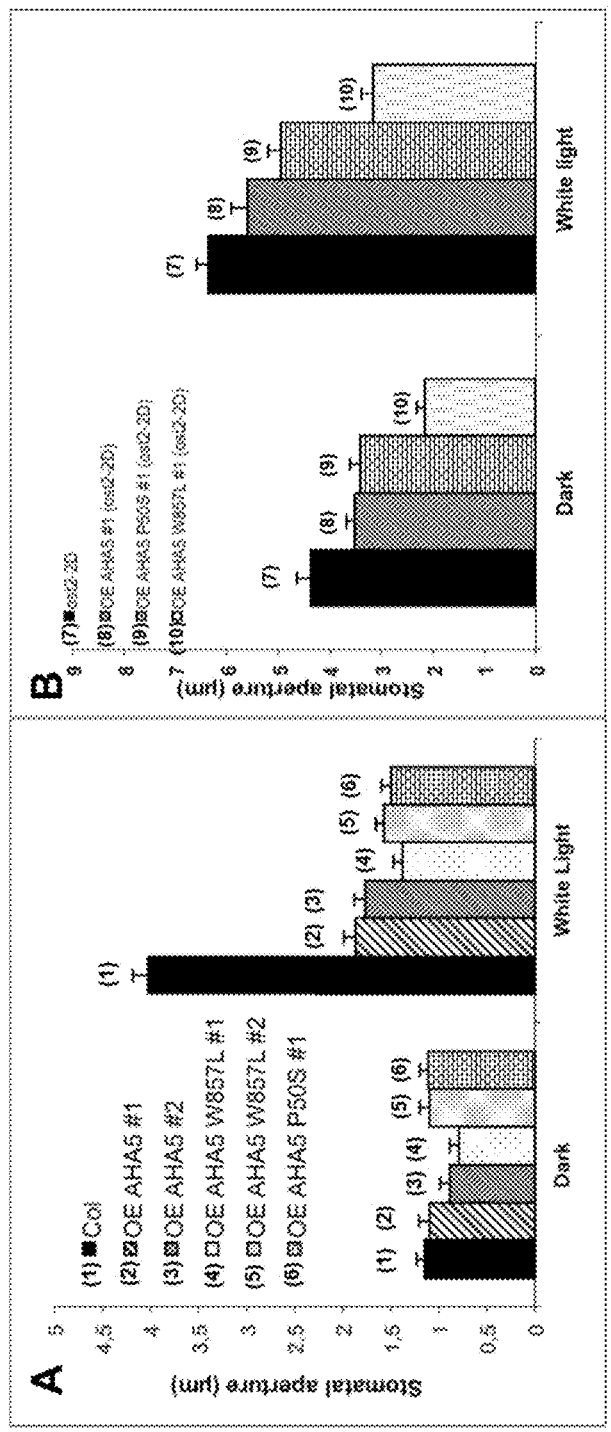
FIGS. 7A and B: Measurement of stomatal movements in response to light in plants transformed with AtAHA5, AtAHA5$_{P50S}$ or AtAHA5$_{W857L}$ under the control of the 35S promoter (OE means overexpression).

Example 9: Comparison of the Stomatal Aperture in Normal Conditions or with ABA The opening and closing of stomata are controlled by environmental factors, including light, humidity and $CO_2$ concentration, as well as by phytohormones, such as ABA (abscisic acid). Because the AtAHA5 over-expression lines exhibit a slower rate of water loss, the stomatal movement of the transformed plants was tested to compare with the controls (Col0 or ost2-2D). Stomatal aperture measurements were done on epidermis from leaves of 3-4 week-old-plants grown on soil in growth chamber (21° C., 70% relative humidity, 8 h/16 h light/dark, 300 µmol·m-2·s-1). After 30 min in darkness in 30 mM KCl, 10 mM MES-Tris pH6.0, stomatal apertures were measured. In light-induced stomatal opening experiments, epidermal peels were incubated 3 h under light (300 µmol·m-2·s-1) at 22° C. and then stomatal apertures were measured. Each value presented is the mean of at least 60 apertures from at least three independent experiments. Error bars represent standard errors to the mean (SEM) with a confidence interval of 95%. Data represent means±sem of 3 independent repetitions. Results are shown on FIG. 7.

Thus, the stomatal aperture of the transformed plants with several versions of AtAHA5 under the control of the 35S promoter was measured in different conditions and compared to wild-type (FIG. 7A) or ost2-2D (FIG. 7B).

In the dark, the apertures of all plants were similar compare to wild type plants but strongly affected in ost2-2D mutants suggesting that the AtAHA5 proton pump activity abolish the ost2-2D phenotype. After a 3 hours illumination, the stomatal aperture in the AtAHA5 over-expression lines was found to be greatly reduced compared to wild-type (FIG. 7A) or ost2-2D plants (FIG. 7B). Altogether, these results demonstrate that AtAHA5 activity inhibits light-induce stomatal opening. The size of the guard cells and the density of stomata were determined and both parameters are similar between transgenic lines and wild-type plants (data not shown).

Example 10: Biomass Experiments

Plant stomata control both carbon uptake and transpiration via opening and closure. Therefore when stomatal pore aperture is reduced due to stomatal closure, gas exchanges may be affected putatively limiting carbon uptake. Such reduction of gas exchanges may be translated in a lower photosynthesis rate and plant biomass. In order to evaluate the impact of the ectopic expression of AtAHA5 or its constitutively active variant on plant biomass, *Arabidopsis* plants (Col0 or ost2-2D) transformed with AtAHA5, AtAHA5$_{P50S}$ or AtAHA5$_{W857L}$ under the control of the 35S promoter, were grown on soil in growth chamber (21° C., 70% relative humidity, 8 h/16 h light/dark, 300 µmol·m-2·s-1) during 4 weeks and rosettes were excised at least 4 h after the beginning of the light period and transferred to darkness. The fresh weight of the excised rosettes was measured. Means and standard deviation are given (n≥6 plant repeats).

Figure 8:
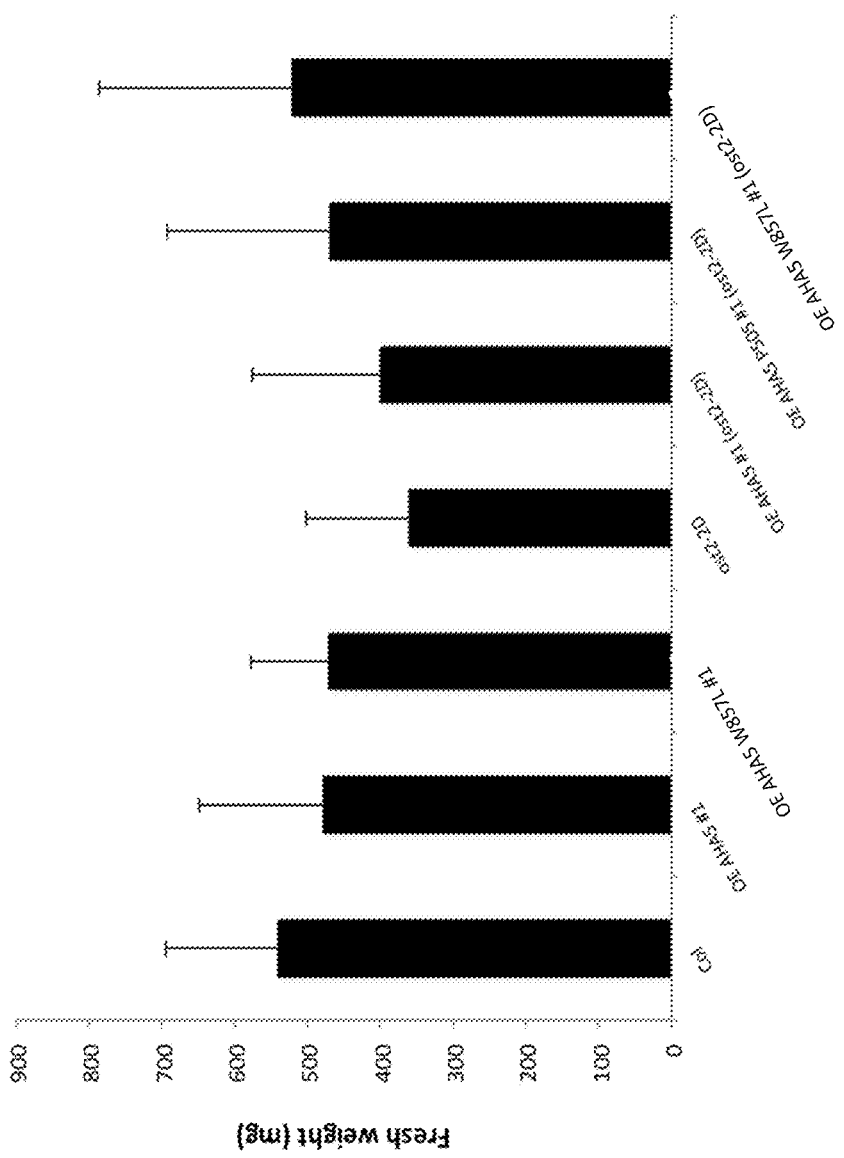
FIG. 8: Measurement of rosette fresh weight in plants transformed with AtAHA5, AtAHA5$_{P50S}$ or AtAHA5$_{W857L}$ under the control of the 35S promoter (OE means overexpression).

The increase activity of AtAHA5 or a constitutive variant AtAHA5 does not affect plant biomass in standard conditions. The biomass of the plants over-expressing AtAHA5 or its constitutive variant is not affected (FIG. 8)

Example 11: Characterization of the Promoter SbMYB60

Segregating T1 or T2 seeds expressing the pSbMYB60: ZsGreen cassette and nulls are sowed in pots with fertilizer and placed in a greenhouse controlled environment. Selection of the transgenic plants was carried out through herbicide resistance test.

12 transgenic plants per events are grown under normal irrigation of 5 minutes twice a day until the emergence of the 15th leaf. Then two lots of 6 plants per event undergo two different irrigation treatments. A lot is irrigated as explained above while the irrigation of the second lot is reduced to 1 minute 30 twice a day until panicle emergence then stopped until flowering stage. The leaf sampling is performed once plants are severely stressed at flowering stage.

In order to evaluate ZsGreen (Clonetech; Matz et al., 1999) expression in response to water deficit on younger leaf, drought stress experiments were also carried out on maize seedlings. Leaf 4 of 7 events were sampled concomitantly.

A—RT-PCR Analysis

Total RNAs are purified using SV 96 Total RNA Isolation System (Promega). A DNase treatment is applied and the integrity of the RNA is controlled. The cDNA are synthesized by reverse transcription using MultiScribe™ Reverse Transcriptase (Thermo Fisher Scientific).

ZsGreen transcripts are quantified by quantitative RT-PCR (cycle of 10 minutes at 25° C., 2 hours at 37° C., 5 minutes at 85° C.). Relative expression was normalized to ZmUbiquitin (GRMZM2G110983) and ZmEF1α (GRMZM2G001327) and calculated according to ΔΔCt method (Livak et al, 2001).

Figure 9:
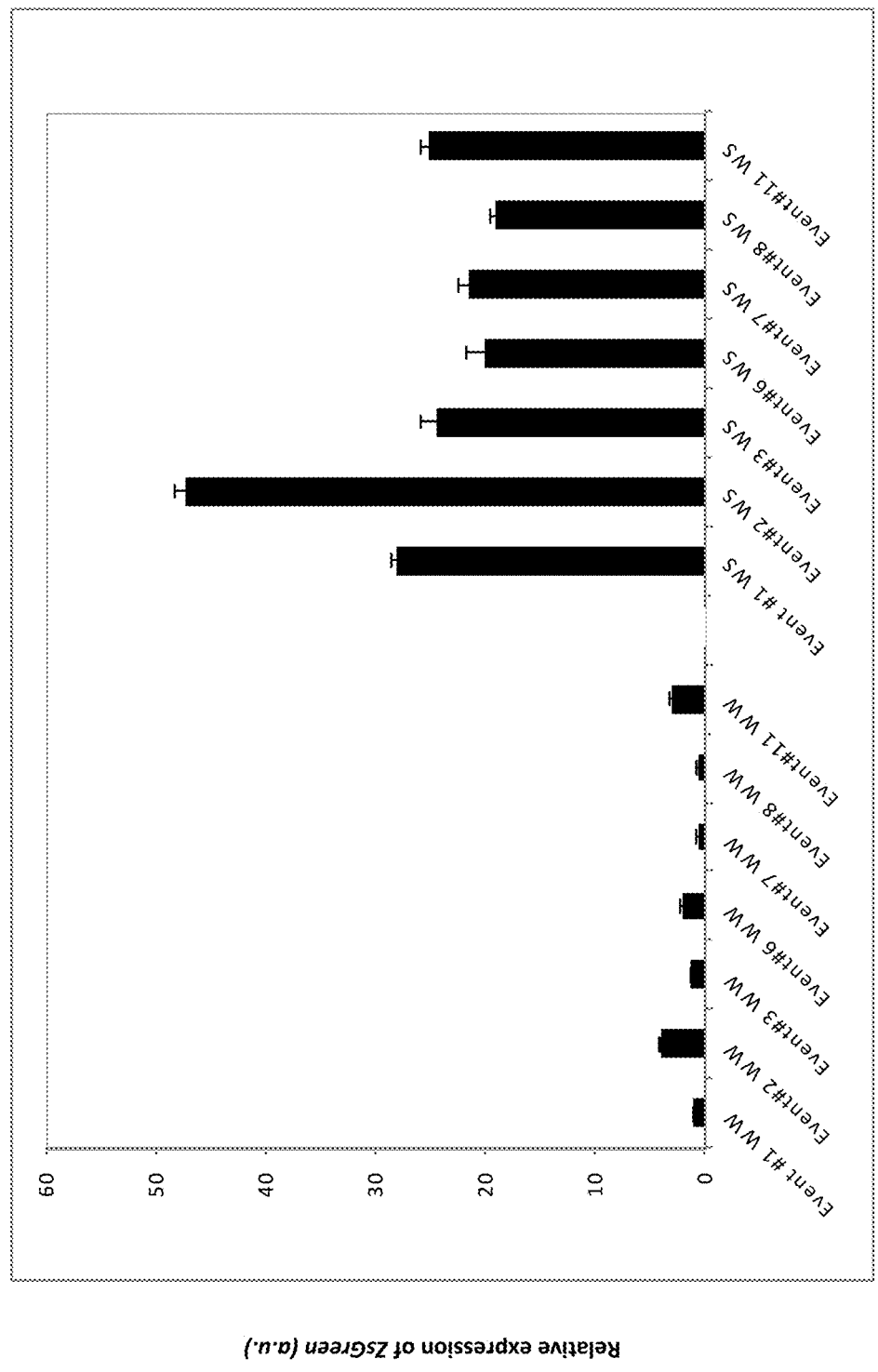
FIG. 9: Relative expression of ZsGreen expressed under the control of the promoter pSbMYB60 in the fourth leaf of transgenic maize plantlets grown under well-watered (WW) or water stress (WS) conditions.
Figure 10:
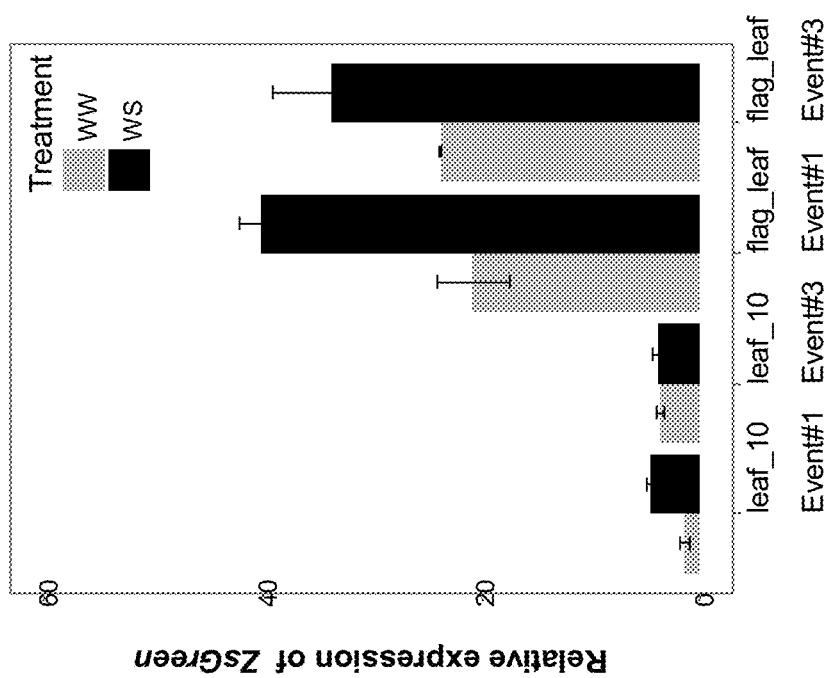
FIG. 10: Relative expression of ZsGreen expressed under the control of the promoter pSbMYB60 in the tenth leaf and the flag leaf of transgenic maize plants grown under well-watered (WW) or water stress (WS) conditions.

As seen in FIG. 9, expression of ZsGreen is significantly up-regulated at about 30 fold under stress conditions in young leaf (leaf #4) and reaching 50 fold for event 2. As seen in FIG. 10, expression of ZsGreen is found up-regulated at about 1.5 to 2 fold in older leaf (leaf #10 and flag leaf). Results are significant (p-value >0.01) except for leaf #10 of event 003. The level of ZsGreen cDNA in the tenth leaf of the stressed plants is statistically higher than in irrigated ones. This observation is identical for the flag leaf.

B—Confocal Microscopy Observation

Plants are grown as described above and confocal microscopy observation is carried out once plants are severely stressed. Adaxial transgenic plant leaf epidermis are isolated on a microscope slide. Slide are mounted in a mounting buffer (glycerol 50%, PBS 0.5×). The stomata are observed by confocal microscopy using a LSM 800 Airyscan (Carl Zeiss), excitation wavelength was 488 nm, a pinhole of 38 µm at 1 airy unit, emission was detected between 494 and 520 nm.

Figure 11:
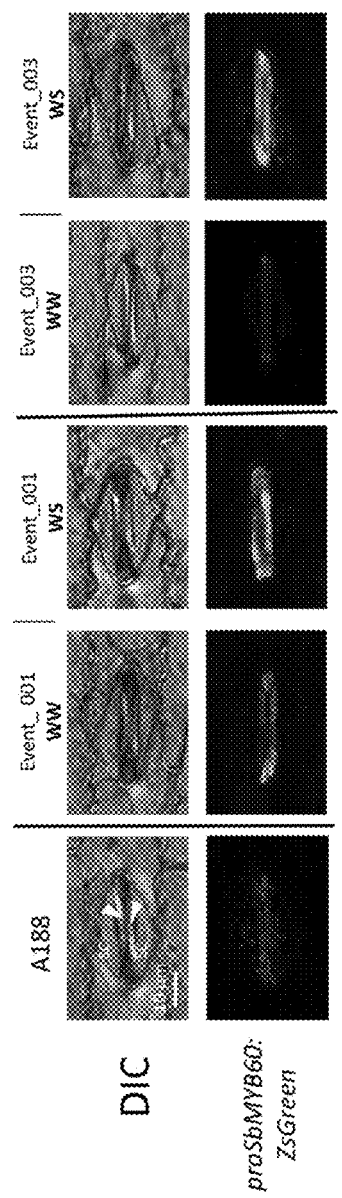
FIG. 11: Confocal microscopy imaging of ZsGreen fluorescence in the tenth leaf of transgenic maize plants grown under well-watered (WW) or water stress (WS) conditions. Scale bar, 10 μm.

As seen in FIG. 11, the fluorescence signal detected from observation of stressed plants guard cells is greater than that of well irrigated plants guard cells showing that the ZsGreen was more up-regulated in stressed plants.

These results indicate that the fragment of pSbMYB60 promoter used for transformation not only drives a guard-cell specific expression but yet drives an up-regulation of the downstream gene in response to water deficit. This promoter can be considered as a new drought inducible promoter.

REFERENCES

Patent Literature

EP2995680
WO2014/012145

EP1033405
US20130074202
US20090217414
U.S. Pat. No. 8,577,624

Non-Patent Literature

Alsterfjord et al. Plant Cell Physiol (2004) 45 (9): 1202-1210
Axelsen et al. Plant Physiology 2001 June; 126 (2): 696-706
Baunsgaard et al. The Plant Journal Volume 10, Issue 3 Sep. 1996 Pages 451-458
Baxter et al. PNAS (2005) vol. 102 no. 7 2649-2654
Caldeira et al. Plant Physiology 2014 April; 164 (4): 1718-30
Cid et al. Current Genetics June 1987, Volume 12, Issue 2, pp 105-110
Clément M et al. Plant Physiology 2011 July; 156 (3): 1481-92
DeWitt et al. The Plant Cell, Vol. 7, 2053-267 December 1995
Gouy M., Guindon S. & Gascuel O. (2010) Molecular Biology and Evolution 27 (2): 221-224
Guindon S., Dufayard J. F., Lefort V., Anisimova M., Hordijk W., Gascuel O. 2010, Systematic Biology, 59 (3): 307-21
Haruta et al. J Biol Chem. 2010 Jun. 4; 285 (23): 17918-17929.
Haruta et al. Curr Opin Plant Biol. 2015 December;28:68-75
Houlne et al. The Plant Journal Volume 5, Issue 3 Mar. 1994 Pages 311-317
Ishida et al. Nature Biotechnology, 14, 745-750, 1996
Jenkins et al. Plant, Cell and Environment (1999) 22, 159-167
Komari et al. (1996) The Plant Journal (1996) 10 (1), 165-174
Leonhardt N et al. Proc Natl Acad Sci USA. 1997 Dec. 9;94 (25): 14156-61
Leonhardt et al, The Plant Cell, Vol. 11, 1141-1151 June 1999
Livak et al, Methods 25, 402-408 (2001)
Matsuoka and Sanada, 1991 Mol Gen Genet. 225:411-9
Matz et al. 1999 Nature Biotechnology 17, 969-973
McElroy et al 1990 The Plant Cell, Vol. 2, 163-171, February 1990
Merlot S et al. (2002) Plant Journal 30:601-609
Merlot et al., 2007 The EMBO Journal Volume 26, Issue 13, 11 Jul. 2007, pp 3039-3271
Perfus-Barbeoch L et al. Plant J. 2002 November;32 (4): 539-48
Rusconi et al. 2013 J. Exp. Bot. 64:3361-71
Ueno et al. Plant Cell Physiol (2005) 46 (6): 955-963
Verdaguer et al (1996) Plant Molecular Biology September 1996, Volume 31, Issue 6, pp 1129-1139
Vilardell et al. Plant Mol Biol. 17:985-93
Vitart et al. The Plant Journal (2001) 27 (3), 191-201
Weigel and Glazebrook. In Planta Transformation of *Arabidopsis*. 2006 Cold Spring Harbor Protocols

---

The invention claimed is:

1. A method for decreasing water loss in a plant comprising introducing a genetic mutation into a plasma membrane H⁺-ATPase 5 (AHA5) gene of *Arabidopsis* or *Zea Mays* to generate a gene with a genetic mutation, wherein the gene with the genetic mutation encodes a mutated AHA5 protein, in a cell of the plant with gene editing techniques, wherein said mutated AHA5 protein is selected from:
(a) a mutated AHA5 protein comprising the amino acid sequence of SEQ ID NO: 31;
(b) a mutated AHA5 protein comprising the amino acid sequence of SEQ ID NO: 30; and
(c) a mutated AHA5 protein comprising the amino acid sequence of SEQ ID NO: 23; and regenerating said cell to obtain a whole plant, wherein the mutated AHA5 protein is at least expressed in guard cells and wherein said plant has decreased water loss.

2. The method according to claim 1, comprising introducing the genetic mutation into the AHA5 gene in a cell of the plant with CRISPR/Cas9.

3. The method according to claim 1, comprising introducing the genetic mutation into the AHA5 gene in a cell of the plant with TALENs.

4. The method according to claim 1, wherein the *Zea mays* AHA5 gene in the cell of the plant into which the mutation is introduced encodes SEQ ID NO:2.

5. The method according to claim 1, wherein said mutated AHA5 protein is a mutated AHA5 protein comprising the amino acid sequence of SEQ ID NO:31.

6. The method according to claim 1, wherein said mutated AHA5 protein is a mutated AHA5 protein comprising the amino acid sequence of SEQ ID NO:30.

7. The method according to claim 1, wherein said mutated AHA5 protein is a mutated AHA5 protein comprising the amino acid sequence of SEQ ID NO:23.

* * * * *